US008546327B2

(12) United States Patent  (10) Patent No.: US 8,546,327 B2
Dimarchi et al.  (45) Date of Patent: Oct. 1, 2013

(54) GLUCAGON/GLP-1 RECEPTOR CO-AGONISTS

(75) Inventors: Richard D. Dimarchi, Carmel, IN (US);
David L. Smiley, Bloomington, IN (US);
Maria Dimarchi, Carmel, IN (US);
Joseph Chabenne, Fishers, IN (US);
Jonathan Day, Bloomington, IN (US);
James Patterson, Martinsville, IN (US);
Brian Ward, Lebanon, IN (US)

(73) Assignee: Indiana University Research and Technology Corporation, Indianapaolis, IN (US)

( * ) Notice: Subject to any disclaimer, the term of this patent is extended or adjusted under 35 U.S.C. 154(b) by 0 days.

(21) Appl. No.: 12/999,283

(22) PCT Filed: Jun. 16, 2009

(86) PCT No.: PCT/US2009/047438
§ 371 (c)(1),
(2), (4) Date: May 16, 2011

(87) PCT Pub. No.: WO2009/155258
PCT Pub. Date: Dec. 23, 2009

(65) Prior Publication Data
US 2011/0257092 A1  Oct. 20, 2011

Related U.S. Application Data

(60) Provisional application No. 61/073,269, filed on Jun. 17, 2008, provisional application No. 61/078,168, filed on Jul. 3, 2008, provisional application No. 61/090,412, filed on Aug. 20, 2008, provisional application No. 61/177,476, filed on May 12, 2009.

(51) Int. Cl.
*A61K 38/26* (2006.01)
*A61K 38/00* (2006.01)
*A61K 38/16* (2006.01)

(52) U.S. Cl.
USPC ............ 514/7.2; 514/6.9; 514/4.8; 514/21.3; 530/324; 530/308; 530/345

(58) Field of Classification Search
None
See application file for complete search history.

(56) References Cited

U.S. PATENT DOCUMENTS

| | | | |
|---|---|---|---|
| 4,275,152 A | 6/1981 | Esders et al. | |
| 5,359,030 A | 10/1994 | Ekwuribe | |
| 5,510,459 A | 4/1996 | Smith et al. | |
| 5,512,549 A | 4/1996 | Chen et al. | |
| 5,665,705 A | 9/1997 | Merrifield et al. | |
| 5,783,674 A | 7/1998 | Geysen | |
| 6,191,102 B1 | 2/2001 | DiMarchi et al. | |
| 6,583,111 B1 | 6/2003 | DiMarchi et al. | |
| 6,677,136 B2 | 1/2004 | Marshall et al. | |
| 7,192,922 B2 | 3/2007 | Shannon et al. | |
| 7,211,557 B2 | 5/2007 | DiMarchi et al. | |
| 7,576,059 B2 | 8/2009 | Jonassen et al. | |
| 2003/0021795 A1 | 1/2003 | Houston et al. | |
| 2003/0143183 A1 | 7/2003 | Knudsen et al. | |
| 2003/0204063 A1 | 10/2003 | Gravel et al. | |
| 2004/0002468 A1 | 1/2004 | Wadsworth | |
| 2004/0235710 A1 | 11/2004 | DeFelippis et al. | |
| 2005/0070469 A1 | 3/2005 | Bloom et al. | |
| 2005/0095679 A1 | 5/2005 | Prescott et al. | |
| 2005/0124550 A1 | 6/2005 | Peri | |
| 2005/0153890 A1 | 7/2005 | Pan et al. | |
| 2005/0288248 A1 | 12/2005 | Pan et al. | |
| 2006/0003417 A1 | 1/2006 | Pan et al. | |
| 2006/0003935 A1 | 1/2006 | Pan et al. | |
| 2006/0171920 A1 | 8/2006 | Shechter et al. | |
| 2006/0210534 A1 | 9/2006 | Lee et al. | |
| 2006/0252916 A1 | 11/2006 | DiMarchi et al. | |
| 2006/0286129 A1 | 12/2006 | Sarubbi | |
| 2007/0042956 A1 | 2/2007 | Johansen et al. | |
| 2007/0173452 A1 | 7/2007 | DiMarchi et al. | |
| 2007/0203058 A1 | 8/2007 | Lau et al. | |
| 2007/0287670 A1 | 12/2007 | Natarajan et al. | |
| 2008/0113905 A1 | 5/2008 | DiMarchi et al. | |
| 2008/0125574 A1 | 5/2008 | Sheffer et al. | |
| 2008/0318837 A1 | 12/2008 | Quay et al. | |
| 2009/0036364 A1 | 2/2009 | Levy et al. | |
| 2009/0054305 A1 | 2/2009 | Schlein et al. | |

(Continued)

FOREIGN PATENT DOCUMENTS

CA 2024855 3/1992
EP 0220958 5/1987

(Continued)

OTHER PUBLICATIONS

Sloop et al. 2005. Expert Opin Ther Targets. 9:593-600.*
Zhang et al. 2000. Current Opin in Chem Biol. 4:461-467.*
Ahn, J.M. et al., Development of potent truncated glucagon antagonists, *J. Med. Chem.*, 44(9): 1372-9, Apr. 26, 2001. (Abstract).
Ahn, J.M. et al., A new approach to search for the bioactive conformation of glucagon: positional cyclization scanning, *J. Med. Chem.*, 44(19): 3109-16, Sep. 13, 2001. (Abstract).
Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

(Continued)

Primary Examiner — Shulamith H Shafer
(74) Attorney, Agent, or Firm — Barnes & Thornburg LLP

(57) ABSTRACT

Modified glucagon peptides are disclosed having enhanced potency at the glucagon receptor relative to native glucagon. Further modification of the glucagon peptides by forming intramolecular bridges or the substitution of the terminal carboxylic acid with an amide group produces peptides exhibiting glucagon/GLP-1 receptor co-agonist activity. The solubility and stability of these high potency glucagon analogs can be further improved by modification of the polypeptides by pegylation, acylation, alkylation, substitution of carboxy terminal amino acids, C-terminal truncation, or the addition of a carboxy terminal peptide selected from the group consisting of SEQ ID NO: 26 (GPSSGAPPPS), SEQ ID NO: 27 (KRNRNNIA) and SEQ ID NO: 28 (KRNR).

20 Claims, 49 Drawing Sheets

(56) References Cited

U.S. PATENT DOCUMENTS

| | | |
|---|---|---|
| 2009/0062192 A1 | 3/2009 | Christensen et al. |
| 2009/0074769 A1 | 3/2009 | Glaesner et al. |
| 2009/0137456 A1 | 5/2009 | DiMarchi et al. |
| 2009/0192072 A1 | 7/2009 | Pillutla et al. |
| 2010/0190699 A1 | 7/2010 | DiMarchi et al. |
| 2010/0190701 A1 | 7/2010 | Day et al. |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| EP | 0479210 | 4/1992 |
| EP | 0815135 | 9/1996 |
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| WO | WO96/29342 | 9/1996 |
| WO | WO 9707814 | 3/1997 |
| WO | 97/29180 | 8/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO 0020592 | 4/2000 |
| WO | WO00/42026 | 7/2000 |
| WO | WO 0058360 | 10/2000 |
| WO | 01/83527 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO2004000354 | 12/2003 |
| WO | 2004/022004 | 3/2004 |
| WO | 2004/067548 | 8/2004 |
| WO | WO 2004078777 | 9/2004 |
| WO | 2004/093823 | 11/2004 |
| WO | 2004/105781 | 12/2004 |
| WO | 2004/105790 | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | 2007/022123 | 2/2007 |
| WO | WO 2007028632 | 3/2007 |
| WO | WO2007028633 | 3/2007 |
| WO | 2007/056362 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | WO2009/058734 | 5/2009 |
| WO | 2009/095479 | 8/2009 |
| WO | 2009/099763 | 8/2009 |
| WO | WO/2009/009763 | 8/2009 |
| WO | 2009/155257 | 12/2009 |
| WO | 2009/155258 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |
| WO | 2011/094337 | 8/2011 |
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

Azizeh et al., "Pure glucagon antagonists: biological activities and cAMP accumulation using phosphodiesterase inhibitors," Peptides 1997, vol. 18, No. 5, pp. 633-641.

Chabenne et al., Optimization of the native glucagon sequence for medicinal purposes, J. Diabetes. Sci. Technol., 4(6): 1322-31, Nov. 1, 2010.

Day, et al., "A New Glucagon and GLP-1 Co-agonist Eliminates Obesity in Rodents," Nature Chemical Biology, vol. 5, No. 10, pp. 749-757 (Jul. 13, 2009).

Day et al., Charge inversion at position 68 of the glucagon and glucagon-like peptide-I receptors supports selectivity in hormone action. J. Pept. Sci., 17(3): 218-25, Nov. 30, 2010.

De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

De et al., Synthesis and characterization of ester-based prodrugs of glucagon-like peptide 1, *Biopolymers*, 94(4): 448-56 (2010).

Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.

Gelfanov, et al., "Discovery and Structural Optimization of High Affinity Co-Agonists at the Glucagon and GLP-1 Receptors," Understanding Biology Using Peptides, Springer, pp. 763-764 (Jun. 23, 2005).

GenBank entry AAH05278. Jul. 15, 2006. [Retrieved from the Internet Jun. 18, 2009: ~http://www._ncbi._nim.n_ih.gov/protein/13528972>].

Habegger et al., The metabolic actions of glucagon revisited, *Nat. Rev. Endocrinol.*, 6(12): 689-97, Oct. 19, 2010.

Harris, J. Milton, Final Word: PEGylation—A "Sunset" Technology? <http://licence.icopyright.net/user/viewFreeUse.act?fuid=OTUINjY3OA%3D%3D>, BioPharm International, Jun. 1, 2004.

Heppner et al., Glucagon regulation of energy metabolism, *Physiol Behav.*, 100(5): 545-8, Apr. 8, 2010.

Hruby, et al., "The Design and Biological Activities of Glucagon Agonists and Antagonists, and Their Use in Examining the Mechanisms of Glucose Action," Curr. Med. Chem. Imm., Endoc. & Metab. Agents, 1, pp. 199-215, (2001).

Joshi, et al., "The Degradation Pathways of Glucagon in Acidic Solutions," International Journal of Pharmaceutics, 203, pp. 115-125 (2000).

Joshi, et al., "The Estimation of Glutaminyl Deamidation and Aspartyl Cleavage Rates in Glucagon," International Journal of Pharmaceutics, 273, pp. 213-219 (2004).

Joshi et al., "Studies on the Mechanism of Aspartic Acid Cleavage and Glutamine Deamidation in the Acidic Degradation of Glucagon," Journal of Pharmaceutical Sciences, vol. 94, No. 9, pp. 1912-1927 (Sep. 2005).

Krstenansky, et al., "Importance of the C-terminal α-helical structure for glucagon's biological activity," Int. J. Peptide Protein Res., 32, pp. 468-475 (1988).

Lee, et al., "Synthesis, Characterization, and Pharmacokinetic Studies of PEGylated Glucagon-like Peptide-I," Bioconjugate Chemistry, vol. 16, No. 2, Mar. 1, 2005, pp. 377-382.

Levy et al., Optimization of the C-terminal Sequence in Glucagon to Maximize Receptor Affinity, Poster Presentation. Jun. 19, 2005.

Levy et al., Optimization of the C-terminal Sequence in Glucagon to Maximize Receptor Affinity, *Understanding Biology Using Peptides*, American Peptide Society, Apr. 2006.

Li et al., Design, synthesis and crystallization of a novel glucagon analog as a therapeutic agent, *Acta Crystallogr. Sect. F Struct. Biol. Cryst. Commun.*, 63(Pt 7):599-601, Jun. 15, 2007.

Li et al., Crystallization and preliminary X-ray analysis of anti-obesity peptide hormone oxyntomodulin, *Protein & Peptide Letters*, 15(2): 232-4 (2008).

Li et al., Structural Basis for Enhanced Solublity of a C-Terminally Extended Glucagon Analog, *Biopolymers*., 96(4): 480 (2011).

Madsen at al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.

McKee, et al., "Receptor Binding and Adenylate Cyclase Activities of Glucagon Analogues Modified in the N-Terminal Region," Biochemistry, vol. 25, pp. 1650-1656 (1986).

Murphy, et al., "Potent Long-Acting Alkylated Analogs of Growth Hormone-Releasing Factor," Pept. Res., vol. 1, No. 1, pp. 36-41 (1988).

Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.

Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.

Pan et al., "Design of a Long Acting Peptide Functioning as Both a Glucagon-like Peptide-1 Receptor Agonist and a Glucagon Receptor Agonist," J. Biol. Chem..; May 5, 2006, vol. 281, No. 18, pp. 12506-12515, Table 1.

Pan, et al., "Synthesis of Cetuximab-Immunoliposomes via a Cholesterol-Based Membrane Anchor for Targeted Delivery of a Neuron Capture Therapy (NCT) Agent to Glioma Cells," Bioconjug. Chem., vol. 18, No. 1, pp. 101-108 (Jan. 2007).

Patterson et al., A novel human-based receptor antagonist of sustained action reveals body weight control by endogenous GLP-1, *ACS Chem Biol.*, 6(2): 135-45 Nov. 4, 2010.

Patterson et al., Functional association of the N-terminal residues with the central region in glucagon-related peptides, *J. Peptide Sci.*, First published online Jun. 10, 2011.

PCT International Search Report for PCT/US2008/050099 completed by the US Searching Authority on 1 Sep. 1 2008.

PCT International Search Report for PCT/US2008/081333 completed by the US Searching Authority on Mar. 12, 2009.

PCT International Search Report for PCT/US2008/080973 completed by the US Searching Authority on Jun. 6, 2009.

PCT International Search Report for PCT/US2009/031593 completed by the US Searching Authority on Jun. 18, 2009.

PCT International Search Report for PCT/US2009/047438 completed by the US Searching Authority on Nov. 16, 2009.

PCT International Search Report for PCT/US2009/068678 completed by the US Searching Authority on Apr. 20, 2010.

PCT International Search Report for PCT/US2009/034448 completed by the US Searching Authority on May 10, 2010.

PCT International Search Report for PCT/US2010/038825 completed by the US Searching Authority on Aug. 23, 2010.

PCT International Search Report for PCT/US2010/059724 completed by the US Searching Authority on May 26, 2011.

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

Phillips et al., "Supramolecular Protein Engineering: Design of Zinc-Stapled Insulin Hexamers As A Long Acting Depot," J. Biol. Chem., vol. 285, No. 16, Apr. 16, 2010, pp. 11755-11759.

Robberecht, P., et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, vol. 21, pp. 117-128 (1988).

Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Sapse, et al., "The Role of Sale Bridge Formation in Glucagon: An Experimental and Theoretical Study of Glucagon Analogs and Peptide Fragments of Glucagon," Molecular Medicine, Blackwell Science, Cambridge, MA, vol. 8, No. 5, pp. 251-262 (May 1, 2002).

Stigsnaes, et al., "Characterization and Physical Stability of PEGylated Glucagon," Intl. J. of Pharamceutics, vol. 330, pp. 87-98, (2007).

Traylor et al., Identification of the High Potency Glucagon Agonist with Enhanced Biophysical Stability and Aqueous Solubility, Poster Abstract PY 10, pp. 505-506, Jun. 10, 2005.

Trivedi, D. et al., Design and synthesis of conformationally constrained glucagon analogues, *J. Med. Chem.*, 43(9): 1714-22, May 4, 2000 (Abstract).

Tschoep et al., A Novel Glucagon/GLP-1 Co-Agonist Eliminates Obesity in Rodents, Diabetes, 58 (Supp. 1): A83 (2009).

Unson et al., "Glucagon antagonists: Contribution to binding and activity of the amino-terminal sequence 1-5, position 12 and the putative alpha-helical segment 19-27," J. Biol. Chem.v264, pp. 789-794, Jan. 15, 1989, p. 792, para 1, Table 1.

Unson, et al., "Positively Charged Residues at Positions 12, 17 and 18 of Glucagon Ensure Maximum Biological Potency," J. Biol. Chem., vol. 273, No. 17, pp. 10308-10312 (1998).

Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.

Wynne, et al., "Subcutaneous Oxyntomodulin Reduces Body Weight in Overweight and Obese Subjects," Diabetes, vol. 54, pp. 2390-2395 (Aug. 2005).

Yang et al., Synthesis and Biological Assessment of Sulfonic Acid-Based Glucagon Antagonists, Understanding Biology Using Peptides, American Peptide Symposia, 9(Part 6): 305-6 (2006).

Zhang et al., Design and synthesis of novel GLP1 analogues with significantly prolonged time action, Biopolymers., 80(4): 555 (2005).

De, et al., "Investigation of the feasibility of an amide-based prodrug under physiological conditions," Int. J. Pept. Res. Ther., 14, pp. 255-262 (2008).

Madsen, et al., "Structure-activity and protraction relationship of long-acting glucagon-like peptide-1 derivatives: Importance of fatty acid length, polarity, and bulkiness," J. Med. Chem., 50, pp. 6126-6132 (2007).

PCT International Search Report for PCT/US2011/041601 completed by the US Searching Authority on Nov. 10, 2011.

Evans et al., "Effect of β-Endorphin C-Terminal Peptides on Glucose Uptake in Isolated Skeletal Muscles of the Mouse," Peptides, vol. 18, No. 1, pp. 165-167, (1997).

PCT International Search Report for PCT/US2008/053857 completed by the US Searching Authority on Sep. 16, 2008.

Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.

Gysin et al., "Design and Synthesis of Glucagon Partial Agonists and Antagonists," Biochemistry, 25, (1986), pp. 8278-8284.

PCT International Search Report for PCT/US2009/047437 completed by the US Searching Authority on Nov. 3, 2009.
Supplemental European Search Report issued in connection with EP Application No. 09767567.2 issued on Jun. 17, 2011.
Extended EP Search Report completed by the EP Searching Authority on Apr. 6, 2011 in connection with EP Patent Application No. 08845852.6.
DatabaseEMBL, Jul. 16, 2007, Richard DiMarchi and David Smiley, "Human Glucagon Peptide SEQ ID No. 1," XP002631582, retrieved from EBI, Database Accession No. AGB07042, Abstract.
Day et al., "A new glucagon and GLP-1 co-agonist eliminates obesity in rodents", Nature Chemical Biology (2009), 5(10), 749-757.
Day, J.; Patterson, J.; Gelfanov, V. and DiMarchi, Richard Molecular-basis for Specificity in Biological Action at the Homologous Glucagon and GLP-1 Receptors, (2009) Proceedings of the $21^{st}$ American Peptide Society 142-143.
De, A. and DiMarchi, R. Synthesis & Analysis of Peptide Hormone-based prodrugs, (2009) Proceedings of the 21st American Peptide Society 160-161.
De, Arnab; DiMarchi, Richard D. Investigation of the feasibility of an amide-based prodrug under physiological conditions. International Journal of Peptide Research and Therapeutics (2008), 14(4), 393.
DiMarchi, Richard, "The Use of Bioproducts in the Treatments of Metabolic Diseases" presentation slides for the Keystone Symposia (Jan. 25, 2009, Banff, Alberta).
Finan, B.; Gelfanov, V. and DiMarchi, R. Assessment of a Tat-Derived Peptide as a Vector for Hormonal Transport, (2009) Proceedings of the 21st American Peptide Society 321-322.
Kukuch, A.; Patterson, J.; DiMarchi, R. and Tolbert, T Immunoglobulin Fc-based Peptide Fusion Proteins as a Basis for Optimizing In Vivo Pharmacology, (2009) Proceedings of the $21^{st}$ American Peptide Society 177-178.
Ma, T.; Day, J.; Gelfanov, V. and DiMarchi, R. Discovery and Structural Optimization of High Affinity Co-Agonists at the Glucagon and GLP-1 Receptors, (2009) Proceedings of the $21^{st}$ American Peptide Society 146-147.
Ouyang et al., "Synthesis and Characterization of Peptides with Glucagon Antagonism and GLP-1 Agonism," poster presentation at the $21^{st}$ American Peptide Symposium (Jun. 7-12, 2009, Bloomington, IN).
Tschoep et al., "A Novel Glucagon/GLP-1 Co-Agonist Eliminates Obesity in Rodents," American Diabetes Association Abstract No. 313-OR (2009).
Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).
Tschoep, Matthias, "Afferent Gut Hormones in the Control of Energy Balance and Metabolism" presentation slides for the 21st American Peptide Symposium (Jun. 7-12, 2009, Bloomington, IN).
Ward, B.; Finan, B.; Gelfanov, V. and DiMarchi, R. Exploring the N-terminal Hydrophobic Faces of Glucagon and Glucagon-like Peptide-1, (2009) Proceedings of the $21^{st}$ American Peptide Society 153-154.
Yang, B. and DiMarchi, R.D. (2005). A Novel Approach to Resin-based Cysteine Alkylation Peptides: Chemistry, Structure and Biology, Proceedings of the XIX American Peptide Symposium, (88-89).
Irwin et al., "Early administration of the glucose-dependent insulinotropic polypeptide receptor antagonist ($Pro^3$) GIP prevents the development of diabetes and related metabolic abnormalities associated with genetically inherited obesity in ob/ob mice," Diabetologia 50:1532-1540 (2007).
Kulkarni, "GIP: No Longer the Neglected Incretin Twin?," Science Translational Medicine 2(49): p. 47, Sep. 15, 2010.
Montrose-Rafizadeh et al., "High Potency Antagonists of the Pancreatic Glucagon-like Peptide-1 Receptor," Journal of Biological Chemistry, 272(34) 21201-21206 (1997).
Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.
Habi et al., Peptide Science, vol. 80, Issue 4, pp. 608 and 579 (abstracts only), 2005.
Habi, "Special Issue: Program and Abstracts for the 19th American Peptide Symposium, 2005, Abstracts of Poster Section C," (pp. 574-603) Article first published online: Jun. 10, 2005 | DOI: 10.1002/bip.20325.
Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.
Vijayalakshmi et al., "Comparison of Helix-Stabilizing Effects of α, α-dialkyl Glycines with Linear and Cycloalkyl Side Chains", Biopolymers 53: 84-98 (Jan. 21, 2000).
Andrews et al., "Forming Stable Helical Peptides Using Natural and Artificial Amino Acids", Tetrahedron 55: 11711-11743, (1999).
Battersby et al., "Diketopiperazine Formation and N-Terminal Degradation in Recombinant Human Growth Hormone", International Journal of Peptide & Protein Research 44: 215-222, (1994).
Eriksson et al., "hPEPT1 Affinity and Translocation of Selected Gln-Sar and Glu-Sar Dipeptide Derivatives", Molecular Pharmaceutics vol. 2, No. 3: 242-249 (May 10, 2005).
Garcia-Aparicio et al., "Design and Discovery of a Novel Dipeptidyl-peptidase IV (CD26)-Based Prodrug Approach", J. Med. Chem. 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", AAPS Pharmsci 2000 2(1) article 5: 1-6 (Mar. 17, 2000).
Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).
Schafmeister et al., "An All-Hydrocarbon Cross-Linking System for Enhancing the Helicity and Metabolic Stability of Peptides", J. Am. Chem. Soc. 122: 5891-5892 (2000).
Walensky et al., "Activation of Apoptosis in Vivo by a Hydrocarbon-Stapled BH3 Helix", Science 205: 1466-1470 (Sep. 3, 2004).
Lebl, Michal, "Peptides: Breaking Away: The Proceedings of the Twenty-First American Peptide Symposium", Prompt Scientific Publishing (2009).
"Legacy Products—'Back to the Future'," presentation to Eli Lilly and Co., Sep. 22, 2005.
"Application of Chemical Biotechnology to Optimization of Endocrine Hormones," Carothers Lecture, Mar. 22, 2007.
"The Emergence of Chemical Biotechnology & Its Application to Optimization of Endocrine Hormones," UMBC presentation, Mar. 26, 2008.
"Emergence of Chemical Biotechnology," Eli Lilly and Co. presentation, Jun. 22, 2009.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," AAPS May 2010.
"Two for the Money" Gut Hormone Hybrids, Tschoep, ADA meeting, Jun. 25-29, 2010, Orlando, FL.
"Biotechnology—A Basis for Better Health & Economic Prosperity," Ohio State University presentation, Aug. 28, 2010.
"Novel Glucagon-Based Peptides—Virtues of Combinatorial Pharmacology," European Peptide Symposium, Sep. 5-9, 2010, Copenhagen, Denmark.
"Biotechnology—A Basis for Better Health & Economic Prosperity," Indiana University television presentation, Nov. 2010.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Speaking From the Gut: From Gastrointestinal Hormones to Combinatorial Therapies," Presentation to American Diabetes Association, Jun. 25, 2011.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
"The Pursuit of Transformational Medicines," Keystone presentation, Jan. 29-Feb. 3, 2012, Santa Fe, NM.

"Novel Glucagon Peptides That Demonstrate the Virtues of Combinatorial Pharmacology," University of Toledo, Mar. 22, 2012.

Althage et al., JBC "Targeted Ablation of GIP-Producing Cells in Transgenic mice reduces obesity and insulin resistance induced by a high fat diet" 2008).

Chia et al., "Exogenous glucose-dependent insulinotropic polypeptide worsens post-prandial hyperglycemia in type 2 diabetes," Diabetes, 58: 1342-1349 (2009).

Drucker, "Glucagon Gene Expression in Vertebrate Brain," The Journal of Biological Chemistry, vol. 263, No. 27, pp. 13475-13478, 1988.

Drucker, "The biology of incretin hormones," Cell Metabolism 3:153-165 (2006).

PCT International Search Report for PCT/US2009/047447 completed by the US Searching Authority on Mar. 19, 2010.

Collie et al., "Purification and sequence of rat oxyntomodulin," Proc. Natl. Acad. Sci. USA, vol. 91, pp. 9362-9366, Sep. 1994.

Sueiras-Diaz et al., "Structure-Activity Studies on the N-Terminal Region of Glucagon," J. Med. Chem., 27, pp. 310-315, 1984.

Hjorth et al., "Glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.

Unson et al., "Role of Histidine-1 in Glucagon Action," Archives of Biochemistry and Biophysics, vol. 300, No. 2, pp. 747-750, Feb. 1, 1993.

Sato, II., "Enzymatic procedure for site-specific pegylation of proteins," Advanced Drug Delivery Reviews 54, pp. 487-504 (2002).

"Novel Glucagon-Like Chimera Peptides—Virtues of Combinatorial Pharmacology," University of Cincinnati, Jun. 2010.

"Molecular Miracles," Indiana University, Apr. 13, 2011.

"Novel Glucagon-Based Peptides—Virtues of Combinatorial Pharmacology," Aug. 31, 2011, Berlin.

Ward, "Fatty Acid Acylation of Peptides: Developing strategies to enhance medicines for treating metabolic disorders," Jan. 14, 2009.

DiMarchi, "Peptides—Development of Prodrug Chemistry," RBF Symposium Feb. 1-4, 2011 India.

Tschoep, "CNS Integration of Systems Metabolism: Target Opportunities for Diabetes Prevention and Therapy," RBF Symposium Feb. 1-4, 2011 India.

Yang et al., "Synthesis and Biological Assessment of Sulfonic Acid-Based Glucagon Antagonists," American Peptide Society, 2005.

Yang et al., "A Novel Approach to Resin-Based Cysteine Alkylation," American Peptide Society, 2005.

Yang et al., "Synthesis and Biological Assessment of Sulfonic Acid-Based Glucagon Antagonists," poster presentation to American Peptide Society, 2005.

Yang et al., "A Novel Approach to Resin-Based Cysteine Alkylation," poster presentation to American Peptide Society, 2005.

Wibowo, Synthesis, Purification, and Biological Activity of AIB Substituted Glucagon and GLP-1 Peptide Analogues (2005-2006) vol. 45, 707=738, accessed https://scholarworks.iu.edu/dspce/handle/2022/326 on Jul. 17, 2012.

O'Brien, Assay for DPPIV Activity using Homogenous, Luminescent Method, Cell Notes 2005, 11:8-11.

Hansen et al., "Incretin hormones and insulin sensitivity," Trends in Endocrinology and Metabolism, vol. 16, No. 4, May/Jun. 2005, pp. 135-136.

Jax® Diet-Induced Obesity (DIO) Models, Retrieved from the internet on Feb. 4, 2013 (http://jaxmice.jax.org/diomice/index.html).

Parekh et al, Reversal of diet-induced obesity and diabetes in C57BL/6J mice. Metabolism. Sep. 1998;47(9):1089-96, Abstract only.

Samson et al, Gene Therapy for Diabetes: Metabolic Effects of Helper-dependent Adenoviral Exendin 4 Expression in a Diet-induced Obesity Mouse Model Mol Ther. Nov. 2008; 16(11): 1805-1812.

* cited by examiner

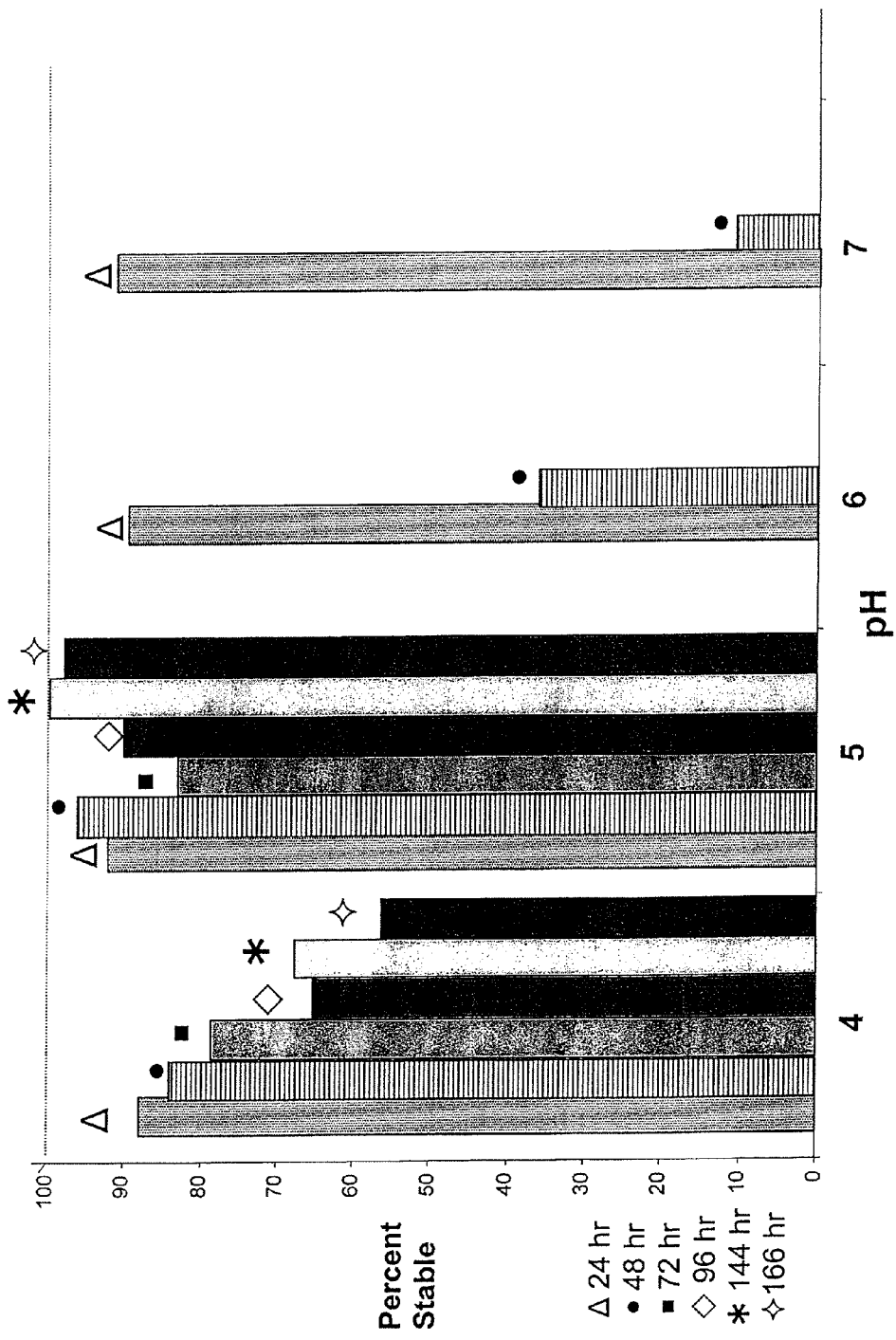

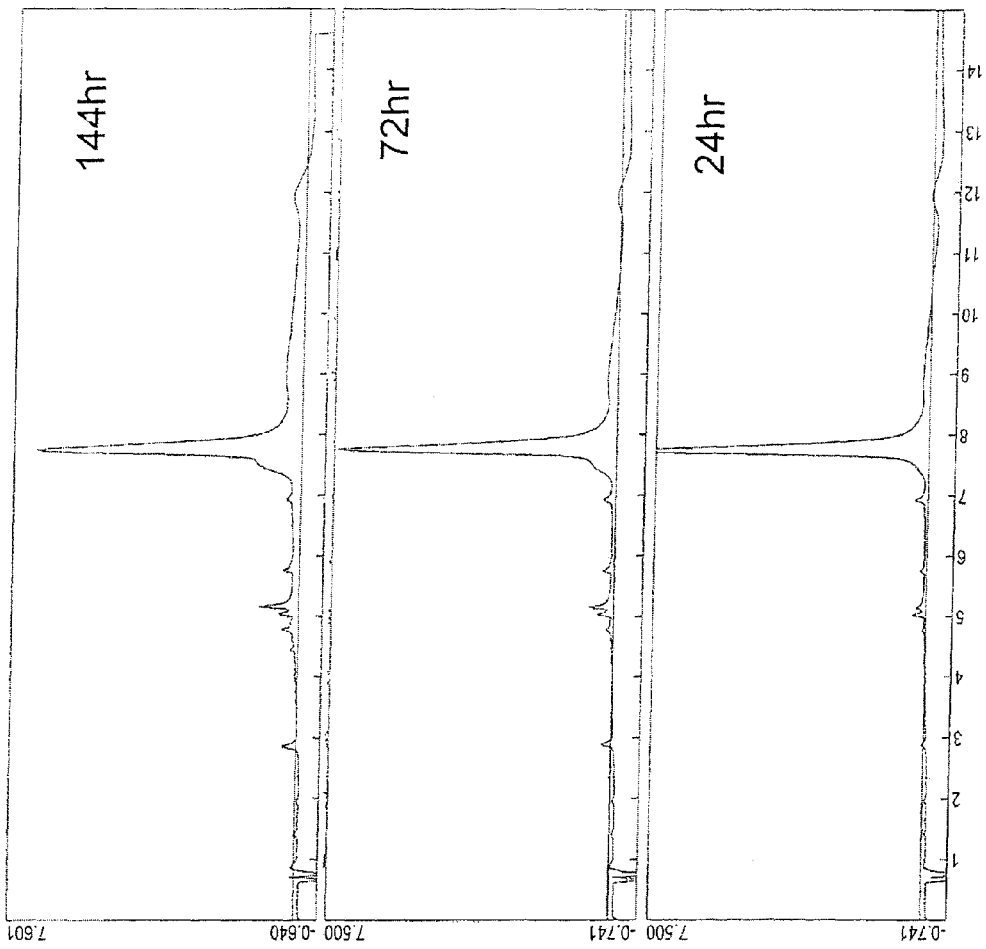

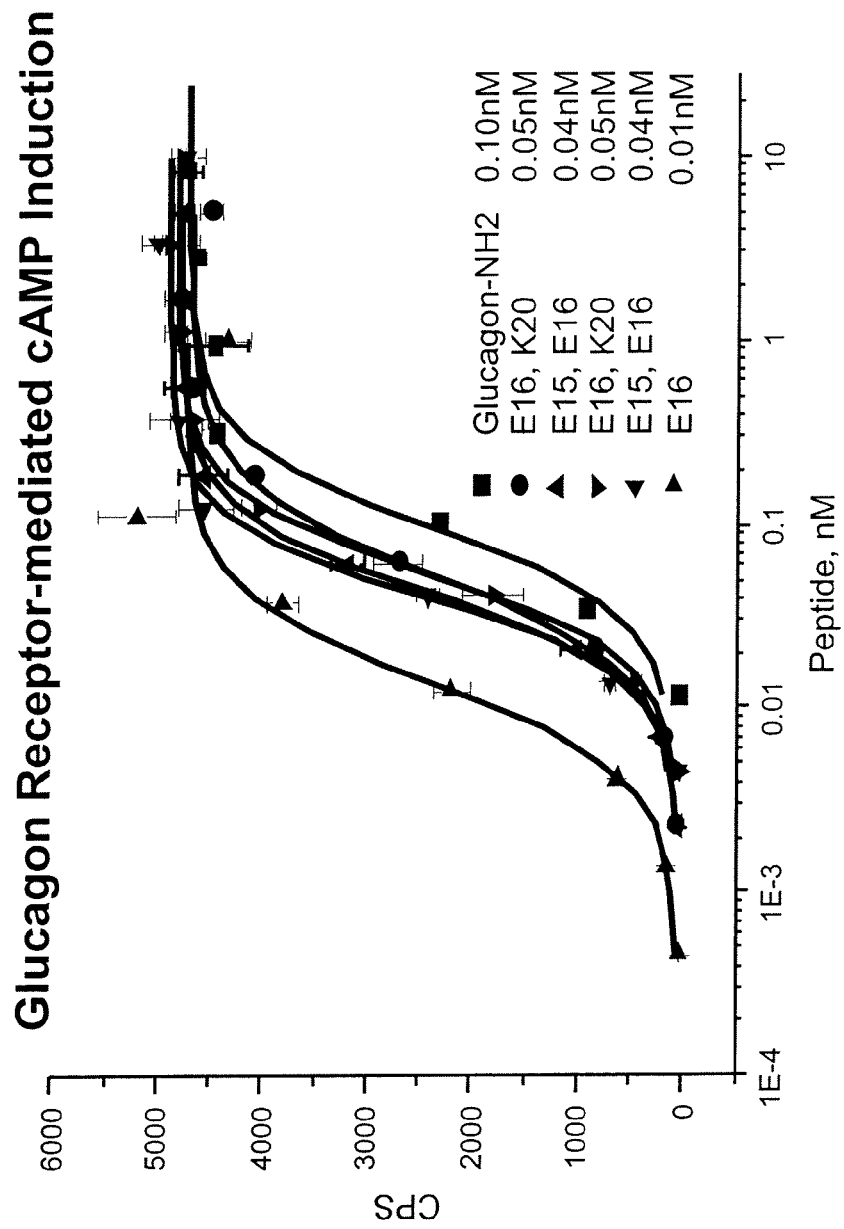
Fig. 3 Glucagon Receptor-mediated cAMP Induction

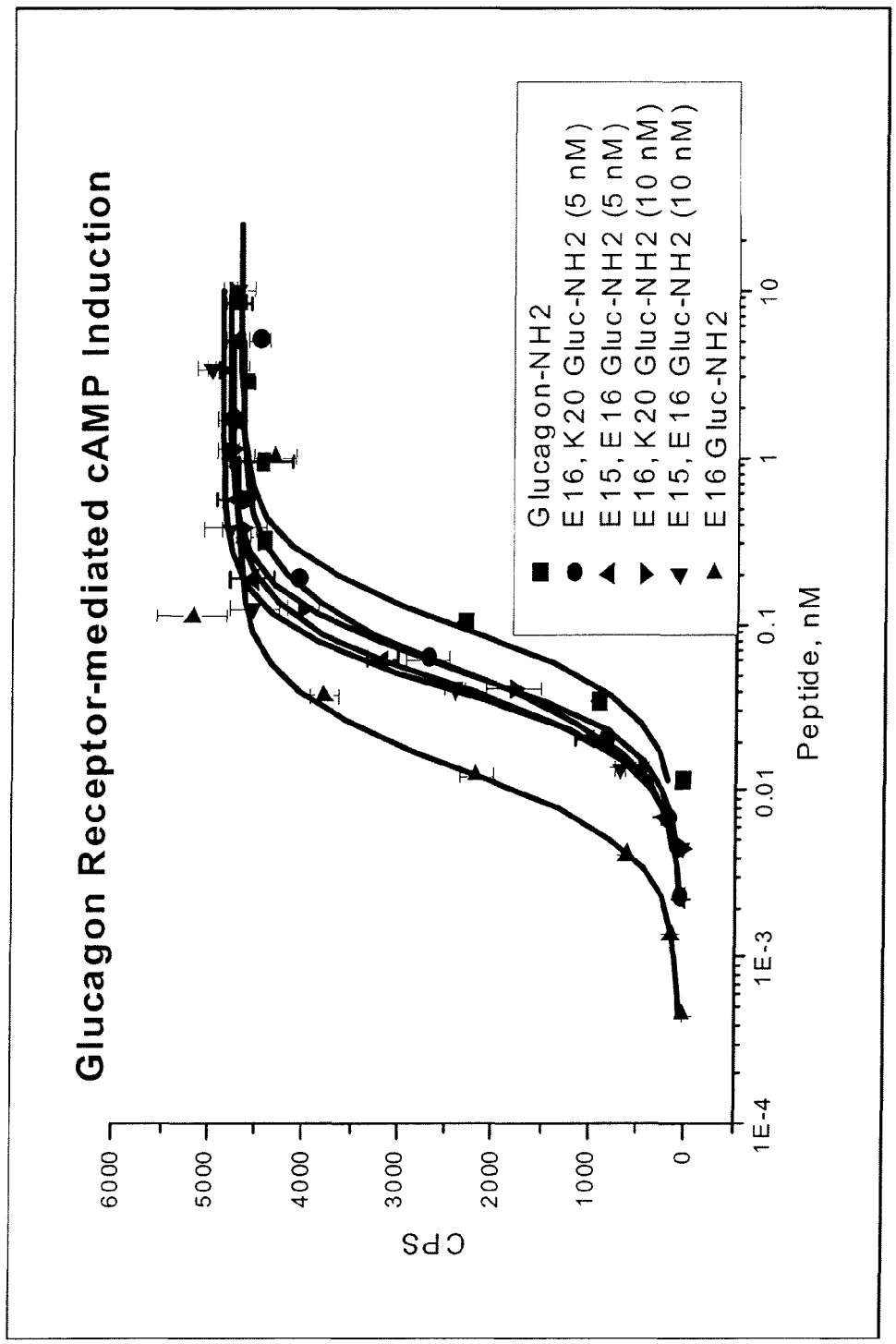

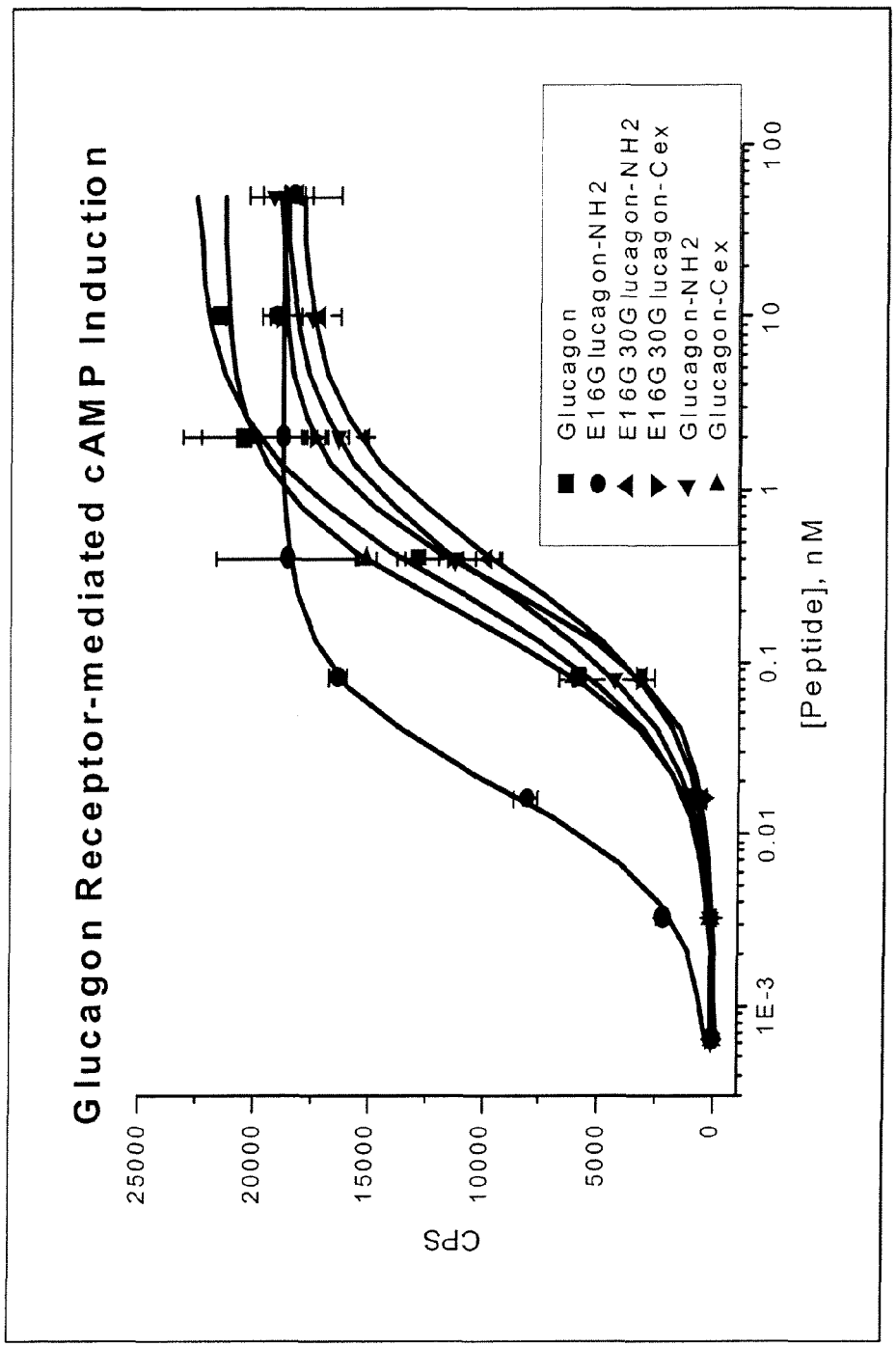
Fig.8A: Position 16 and C-terminal Modification of Glucagon

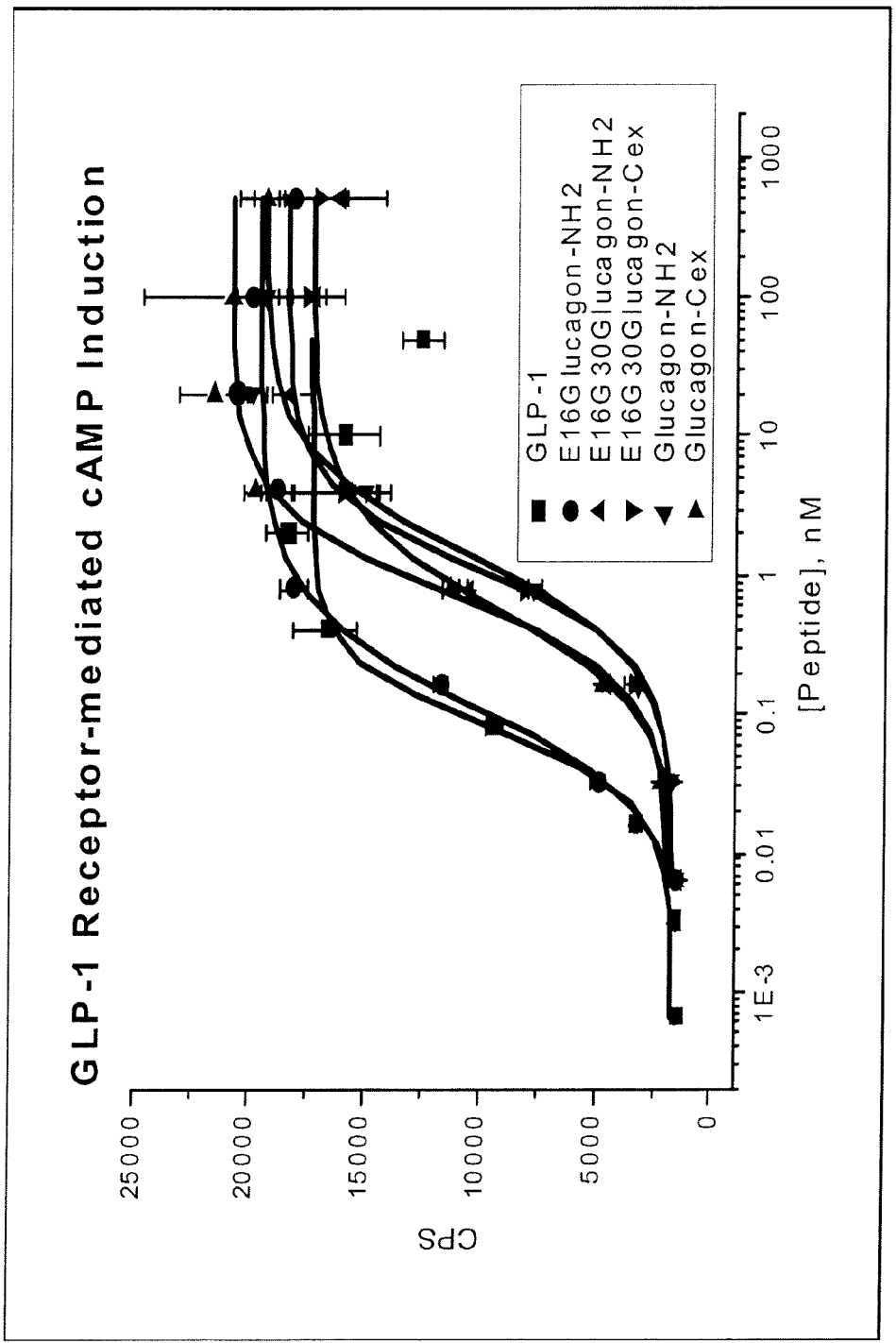
Fig. 8B: Position 16 and C-terminal Modification of Glucagon

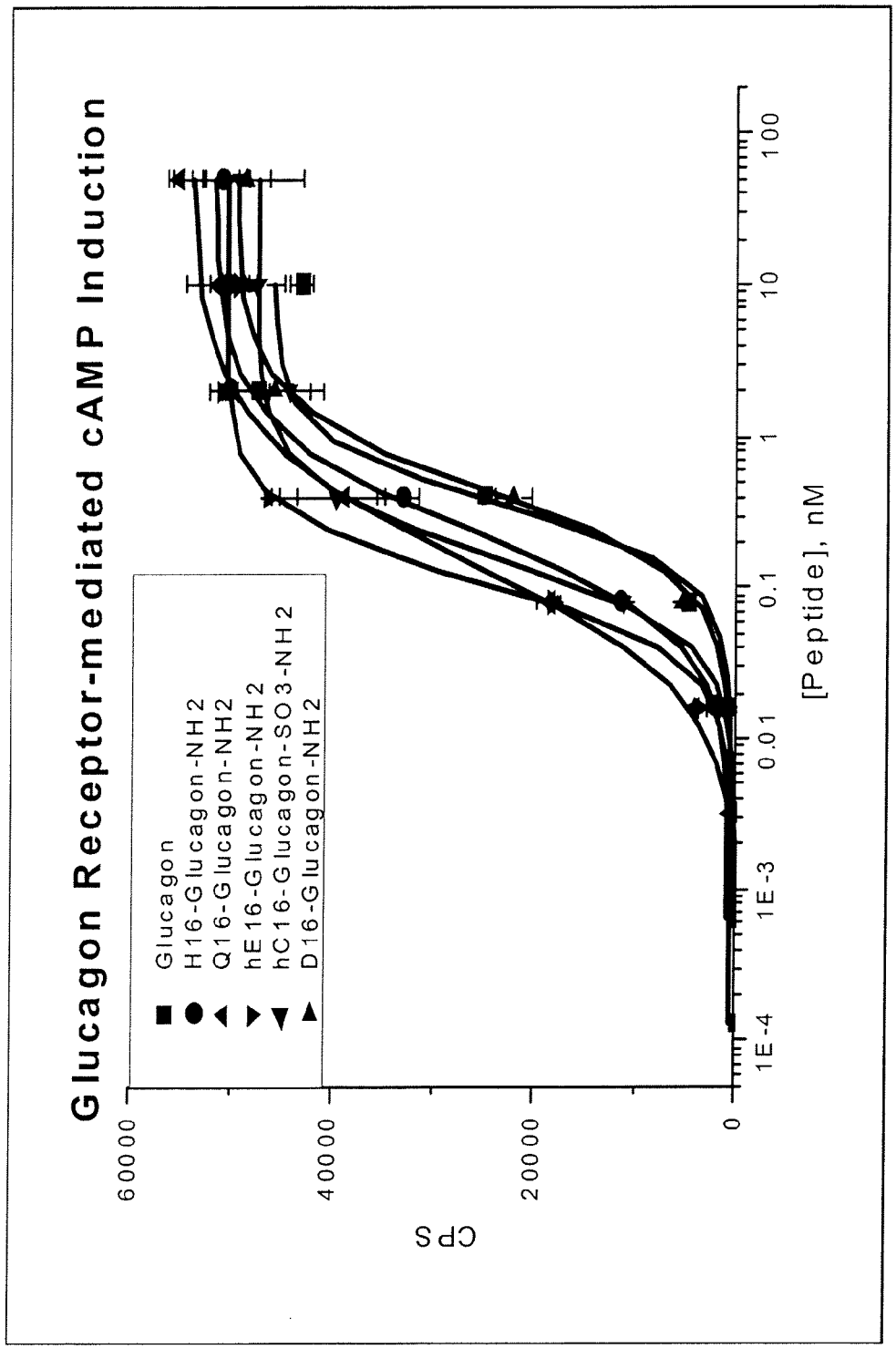
Fig. 8C: Substitutions at Position 16 of Glucagon

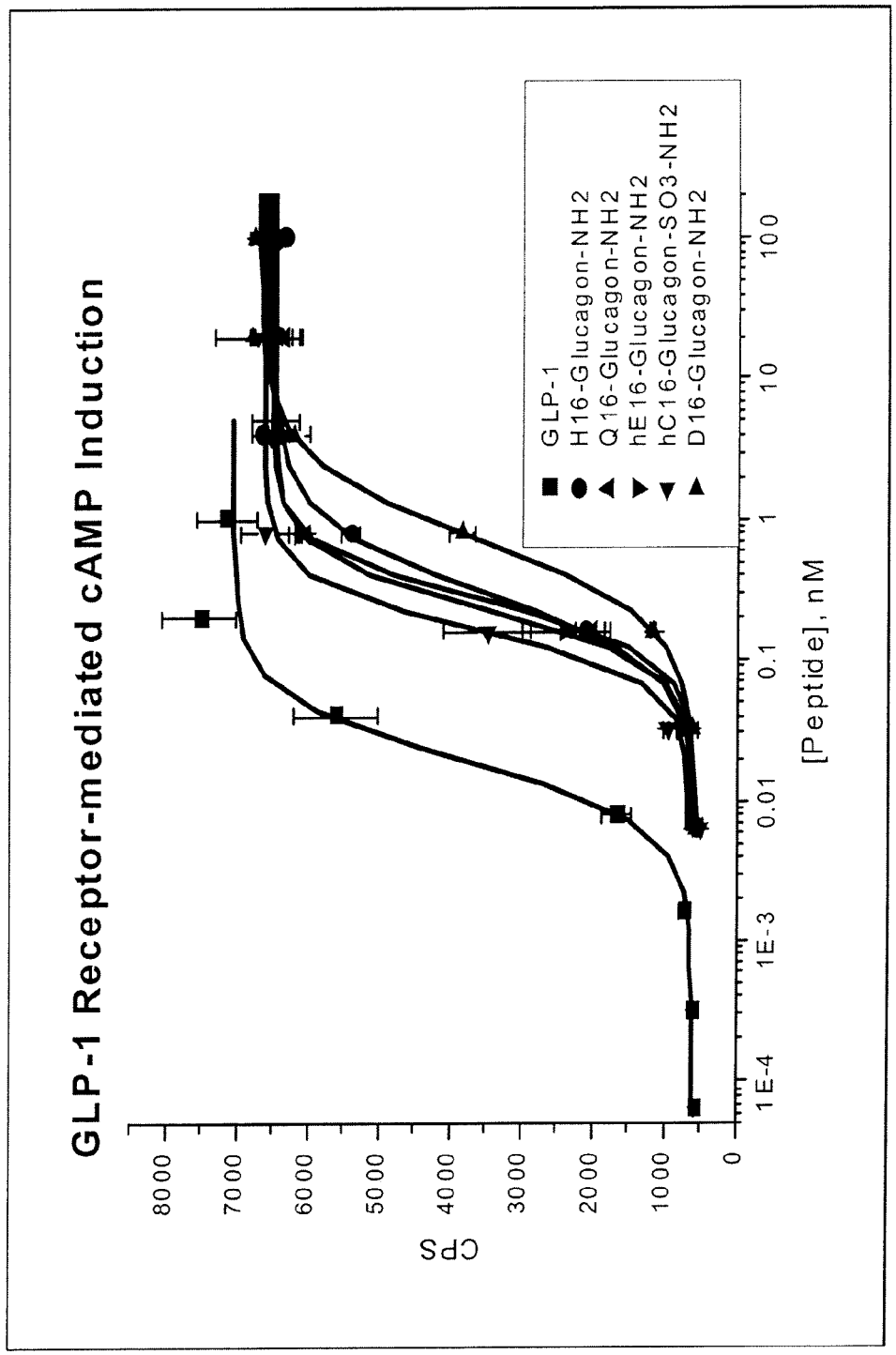

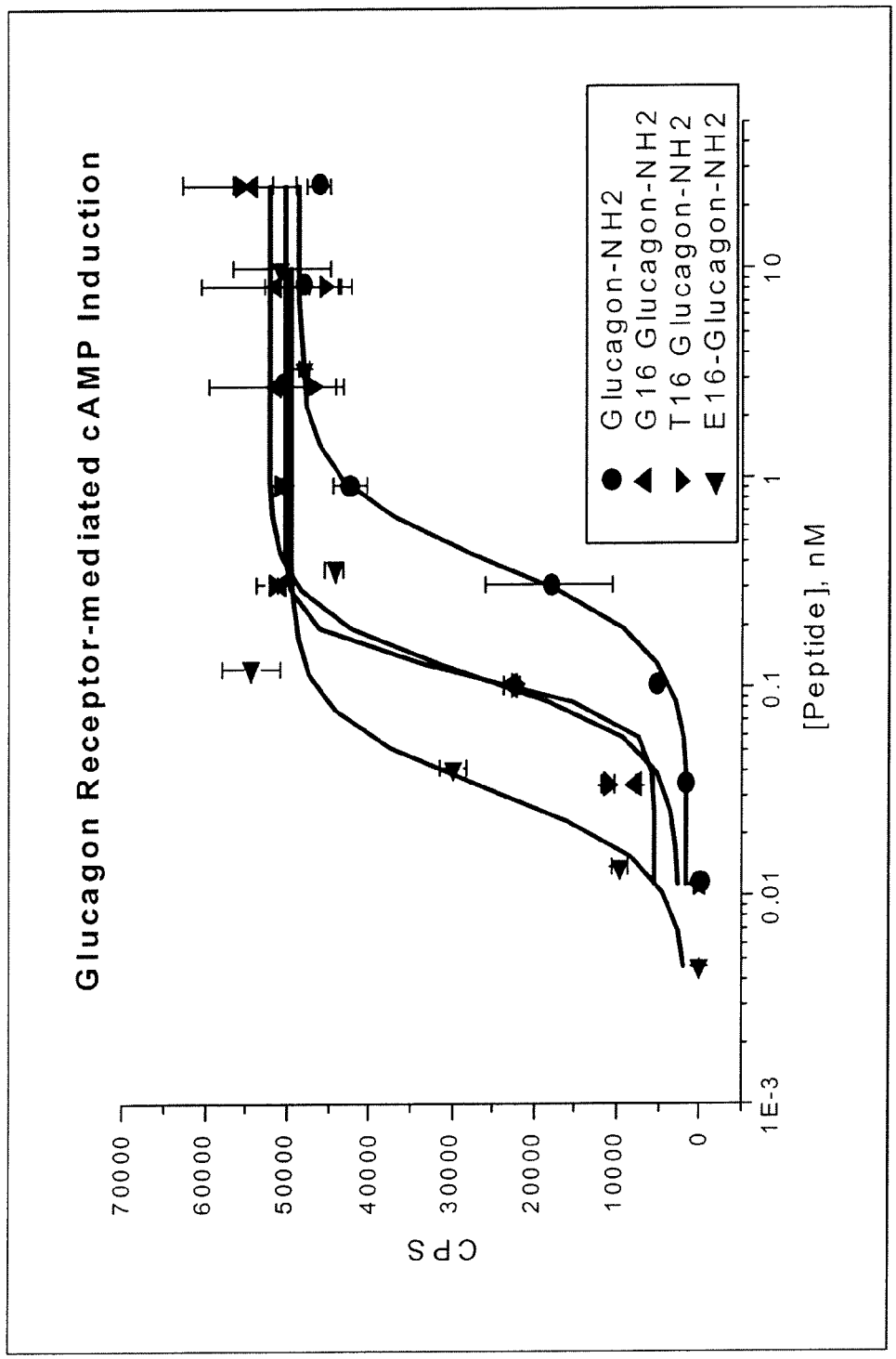
Fig. 8E: Substitutions at Position 16 of Glucagon

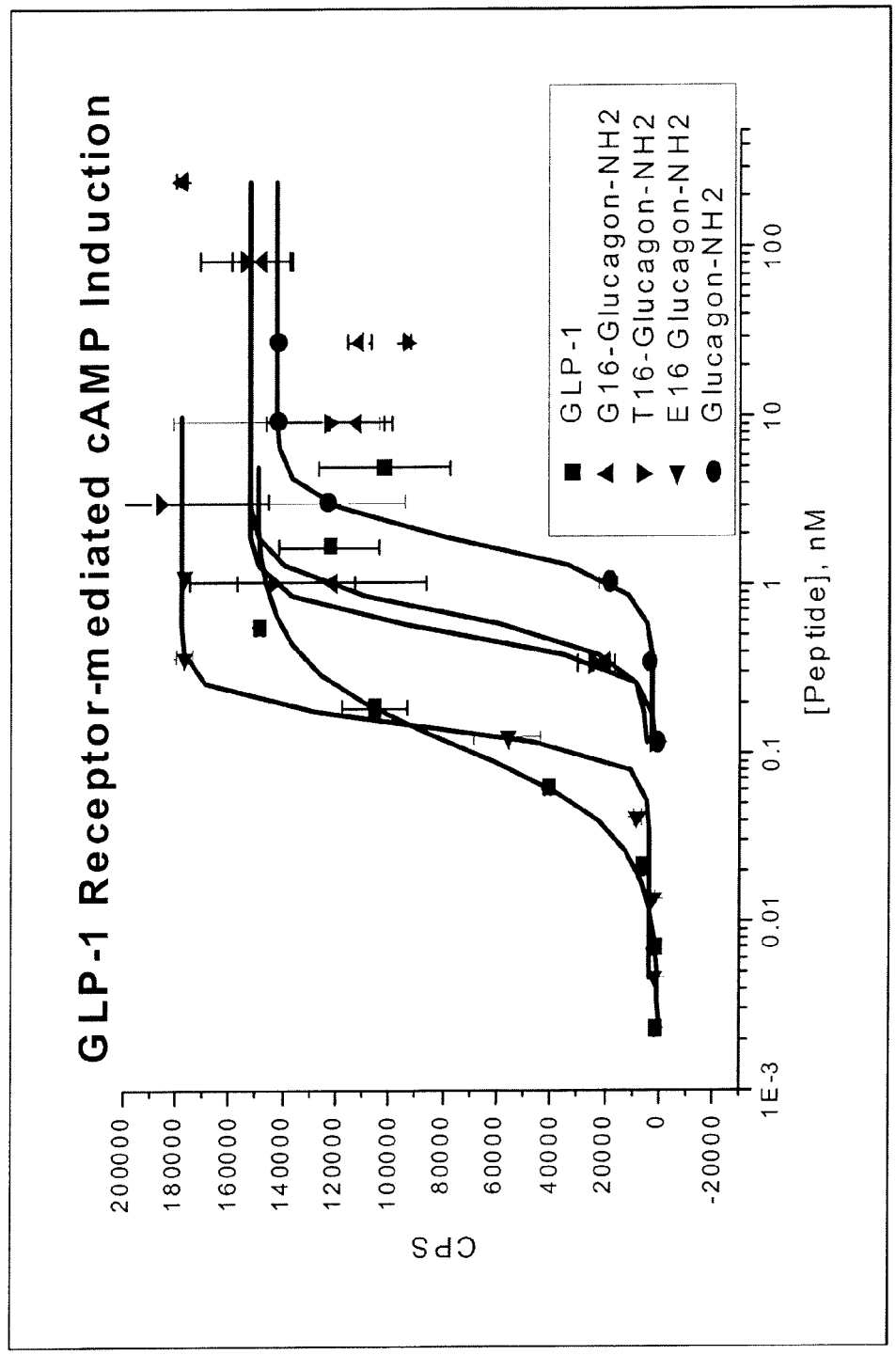
Fig. 8F Substitutions at Position 16 of Glucagon

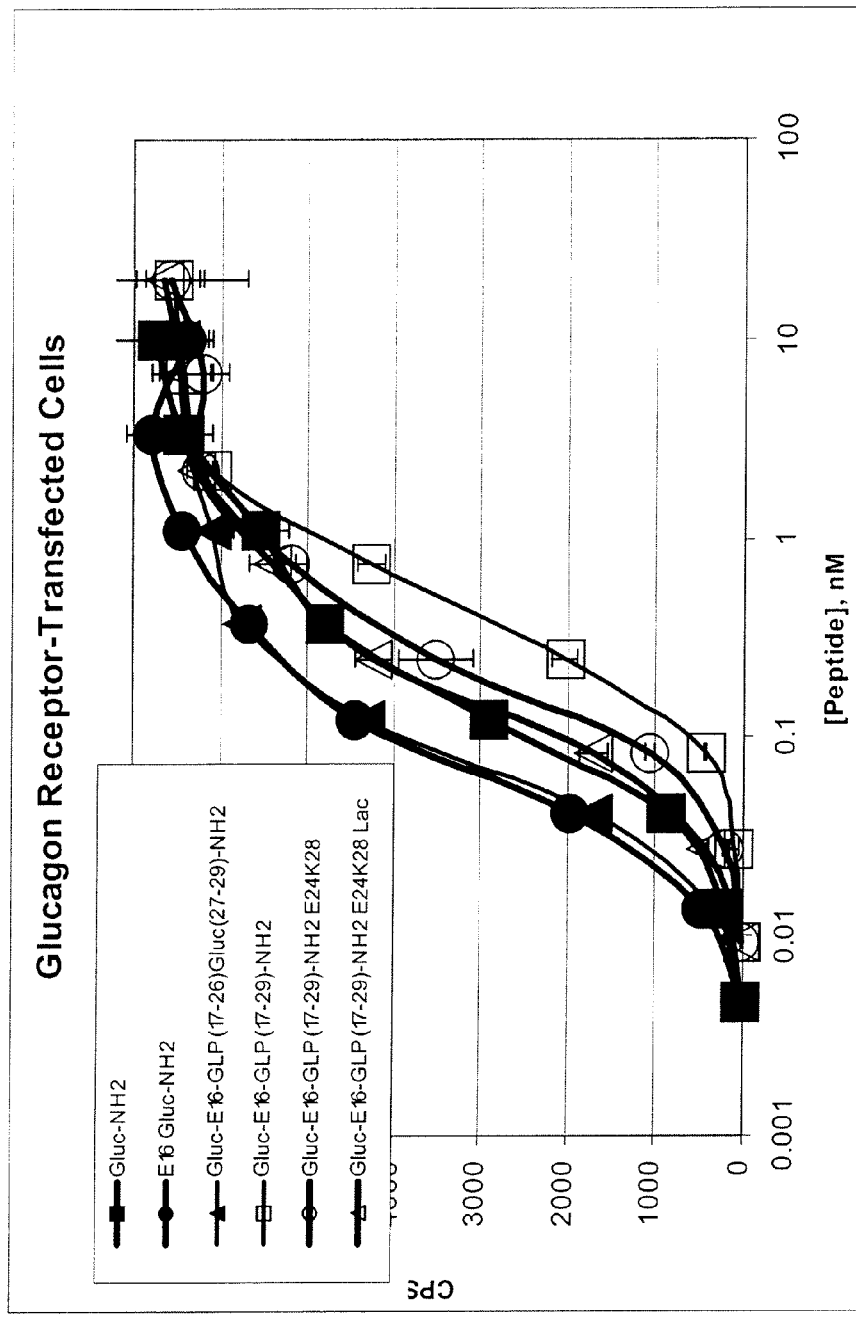

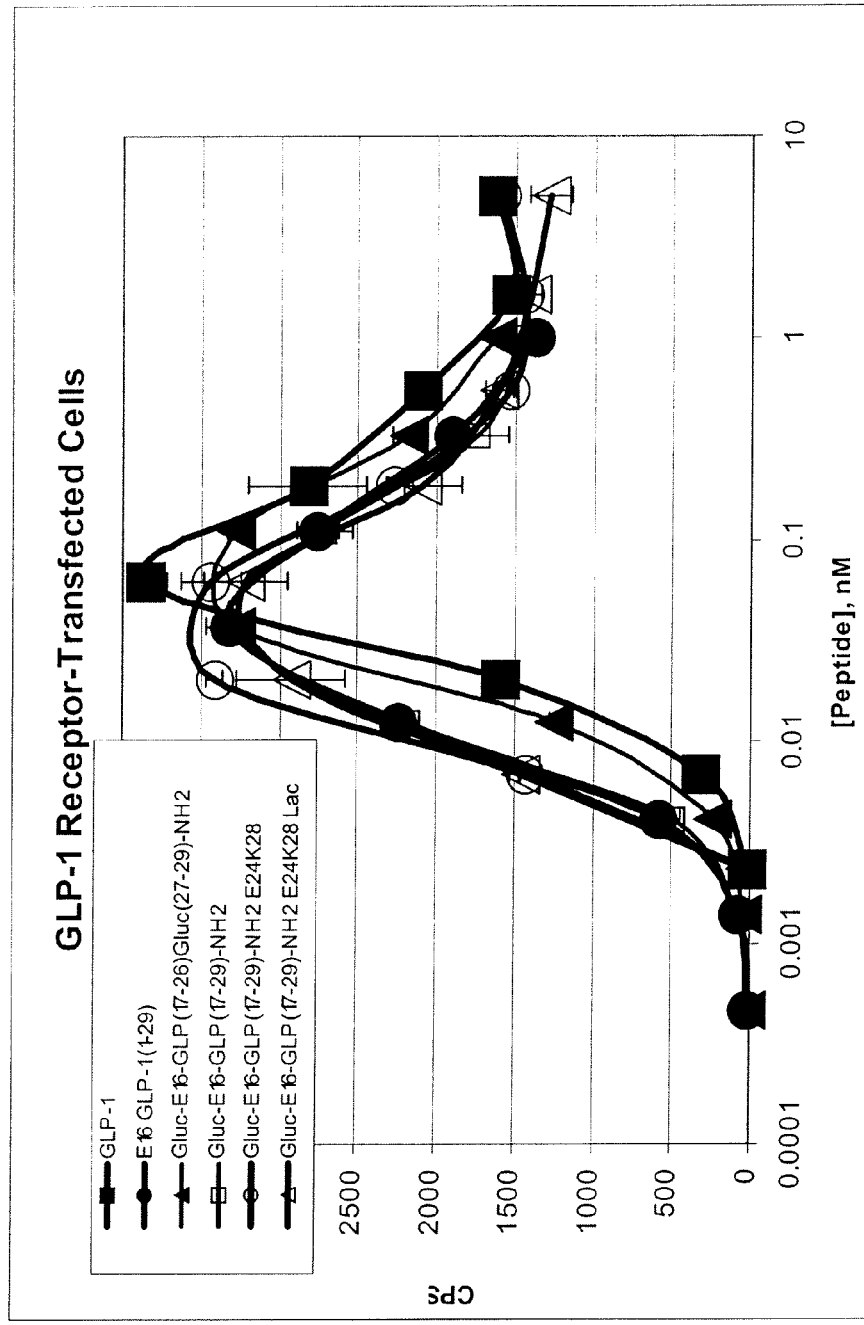
Fig. 9B: cAMP Induction by GLP-1 17-26 Glucagon Analogs

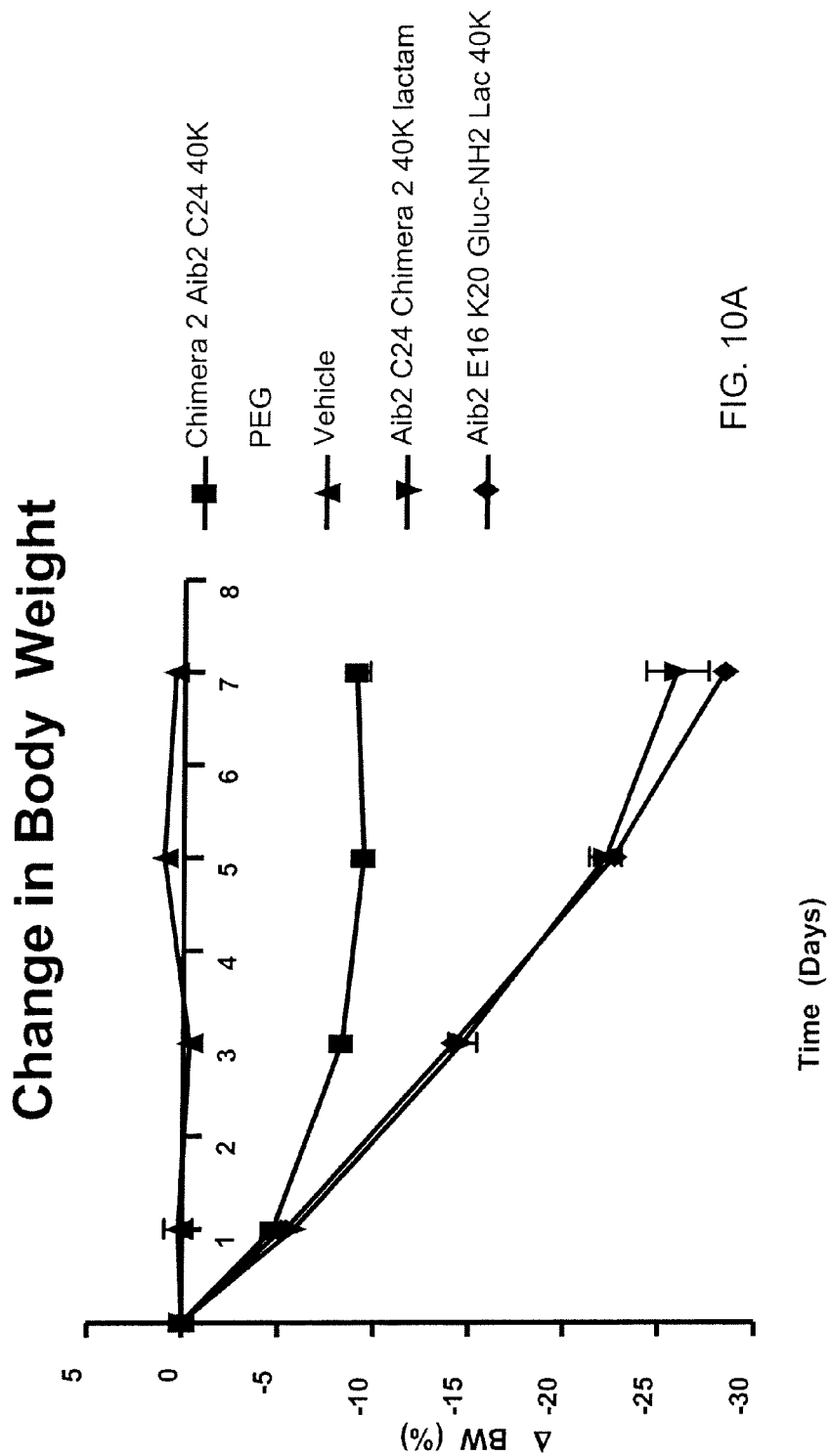

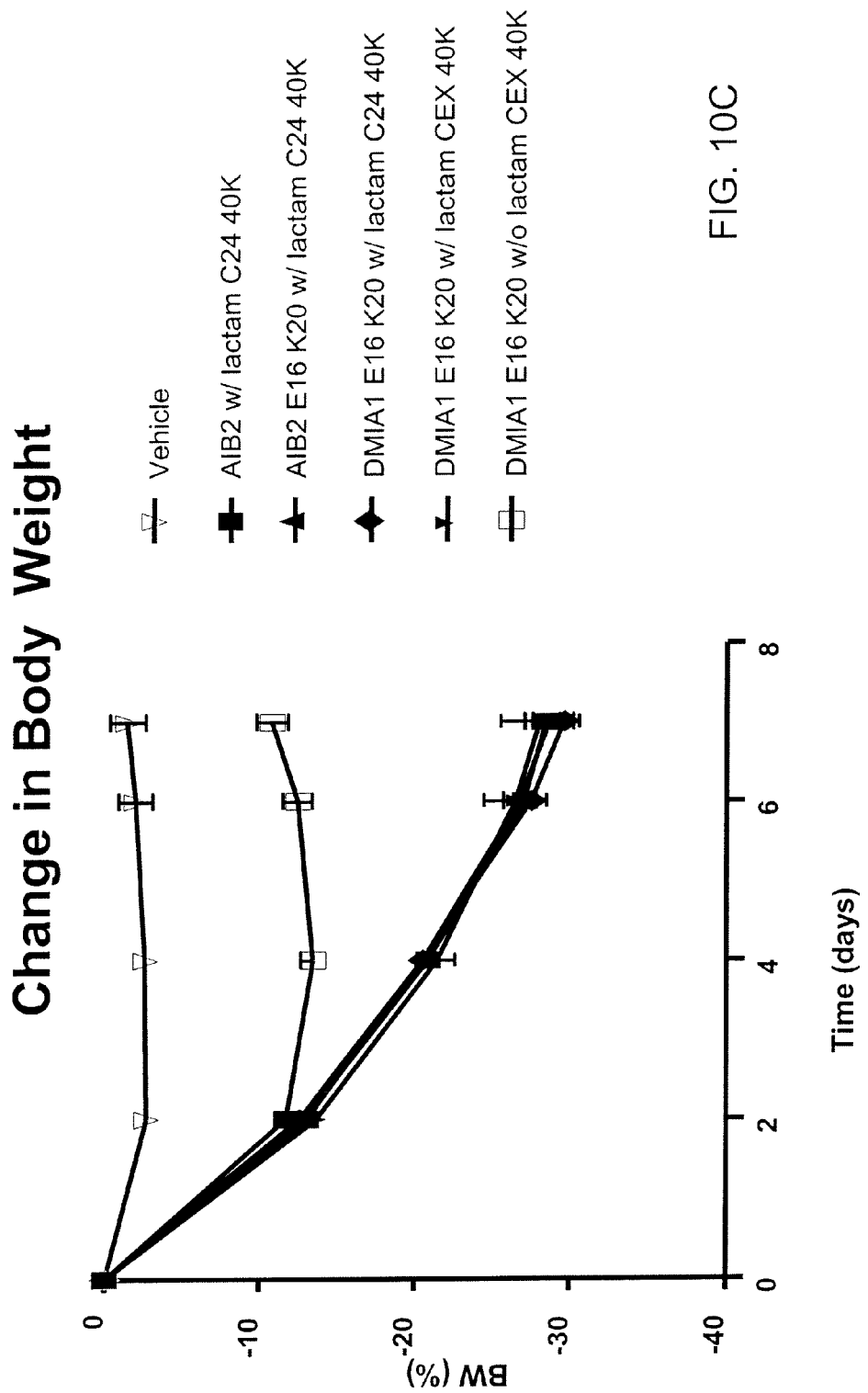

FIG. 25 CD Spectra of PEGylated Peptides in 10 mM Phosphate pH 5.9

GLUCAGON/GLP-1 RECEPTOR CO-AGONISTS

CROSS REFERENCE TO RELATED APPLICATIONS

This application is a U.S. national counterpart application of international application serial No. PCT/US2009/047438 filed Jun. 16, 2009, which claims priority to U.S. Provisional Patent Application Nos. 61/073,269, 61/078,168, 61/090,412, and 61/177,476 filed Jun. 17, 2008, Jul. 3, 2008, Aug. 20, 2008, and May 12, 2009 (respectively). The entire disclosures of PCT/US2009/047438 and USSN(s) 61/073,269, 61/078,168, 61/090,412, and 61/177,476 are hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 379 KB ACII (Text) file named 214786SL.txt created on Nov. 22, 2010.

BACKGROUND

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1(7-36) amide or GLP-1(7-37) acid are biologically potent forms of GLP-1, that demonstrate essentially equivalent activity at the GLP-1 receptor.

Hypoglycemia occurs when blood glucose levels drops too low to provide enough energy for the body's activities. In adults or children older than 10 years, hypoglycemia is uncommon except as a side effect of diabetes treatment, but it can result from other medications or diseases, hormone or enzyme deficiencies, or tumors. When blood glucose begins to fall, glucagon, a hormone produced by the pancreas, signals the liver to break down glycogen and release glucose, causing blood glucose levels to rise toward a normal level. Thus, glucagon's most recognized role in glucose regulation is to counteract the action of insulin and maintain blood glucose levels. However for diabetics, this glucagon response to hypoglycemia may be impaired, making it harder for glucose levels to return to the normal range.

Hypoglycemia is a life threatening event that requires immediate medical attention. The administration of glucagon is an established medication for treating acute hypoglycemia and it can restore normal levels of glucose within minutes of administration. When glucagon is used in the acute medical treatment of hypoglycemia, a crystalline form of glucagon is solubilized with a dilute acid buffer and the solution is injected intramuscularly. While this treatment is effective, the methodology is cumbersome and dangerous for someone that is semi-conscious. Accordingly, there is a need for a glucagon analog that maintains or exceeds the biological performance of the parent molecule but is sufficiently soluble and stable, under relevant physiological conditions, that it can be pre-formulated as a solution, ready for injection.

Additionally, diabetics are encouraged to maintain near normal blood glucose levels to delay or prevent microvascular complications. Achievement of this goal usually requires intensive insulin therapy. In striving to achieve this goal, physicians have encountered a substantial increase in the frequency and severity of hypoglycemia in their diabetic patients. Accordingly, improved pharmaceuticals and methodologies are needed for treating diabetes that are less likely to induce hypoglycemia than current insulin therapies.

GLP-1 has different biological activities compared to glucagon. Its actions include stimulation of insulin synthesis and secretion, inhibition of glucagon secretion, and inhibition of food intake. GLP-1 has been shown to reduce hyperglycemia (elevated glucose levels) in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Accordingly, there remains a need for alternative and preferably improved methods for treating diabetes and obesity.

SUMMARY

As described herein, high potency glucagon agonists analogs are provided that also exhibit increased activity at the glucagon receptor, and in further embodiments exhibit enhanced biophysical stability and/or aqueous solubility. In addition, in accordance with another aspect of the invention, glucagon agonist analogs are provided that have lost native glucagon's selectivity for the glucagon receptor verses the GLP-1 receptor, and thus represent co-agonists of those two receptors. Selected amino acid modifications within the glucagon analogs can control the relative activity of the analog at the GLP-1 receptor verses the glucagon receptor. Thus, yet another aspect of the invention provides glucagon co-agonist analogs that have higher activity at the glucagon receptor versus the GLP-1 receptor, glucagon co-agonist analogs that have approximately equivalent activity at both receptors, and glucagon co-agonist analogs that have higher activity at the GLP-1 receptor versus the glucagon receptor. The latter category of co-agonist can be engineered to exhibit little or no activity at the glucagon receptor, and yet retain ability to activate the GLP-1 receptor with the same or better potency than native GLP-1. Any of these analogs may also include modifications that confer enhanced biophysical stability and/or aqueous solubility.

Glucagon analogs that demonstrate co-agonism at the glucagon and GLP-1 receptors are advantageous for several applications. First of all the use of glucagon to treat hypoglycemia may overcompensate for low blood glucose levels and result in excess blood glucose levels. If a glucagon/GLP-1 receptor co-agonist is administered, the additional GLP-1 stimulation may buffer the glucagon agonist effect to prevent excessive glucose blood levels resulting from treatment of hypoglycemia.

In addition as described herein, glucagon co-agonist analogs of the invention may be used to control hyperglycemia, or to induce weight loss or prevent weight gain, when administered alone or in combination with other anti-diabetic or anti-obesity treatments. Another compound that induces weight loss is oxyntomodulin, a naturally occurring digestive hormone found in the small intestine (see Diabetes 2005; 54:2390-2395). Oxyntomodulin is a 37 amino acid peptide that contains the 29 amino acid sequence of glucagon (i.e., SEQ ID NO: 1) followed by an 8 amino acid carboxy terminal extension of SEQ ID NO: 27 (KRNRNNIA). While the present invention contemplates that glucagon analogs described herein may optionally be joined to this 8 amino acid carboxy terminal extension (SEQ ID NO: 27), the invention in some embodiments also specifically contemplates analogs and uses of analogs lacking the 8 contiguous carboxy amino acids of SEQ ID NO: 27.

The compounds can be customized by amino acid modifications to regulate the GLP-1 activity of the peptide, and thus the glucagon analogs of the present can be tailored to treat a particular condition or disease. More particularly, glucagon analogs are provided herein wherein each analog displays a characteristic relative level of activity at the respective glucagon and GLP-1 receptors. For example, modifications can be made to each peptide to produce a glucagon peptide having anywhere from at least about 1% (including at least about 1.5%, 2%, 5%, 7%, 10%, 20%, 30%, 40%, 50%, 60%, 75%, 100%, 125%, 150%, 175%) to about 200% or higher activity at the GLP-1 receptor relative to native GLP-1 and anywhere from at least about 1% (including about 1.5%, 2%, 5%, 7%, 10%, 20%, 30%, 40%, 50%, 60%, 75%, 100%, 125%, 150%, 175%, 200%, 250%, 300%, 350%, 400%, 450%) to about 500% or higher activity at the glucagon receptor relative to native glucagon. In some embodiments, the glucagon peptides described herein exhibit no more than about 100%, 1000%, 10,000%, 100,000%, or 1,000,000% of the activity of native glucagon at the glucagon receptor. In some embodiments, the glucagon peptides described herein exhibit no more than about 100%, 1000%, 10,000%, 100,000%, or 1,000,000% of the activity of native GLP-1 at the GLP-1 receptor. The amino acid sequence of native glucagon is SEQ ID NO: 1, the amino acid sequence of GLP-1(7-36)amide is SEQ ID NO: 52, and the amino acid sequence of GLP-1(7-37) acid is SEQ ID NO: 50. In exemplary embodiments, a glucagon peptide may exhibit at least 10% of the activity of native glucagon at the glucagon receptor and at least 50% of the activity of native GLP-1 at the GLP-1 receptor, or at least 40% of the activity of native glucagon at the glucagon receptor and at least 40% of the activity of native GLP-1 at the GLP-1 receptor, or at least 60% of the activity of native glucagon at the glucagon receptor and at least 60% of the activity of native GLP-1 at the GLP-1 receptor.

Selectivity of a glucagon peptide for the glucagon receptor versus the GLP-1 receptor can be described as the relative ratio of glucagon/GLP-1 activity (the peptide's activity at the glucagon receptor relative to native glucagon, divided by the peptide's activity at the GLP-1 receptor relative to native GLP-1). For example, a glucagon peptide that exhibits 60% of the activity of native glucagon at the glucagon receptor and 60% of the activity of native GLP-1 at the GLP-1 receptor has a 1:1 ratio of glucagon/GLP-1 activity. Exemplary ratios of glucagon/GLP-1 activity include about 1:1, 1.5:1, 2:1, 3:1, 4:1, 5:1, 6:1, 7:1, 8:1, 9:1 or 10:1, or about 1:10, 1:9, 1:8, 1:7, 1:6, 1:5, 1:4, 1:3, 1:2, or 1:1.5. As an example, a glucagon/GLP-1 activity ratio of 10:1 indicates a 10-fold selectivity for the glucagon receptor versus the GLP-1 receptor. Similarly, a GLP-1/glucagon activity ratio of 10:1 indicates a 10-fold selectivity for the GLP-1 receptor versus the glucagon receptor.

In accordance with one embodiment, analogs of glucagon are provided that have enhanced potency and optionally improved solubility and stability. In one embodiment, enhanced glucagon potency is provided by an amino acid modification at position 16 of native glucagon (SEQ ID NO: 1). By way of nonlimiting example, such enhanced potency can be provided by substituting the naturally occurring serine at position 16 with glutamic acid or with another negatively charged amino acid having a side chain with a length of 4 atoms, or alternatively with any one of glutamine, homoglutamic acid, or homocysteic acid, or a charged amino acid having a side chain containing at least one heteroatom, (e.g. N, O, S, P) and with a side chain length of about 4 (or 3-5) atoms. In one embodiment the enhanced potency glucagon agonist comprises a peptide of SEQ ID NO: 2, SEQ ID NO: 3, SEQ ID NO: 4, SEQ ID NO: 5, SEQ ID NO: 6, SEQ ID NO: 7 or a glucagon agonist analog of SEQ ID NO: 5. In accordance with one embodiment a glucagon analog protein having enhanced potency at the glucagon receptor relative to wild type glucagon is provided wherein the peptide comprises the sequence of SEQ ID NO: 7, SEQ ID NO: 8, SEQ ID NO: 9 or SEQ ID NO: 10, wherein the glucagon peptide retains its selectivity for the glucagon receptor relative to the GLP-1 receptors.

Glucagon receptor activity can be reduced, maintained, or enhanced by an amino acid modification at position 3, e.g. substitution of the naturally occurring glutamine at position 3. In one embodiment, substitution of the amino acid at position 3 with an acidic, basic, or hydrophobic amino acid (glutamic acid, ornithine, norleucine) has been shown to substantially reduce or destroy glucagon receptor activity. The analogs that are substituted with, for example, glutamic acid, ornithine, or norleucine have about 10% or less of the activity of native glucagon at the glucagon receptor, e.g. about 1-10%, or about 0.1-10%, or greater than about 0.1% but less than about 10%, while exhibiting at least 20% of the activity of GLP-1 at the GLP-1 receptor. For example, exemplary analogs described herein have about 0.5%, about 1% or about 7% of the activity of native glucagon, while exhibiting at least 20% of the activity of GLP-1 at the GLP-1 receptor.

In another embodiment, the naturally occurring glutamine at position 3 of the glucagon peptide can be substituted with a glutamine analog without a substantial loss of activity at the glucagon receptor, and in some cases, with an enhancement of glucagon receptor activity. For example, a glucagon peptide comprising a glutamine analog at position 3 may exhibit about 5%, about 10%, about 20%, about 50%, or about 85% or greater the activity of native glucagon (e.g. SEQ ID NO: 1) at the glucagon receptor. In some embodiments a glucagon peptide comprising a glutamine analog at position 3 may exhibit about 20%, about 50%, about 75%, about 100%, about 200% or about 500% or greater the activity of a corresponding glucagon peptide having the same amino acid sequence as the peptide comprising the glutamine analog, except for the modified amino acid at position 3 (e.g. SEQ ID NO: 601 or SEQ ID NO: 602) at the glucagon receptor. In some embodiments, a glucagon peptide comprising a glutamine analog at position 3 exhibits enhanced activity at the glucagon receptor, but the enhanced activity is no more than 1000%, 10,000%, 100,000%, or 1,000,000% of the activity of native glucagon or of a corresponding glucagon peptide having the same amino acid sequence as the peptide comprising the glutamine analog, except for the modified amino acid at position 3. In some embodiments, the glutamine analog is a naturally occurring or a non-naturally occurring amino acid comprising a side chain of Structure I, II or III:

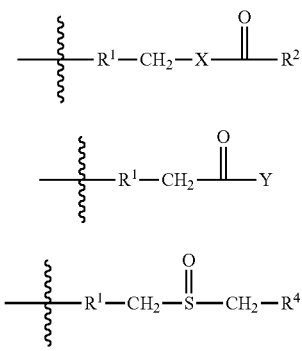

Structure I

Structure II

Structure III wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R^1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl. In exemplary embodiments, an amino acid comprising a side chain of Structure I is provided where, $R^1$ is $CH_2$—S, X is NH, and $R^2$ is $CH_3$ (acetamidomethyl-cysteine, C(Acm)); $R^1$ is $CH_2$, X is NH, and $R^2$ is $CH_3$ (acetyldiaminobutanoic acid, Dab(Ac)); $R^1$ is $C_0$ alkyl, X is NH, $R^2$ is $NHR^4$, and $R^4$ is H (carbamoyl-diaminopropanoic acid, Dap(urea)); or $R^1$ is $CH_2$—$CH_2$, X is NH, and $R^2$ is $CH_3$ (acetylornithine, Orn(Ac)). In exemplary embodiments, an amino acid comprising a side chain of Structure II is provide where, $R^1$ is $CH_2$, Y is $NHR^4$, and $R^4$ is $CH_3$ (methylglutamine, Q(Me)); In exemplary embodiments, an amino acid comprising a side chain of Structure III is provided where, $R^1$ is $CH_2$ and $R^4$ is H (methionine-sulfoxide, M(O)); In specific embodiments, the amino acid at position 3 is substituted with Dab(Ac) For example, glucagon agonists can comprise the amino acid sequence of SEQ ID NO: 595, SEQ ID NO: 601 SEQ ID NO: 603, SEQ ID NO: 604, SEQ ID NO: 605, and SEQ ID NO: 606.

In another embodiment analogs of glucagon are provided that have enhanced or retained potency at the glucagon receptor relative to the native glucagon peptide, but also have greatly enhanced activity at the GLP-1 receptor. Glucagon normally has about 1% of the activity of native-GLP-1 at the GLP-1 receptor, while GLP-1 normally has less than about 0.01% of the activity of native glucagon at the glucagon receptor. Enhanced activity at the GLP-1 receptor is provided by replacing the carboxylic acid of the C-terminal amino acid with a charge-neutral group, such as an amide or ester. In one embodiment, these glucagon analogs comprise a sequence of SEQ ID NO: 20 wherein the carboxy terminal amino acid has an amide group in place of the carboxylic acid group found on the native amino acid. These glucagon analogs have strong activity at both the glucagon and GLP-1 receptors and thus act as co-agonists at both receptors. In accordance with one embodiment a glucagon and GLP-1 receptor co-agonist is provided wherein the peptide comprises the sequence of SEQ ID NO: 20, wherein the amino acid at position 28 is Asn or Lys and the amino acid at position 29 is Thr-amide.

Enhanced activity at the GLP-1 receptor is also provided by stabilizing the alpha-helix structure in the C-terminal portion of glucagon (around amino acids 12-29), through formation of an intramolecular bridge between the side chains of two amino acids that are separated by three intervening amino acids, i.e., an amino acid at position "i" and an amino acid at position "i+4", wherein i is any integer between 12 and 25, by two intervening amino acids, i.e., an amino acid at position "j" and an amino acid at position "j+3," wherein j is any integer between 12 and 27, or by six intervening amino acids, i.e., an amino acid at position "k" and an amino acid at position "k+7," wherein k is any integer between 12 and 22. In exemplary embodiments, the bridge or linker is about 8 (or about 7-9) atoms in length and forms between side chains of amino acids at positions 12 and 16, or at positions 16 and 20, or at positions 20 and 24, or at positions 24 and 28. The side chains of these amino acids can be linked to one another through non-covalent bonds, e.g., hydrogen-bonding or ionic interactions, such as the formation of salt bridges, or by covalent bonds.

In accordance with one embodiment a glucagon agonist is provided comprising a glucagon peptide of SEQ ID NO: 20, wherein a lactam ring is formed between the side chains of a lysine residue, located at position 12, 20 or 28, and a glutamic acid residue, located at position 16 or 24, wherein the two amino acids of the glucagon peptide whose side chains participate in forming the lactam ring are spaced from one another by three intervening amino acids. In accordance with one embodiment the lactam bearing glucagon analog comprises an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18. In one embodiment the carboxy terminal amino acid of the lactam bearing peptide comprises an amide group or an ester group in place of the terminal carboxylic acid. In one embodiment a glucagon peptide of SEQ ID NO: 11, SEQ ID NO: 12, SEQ ID NO: 13, and SEQ ID NO: 14, SEQ ID NO: 15, SEQ ID NO: 16, SEQ ID NO: 17 and SEQ ID NO: 18 further comprises an additional amino acid covalently bound to the carboxy terminus of SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18. In a further embodiment a glucagon peptide is provided comprising a sequence selected from the group consisting of SEQ ID NO: 66, SEQ ID NO: 67, SEQ ID NO: 68 and SEQ ID NO: 69 further comprises an additional amino acid covalently bound to the carboxy terminus of SEQ ID NO: 66, SEQ ID NO: 67, SEQ ID NO: 68 and SEQ ID NO: 69. In one embodiment the amino acid at position 28 is asparagine or lysine and the amino acid at position 29 is threonine.

In some specific embodiments, stabilization of the alpha helix structure in the C-terminal portion of the glucagon agonist peptide is achieved through the formation of a covalent intramolecular bridge other than a lactam bridge. For example, suitable covalent bonding methods (i.e., means of forming a covalent intramolecular bridge) include any one or more of olefin metathesis, lanthionine-based cyclization, disulfide bridge or modified sulfur-containing bridge formation, the use of α, ω-diaminoalkane tethers, the formation of metal-atom bridges, and other means of peptide cyclization are used to stabilize the alpha helix.

Enhanced activity at the GLP-1 receptor is also provided by stabilizing the alpha-helix structure in the C-terminal portion of the glucagon peptide (around amino acids 12-29) through introduction of one or more α,α-disubstituted amino acids at positions that retain the desired activity. In some aspects, stabilization of the alpha-helix is accomplished in this manner without purposeful introduction of an intramolecular bridge such as a salt bridge or covalent bond. Such peptides may be considered herein as a peptide lacking an intramolecular bridge. In specific aspects, stabilization of the alpha-helix is accomplished by introducing one or more α,α-disubstituted amino acids without introduction of a covalent intramolecular bridge, e.g., a lactam bridge, a disulfide bridge. Such peptides may be considered herein as a peptide lacking a covalent intramolecular bridge. In some embodiments, one, two, three, four or more of positions 16, 17, 18, 19, 20, 21, 24 or 29 of a glucagon peptide is substituted with an α,α-disubstituted amino acid. For example, substitution of position 16 of the glucagon peptide with amino iso-butyric acid (AIB) enhances GLP-1 activity, in the absence of a salt bridge or lactam. In some embodiments, one, two, three or more of positions 16, 20, 21 or 24 are substituted with AIB.

Enhanced activity at the GLP-1 and glucagon receptors for glucagon analog peptides lacking an intramolecular bridge (e.g., a covalent intramolecular bridge) is provided by the addition of an acyl or alkyl group to the side chain of the amino acid at position 10 of the peptide. In some aspects, the acyl or alkyl group is not naturally-occurring on an amino acid. In specific aspects, the acyl or alkyl group is non-native to any naturally-occurring amino acid. In some embodiments, the acyl group is a fatty acyl group, e.g., a C4 to C30 fatty acyl group. For example, provided herein is a glucagon analog peptide lacking a covalent intramolecular bridge comprising AIB at position 16 and a C14, C16, or C18 fatty acyl group covalently attached to a Lys residue at position 10. Also provided is a glucagon analog peptide lacking an intramolecular bridge (e.g., a covalent intramolecular bridge) comprising AIB at positions 2 and 16 and a C14, C16, or C18 fatty acyl group covalently attached to a Lys residue at position 10. Such acylated glucagon analog peptides lacking an intramolecular bridge (e.g., a covalent intramolecular bridge) may be pegylated as further described herein.

A further enhancement in GLP-1 activity and glucagon activity for acylated glucagon analog peptides lacking an intramolecular bridge (e.g., an intramolecular bridge) may be achieved by incorporating a spacer between the acyl or alkyl group and the side chain of the amino acid at position 10. In accordance with some embodiments, the spacer (e.g., an amino acid, a dipeptide, a tripeptide, a hydrophilic bifunctional spacer, or a hydrophobic bifunctional spacer) is 3 to 10 atoms (e.g., 6 to 10 atoms) in length. In accordance with certain specific embodiments, the total length of the spacer and acyl or alkyl group is 14 to 28 atoms, e.g., 17 to 28, 19 to 26 atoms, 19 to 21 atoms. Suitable spacers for purposes of enhancing GLP-1 activity and glucagon activity for acylated or alkylated peptides lacking an intramolecular bridge (e.g., a covalent intramolecular bridge) are further described herein.

For example, provided herein is a non-native glucagon peptide that differs from SEQ ID NO: 1 by no more than 10 amino acid modifications, comprising an acyl group or alkyl group, wherein the acyl or alkyl group is attached to a spacer and the spacer is attached to the side chain of an amino acid at position 10 of the glucagon peptide, wherein, when said glucagon peptide lacks a hydrophilic moiety, e.g., PEG, said glucagon peptide exhibits at least 20% (e.g., at least 30%, at least 40%, at least 50%, at least 60%, at least 75%, at least 80%, at least 90% at least 95%, at least 98%, at least 99%, about 100%, about 150%, about 200%, about 400%, about 500% or more) of the activity of native GLP-1 at the GLP-1 receptor. In some embodiments, the glucagon peptide exhibits at least 0.5% (e.g., at least 1%, at least 2%, at least 3%, at least 4%, at least 5%, at least 10%, at least 20%) of the activity of native glucagon at the glucagon receptor, when the glucagon peptide lacks a hydrophilic moiety, e.g., PEG. In some embodiments, the glucagon peptides described above may exhibit any of the above indicated activities and no more than 1000%, 10,000%, 100,000%, or 1,000,000% of the activity of native glucagon at the glucagon receptor. In some embodiments, the glucagon peptides described above may exhibit any of the above indicated activities and no more than 1000%, 10,000%, 100,000%, or 1,000,000% of the activity of native GLP-1 at the GLP-1 receptor.

Enhanced activity at the GLP-1 receptor is also provided by an amino acid modification at position 20. In one embodiment, the glutamine at position 20 is replaced with another hydrophilic amino acid having a side chain that is either charged or has an ability to hydrogen-bond, and is at least about 5 (or about 4-6) atoms in length, for example, lysine, citrulline, arginine, or ornithine.

Any of the modifications described above which increase or decrease glucagon receptor activity and which increase GLP-1 receptor activity can be applied individually or in combination. Combinations of the modifications that increase GLP-1 receptor activity may provide higher GLP-1 activity than any of such modifications taken alone. For example, the invention provides glucagon analogs that comprise modifications at position 16, at position 20, and at the C-terminal carboxylic acid group, optionally with a covalent bond between the amino acids at positions 16 and 20; glucagon analogs that comprise modifications at position 16 and at the C-terminal carboxylic acid group; glucagon analogs that comprise modifications at positions 16 and 20, optionally with a covalent bond between the amino acids at positions 16 and 20; and glucagon analogs that comprise modifications at position 20 and at the C-terminal carboxylic acid group; optionally with the proviso that the amino acid at position 12 is not Arg; or optionally with the proviso that the amino acid at position 9 is not Glu.

Other modifications at position 1 or 2, as described herein, can increase the peptide's resistance to dipeptidyl peptidase IV (DPP IV) cleavage. For example, the amino acid at position 2 may be substituted with D-serine, D-alanine, valine, glycine, N-methyl serine, N-methyl alanine, or amino isobutyric acid. Alternatively, or in addition, the amino acid at position 1 may be substituted with D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

It was observed that modifications at position 2 (e.g. AIB at position 2) and in some cases modifications at position 1 may reduce glucagon activity, sometimes significantly; surprisingly, this reduction in glucagon activity can be restored by stabilizing the alpha-helix in the C-terminal portion of glucagon, e.g. through a covalent bond between amino acids at positions "i" and "i+4", e.g., 12 and 16, 16 and 20, or 20 and 24. In some embodiments, this covalent bond is a lactam bridge between a glutamic acid at position 16 and a lysine at position 20. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

Glucagon peptides with GLP-1 activity that contain a non-conservative substitution of His at position 1 with a large, aromatic amino acid (e.g., Tyr) can retain GLP-1 activity provided that the alpha-helix is stabilized via an intramolecular bridge, e.g. through a covalent bond between amino acids at positions "i" and "i+4", e.g., 12 and 16, 16 and 20, or 20 and 24. In some embodiments, this covalent bond is a lactam bridge between a glutamic acid at position 16 and a lysine at position 20. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

In yet further exemplary embodiments, any of the foregoing compounds can be further modified to improve stability by modifying the amino acid at position 15 of SEQ ID NO: 1 to reduce degradation of the peptide over time, especially in acidic or alkaline buffers.

In another embodiment the solubility of the glucagon peptides disclosed herein are enhanced by the covalent linkage of a hydrophilic moiety to the peptide. In one embodiment the hydrophilic moiety is a polyethylene glycol (PEG) chain, optionally linked to the peptide at one or more of positions 16, 17, 21, 24, 29, within a C-terminal extension, or at the C-terminal amino acid. In some embodiments, the native amino acid at that position is substituted with an amino acid having a side chain suitable for crosslinking with hydrophilic moieties, to facilitate linkage of the hydrophilic moiety to the peptide. In other embodiments, an amino acid modified to comprise a hydrophilic group is added to the peptide at the C-terminal amino acid. In one embodiment the peptide co-agonist comprises a sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19 wherein the side chain of an amino acid residue at one of position 16, 17, 21 or 24 of said glucagon peptide further comprises a polyethylene glycol chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons. In yet other exemplary embodiments the polyethylene glycol chain has a molecular weight of about 20,000 to about 40,000 Daltons.

In another embodiment the solubility of any of the preceding glucagon analogs can be improved by amino acid substitutions and/or additions that introduce a charged amino acid into the C-terminal portion of the peptide, preferably at a position C-terminal to position 27 of SEQ ID NO: 1. Optionally, one, two or three charged amino acids may be introduced within the C-terminal portion, preferably C-terminal to position 27. In accordance with one embodiment the native amino acid(s) at positions 28 and/or 29 are substituted with a charged amino acids, and/or in a further embodiment one to three charged amino acids are also added to the C-terminus of the peptide. In exemplary embodiments, one, two or all of the charged amino acids are negatively charged. Additional modifications, e.g. conservative substitutions, may be made to the glucagon peptide that still allow it to retain glucagon activity. In one embodiment an analog of the peptide of SEQ ID NO: 20 is provided wherein the analog differs from SEQ ID NO: 20 by 1 to 2 amino acid substitutions at positions 17-26, and in one embodiment the analog differs from the peptide of SEQ ID NO: 20 by an amino acid substitution at position 20.

In accordance with some embodiments, the glucagon peptides disclosed herein are modified by truncation of the C-terminus by one or two amino acid residues. Such modified glucagon peptides, as shown herein, retain similar activity and potency at the glucagon receptor and GLP-1 receptor. In this regard, the glucagon peptides can comprise amino acids 1-27 or 1-28 of the native glucagon peptide (SEQ ID NO: 1), optionally with any of the additional modifications described herein.

In accordance with one embodiment the glucagon peptides disclosed herein are modified by the addition of a second peptide to the carboxy terminus of the glucagon peptide, for example, SEQ ID NO: 26, SEQ ID NO: 27 or SEQ ID NO: 28. In one embodiment a glucagon peptide having a peptide sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 66, SEQ ID NO: 67, SEQ ID NO: 68, and SEQ ID NO: 69 is covalently bound through a peptide bond to a second peptide, wherein the second peptide comprises a sequence selected from the group consisting of SEQ ID NO: 26, SEQ ID NO: 27 and SEQ ID NO: 28. In a further embodiment, in glucagon peptides which comprise the C-terminal extension, the threonine at position 29 of the native glucagon peptide is replaced with a glycine. A glucagon analog having a glycine substitution for threonine at position 29 and comprising the carboxy terminal extension of SEQ ID NO: 26 is four times as potent at the GLP-1 receptor as native glucagon modified to comprise the carboxy terminal extension of SEQ ID NO: 26. Potency at the GLP-1 receptor can be further enhanced by an alanine substitution for the native arginine at position 18.

Any of the glucagon peptides disclosed herein can be modified to comprise an acyl group or alkyl group, e.g., a C4 to C30 acyl or alkyl group. In some aspects, the acyl group or alkyl group is non-native to any naturally-occurring amino acid. Acylation or alkylation can increase the half-life of the glucagon peptides in circulation. Acylation or alkylation can advantageously delay the onset of action and/or extend the duration of action at the glucagon and/or GLP-1 receptors and/or improve resistance to proteases such as DPP-IV. As shown herein, the activity at the glucagon receptor and GLP-1 receptor of the glucagon peptide is maintained, if not substantially enhanced, after acylation. Further, the potency of the acylated glucagon peptides were comparable to the unacylated versions of the glucagon peptides, if not substantially enhanced. Glucagon peptides may be acylated or alkylated at the same amino acid position where a hydrophilic moiety is linked, or at a different amino acid position. In some embodiments, the invention provides a glucagon peptide modified to comprise an acyl group or alkyl group covalently linked to the amino acid at position 10 of the glucagon peptide. The glucagon peptide may further comprise a spacer between the amino acid at position 10 of the glucagon peptide and the acyl group or alkyl group. In some embodiments, the acyl group is a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The spacer is any moiety with suitable reactive groups for attaching acyl or alkyl groups. In exemplary embodiments, the spacer comprises an amino acid, a dipeptide, a tripeptide, a hydrophilic bifunctional spacer, or a hydrophobic bifunctional spacer. In some embodiments, the spacer is selected from the group consisting of: Trp, Glu, Asp, Cys and a spacer comprising $NH_2(CH_2CH_2O)n(CH_2)_m COOH$, wherein m is any integer from 1 to 6 and n is any integer from 2 to 12. Such acylated or alkylated glucagon peptides may also further comprise a hydrophilic moiety, optionally a polyethylene glycol. Any of the foregoing glucagon peptides may comprise two acyl groups or two alkyl groups, or a combination thereof.

Thus, as disclosed herein high potency glucagon analogs or glucagon co-agonist analogs are provided that also exhibit improved solubility and/or stability. An exemplary high potency glucagon analog exhibits at least about 200% of the activity of native glucagon at the glucagon receptor, and optionally is soluble at a concentration of at least 1 mg/mL at a pH between 6 and 8, or between 6 and 9, or between 7 and 9 (e.g. pH 7), and optionally retains at least 95% of the original peptide (e.g. 5% or less of the original peptide is degraded or cleaved) after 24 hours at 25.C. As another example, an exemplary glucagon co-agonist analog exhibits greater than about 40% or greater than about 60% activity at both the glucagon and the GLP-1 receptors (at a ratio between about 1:3 and 3:1, or between about 1:2 and 2:1), is optionally soluble at a concentration of at least 1 mg/mL at a pH between 6 and 8 or between 6' and 9, or between 7 and 9 (e.g. pH 7), and optionally retains at least 95% of the original peptide after 24 hours at 25° C. Another exemplary glucagon co-agonist analog exhibits about 175% or more of the activity of native glucagon at the glucagon receptor and about 20% or less of the activity of native GLP-1 at the GLP-1 receptor, is optionally soluble at a concentration of at least 1 mg/mL at a pH between 6 and 8 or between 6 and 9, or between 7 and 9 (e.g. pH 7), and optionally retains at least 95% of the original peptide after 24 hours at 25° C. Yet another exemplary glucagon co-agonist analog exhibits about 10% or less of the activity of native glucagon at the glucagon receptor and at least about 20% of the activity of native GLP-1 at the GLP-1 receptor, is optionally soluble at a concentration of at least 1 mg/mL at a pH between 6 and 8 or between 6 and 9, or between 7 and 9 (e.g. pH 7), and optionally retains at least 95% of the original peptide after 24 hours at 25° C. Yet another exemplary glucagon co-agonist analog exhibits about 10% or less but above 0.1%, 0.5% or 1% of the activity of native glucagon at the glucagon receptor and at least about 50%, 60%, 70%, 80%, 90% or 100% or more of the activity of native GLP-1 at the GLP-1 receptor, is optionally soluble at a concentration of at least 1 mg/mL at a pH between 6 and 8 or between 6 and 9, or between 7 and 9 (e.g. pH 7), and optionally retains at least 95% of the original peptide after 24 hours at 25.C. In some embodiments, the glucagon peptides exhibit no more than about 100%, 1000%, 10,000%, 100,000%, or 1,000,000% of the activity of native GLP-1 at the GLP-1 receptor. In some embodiments, such glucagon analogs retain at least 22, 23, 24, 25, 26, 27 or 28 of the naturally occurring amino acids at the corresponding positions in native glucagon (e.g. have 1-7, 1-5 or 1-3 modifications relative to naturally occurring glucagon).

Any one of the following peptides is excluded from the compounds of the invention, although any of the following peptides comprising one or more further modifications thereto as described herein exhibiting the desired GLP-1 or co-agonist activity, pharmaceutical compositions, kits, and treatment methods using such compounds may be included in the invention: The peptide of SEQ ID NO: 1 with an [Arg12] substitution and with a C-terminal amide; The peptide of SEQ ID NO: 1 with [Arg12,Lys20] substitutions and with a C-terminal amide; The peptide of SEQ ID NO: 1 with [Arg12, Lys24] substitutions and with a C-terminal amide; The peptide of SEQ ID NO: 1 with [Arg12,Lys29] substitutions and with a C-terminal amide; The peptide of SEQ ID NO: 1 with a [Glu9] substitution; The peptide of SEQ ID NO: 1 missing His1, with [Glu9, Glu16, Lys29] substitutions and C-terminal amide; The peptide of SEQ ID NO: 1 with [Glu9, Glu16, Lys29] substitutions and with a C-terminal amide; The peptide of SEQ ID NO: 1 with [Lys13, Glu17] substitutions linked via lactam bridge and with a C-terminal amide; The peptide of SEQ ID NO: 1 with [Lys17, Glu21] substitutions linked via lactam bridge and with a C-terminal amide; The peptide of SEQ ID NO: 1 missing His1, with [Glu20, Lys24] substitutions linked via lactam bridge.

In accordance with one embodiment a pharmaceutical composition is provided comprising any of the novel glucagon peptides disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a glucagon peptide at a concentration of at least A, wherein A is 0.001 mg/ml, 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In other embodiments, such compositions may contain a glucagon peptide at a concentration of at most B, wherein B is 30 mg/ml, 25 mg/ml, 24 mg/ml, 23, mg/ml, 22 mg/ml, 21 mg/ml, 20 mg/ml, 19 mg/ml, 18 mg/ml, 17 mg/ml, 16 mg/ml, 15 mg/ml, 14 mg/ml, 13 mg/ml, 12 mg/ml, 11 mg/ml 10 mg/ml, 9 mg/ml, 8 mg/ml, 7 mg/ml, 6 mg/ml, 5 mg/ml, 4 mg/ml, 3 mg/ml, 2 mg/ml, 1 mg/ml, or 0.1 mg/ml. In some embodiments, the compositions may contain a glucagon peptide at a concentration range of A to B mg/ml, for example, 0.001 to 30.0 mg/ml. In one embodiment the pharmaceutical compositions comprise aqueous solutions that are sterilized and optionally stored within various containers. The compounds of the present invention can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment a method of rapidly increasing glucose level or treating hypoglycemia using a pre-formulated aqueous composition of glucagon peptides of the invention is provided. The method comprises the step of administering an effective amount of an aqueous solution comprising a novel modified glucagon peptide of the present disclosure. In one embodiment the glucagon peptide is pegylated at position 21 or 24 of the glucagon peptide and the PEG chain has a molecular weight of about 500 to about 5,000 Daltons. In one embodiment the modified glucagon solution is prepackaged in a device that is used to administer the composition to the patient suffering from hypoglycemia.

In accordance with one embodiment an improved method of regulating blood glucose levels in insulin dependent patients is provided. The method comprises the steps of administering insulin in an amount therapeutically effective for the control of diabetes and administering a novel modified glucagon peptide of the present disclosure in an amount therapeutically effective for the prevention of hypoglycemia, wherein said administering steps are conducted within twelve hours of each other. In one embodiment the glucagon peptide and the insulin are co-administered as a single composition, wherein the glucagon peptide is pegylated with a PEG chain having a molecular weight selected from the range of about 5,000 to about 40,000 Daltons In another embodiment a method is provided for inducing the temporary paralysis of the intestinal tract. The method comprises the step of administering one or more of the glucagon peptides disclosed herein to a patient.

Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g. high fibrinogen or plasminogen activator inhibitor-1 in blood), and (6) pro-inflammatory state (e.g. elevated C-reactive protein in blood). Other risk factors may include aging, hormonal imbalance and genetic predisposition.

Metabolic Syndrome is associated with an increased the risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B):66B-76B (2004)).

According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m$^2$, or a waist measurement over 37 inches); (b) cholesterol panel showing a triglyceride level of at least 150 mg/dl or an HDL cholesterol lower than 35 mg/dl; (c) blood pressure of 140/90 or more, or on treatment for high blood pressure). (Mathur, Ruchi, "Metabolic Syndrome," ed. Shiel, Jr., William C., MedicineNet.com, May 11, 2009).

For purposes herein, if an individual meets the criteria of either or both of the criteria set forth by the 2001 National Cholesterol Education Program Adult Treatment Panel or the WHO, that individual is considered as afflicted with Metabolic Syndrome.

Without being bound to any particular theory, glucagon peptides described herein are useful for treating Metabolic Syndrome. Accordingly, the invention provides a method of preventing or treating Metabolic Syndrome, or reducing one, two, three or more risk factors thereof, in a subject, comprising administering to the subject a glucagon peptide described herein in an amount effective to prevent or treat Metabolic Syndrome, or the risk factor thereof.

Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, glucagon peptides described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the invention provides a method of preventing or treating Alcoholic Liver Disease, NAFLD, or any stage thereof, in a subject comprising administering to a subject a glucagon peptide described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g. abnormal hepatic enzyme levels (e.g., aspartate aminotransferase AST and/or alanine aminotransferase ALT, or LDH), elevated serum ferritin, elevated serum bilirubin, and/or signs of fibrosis, e.g. elevated TGF-beta levels. In preferred embodiments, the glucagon peptides are used treat patients who have progressed beyond simple fatty liver (steatosis) and exhibit signs of inflammation or hepatitis. Such methods may result, for example, in reduction of AST and/or ALT levels.

In yet another embodiment a method of treating hyperglycemia, or a method of reducing weight gain or inducing weight loss is provided, which involves administering an effective amount of an aqueous solution comprising a glucagon peptide of the invention. In one embodiment either method comprises administering an effective amount of a composition comprising a glucagon agonist selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19. In another embodiment, the method comprises administering an effective amount of a composition comprising a glucagon agonist, wherein the glucagon agonist comprising a glucagon peptide selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 66, SEQ ID NO: 67, SEQ ID NO: 68, and SEQ ID NO: 69, wherein amino acid 29 of the glucagon peptide is bound to a second peptide through a peptide bond, and said second peptide comprises the sequence of SEQ ID NO: 26, SEQ ID NO: 27 or SEQ ID NO: 28. In further embodiments, methods of treating diabetes involving co-administering a conventional dose or a reduced dose of insulin and a glucagon peptide of the invention are provided. Methods of treating diabetes with a glucagon peptide of the invention, without co-administering insulin are also provided.

In yet another aspect, the invention provides novel methods for treating hyperglycemia and novel methods for decreasing appetite or promoting body weight loss that involve administration of a glucagon/GLP-1 co-agonist molecule (including pharmaceutically acceptable salts thereof) that activates both the glucagon receptor and the GLP-1 receptor. Agonism, i.e., activation, of both the glucagon and GLP-1 receptors provides an unexpected improvement compared to GLP-1 agonism alone in treating hyperglycemia. Thus, the addition of glucagon agonism provides an unexpected additive or synergistic effect, or other unexpected clinical benefit(s). Administration with a conventional dose of insulin, a reduced dose of insulin, or without insulin is contemplated according to such methods. Agonism of the glucagon receptor also has an unexpected beneficial effect compared to GLP-1 agonism alone in promoting weight loss or preventing weight gain.

Exemplary glucagon/GLP-1 co-agonist molecules include glucagon peptides of the invention, GLP-1 analogs that activate both GLP-1 and glucagon receptors, fusions of glucagon and GLP-1, or fusions of glucagon analogs and GLP-1 analogs, or chemically modified derivatives thereof. Alternatively, a compound that activates the glucagon receptor can be co-administered with a compound that activates the GLP-1 receptor (such as a GLP-1 analog, an exendin-4 analog, or derivatives thereof). The invention also contemplates co-administration of a glucagon agonist analog with a GLP-1 agonist analog.

Such methods for treating hyperglycemia and/or for decreasing appetite or promoting body weight loss include administration of a glucagon analog with a modification at position 12 (e.g. Arg12), optionally in combination with modifications at position 16 and/or 20. The methods of the invention also include administration of glucagon analogs comprising an intramolecular bridge between the side chains of two amino acids within the region of amino acids 12 and 29 that are separated by three intervening amino acids, e.g. positions 12 and 16, positions 13 and 17 (e.g., Lys13 Glu17 or Glu13 Lys17), positions 16 and 20, positions 17 and 21 (e.g. Lys17 Glu 21 or Glu 17 Lys 21), positions 20 and 24, or positions 24 and 28, with the optional proviso that the amino acid at position 9 is not Glu, and optionally including a C-terminal amide or ester.

In accordance with one embodiment excluded from such glucagon/GLP-1 co-agonist molecules are any glucagon analogs or GLP-1 analogs in the prior art known to be useful in such a method. In another embodiment peptides described in U.S. Pat. No. 6,864,069 as acting as both a GLP-1 agonist and a glucagon antagonist for treating diabetes are also excluded as glucagon/GLP-1 co-agonist molecules. In another embodiment, excluded is the use of glucagon antagonists to treat diabetes, such as the antagonists described in Unson et al., *J. Biol. Chem.*, 264:789-794 (1989), Ahn et al., *J. Med. Chem.*, 44:3109-3116 (2001), and Sapse et al., *Mol. Med.*, 8(5):251-262 (2002). In a further embodiment oxyntomodulin or a glucagon analog that contains the 8 C-terminal amino acids of oxyntomodulin (SEQ ID NO: 27) are also excluded as glucagon/GLP-1 co-agonist molecules.

Such methods for treating hyperglycemia are expected to be useful for a variety of types of hyperglycemia, including diabetes, diabetes mellitus type I, diabetes mellitus type II, or gestational diabetes, either insulin-dependent or non-insulin-dependent, and reducing complications of diabetes including nephropathy, retinopathy and vascular disease. Such methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

All therapeutic methods, pharmaceutical compositions, kits and other similar embodiments described herein contemplate that the use of the term glucagon analogs includes all pharmaceutically acceptable salts or esters thereof.

BRIEF DESCRIPTION OF THE DRAWINGS

FIG. 1 is a bar graph representing the stability of Glucagon Cys$^{21}$maleimidoPEG$_{5K}$ at 37° C. incubated for 24, 48, 72, 96, 144 and 166 hours, respectively.

FIG. 2 represents data generated from HPLC analysis of Glucagon Cys$^{21}$maleimidoPEG$_{5K}$ at pH 5 incubated at 37° C. for 24, 72 or 144 hours, respectively.

FIG. 3 represents data showing receptor mediated cAMP induction by glucagon analogs. More particularly, FIG. 3A compares induction of the glucagon receptor by glucagon analogs E16, K20 ●, E15, E16 ▲, E16, K20 ▼, E15, E16 ◄, E16 ▶ and Gluc-NH$_2$ ■

FIGS. 5A and 5B represents data showing receptor mediated cAMP induction by glucagon analogs. More particularly, FIG. 5A compares induction of the glucagon receptor by glucagon analogs (E16, K20 Gluc-NH$_2$ ● (5 nM, stock solution), E15, E16 Gluc-NH$_2$ ▲ (5 nM, stock solution), E16, K20 Gluc-NH$_2$ ▼ (10 nM, stock solution), E15, E16 Gluc-NH$_2$ ◄ (10 nM, stock solution) and E16 Gluc-NH$_2$ ▶) relative to glucagon-NH$_2$ (■), whereas FIG. 5B compares induction of the GLP-1 receptor by glucagon analogs (E16, K20 Gluc-NH$_2$ ●, E15, E16 Gluc-NH$_2$ ▲, and E16 Gluc-NH$_2$, ▶) relative to GLP-1 (■) and glucagon-NH$_2$ (□).

NH₂ lactam ▼, K20E24-NH₂ lactam ◄ and E24K28-NH₂ lactam ▶) relative to GLP-1 (■).

Figure 4A:
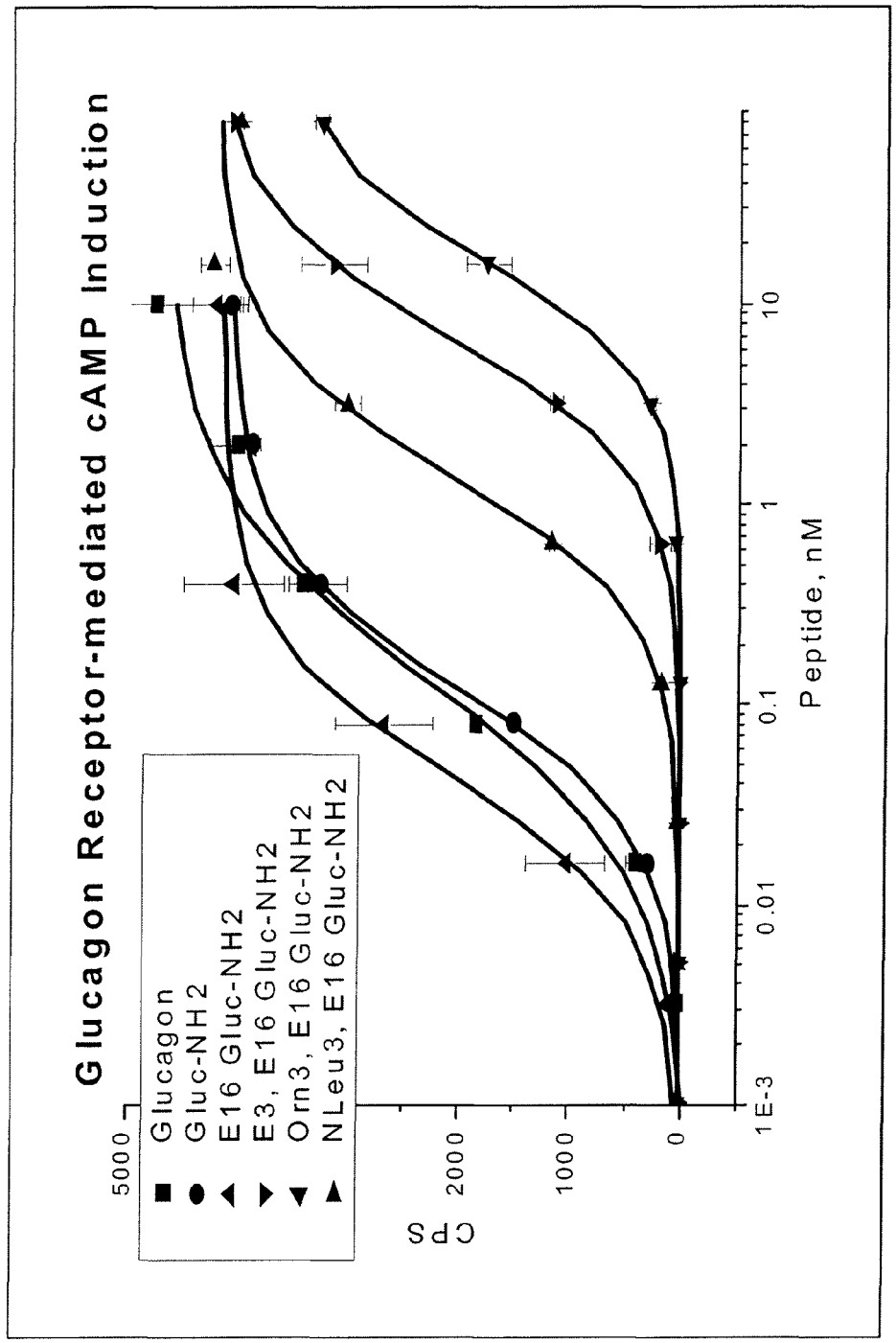
FIGS. 4A and 4B represents data showing receptor mediated cAMP induction by glucagon analogs. More particularly, FIG. 4A compares induction of the glucagon receptor by glucagon analogs Gluc-NH$_2$ ●, E16Gluc-NH$_2$ ▲, E3, E16 Gluc-NH$_2$ ▼, Orn3, E16 Gluc-NH$_2$ ◄ and Nle3, E16 Gluc-NH$_2$, ▶ relative to native glucagon whereas FIG. 4B compares induction of the GLP-1 receptor by glucagon analogs Gluc-NH$_2$ ●, E16 Gluc-NH$_2$ ▲, E3, E16Gluc-NH$_2$ ▼, Orn3, E16 Gluc-NH$_2$ ◄ and Nle3, E16 Gluc-NH$_2$, ▶ relative to native GLP-1 ■.
Figure 4B:
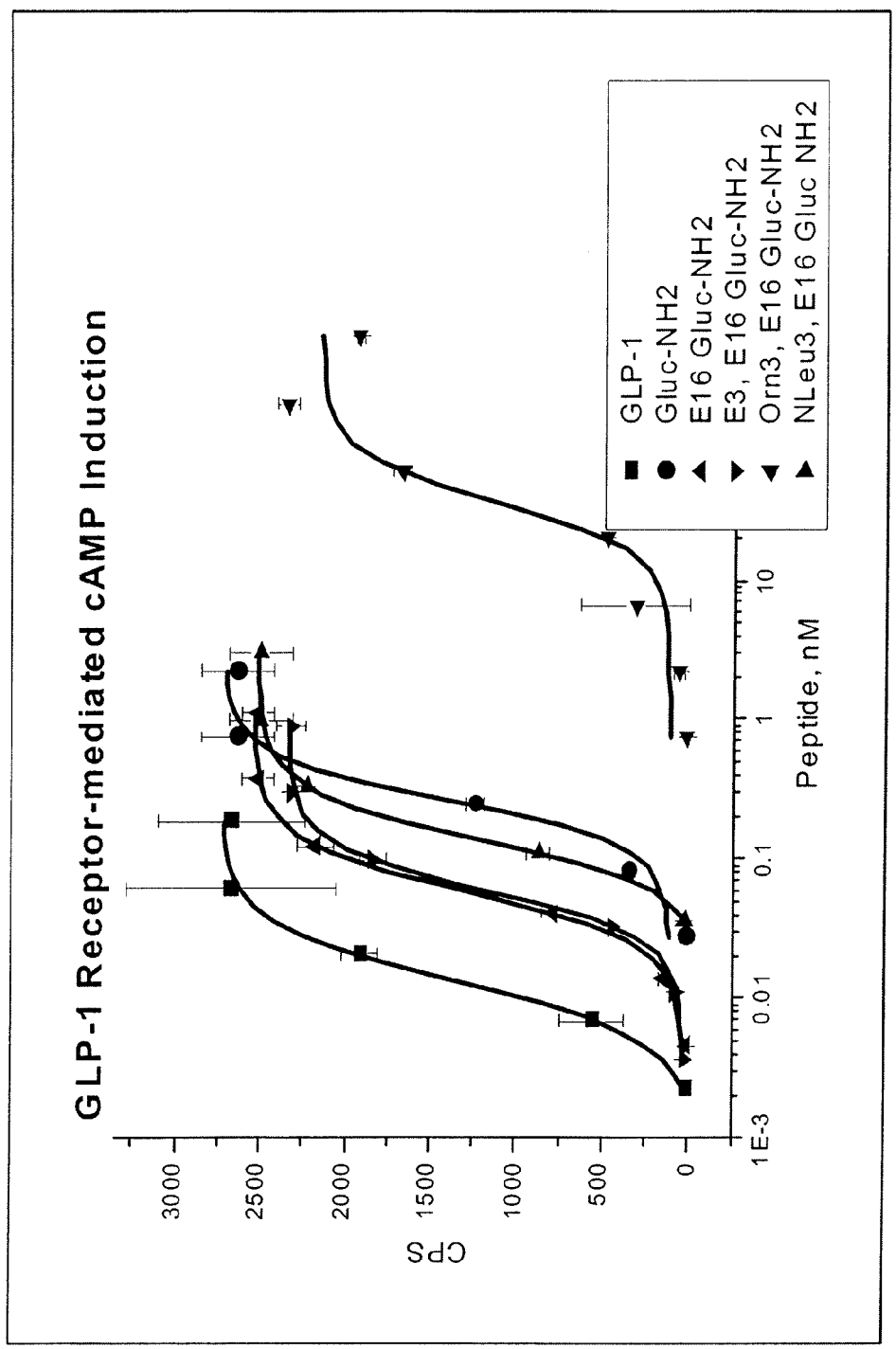
Figure 5B:
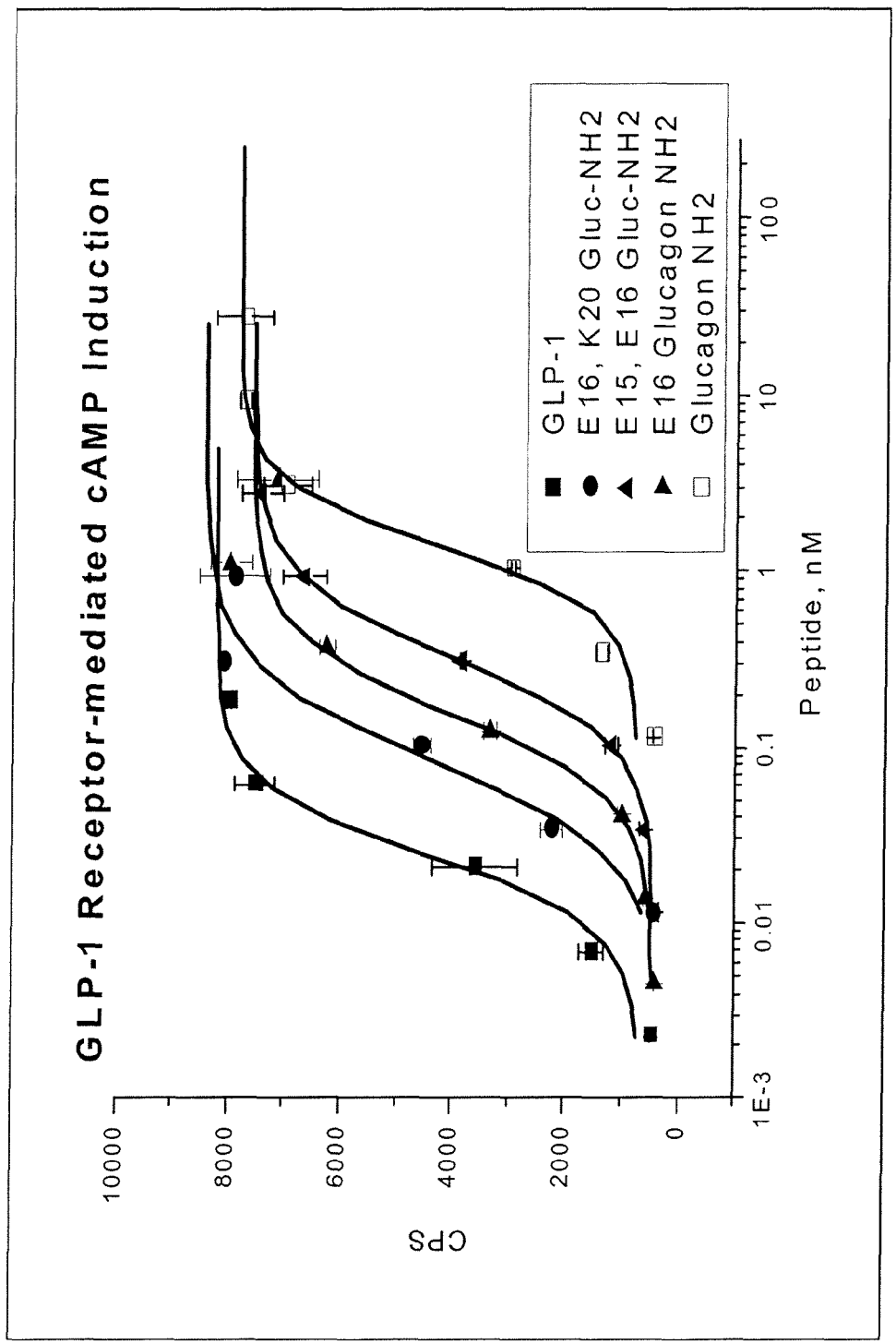
Figure 6A:
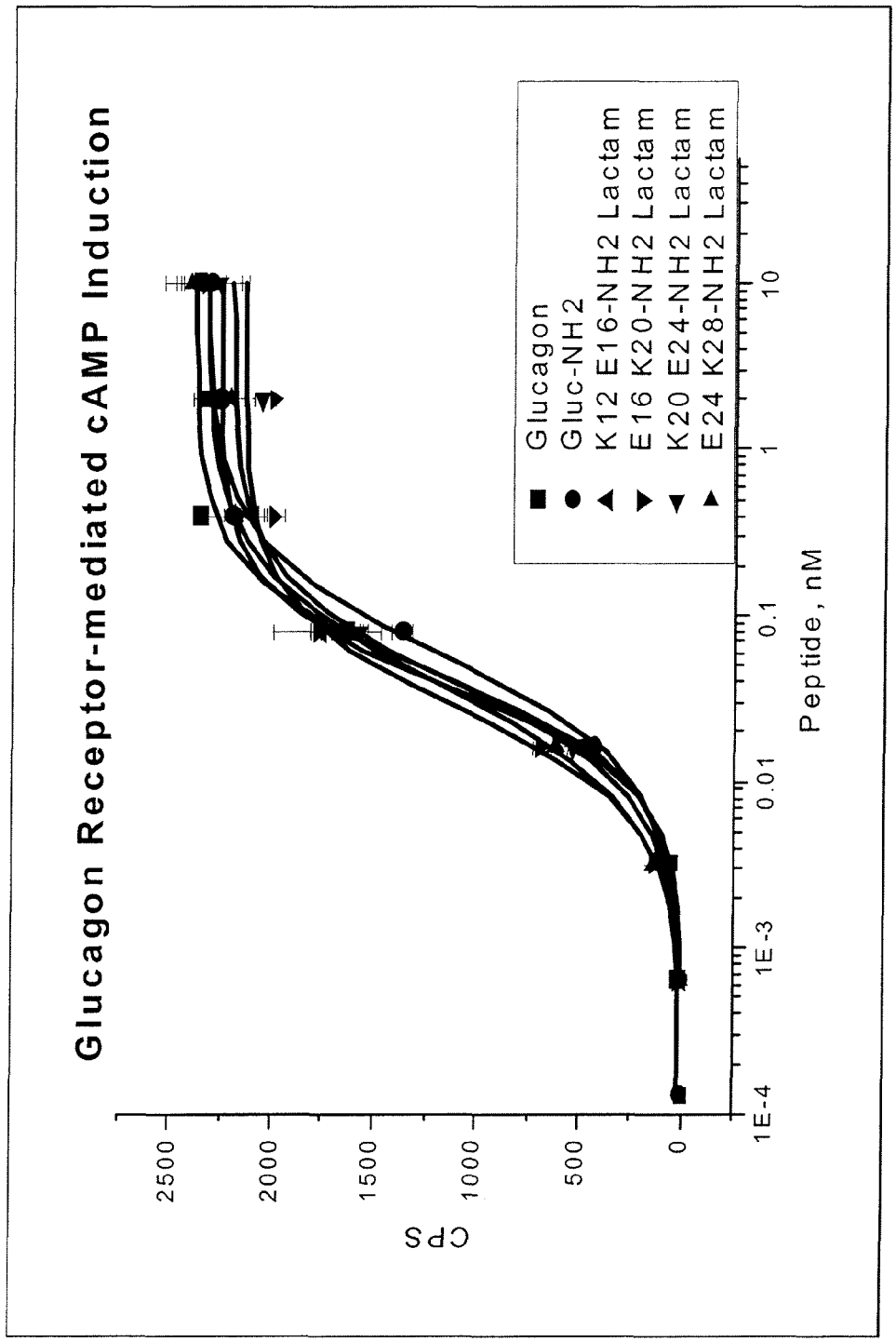
FIGS. 6A and 6B represents data showing receptor mediated cAMP induction by glucagon analogs. More particularly, FIG. 6A compares induction of the glucagon receptor by glucagon analogs (Gluc-NH$_2$ ●, K12E16-NH$_2$ lactam ▲, E16K2O—NH$_2$ lactam ▼, K20E24-NH$_2$ lactam ◄ and E24K28-NH$_2$ lactam ▶) relative to glucagon (■), whereas FIG. 6B compares induction of the GLP-1 receptor by glucagon analogs (Gluc-NH$_2$ ●, K12E16-NH$_2$ lactam ▲, E16K20-
Figure 6B:
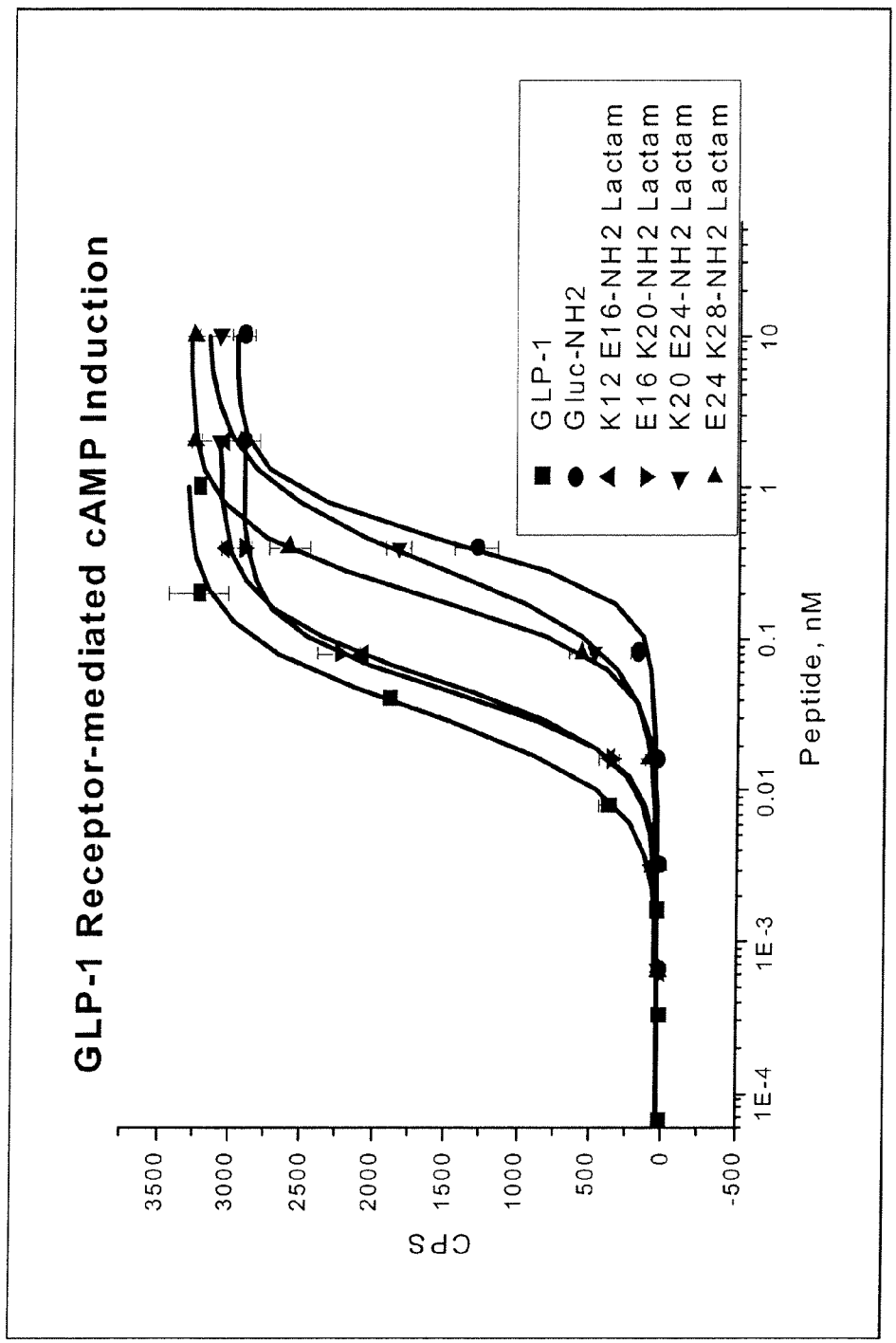
Figure 7A:
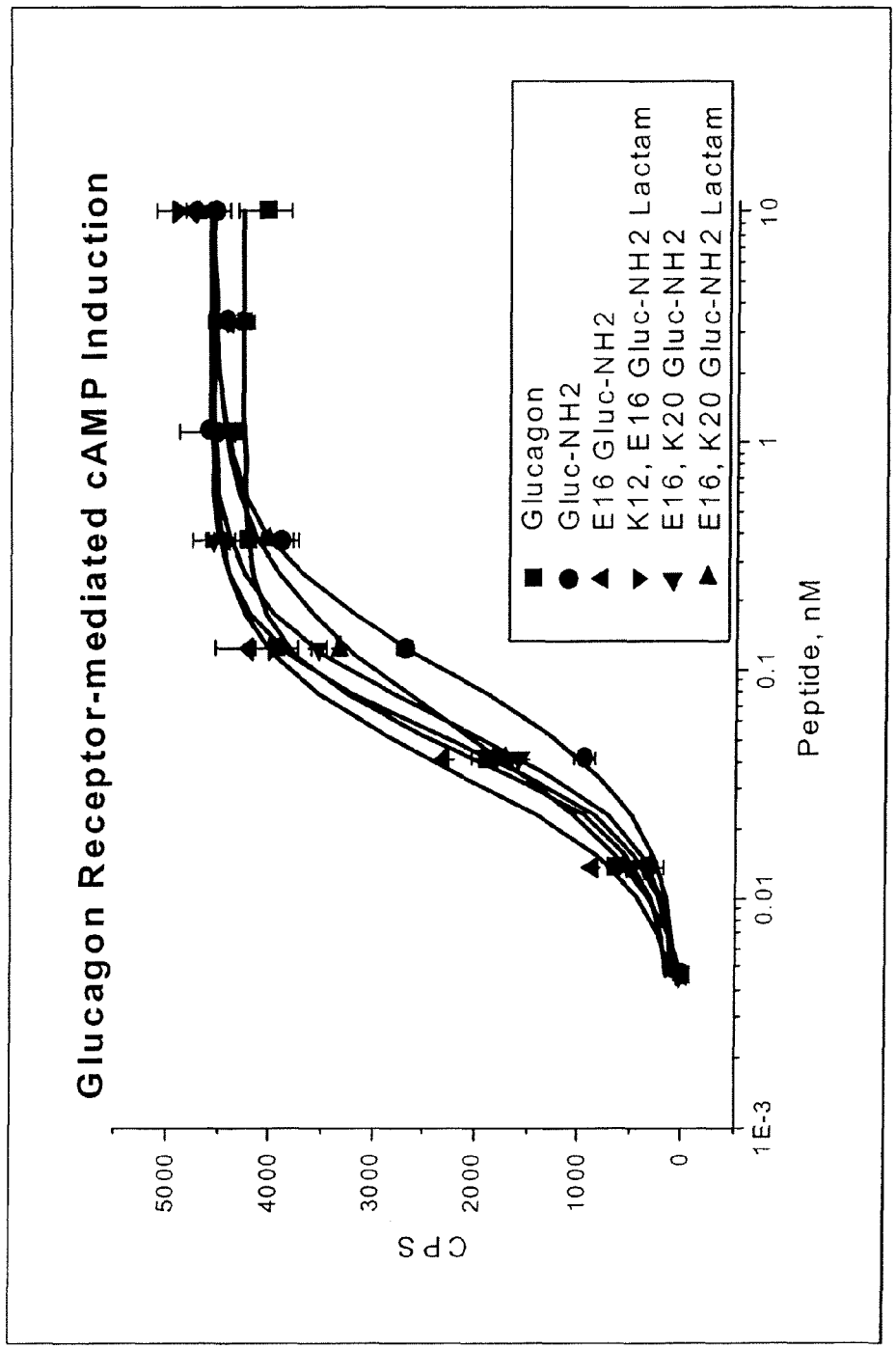
Figure 7B:
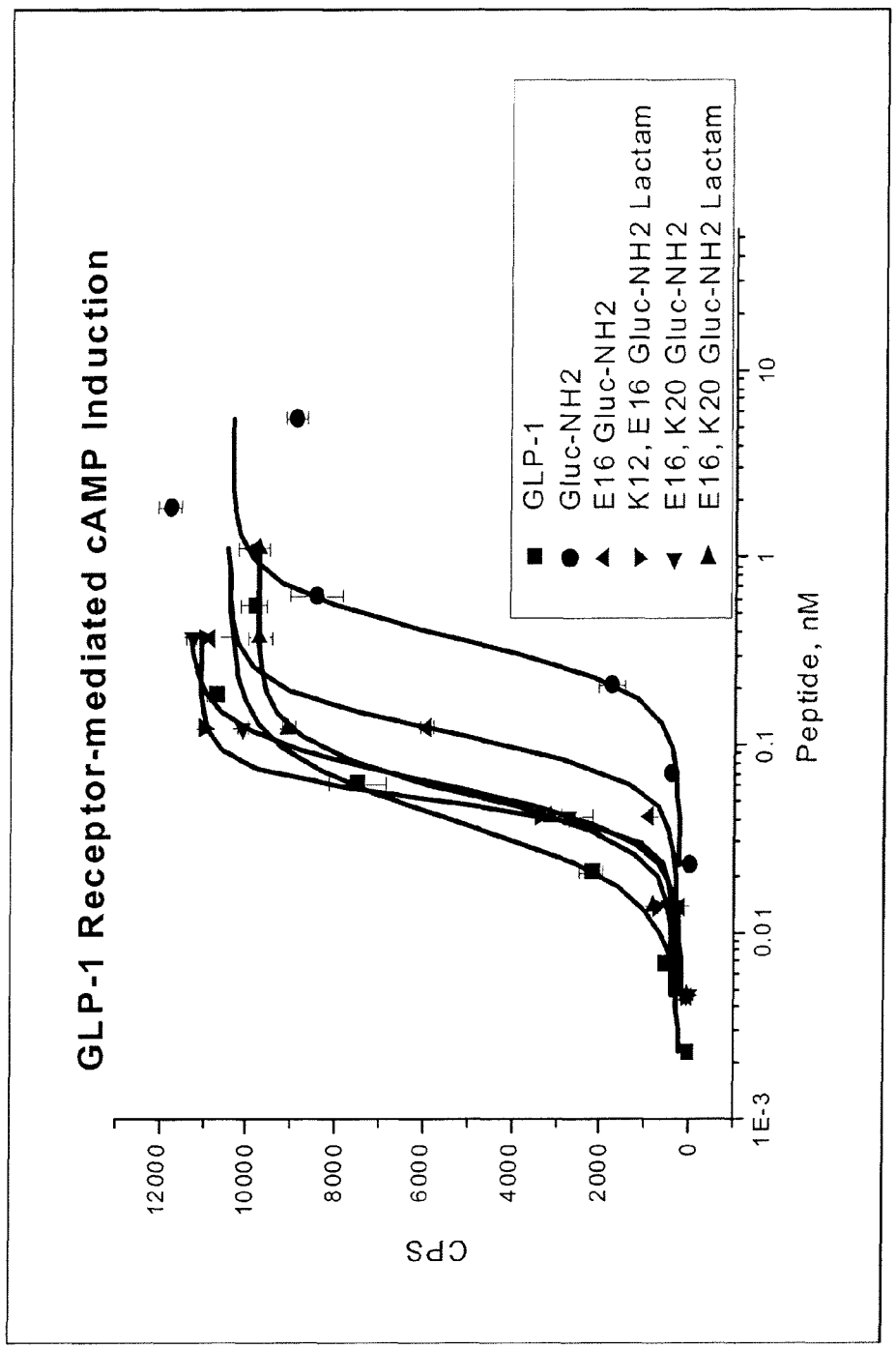

FIGS. 7A and 7B represents data showing receptor mediated cAMP induction by glucagon analogs. More particularly, FIG. 7A compares induction of the glucagon receptor by glucagon analogs (Gluc-NH₂ ●, E16 Gluc-NH₂, ▲, K12, E16 Gluc-NH₂ lactam ▼, E16, K20 Gluc-NH₂ ◄ and E16, K20 Gluc-NH₂ lactam ▶) relative to glucagon (■), whereas FIG. 7B compares induction of the GLP-1 receptor by glucagon analogs (Gluc-NH₂ ●, E16 Gluc-NH₂, ▲, K12, E16 Gluc-NH₂ lactam ▼, E16, K20 Gluc-NH₂ ◄ and E16, K20 Gluc-NH₂ lactam ▶) relative to GLP-1 (■).

FIGS. 8A-8F represent data showing receptor mediated cAMP induction by glucagon analogs at the glucagon receptor (FIGS. 8A, 8C and 8E) or the GLP-1 receptor (FIGS. 8B, 8C and 8F) wherein hE=homoglutamic acid and hC=homocysteic acid.

FIGS. 9A and 9B: represent data showing receptor mediated cAMP induction by GLP (17-26) glucagon analogs, wherein amino acid positions 17-26 of native glucagon (SEQ ID NO: 1) have been substituted with the amino acids of positions 17-26 of native GLP-1 (SEQ ID NO: 50). More particularly, FIG. 9A compares induction of the glucagon receptor by the designated GLP (17-26) glucagon analogs, and FIG. 9B compares induction of the GLP-1 receptor by the designated GLP (17-26) glucagon analogs.

Figure 10B:
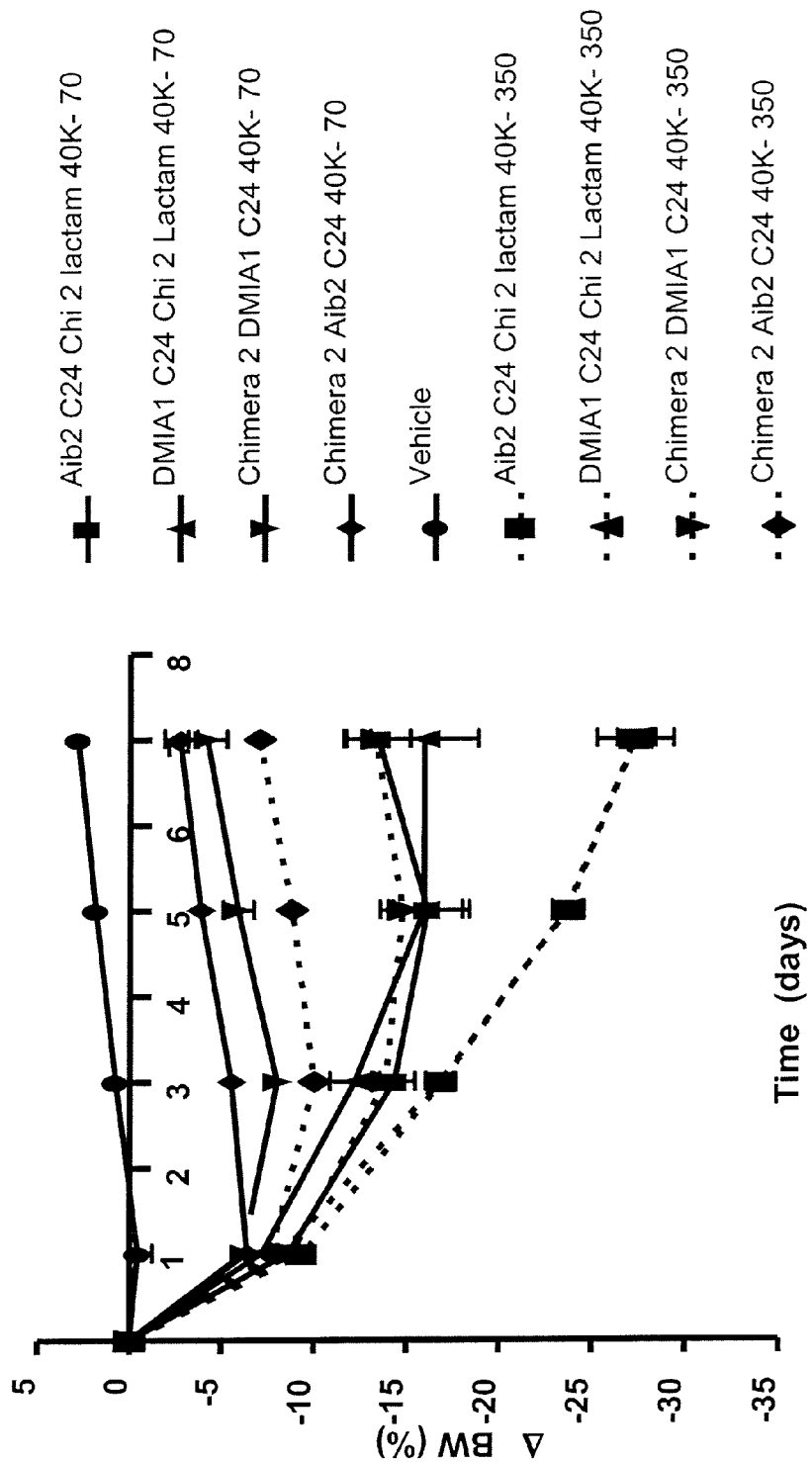
Figure 10D:
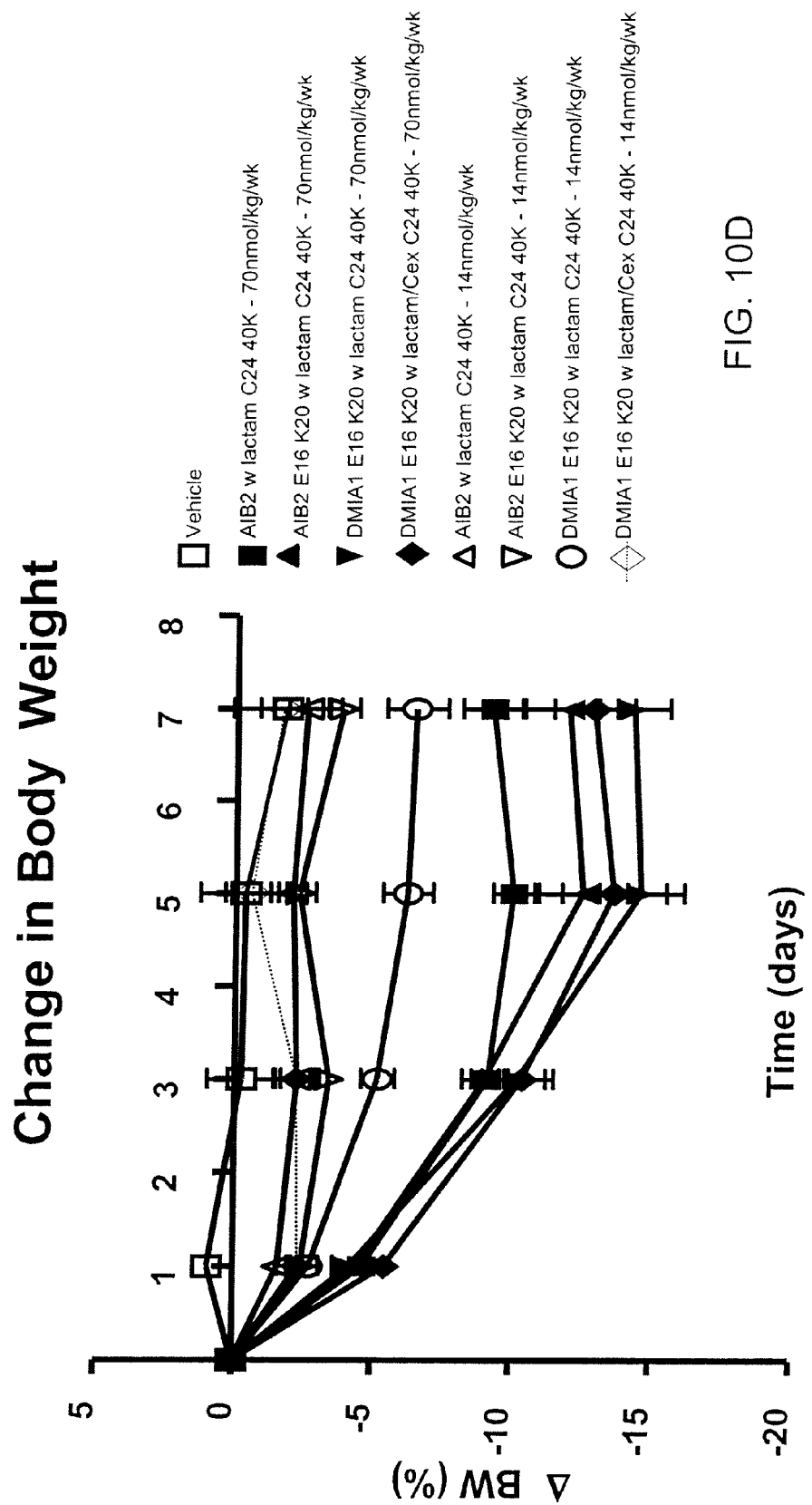
Figure 10E:
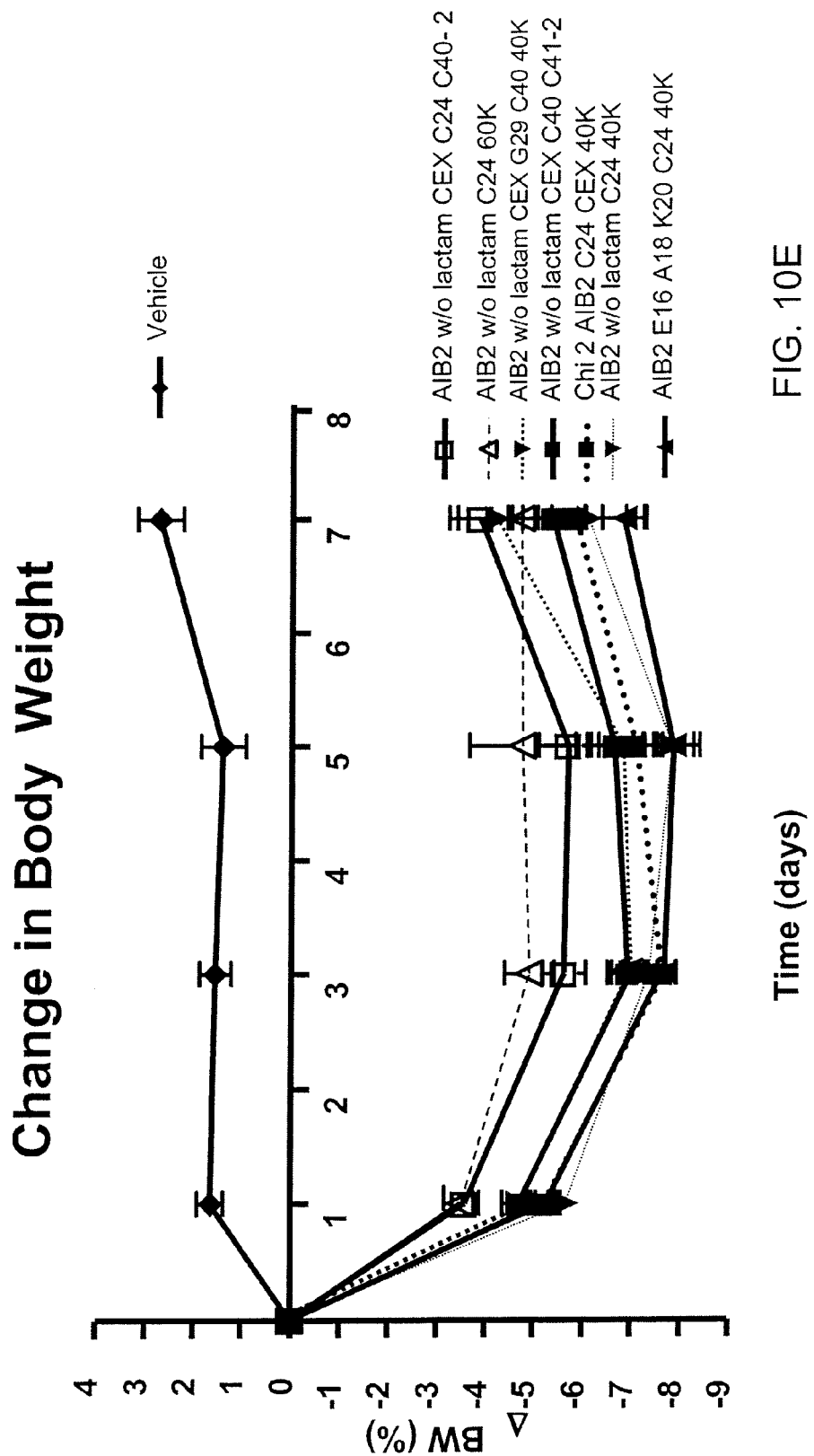

FIGS. 10A-E: are graphs providing in vivo data demonstrating the ability of the glucagon peptides of the present invention to induce weight loss in mice injected subcutaneously with the indicated amounts of the respective compounds. Sequence Identifiers for the glucagon peptide listed in FIGS. 10A-10E are as follows, for FIG. 10A: Chimera 2 Aib2 C24 40K PEG (SEQ ID NO: 486), Aib2 C24 Chimera 2 40K lactam (SEQ ID NO: 504) and Aib2 E16 K20 Gluc-NH2 Lac 40K (SEQ ID NO: 528); FIG. 10B: Aib2 C24 Chi 2 lactam 40K (SEQ ID NO: 504), DMIA1 C24 Chi 2 Lactam 40K (SEQ ID NO: 505), Chimera 2 DMIA1 C24 40K (SEQ ID NO: 519), and Chimera 2 Aib2 C24 40K (SEQ ID NO: 486), wherein the number at the end of the sequence designates the dosage used, either 70 or 350 nmol/kg; FIG. 10C: AIB2 w/ lactam C24 40K (SEQ ID NO: 504), AIB2 E16 K20 w/ lactam C24 40K (SEQ ID NO: 528), DMIA1 E16 K20 w/ lactam C24 40K (SEQ ID NO: 510), DMIA1 E16 K20 w/ lactam CEX 40K (SEQ ID NO: 513) and DMIA1 E16 K20 w/o lactam CEX 40K (SEQ ID NO: 529); FIG. 10D: AIB2 w lactam C24 40K (SEQ ID NO: 504), AIB2 E16 K20 w lactam C24 40K (SEQ ID NO: 528), DMIA1 E16 K20 w lactam C24 40K (SEQ ID NO: 510) and DMIA1 E16 K20 w lactam/Cex C24 40K (SEQ ID NO: 513), wherein the number at the end of the sequence designates the dosage used, either 14 or 70 nmol/kg/wk; FIG. 10E: AIB2 w/o lactam C24 40K (SEQ ID NO: 486), Chi 2 AIB2 C24 CEX 40K (SEQ ID NO: 533), AIB2 E16 A18 K20 C24 40K (SEQ ID NO: 492), AIB2 w/o lactam CEX G29 C40 40K (SEQ ID NO: 488), AIB2 w/o lactam CEX C40 C41-2 (SEQ ID NO: 532), AIB2 w/o lactam CEX C24 C40-2 (SEQ ID NO: 531) and AIB2 w/o lactam C24 60K (SEQ ID NO: 498), wherein the designation 40K or 60K represents the molecular weight of the polyethylene chain attached to the glucagon peptide.

Figure 11:
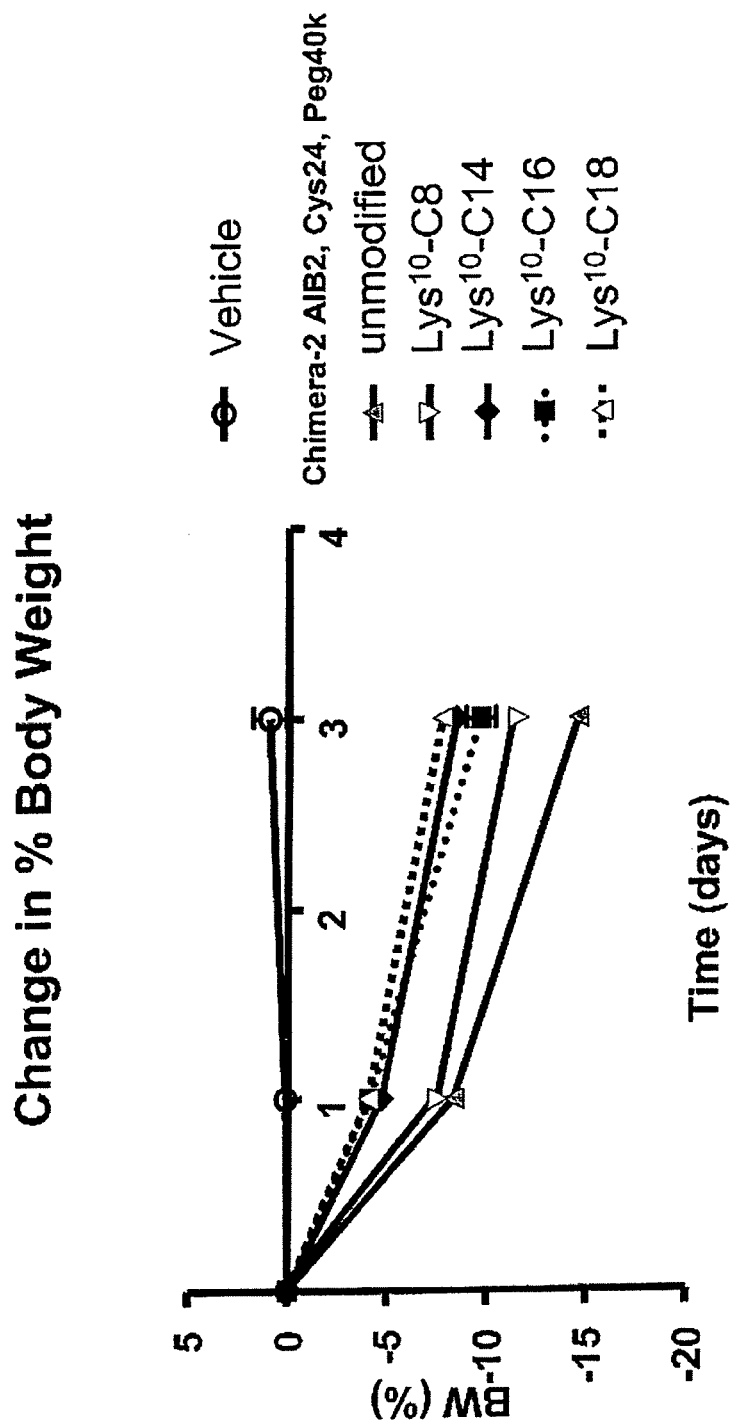
Figure 12:
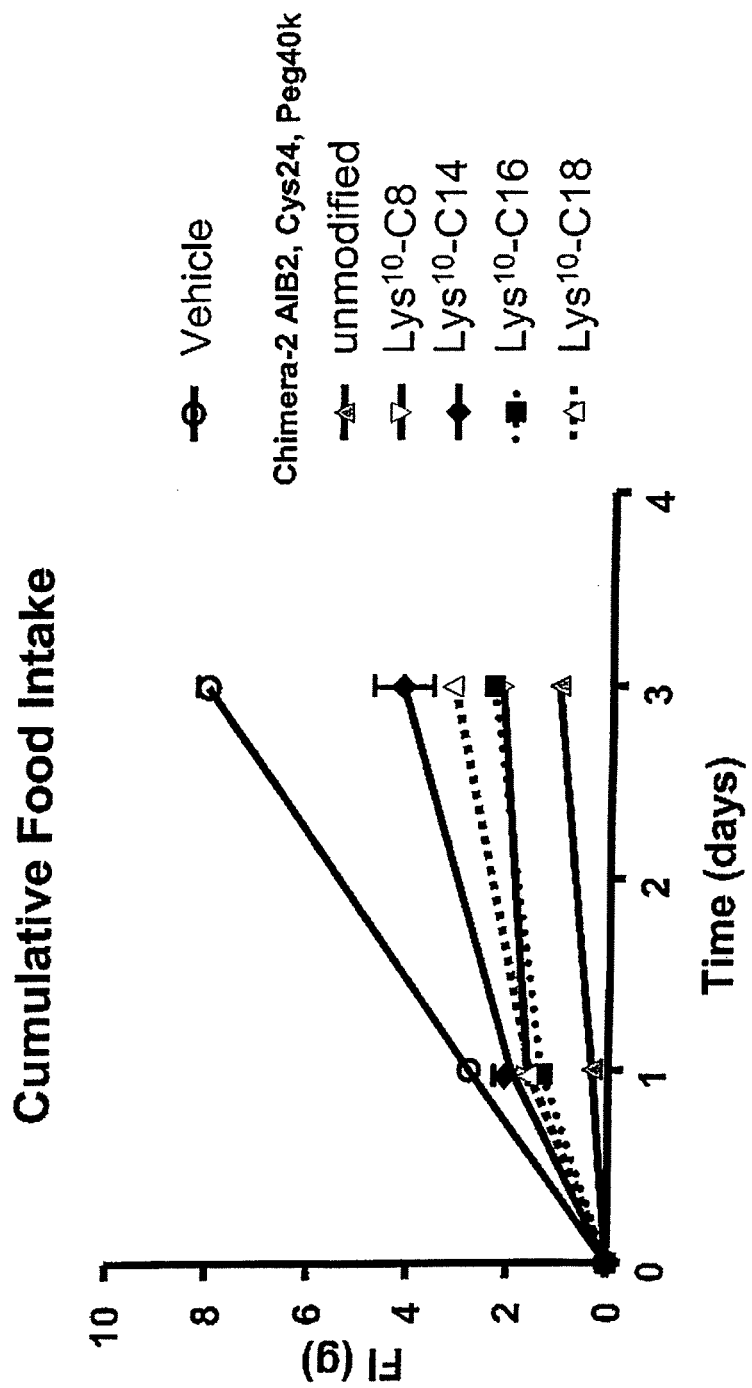
Figure 13:
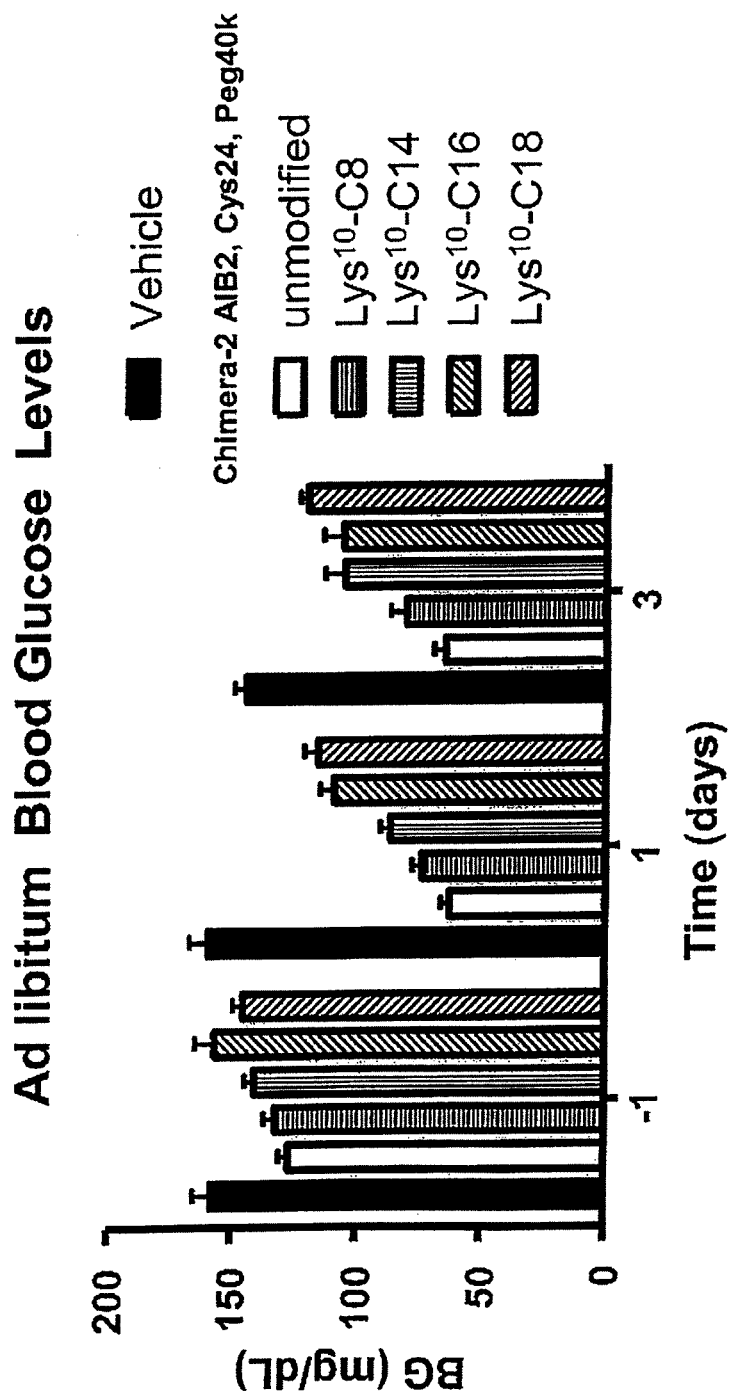

FIGS. 11-13 are graphs providing in vivo data demonstrating the ability of acylated glucagon peptides to induce weight loss (FIG. 11), reduce food intake (FIG. 12), and reduce blood glucose levels (FIG. 13) in mice injected subcutaneously with the indicated amounts of the compounds.

Figure 14:
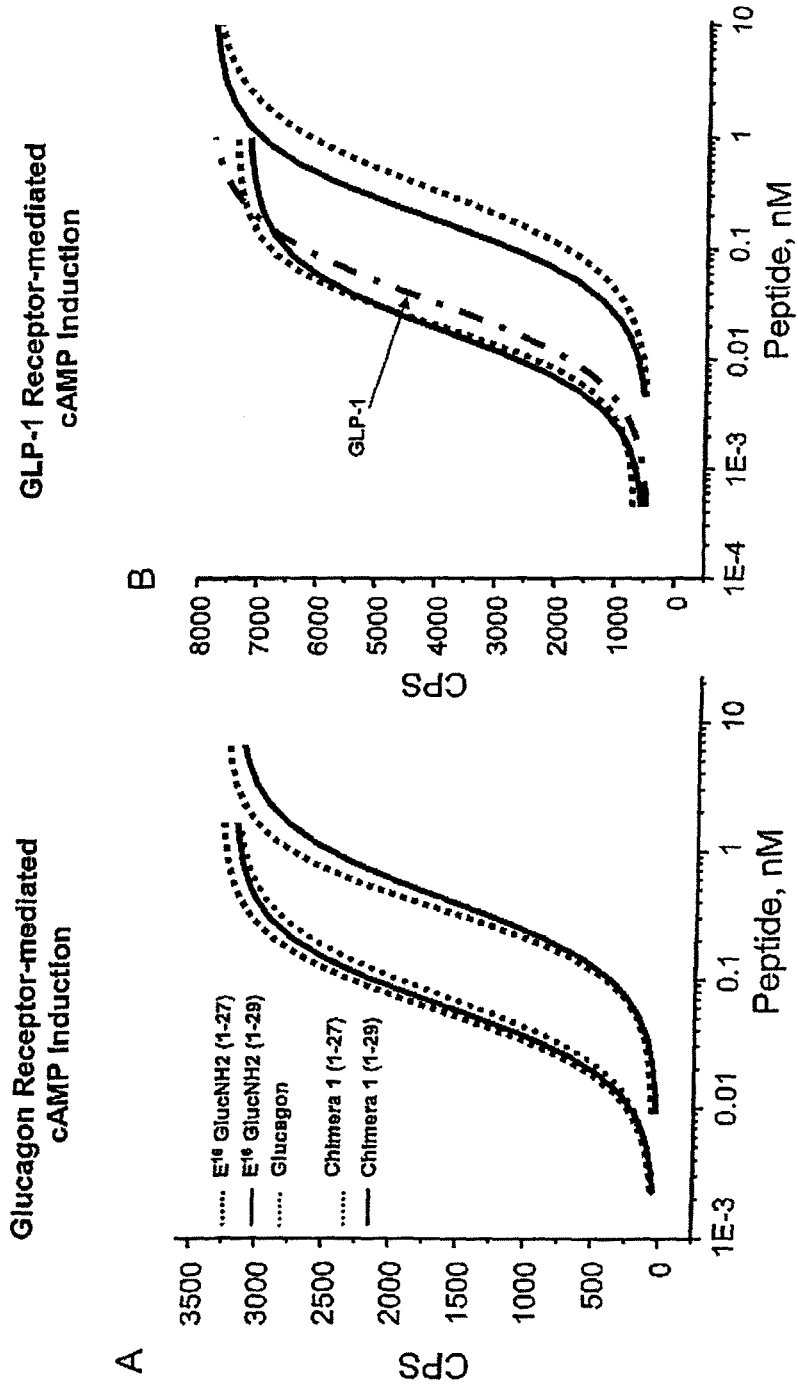

FIGS. 14A and 14B represent data showing glucagon and GLP-1 receptor mediated cAMP induction, respectively, by glucagon analogs.

Figure 15:
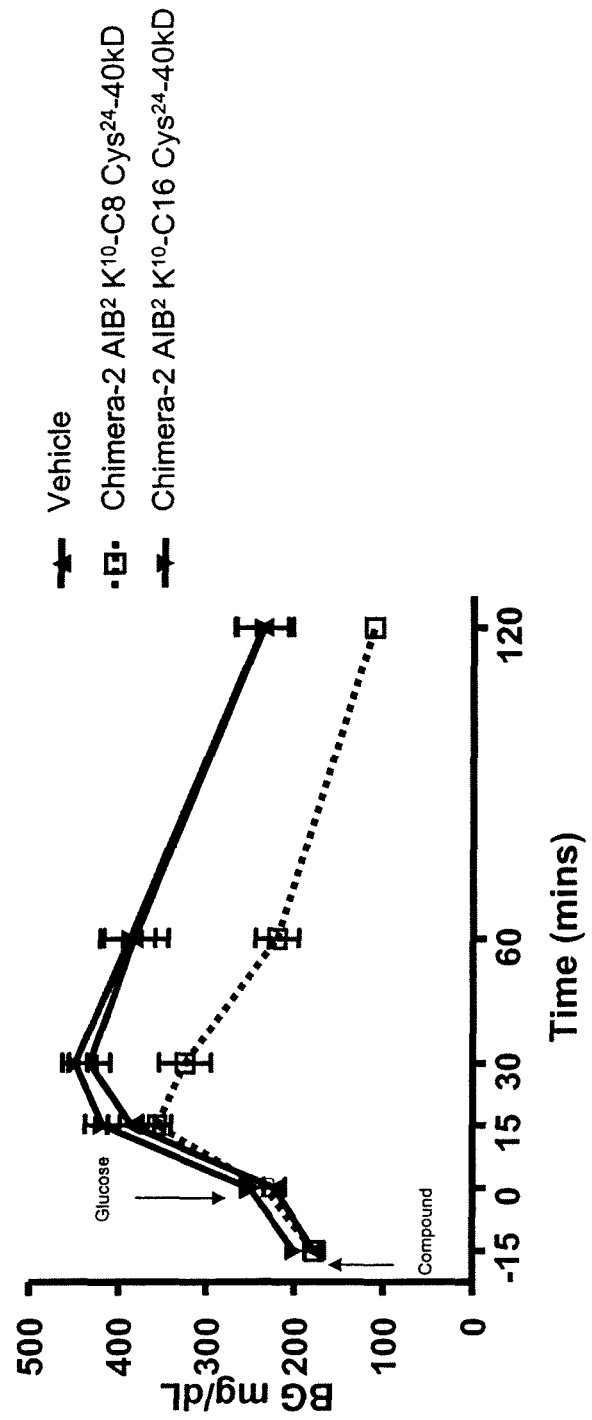

FIG. 15 represents a graph of blood glucose (mg/dL) as a function of time (mins) in DIO mice treated with 2 nmol/kg of vehicle only (triangles), Chimera-2 AIB², K¹⁰-C8 Cys²⁴-40 kD PEG (open squares), or Chimera-2 AIB², K¹⁰-C16 Cys²⁴-40 kD PEG (inverted triangles) followed by glucose challenge 15 mins after administration of the peptide.

Figure 16:
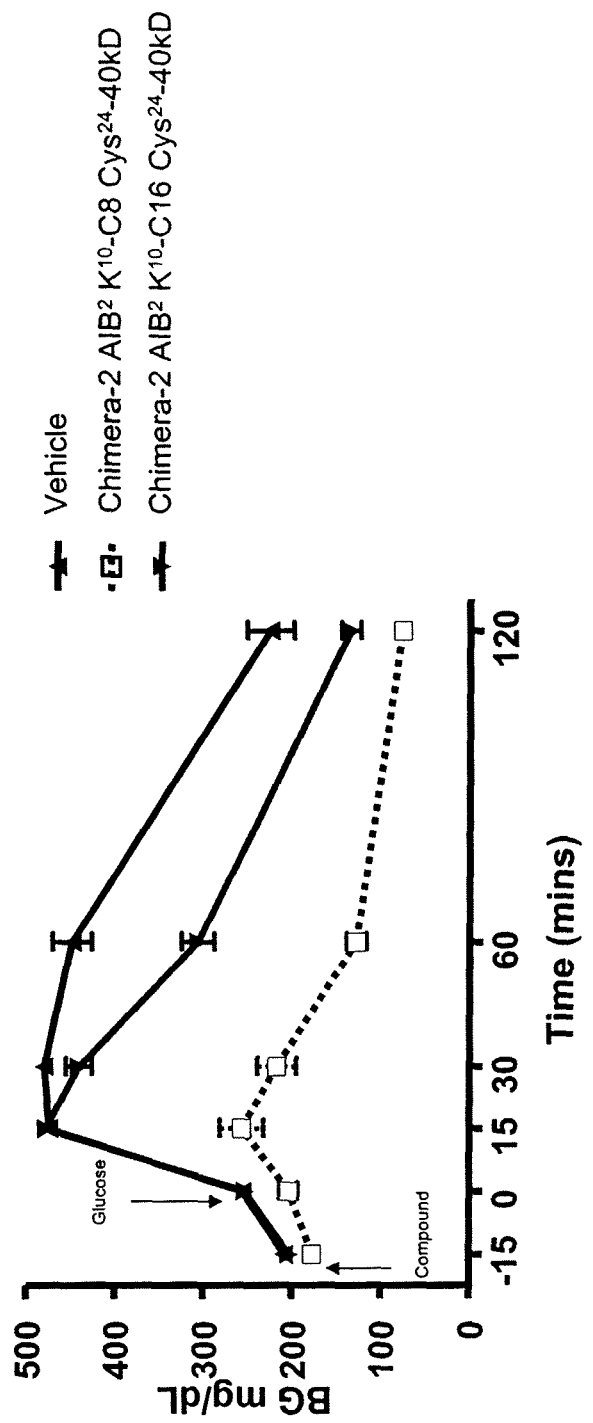

FIG. 16 represents a graph of blood glucose (mg/dL) as a function of time (mins) in DIO mice treated with 20 nmol/kg of vehicle only (triangles), Chimera-2 AIB², K¹⁰-C8 Cys²⁴-40 kD PEG (open squares), or Chimera-2 AIB², K¹⁰-C16 Cys²⁴-40 kD PEG (inverted triangles) followed by glucose challenge 15 mins after administration of the peptide.

Figure 17:
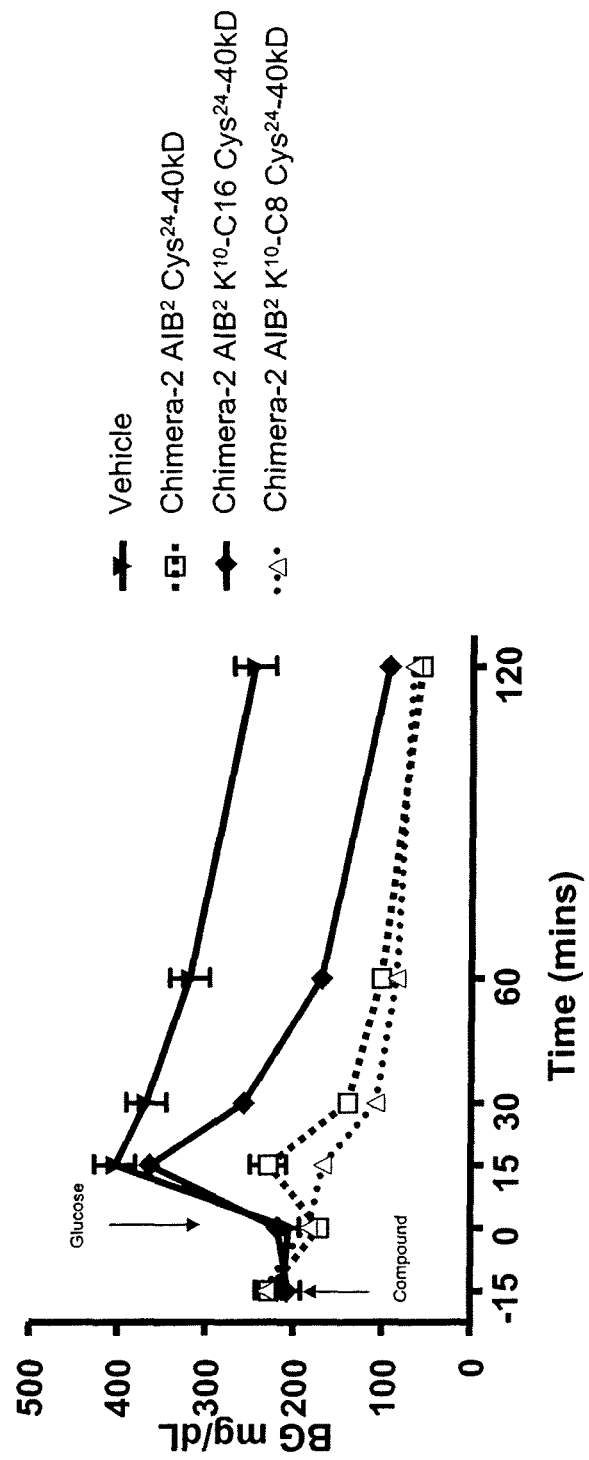

FIG. 17 represents a graph of blood glucose (mg/dL) as a function of time (mins) of DIO mice treated with 70 nmol/kg of vehicle only (inverted triangles), Chimera-2 AIB², K¹⁰-C8 Cys²⁴-40 kD PEG (open triangles), Chimera-2 AIB², K¹⁰-C16 Cys²⁴-40 kD PEG (diamonds), or Chimera-2 AIB², Cys²⁴-40 kD PEG (open squares) followed by glucose challenge 15 mins after administration of the peptide.

Figure 18:
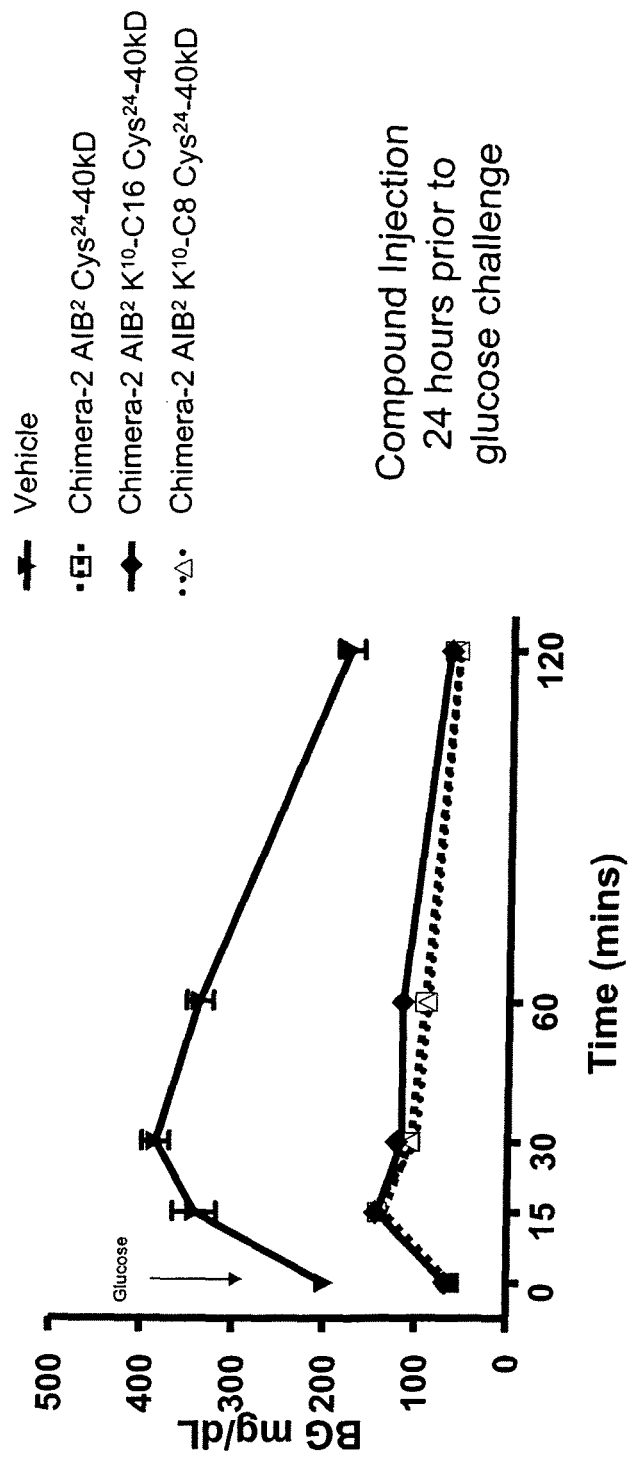

FIG. 18 represents a graph of blood glucose (mg/dL) as a function of time (mins) of DIO mice treated with 70 nmol/kg of vehicle only (inverted triangles), Chimera-2 AIB², K¹⁰-C8 Cys²⁴-40 kD PEG (open triangles), Chimera-2 AIB², C16 Cys²⁴-40 kD PEG (diamonds), or Chimera-2 AIB², Cys²⁴-40 kD PEG (open squares) followed by glucose challenge 24 hours after administration of the peptide.

Figure 19:
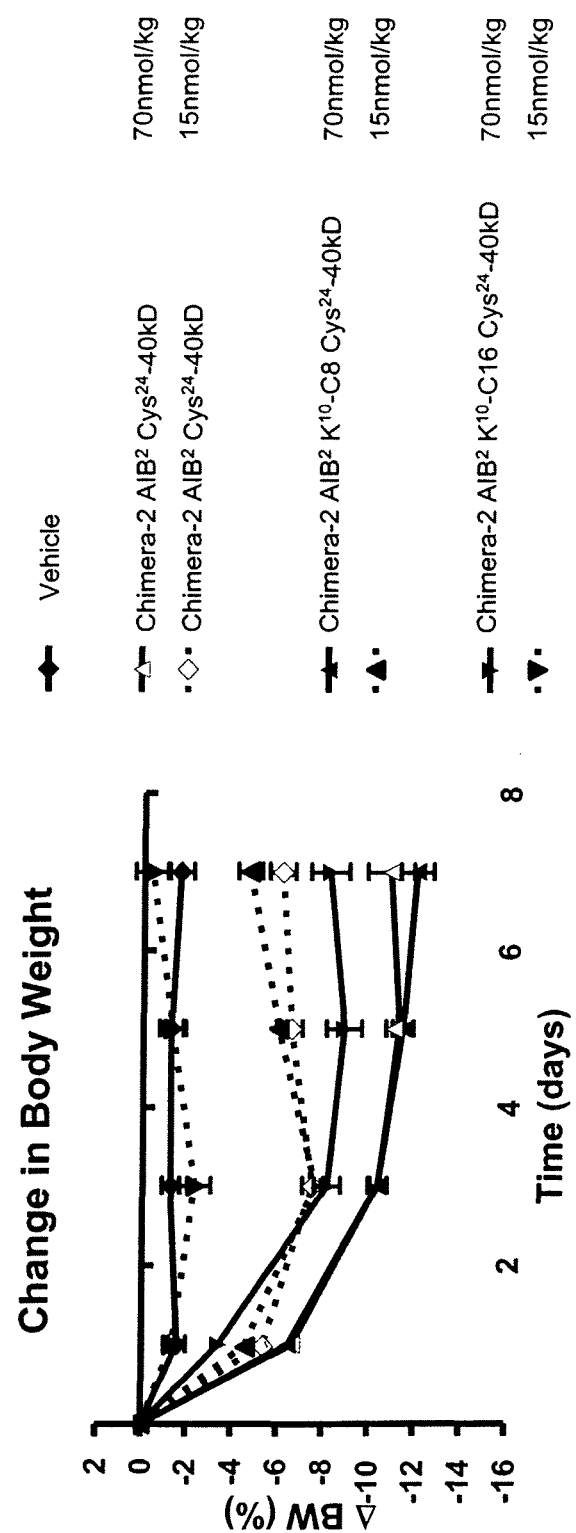

FIG. 19 represents a graph of the change in body weight (%) as a function of time (days) in DIO mice treated with 15 or 70 nmol/kg of vehicle only (diamonds with solid line); Chimera-2 AIB², Cys²⁴-40 kD PEG (15 nmol/kg, open diamonds with dotted line; 70 nmol/kg, open triangles with solid line); Chimera-2 AIB², K¹⁰-C8 Cys²⁴-40 kD PEG (15 nmol/kg, closed triangle with dotted line; 70 nmol/kg, closed triangle with solid line); Chimera-2 AIB², K¹⁰-C16 Cys²⁴-40 kD Peg (15 nmol/kg, inverted triangle with dotted line; 70 nmol/kg; inverted triangle with solid line).

Figure 20:
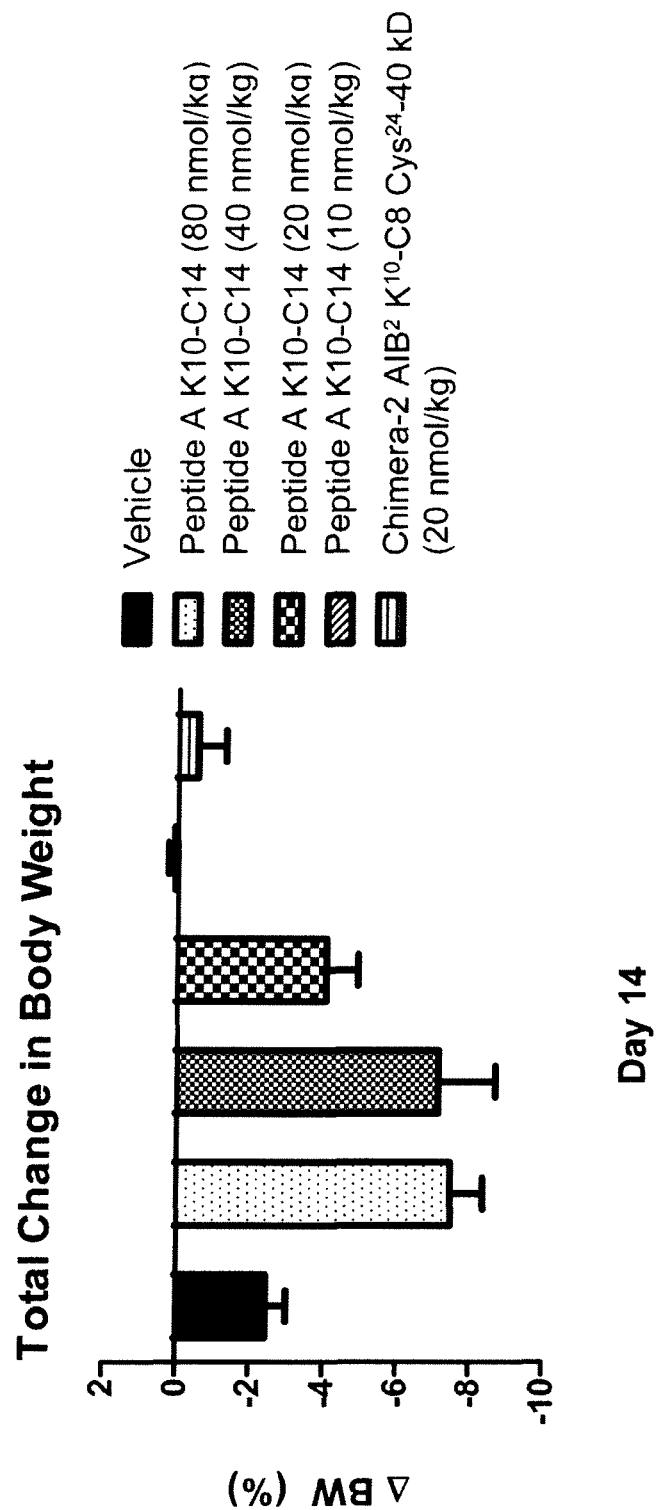
Figure 21:
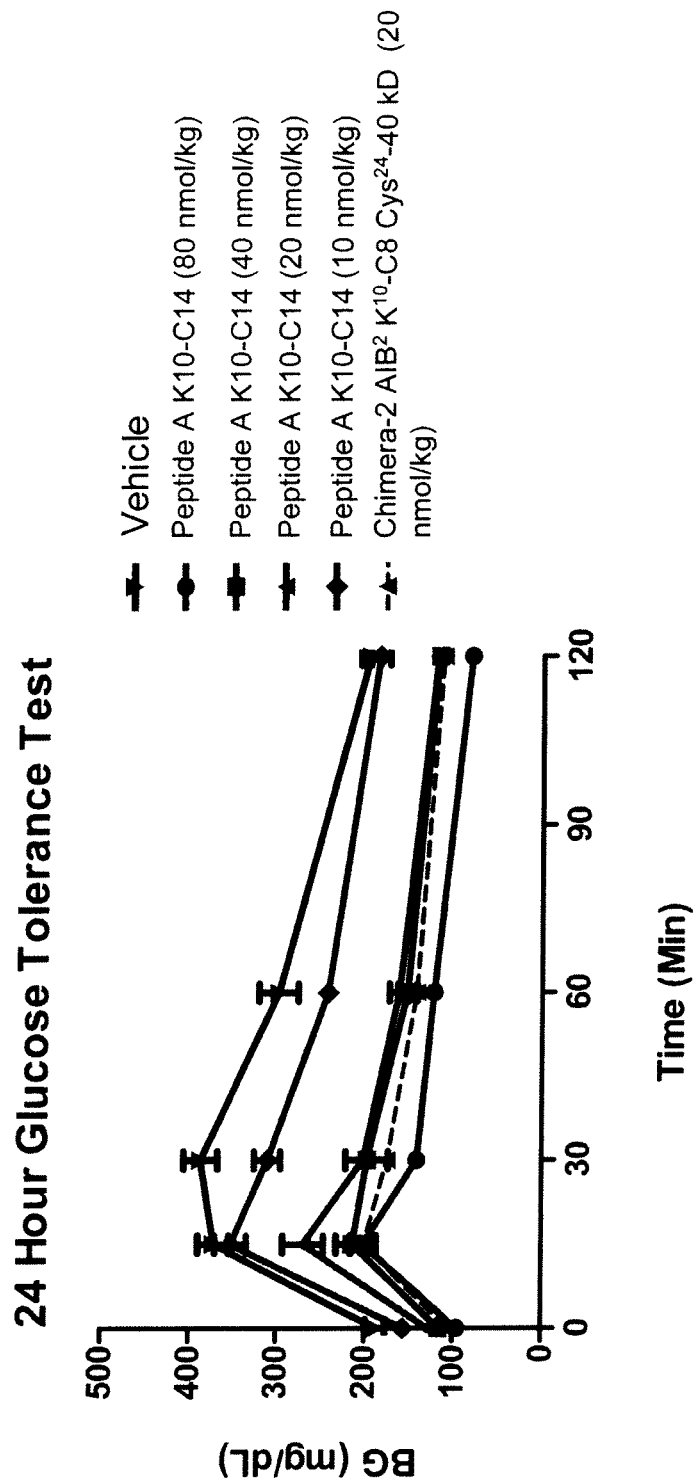

FIG. 20 represents a graph of the total change in body weight (%) in mice 14 days after QW injections of 10, 20, 40, or 80 nmol/kg Peptide A K¹⁰-C₁₄ or 20 nmol/kg Chimera-2 AIB² K¹⁰-C8 Cys²⁴-40 kD or a vehicle control FIG. 21 represents a graph of the blood glucose levels (mg/dL) in response to a glucose injection of mice injected with 10, 20, 40, or 80 nmol/kg Peptide A K¹⁰-C₁₄ or 20 nmol/kg Chimera-2 AIB² K¹⁰-C8 Cys²⁴-40 kD or a vehicle control 24 hours prior to the glucose injection.

Figure 22:
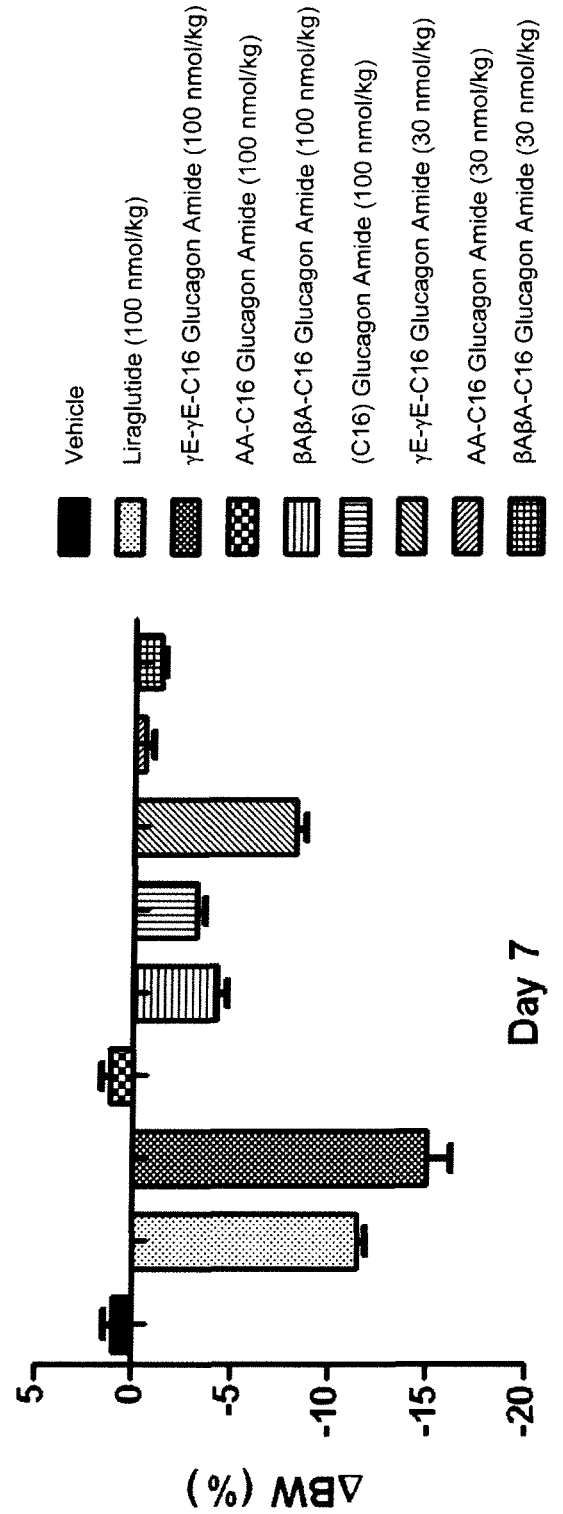

FIG. 22 represents a graph of the total change in body weight (%) of mice injected with vehicle control, Liraglutide, (C16) Glucagon Amide, γE-γE-C 16 Glucagon Amide, AA-C16 Glucagon Amide, or βAβA-C16 Glucagon Amide at the indicated dose.

Figure 23:
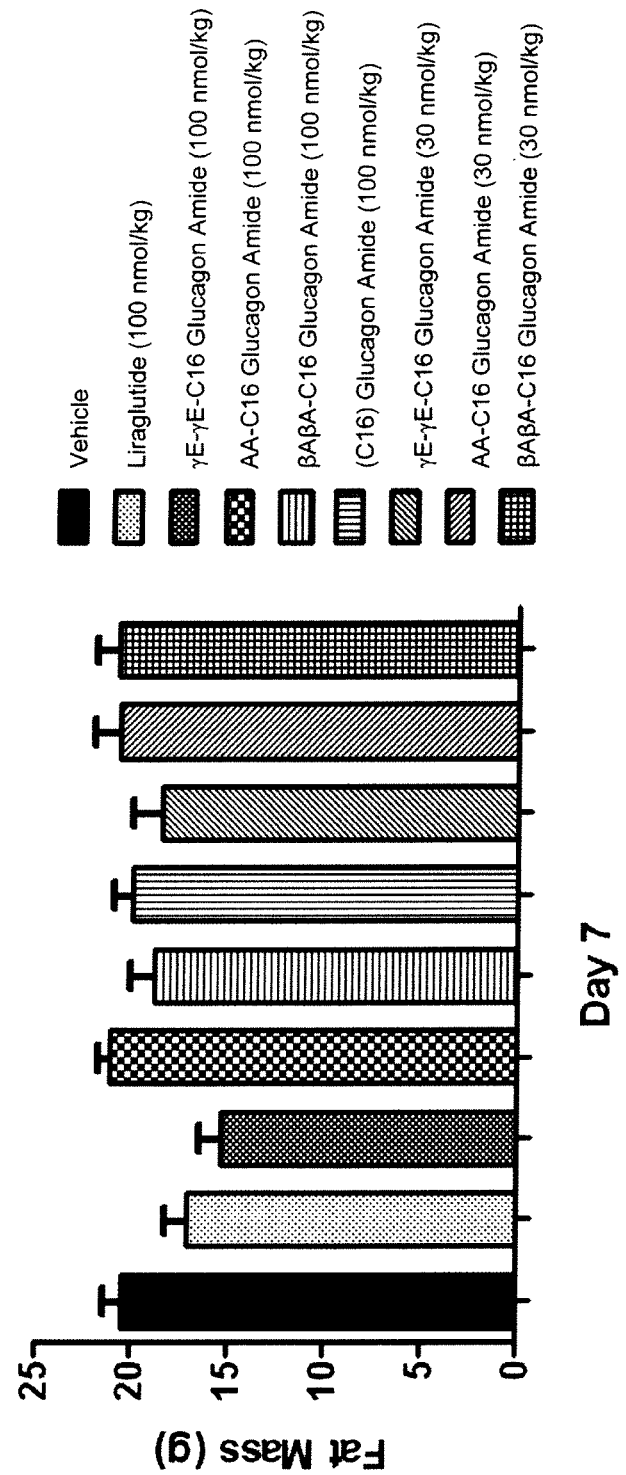

FIG. 23 represents a graph of the fat mass (g) as measured on Day 7 of the study of mice injected with vehicle control, Liraglutide, (C16) Glucagon Amide, γE-γE-C16 Glucagon Amide, AA-C16 Glucagon Amide, or βAβA-C16 Glucagon Amide at the indicated dose.

Figure 24:
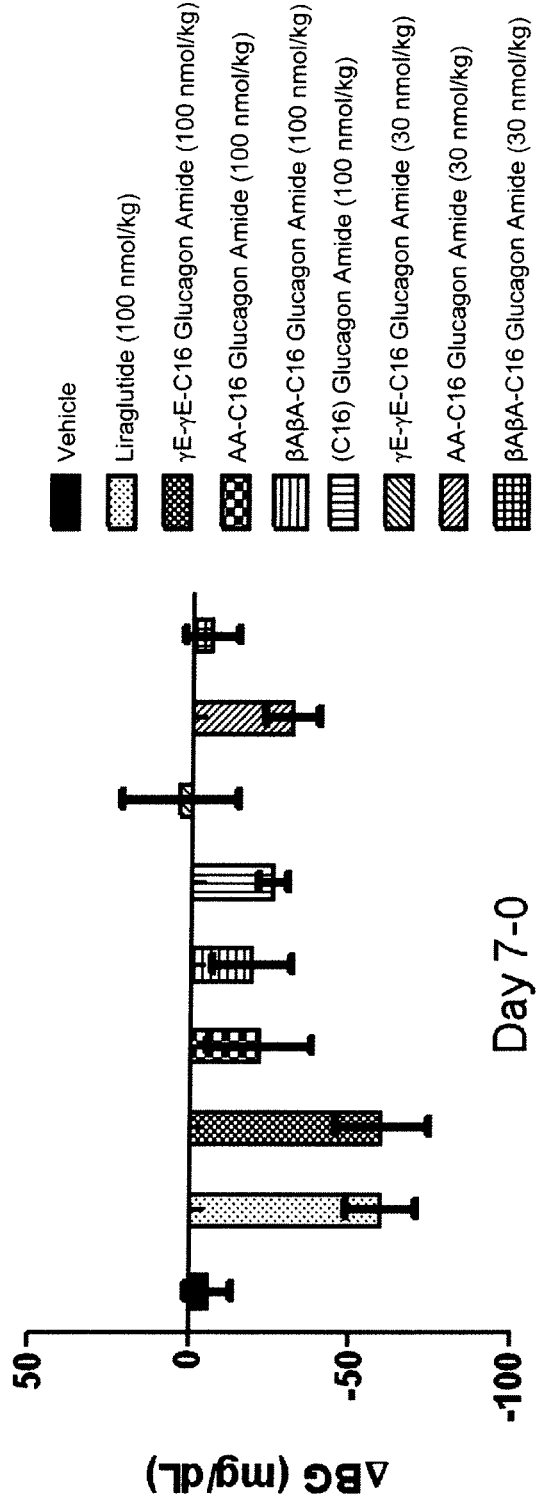

FIG. 24 represents a graph of the change in blood glucose (mg/dL; Day 7 levels minus Day 0 levels) of mice injected with vehicle control, Liraglutide, (C16) Glucagon Amide, γE-γE-C16 Glucagon Amide, AA-C16 Glucagon Amide, or βAβA-C16 Glucagon Amide at the indicated dose.

Figure 25:
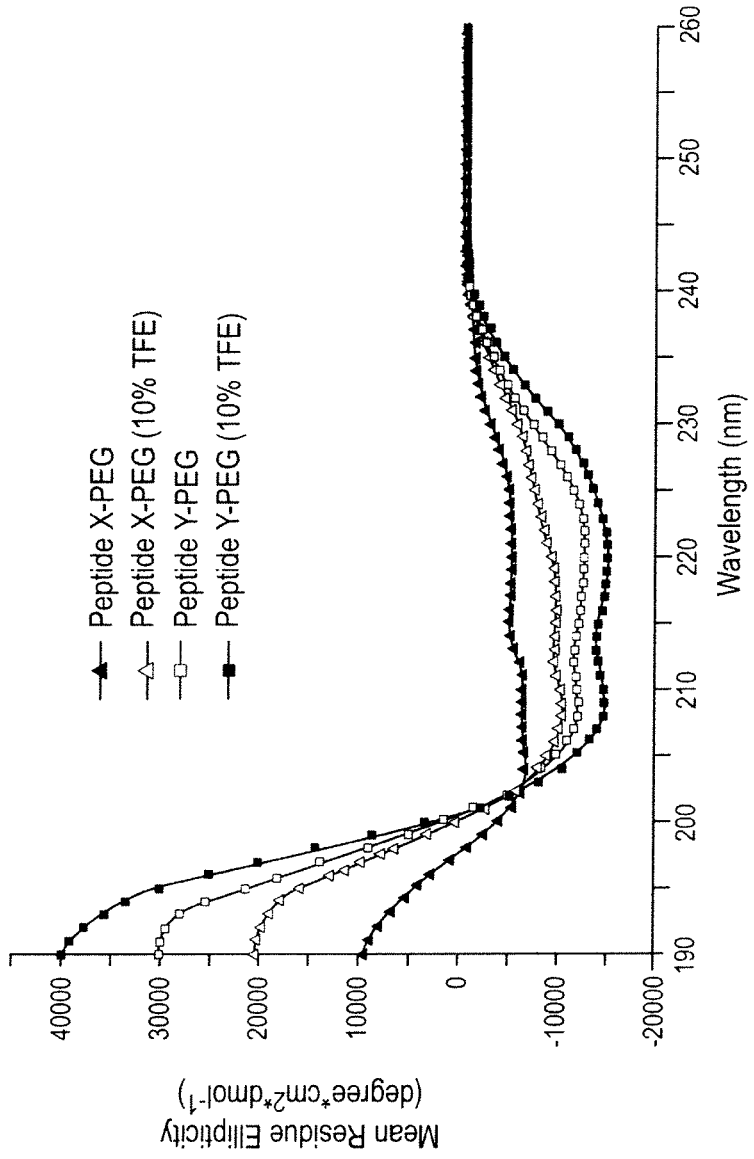

FIG. 25 represents represents a graph of the mean residue ellipticity as a function of wavelength (nm) for Peptide X-PEG or Peptide Y-PEG in 10 mM Phosphate (pH 5.9) either with or without 10% TFE.

Figure 26:
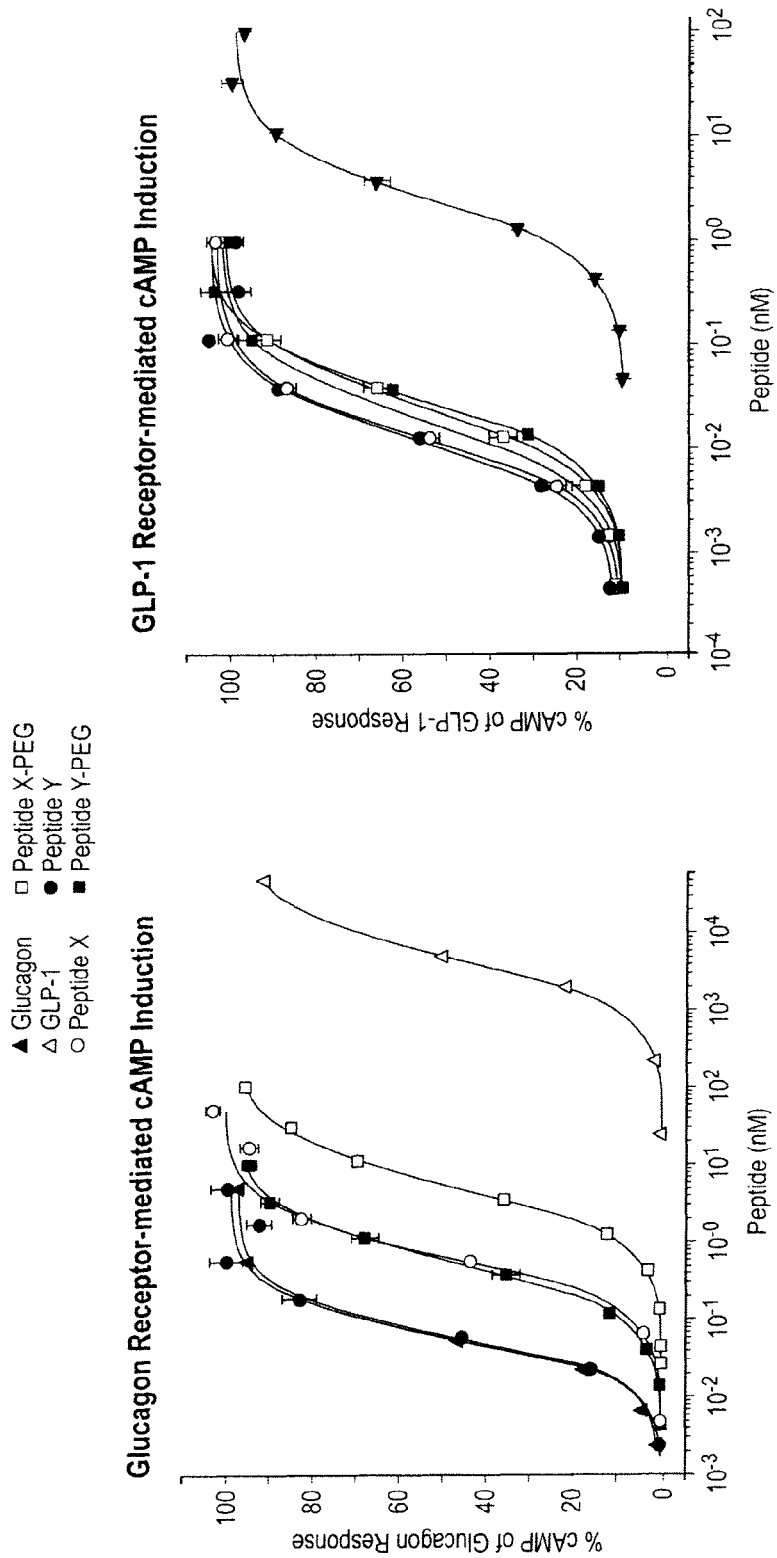

FIG. 26 represents a graph of the % cAMP produced in response to Glucagon, GLP-1, Peptide X, Peptide X-PEG, Peptide Y, or Peptide Y-PEG binding to either the glucagon receptor (left) or GLP-1 receptor (right) as a function of peptide concentration (nM).

Figure 27:
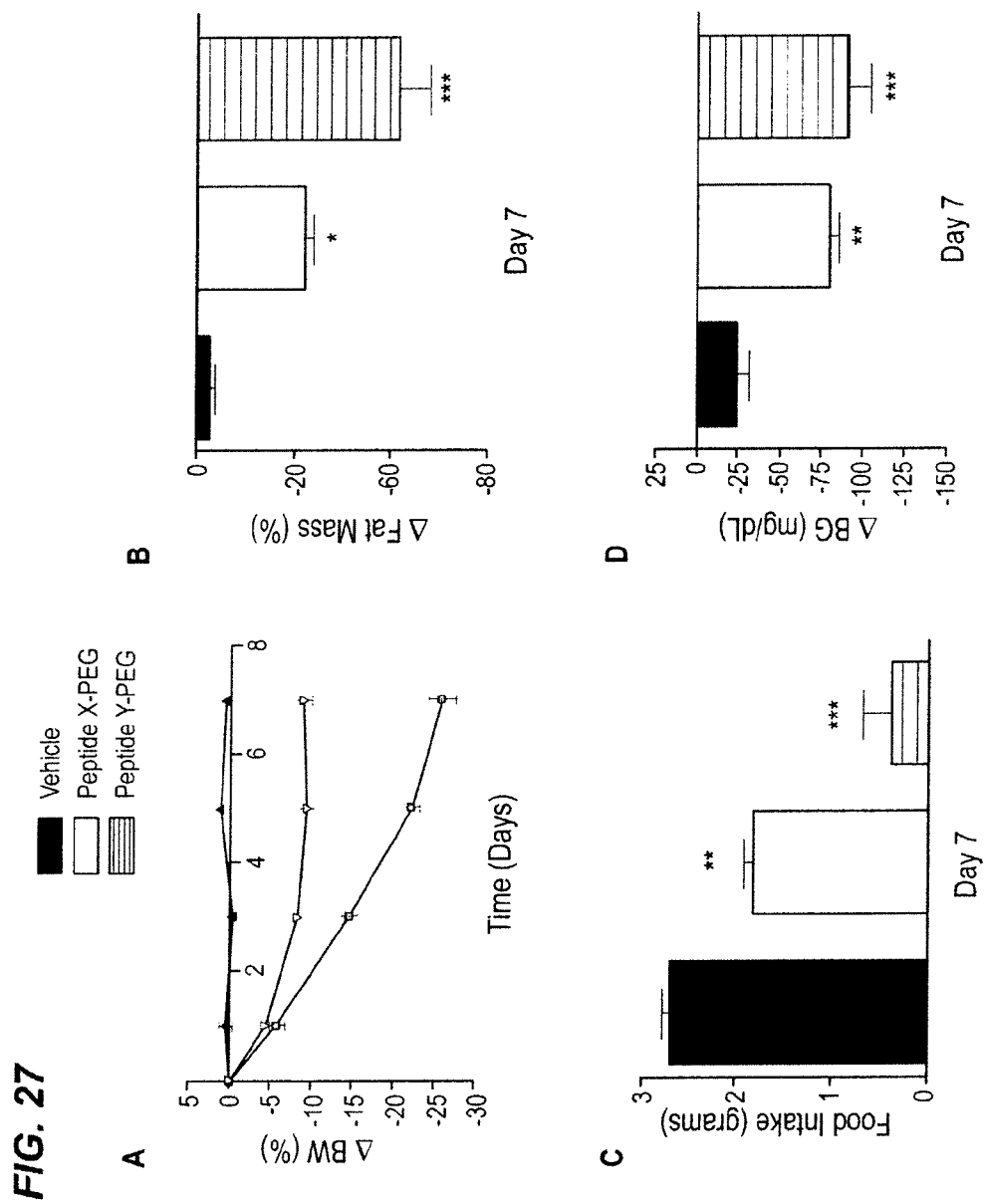

FIG. 27 represents a collection of graphs which demonstrate the in vivo effects on A) body weight, B) fat mass, C) food intake, and D) fasting blood glucose levels in diet induced obese mice treated for one week with vehicle control, Peptide X-PEG, or Peptide Y-PEG. More specifically, FIG. 27A represents a graph of the % change in body weight (BW) as a function of time (days), FIG. 27 B represents a graph of the % change in fat mass as measured on Day 7 (as compared to initial fat mass measurements), FIG. 27C represents a graph of the total food intake (g) over the course of the study as measured on Day 7, and FIG. 27D represents a graph of the change in blood glucose (mg/dL) as measured on Day 7 (in comparison to initial blood glucose levels).

Figure 28:
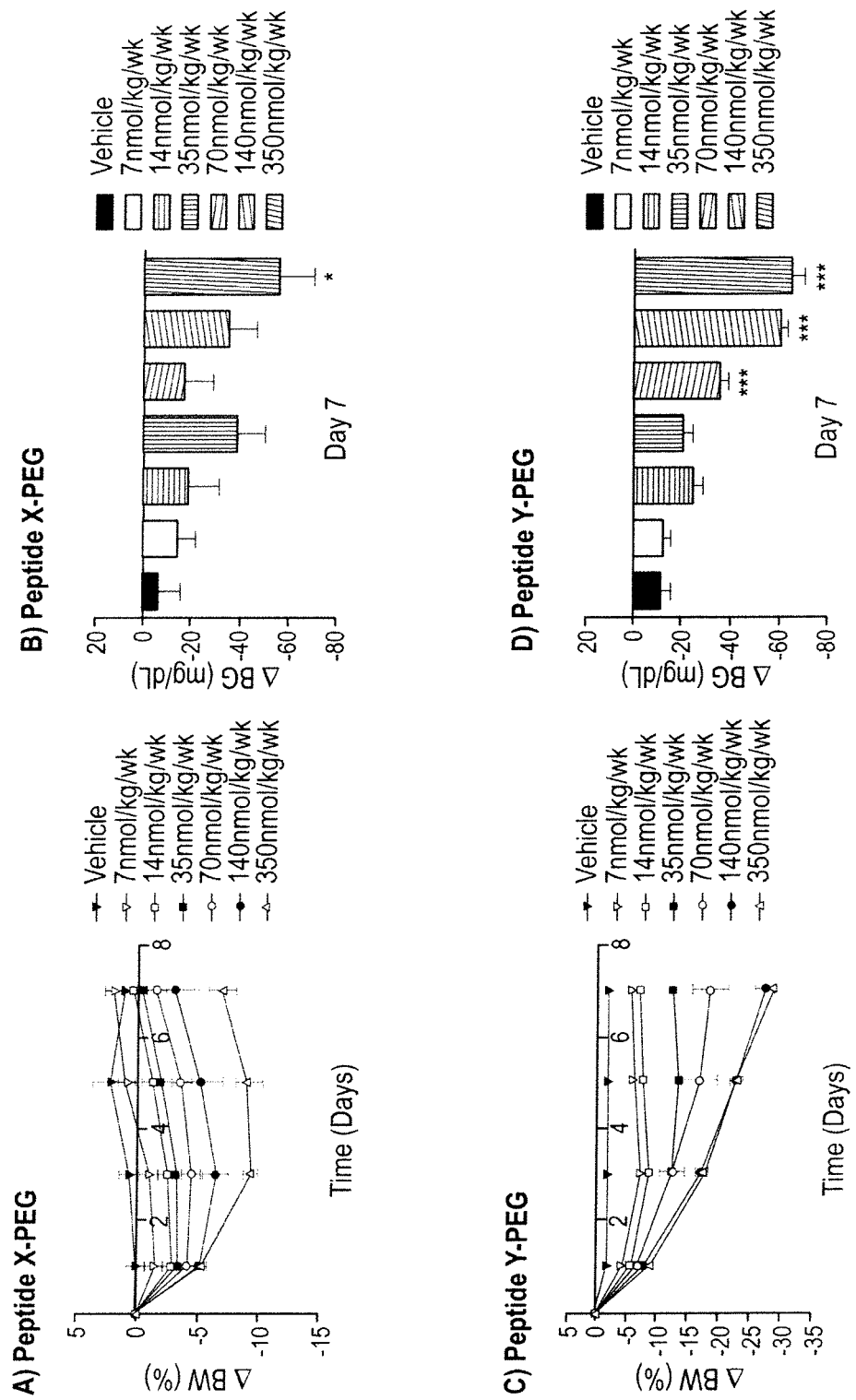

FIG. 28 represents a collection of graphs which demonstrate the in vivo effects on body weight (FIGS. 28A and 28C) and fasting blood glucose levels (FIGS. 28B and 28D) in mice treated with either Peptide X-PEG (FIGS. 28A and 28B) or Peptide Y-PEG (FIGS. 28C and 28D) at varying doses (nmol/kg/week).

Figure 29:
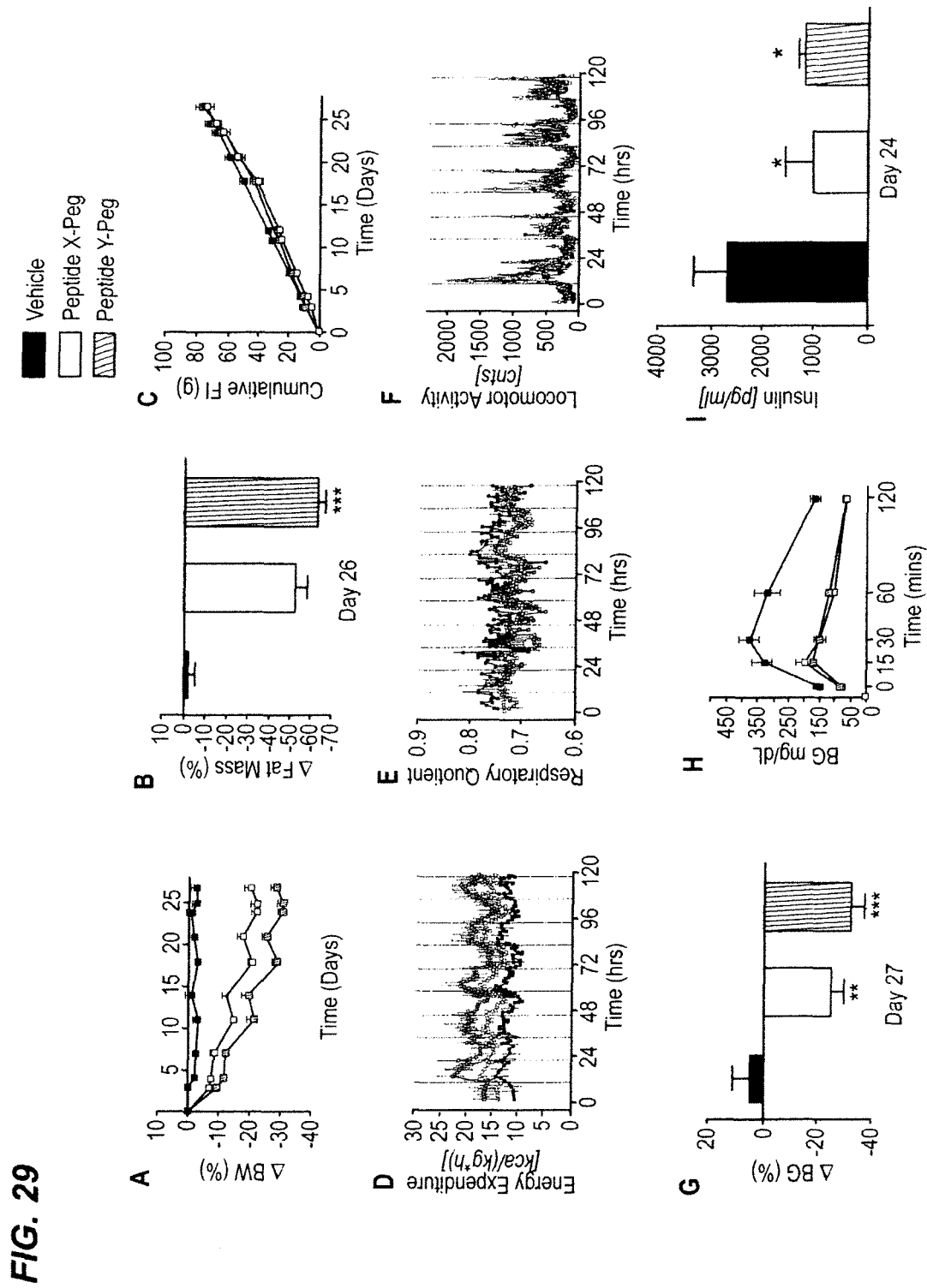

FIG. 29 represents a collection of graphs showing the in vivo effects on A) body weight (BW), B) body fat mass, C) overall food intake, D) energy expenditure, E) respiratory quotient, F) locomotor activity, G) fasting blood glucose, H) glucose tolerance, and I) total plasma insulin levels in diet induced obese mice treated for one month with a vehicle control, Peptide X-PEG, or Peptide Y-PEG.

Figure 30:
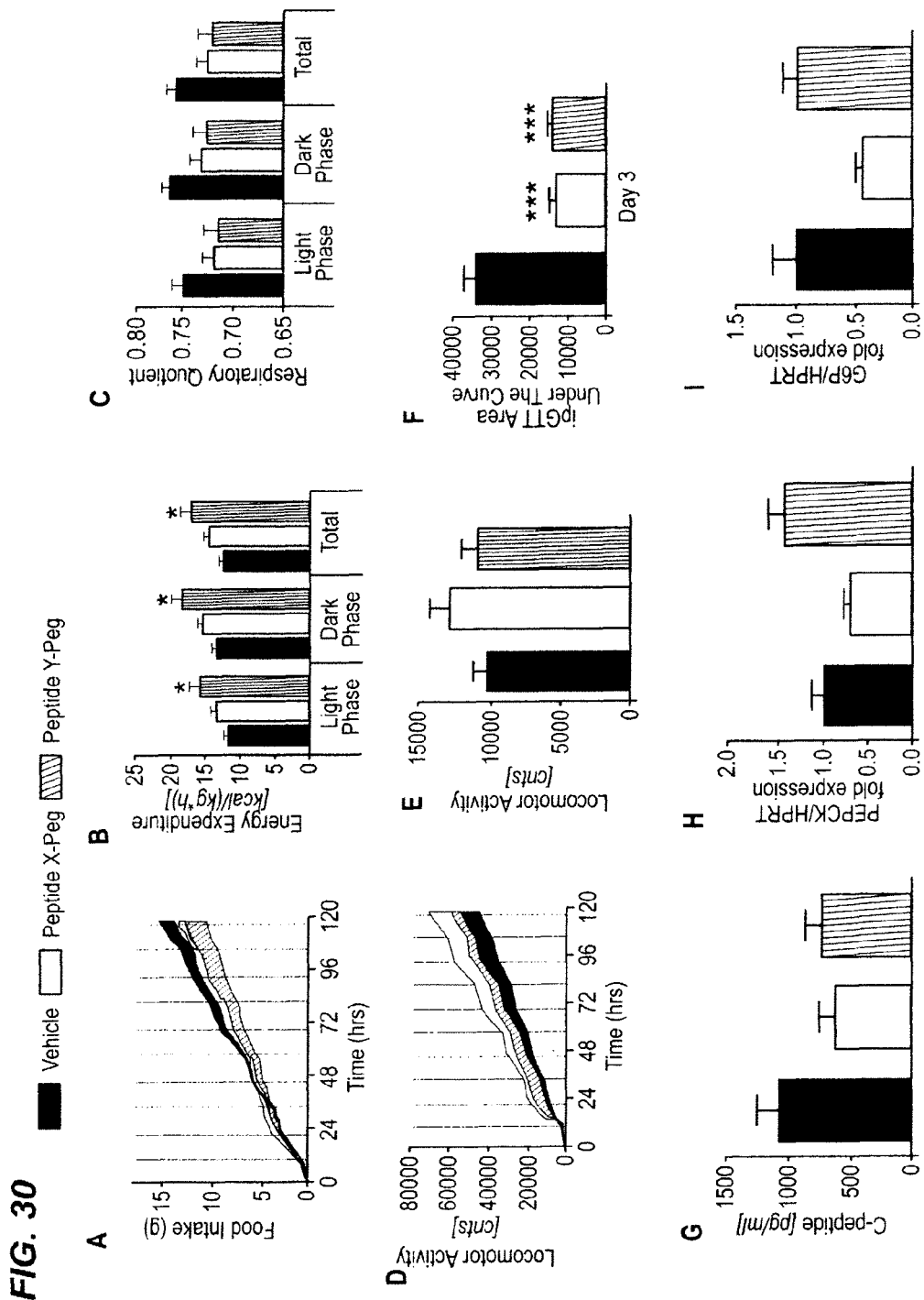

FIG. 30 represents a collection of graphs showing the in vivo Week 3 effects on calorimetric measurements of A) food intake, B) total energy expenditure, C) total respiratory quotient, D) locomotor activity, E) total locomotor activity, F) area under the curve ipGTT, G) plasma C-peptide levels, H) PEPCK/HPRT fold expression, and I) G6P/HPRT fold expression levels in diet induced obese mice treated for one month with a vehicle control, Peptide X-PEG, or Peptide Y-PEG.

Figure 31:
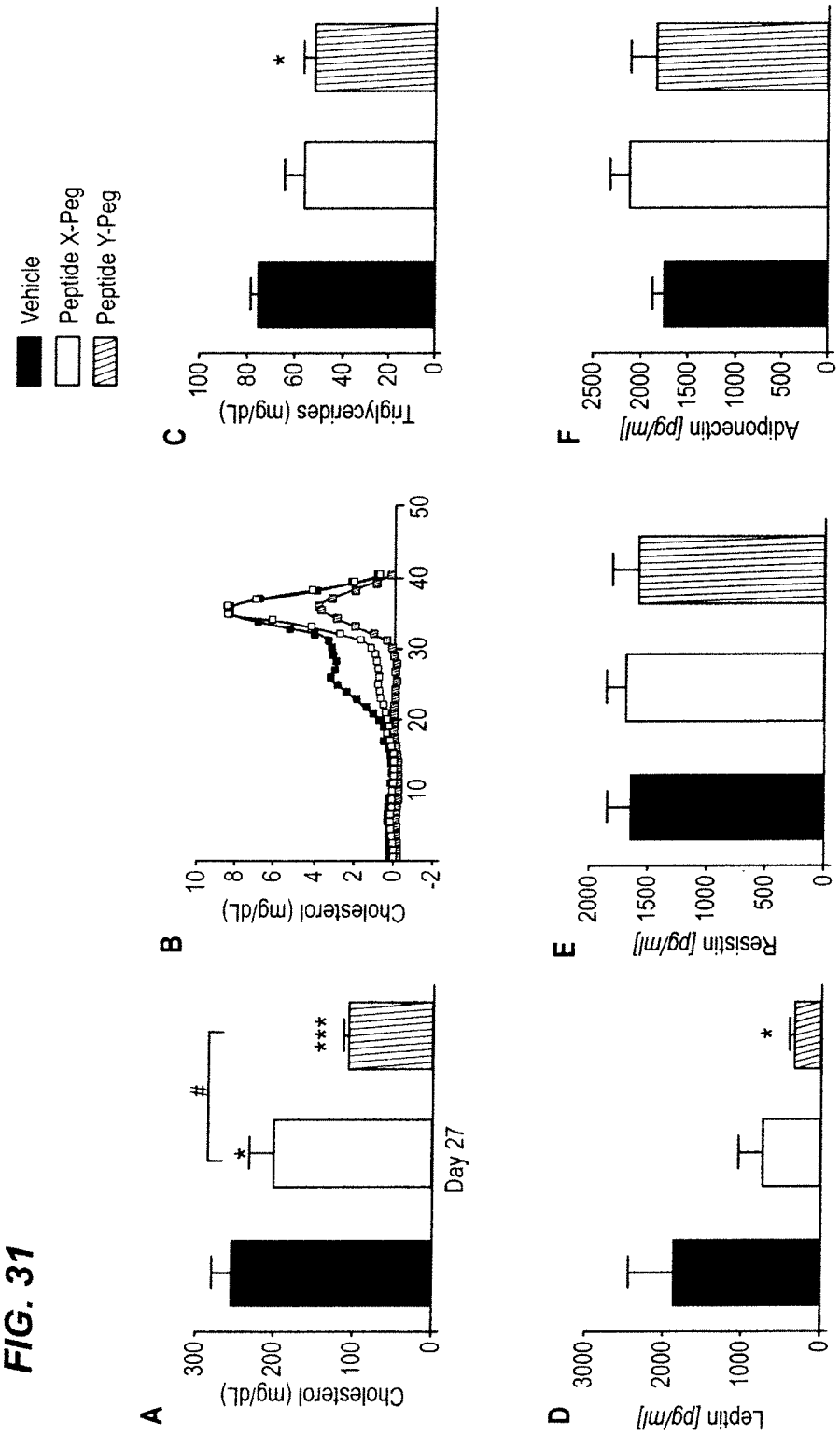

FIG. 31 represents a collection of graphs demonstrating the in vivo effects on plasma A) cholesterol, B) cholesterol FPLC, C) triglycerides, D) leptin., E) resistin, and F) adiponectin in diet induced obese mice treated for one month with a vehicle control, Peptide X-PEG, or Peptide Y-PEG.

Figure 32:
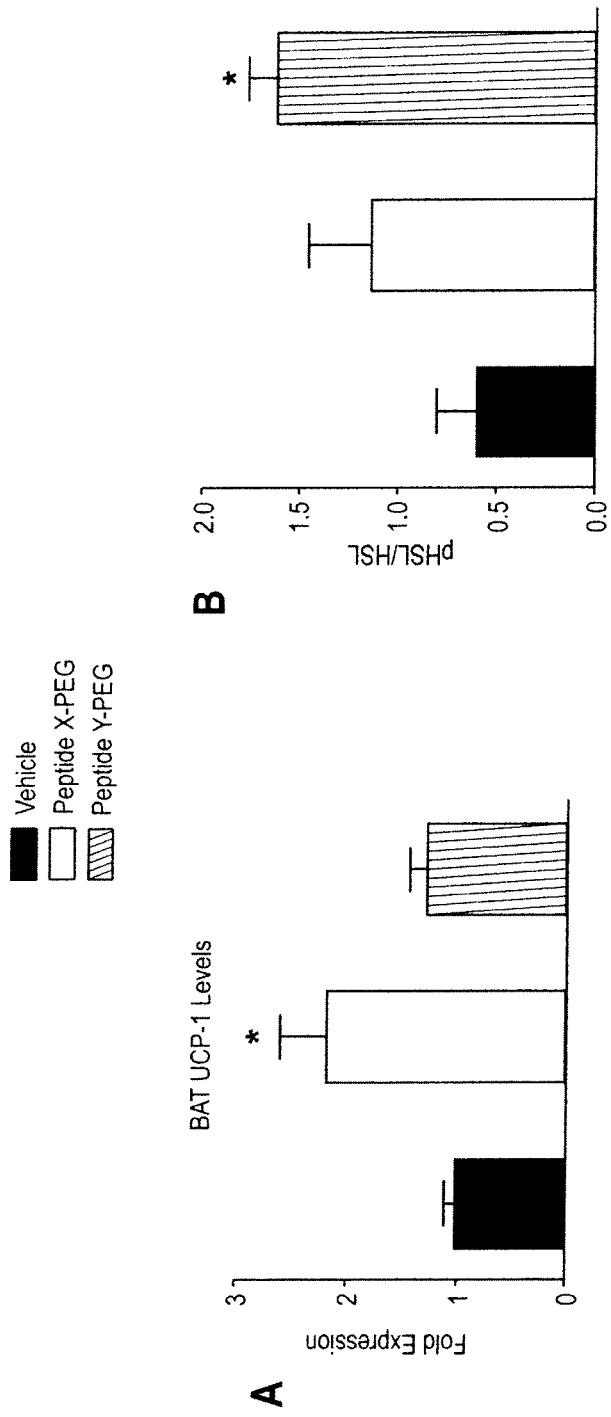

FIG. 32 represents a collection of graphs demonstrating the in vivo effects on A) BAT UCP-1 expression levels and B) white adipose tissue as reflected by phosphorylation of hormone sensitive lipase (pHSL) in mice treated with a vehicle control, Peptide X-PEG, or Peptide Y-PEG.

Figure 33:
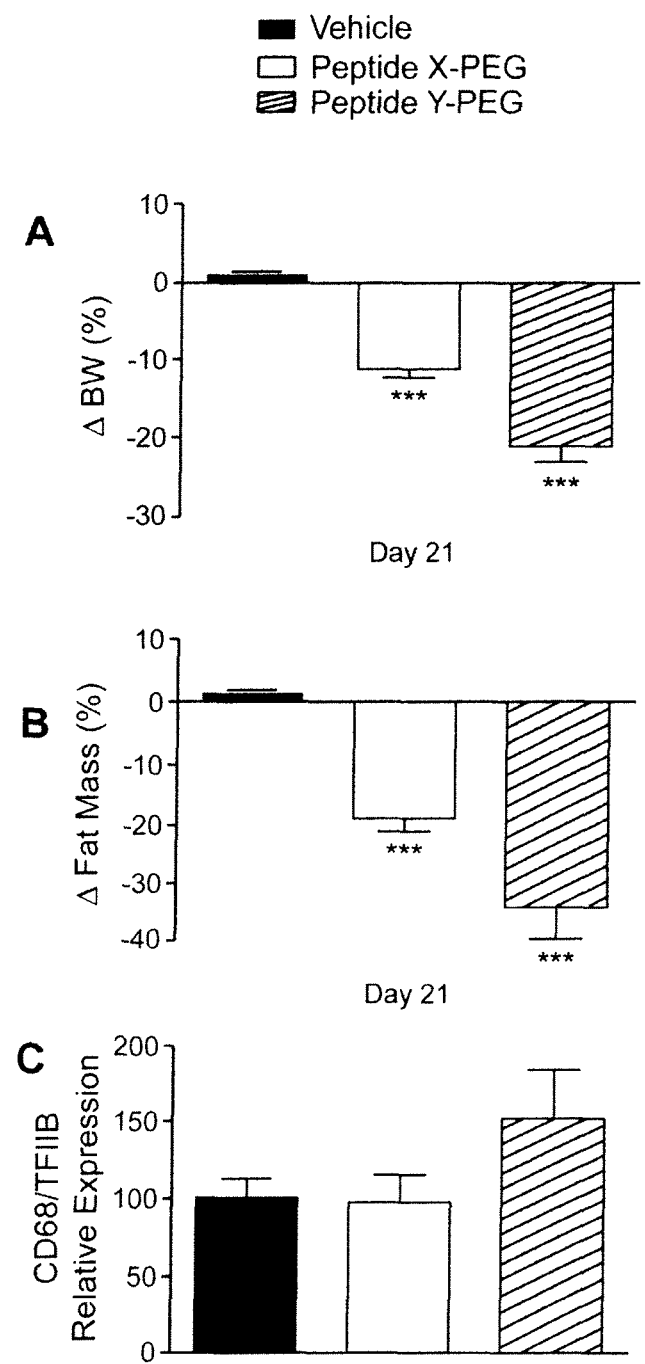

FIG. 33 represents a collection of graphs demonstrating the in vivo effects of a vehicle control, Peptide X-PEG, or Peptide Y-PEG in DIO rats on A) body weight and B) fat mass. FIG. 33C represents a graph of the relative expression of CD68 to TFIIB as quantitatively assessed by real-time RT-PCR in epidiymal adipose tissue isolated from mice treated for two weeks with Peptide Y-PEG, Peptide X-PEG, or vehicle. Data are presented as relative CD68 mRNA expression normalized to TF1IB mRNA expression and expressed as mean±SEM.

Figure 34:
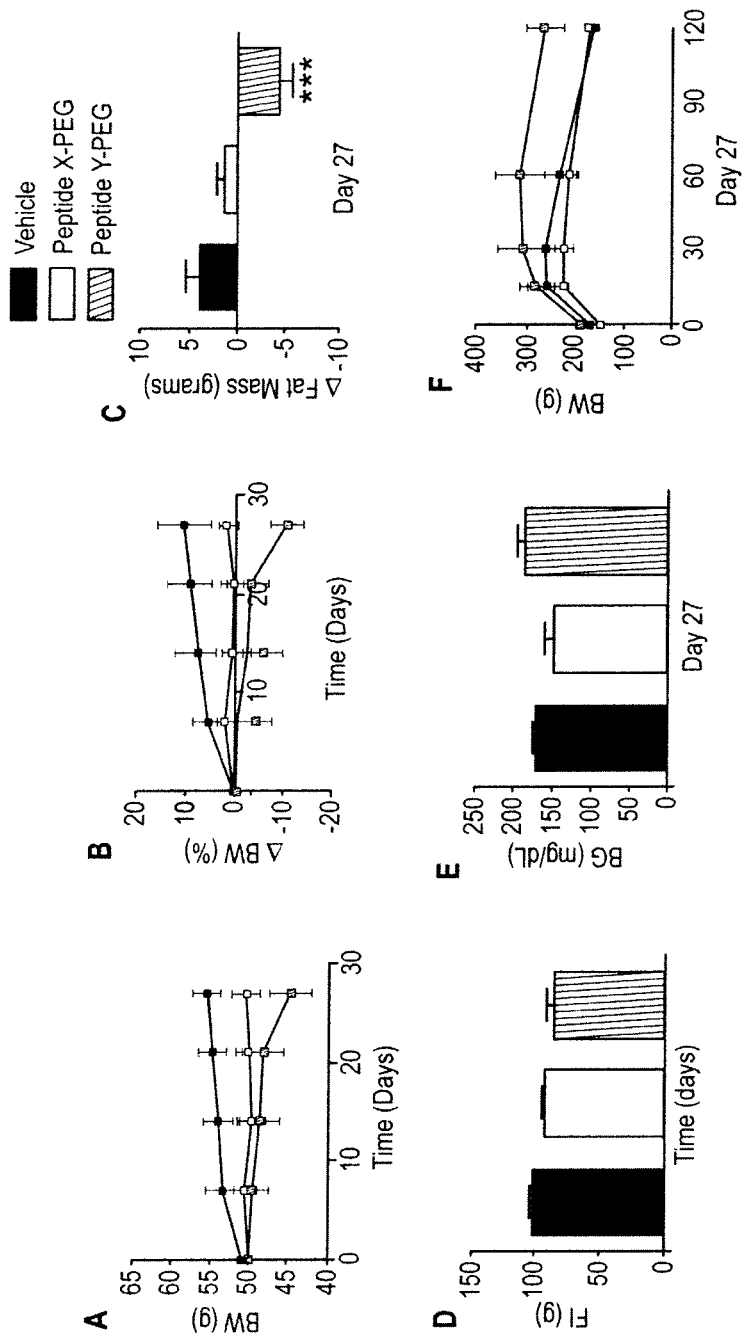
Figure 35:
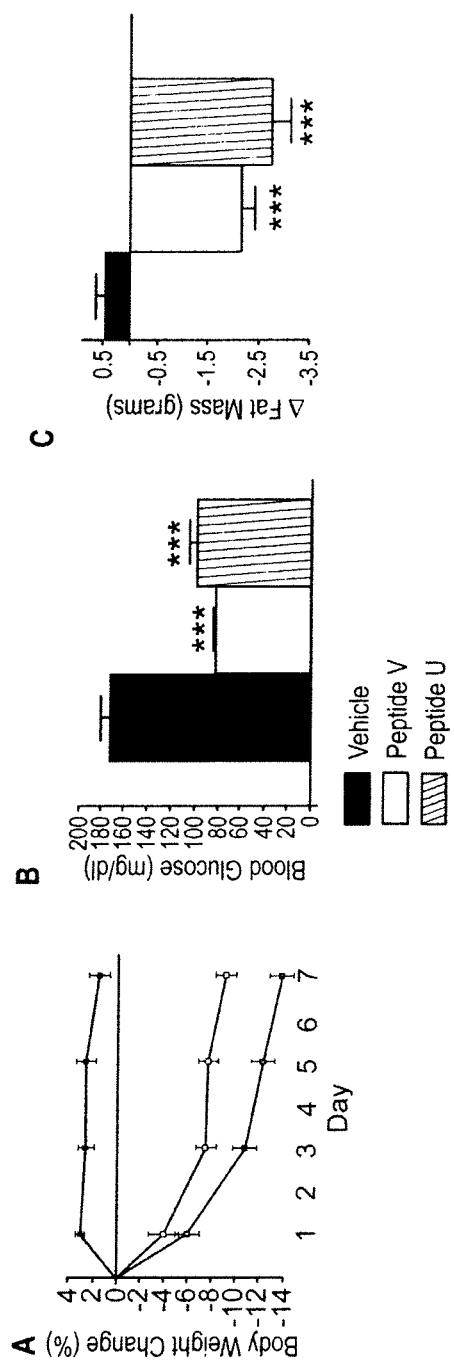

FIGS. 34A to 34F represent a collection of graphs demonstrating the in vivo effects on body weight (BW; 34A and 34B), fat mass (34C), food intake (34D), and blood glucose levels (34E and 34F) in GLP-1-R knock out mice treated with a vehicle control, Peptide X-PEG, or Peptide Y-PEG FIGS. 35A to 35C represent a series of graphs demonstrating the in vivo effects on body weight (35A), blood glucose (35B), and fat mass (35C) in DIO mice treated with vehicle control, Peptide V, or Peptide U.

DETAILED DESCRIPTION

Definitions

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia, as measured, for example, by an increase in blood glucose level. An alternative desired effect for the co-agonist analogs of the present disclosure would include treating hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

A "glucagon peptide" as used herein includes any peptide comprising, either the amino acid sequence of SEQ ID NO: 1, or any analog of the amino acid sequence of SEQ ID NO: 1, including amino acid substitutions, additions, deletions or post translational modifications (e.g., methylation, acylation, ubiquitination, intramolecular covalent bonding such as lactam bridge formation, PEGylation, and the like) of the peptide, wherein the analog stimulates glucagon or GLP-1 receptor activity, e.g., as measured by cAMP production using the assay described in Example 14.

The term "glucagon agonist" refers to a complex comprising a glucagon peptide that stimulates glucagon receptor activity, e.g., as measured by cAMP production using the assay described in Example 14.

As used herein a "glucagon agonist analog" is a glucagon peptide comprising a sequence selected from the group consisting of SEQ ID NO: 10, SEQ ID NO: 11, SEQ ID NO: 12, SEQ ID NO: 13, SEQ ID NO: 14 and SEQ ID NO: 15, or an analog of such a sequence that has been modified to include one or more conservative amino acid substitutions at one or more of positions 2, 5, 7, 10, 11, 12, 13, 14, 17, 18, 19, 20, 21, 24, 27, 28 or 29.

As used herein an amino acid "modification" refers to a substitution, addition or deletion of an amino acid, and includes substitution with or addition of any of the 20 amino acids commonly found in human proteins, as well as atypical or non-naturally occurring amino acids. Throughout the application, all references to a particular amino acid position by number (e.g. position 28) refer to the amino acid at that position in native glucagon (SEQ ID NO:1) or the corresponding amino acid position in any analogs thereof. For example, a reference herein to "position 28" would mean the corresponding position 27 for a glucagon analog in which the first amino acid of SEQ ID NO: 1 has been deleted. Similarly, a reference herein to "position 28" would mean the corresponding position 29 for a glucagon analog in which one amino acid has been added before the N-terminus of SEQ ID NO: 1. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from other amino acids.

As used herein a "glucagon co-agonist" is a glucagon peptide that exhibits activity at the glucagon receptor of at least about 10% to about 500% or more relative to native glucagon and also exhibits activity at the GLP-1 receptor of about at least 10% to about 200% or more relative to native GLP-1.

As used herein a "glucagon/GLP-1 co-agonist molecule" is a molecule that exhibits activity at the glucagon receptor of at least about 10% relative to native glucagon and also exhibits activity at the GLP-1 receptor of at least about 10% relative to native GLP-1.

As used herein the term "native glucagon" refers to a peptide consisting of the sequence of SEQ ID NO: 1, and the term "native GLP-1" is a generic term that designates GLP-1(7-36)amide (consisting of the sequence of SEQ ID NO: 52), GLP-1(7-37)acid (consisting of the sequence of SEQ ID NO: 50) or a mixture of those two compounds. As used herein, a general reference to "glucagon" or "GLP-1" in the absence of any further designation is intended to mean native glucagon or native GLP-1, respectively.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
   Ala, Ser, Thr, Pro, Gly;
II. Polar, negatively charged residues and their amides and esters:
   Asp, Asn, Glu, Gln, cysteic acid and homocysteic acid;
III. Polar, positively charged residues:
   His, Arg, Lys; Ornithine (Orn)
IV. Large, aliphatic, nonpolar residues: Met, Leu, Ile, Val, Cys, Norleucine (Nle), homocysteine
V. Large, aromatic residues:
   Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol chain" or "PEG chain" is used in combination with a numeric suffix to indicate the approximate average molecular weight thereof. For example, PEG-5,000 refers to polyethylene glycol chain having a total molecular weight average of about 5,000.

As used herein the term "pegylated" and like terms refers to a compound that has been modified from its native state by linking a polyethylene glycol chain to the compound. A "pegylated glucagon peptide" is a glucagon peptide that has a PEG chain covalently bound to the glucagon peptide.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

As used herein the term "charged amino acid" refers to an amino acid that comprises a side chain that is negatively charged (i.e., de-protonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acidscommonly found in human proteins, as well as atypical or non-naturally occurring amino acids.

As used herein the term "acidic amino acid" refers to an amino acid that comprises a second acidic moiety, including for example, a carboxylic acid or sulfonic acid group.

The term "alkyl" refers to a linear or branched hydrocarbon containing the indicated number of carbon atoms. Exemplary alkyls include methyl, ethyl, and linear propyl groups.

The term "heteroalkyl" refers to a linear or branched hydrocarbon containing the indicated number of carbon atoms and at least one heteroatom in the backbone of the structure. Suitable heteroatoms for purposes herein include but are not limited to N, S, and O.

Embodiments

The invention provides glucagon peptides with increased or decreased activity at the glucagon receptor, or the GLP-1 receptor, or at both receptors. The invention also provides glucagon peptides with altered selectivity for the glucagon receptor versus the GLP-1 receptor.

Increased activity at the glucagon receptor is provided by an amino acid modification at position 16 of native glucagon (SEQ ID NO: 1) as described herein.

Maintained or increased activity at the glucagon receptor is also provided by an amino acid modification at position 3 of native glucagon with a glutamine analog (e.g. (Dab(Ac)).

Reduced activity at the glucagon receptor is provided, e.g., by substitution of the amino acid at position 3 with an acidic, basic, or hydrophobic amino acid as described herein.

Increased activity at the GLP-1 receptor is provided by replacing the carboxylic acid of the C-terminal amino acid with a charge-neutral group, such as an amide or ester.

Increased activity at the GLP-1 receptor is provided by modifications that stabilize the alpha helix in the C-terminal portion of glucagon (e.g. around residues 12-29). In some embodiments, such modifications permit formation of an intramolecular bridge between the side chains of two amino acids that are separated by three intervening amino acids, for example, positions 12 and 16, or 16 and 20, or and 24, as described herein. In other embodiments, such modifications include insertion or substitution modifications that introduce one or more α,α-disubstituted amino acids, e.g. AIB at one or more of positions 16, 20, 21 or 24.

Increased activity at the GLP-1 and glucagon receptors for peptides lacking an intramolecular bridge, e.g., a covalent intramolecular brige, is provided by covalently attaching an acyl or alkyl group to to the side chain of the amino acid at position 10 of the peptide, wherein the acyl or alkyl group is non-native to the amino acid at position 10. Further increased activity at the GLP-1 and glucagon receptors for such peptides lacking an intramolecular bridge, e.g., a covalent intramolecular bridge, may be achieved by incorporating a spacer between the acyl or alkyl group and the side chain of the amino acid at position 10. Suitable spacers are described herein and include, but not limited to spacers that are 3 to 10 atoms in length.

Increased activity at the GLP-1 receptor is provided by an amino acid modification at position 20 as described herein.

Increased activity at the GLP-1 receptor is provided in glucagon analogs comprising the C-terminal extension of SEQ ID NO: 26. GLP-1 activity in such analogs comprising SEQ ID NO: 26 can be further increased by modifying the amino acid at position 18, 28 or 29, or at position 18 and 29, as described herein.

Restoration of glucagon activity which has been reduced by amino acid modifications at positions 1 and 2 is provided by a covalent bond between the side chains of two amino acids that are separated by three intervening amino acids, for example, positions 12 and 16, or 16 and 20, or 20 and 24, as described herein.

A further modest increase in GLP-1 potency is provided by modifying the amino acid at position 10 to be Trp.

Any of the modifications described above which increase or decrease glucagon receptor activity and which increase GLP-1 receptor activity can be applied individually or in combination. Any of the modifications described above can also be combined with other modifications that confer other desirable properties, such as increased solubility and/or stability and/or duration of action. Alternatively, any of the modifications described above can be combined with other modifications that do not substantially affect solubility or stability or activity. Exemplary modifications include but are not limited to:

(A) Improving solubility, for example, by introducing one, two, three or more charged amino acid(s) to the C-terminal portion of native glucagon, preferably at a position C-terminal to position 27. Such a charged amino acid can be introduced by substituting a native amino acid with a charged amino acid, e.g. at positions 28 or 29, or alternatively by adding a charged amino acid, e.g. after position 27, 28 or 29. In exemplary embodiments, one, two, three or all of the charged amino acids are negatively charged. In other embodiments, one, two, three or all of the charged amino acids are positively charged. Such modifications increase solubility, e.g. provide at least 2-fold, 5-fold, 10-fold, 15-fold, 25-fold, 30-fold or greater solubility relative to native glucagon at a given pH between about 5.5 and 8, e.g., pH 7, when measured after 24 hours at 25.C.

(B) Increasing solubility and duration of action or half-life in circulation by addition of a hydrophilic moiety such as a polyethylene glycol chain, as described herein, e.g. at position 16, 17, 20, 21, 24 or 29, or at the C-terminal amino acid of the peptide.

(C) Increasing, by modification of the aspartic acid at position 15, for example, by deletion or substitution with glutamic acid, homoglutamic acid, cysteic acid or homocysteic acid. Such modifications can reduce degradation or cleavage at a pH within the range of 5.5 to 8, for example, retaining at least 75%, 80%, 90%, 95%, 96%, 97%, 98% or 99% of the original peptide after 24 hours at 25° C.

(D) Increasing stability by modification of the methionine at position 27, for example, by substitution with leucine or norleucine. Such modifications can reduce oxidative degradation. Stability can also be increased by modification of the Gln at position 20 or 24, e.g. by substitution with Ala, Ser, Thr, or AIB. Such modifications can reduce degradation that occurs through deamidation of Gln. Stability can be increased by modification of Asp at position 21, e.g. by substitution with Glu. Such modifications can reduce degradation that occurs through dehydration of Asp to form a cyclic succinimide intermediate followed by isomerization to iso-aspartate.

(E) Increasing resistance to dipeptidyl peptidase IV (DPP IV) cleavage by modification of the amino acid at position 1 or 2 as described herein.

(F) Conservative or non-conservative substitutions, additions or deletions that do not affect activity, for example, conservative substitutions at one or more of positions 2, 5, 7, 10, 11, 12, 13, 14, 16, 17, 18, 19, 20, 21, 24, 27, 28 or 29; deletions at one or more of positions 27, 28 or 29; or a deletion of amino acid 29 optionally combined with a C-terminal amide or ester in place of the C-terminal carboxylic acid group;

(G) Adding C-terminal extensions as described herein;

(H) Increasing half-life in circulation and/or extending the duration of action and/or delaying the onset of action, for example, through acylation or alkylation of the glucagon peptide, as described herein;

(I) Homodimerization or heterodimerization as described herein.

In exemplary embodiments, the glucagon peptide may comprise a total of 1, up to 2, up to 3, up to 4, up to 5, up to 6, up to 7, up to 8, up to 9, or up to 10 amino acid modifications relative to the native glucagon sequence.

Other modifications include substitution of His at position 1 with a large, aromatic amino acid (e.g., Tyr, Phe, Trp or amino-Phe);

Ser at position 2 with Ala;
substitution of Tyr at position 10 with Val or Phe;
substitution of Lys at position 12 with Arg;
substitution of Asp at position 15 with Glu;
substitution of Ser at position 16 with Thr or AIB.

One embodiment disclosed herein is directed to a glucagon agonist that has been modified relative to the wild type peptide of His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1) to enhance the peptide's potency at the glucagon receptor. Surprisingly, applicants have discovered that the normally occurring serine at position 16 of native glucagon (SEQ ID NO: 1) can be substituted with select acidic amino acids to enhance the potency of glucagon, in terms of its ability to stimulate cAMP synthesis in a validated in vitro model assay (see Example 14). More particularly, this substitution enhances the potency of the analog at least 2-fold, 4-fold, 5-fold, and up to 10-fold greater at the glucagon receptor. This substitution also enhances the analog's activity at the GLP-1 receptor at least 5-fold, 10-fold, or 15-fold relative to native glucagon, but selectivity is maintained for the glucagon receptor over the GLP-1 receptor.

In accordance with one embodiment the serine residue at position 16 of native glucagon is substituted with an amino acid selected from the group consisting of glutamic acid, glutamine, homoglutamic acid, homocysteic acid, threonine or glycine. In accordance with one embodiment the serine residue at position 16 of native glucagon is substituted with an amino acid selected from the group consisting of glutamic acid, glutamine, homoglutamic acid and homocysteic acid, and in one embodiment the serine residue is substituted with glutamic acid. In one embodiment the glucagon peptide having enhanced specificity for the glucagon receptor comprises the peptide of SEQ ID NO: 8, SEQ ID NO: 9, SEQ ID NO: 10 or a glucagon agonist analog thereof, wherein the carboxy terminal amino acid retains its native carboxylic acid group. In accordance with one embodiment a glucagon agonist comprising the sequence of NH$_2$-His-Ser-Gln-Gly-Thr-Phe-Thr-Ser-Asp-Tyr-Ser-Lys-Tyr-Leu-Asp-Glu-Arg-Arg-Ala-Gln-Asp-Phe-Val-Gln-Trp-Leu-Met-Asn-Thr-COOH (SEQ ID NO: 10) is provided, wherein the peptide exhibits approximately fivefold enhanced potency at the glucagon receptor, relative to native glucagon as measured by the in vitro cAMP assay of Example 14.

Hydrophilic Moieties

The glucagon peptides of the present invention can be further modified to improve the peptide's solubility and stability in aqueous solutions at physiological pH, while retaining the high biological activity relative to native glucagon. Hydrophilic moieties such as PEG groups can be attached to the glucagon peptides under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

In a specific aspect of the invention, an amino/acid residue on the glucagon peptide having a thiol is modified with a hydrophilic moiety such as PEG. In some embodiments, the thiol is modified with maleimide-activated PEG in a Michael addition reaction to result in a PEGylated peptide comprising the thioether linkage shown below:

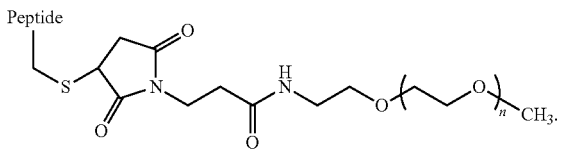

In some embodiments, the thiol is modified with a haloacetyl-activated PEG in a nucleophilic substitution reaction to result in a PEGylated peptide comprising the thioether linkage shown below:

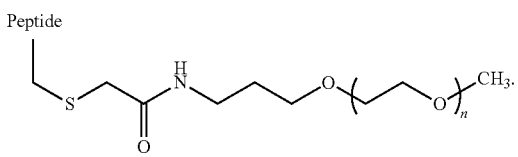

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-($C_1$-$C_{10}$)alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly(.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per peptide.

In accordance with one embodiment, introduction of hydrophilic groups at positions 17, 21, and 24 of the peptide of SEQ ID NO: 9 or SEQ ID NO: 10 are anticipated to improve the solubility and stability of the high potency glucagon analog in solutions having a physiological pH. Introduction of such groups also increases duration of action, e.g. as measured by a prolonged half-life in circulation. Suitable hydrophilic moieties include any water soluble polymers known in the art, including PEG, homo- or co-polymers of PEG, a monomethyl-substituted polymer of PEG (mPEG), or polyoxyethylene glycerol (POG). In accordance with one embodiment the hydrophilic group comprises a polyethylene (PEG) chain. More particularly, in one embodiment the glucagon peptide comprises the sequence of SEQ ID NO: 6 or SEQ ID NO: 7 wherein a PEG chain is covalently linked to the side chains of amino acids present at positions 21 and 24 of the glucagon peptide and the carboxy terminal amino acid of the peptide has the carboxylic acid group.

Conjugates

The present disclosure also encompasses other conjugates in which glucagon peptides of the invention are linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The peptide can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly are reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Exemplary conjugate moieties that can be linked to any of the glucagon peptides described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide of the present invention and a plasma protein, wherein the plasma protein is selected form the group consisting of albumin, transferin, fibrinogen and globulins. In one embodiment the plasma protein moiety of the conjugate is albumin or transferin.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in some embodiments, the glucagon peptides are conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A; E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Fusion Protein and Terminal Extension

The present disclosure also encompasses glucagon fusion peptides or proteins wherein a second peptide or polypeptide has been fused to a terminus, e.g., the carboxy terminus of the glucagon peptide. More particularly, the fusion glucagon peptide may comprise a glucagon agonist of SEQ ID NO: 55, SEQ ID NO: 9 or SEQ ID NO: 10 further comprising an amino acid sequence of SEQ ID NO: 26 (GPSSGAPPPS), SEQ ID NO: 27 (KRNRNNIA) or SEQ ID NO: 28 (KRNR) linked to amino acid 29 of the glucagon peptide. In one embodiment the amino acid sequence of SEQ ID NO: 26 (GPSSGAPPPS), SEQ ID NO: 27 (KRNRNNIA) or SEQ ID NO: 28 (KRNR) is bound to amino acid 29 of the glucagon peptide through a peptide bond. Applicants have discovered that in glucagon fusion peptides comprising the C-terminal extension peptide of Exendin-4 (e.g., SEQ ID NO: 26 or SEQ ID NO: 29), substitution of the native threonine residue at position 29 with glycine dramatically increases GLP-1 receptor activity. This amino acid substitution can be used in conjunction with other modifications disclosed herein to enhance the affinity of the glucagon analogs for the GLP-1 receptor. For example, the T29G substitution can be combined with the S16E and N20K amino acid substitutions, optionally with a lactam bridge between amino acids 16 and 20, and optionally with addition of a PEG chain as described herein. In one embodiment a glucagon/GLP-1 receptor co-agonist is provided, comprising the sequence of SEQ ID NO: 64. In one embodiment the glucagon peptide portion of the glucagon fusion peptide is selected from the group consisting of SEQ ID NO: 55, SEQ ID NO: 2, SEQ ID NO: 3, SEQ ID NO: 4, and SEQ ID NO: 5 wherein a PEG chain, when present at positions 17, 21, 24, or the C-terminal amino acid, or at both 21 and 24, is selected from the range of 500 to 40,000 Daltons. More particularly, in one embodiment the glucagon peptide segment is selected from the group consisting of SEQ ID NO: 7, SEQ ID NO: 8, and SEQ ID NO: 63, wherein the PEG chain is selected from the range of 500 to 5,000. In one embodiment the glucagon peptide is a fusion peptide comprising the sequence of SEQ ID NO: 55 and SEQ ID NO: 65 wherein the peptide of SEQ ID NO: 65 is linked to the carboxy terminus of SEQ ID NO: 55.

Charge Neutral C-terminus

In accordance with one embodiment, an additional chemical modification of the glucagon peptide of SEQ ID NO: 10 bestows increased GLP-1 receptor potency to a point where the relative activity at the glucagon and GLP-1 receptors is virtually equivalent. Accordingly, in one embodiment a glucagon/GLP-1 receptor co-agonist is provided wherein the terminal amino acid of the glucagon peptides of the present invention have an amide group in place of the carboxylic acid group that is present on the native amino acid. The relative activity of the glucagon analog at the respective glucagon and GLP-1 receptors can be adjusted by further modifications to the glucagon peptide to produce analogs demonstrating about 40% to about 500% or more of the activity of native glucagon at the glucagon receptor and about 20% to about 200% or more of the activity of native GLP-1 at the GLP-1 receptor, e.g. 50-fold, 100-fold or more increase relative to the normal activity of glucagon at the GLP-1 receptor. In some embodiments, the glucagon peptides described herein exhibit up to about 100%, 1000%, 10,000%, 100,000%, or 1,000,000% of the activity of native glucagon at the glucagon receptor. In some embodiments, the glucagon peptides described herein exhibit up to about 100%, 1000%, 10,000%, 100,000%, or 1,000,000% of the activity of native GLP-1 at the GLP-1 receptor.

Stabilization of the Alpha Helix/Intramolecular Bridges

In a further embodiment glucagon analogs are provided that exhibit enhanced GLP-1 receptor agonist activity wherein an intramolecular bridge is formed between two amino acid side chains to stabilize the three dimensional structure of the carboxy terminus of the peptide. The two amino acid side chains can be linked to one another through non-covalent bonds, e.g., hydrogen-bonding, ionic interactions, such as the formation of salt bridges, or by covalent bonds. When the two amino acid side chains are linked to one another through one or more covalent bonds, the peptide may be considered herein as comprising a covlent intramolecular bridge. When the two amino acid side chains are linked to one another through non-covalent bonds, e.g., hydrogen bonds, ionic interactions, the peptide may be considered herein as comprising a non-covalent intramolecular bridge.

In some embodiments, the intramolecular bridge is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25). More particularly, the side chains of the amino acid pairs 12 and 16, 16 and 20, 20 and 24 or 24 and 28 (amino acid pairs in which i=12, 16, 20, or 24) are linked to one another and thus stabilize the glucagon alpha helix. Alternatively, i can be 17.

In some specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26). In some specific embodiments, j is 17.

In some specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22). In some specific embodiments, k is 12, 13, or 17. In an exemplary embodiment, k is 17.

Examples of amino acid pairings that are capable of covalently bonding to form a six-atom linking bridge include Orn and Asp, Glu and an amino acid of Formula I, wherein n is 2, and homoglutamic acid and an amino acid of Formula I, wherein n is 1, wherein Formula I is:

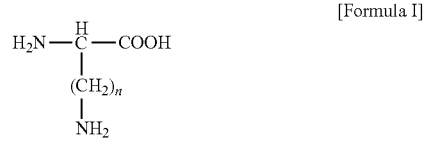

[Formula I]

wherein n = 1 to 4

Examples of amino acid pairing that are capable of covalently bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect. Even without covalent linkage, the amino acid pairings described above or similar pairings that one of ordinary skill in the art can envision may also provide added stability to the alpha-helix through non-covalent bonds, for example, through formation of salt bridges or hydrogen-bonding interactions.

Further exemplary embodiments include the following pairings, optionally with a lactam bridge: Glu at position 12 with Lys at position 16; native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28.

In accordance with one embodiment a glucagon analog is provided that exhibits glucagon/GLP-1 receptor co-agonist activity wherein the analog comprises an amino acid sequence selected from the group consisting of SEQ ID NO: 11, 47, 48 and 49. In one embodiment the side chains are covalently bound to one another, and in one embodiment the two amino acids are bound to one another to form a lactam ring. The size of the lactam ring can vary depending on the length of the amino acid side chains, and in one embodiment the lactam is formed by linking the side chains of a lysine amino acid to a glutamic acid side chain.

The order of the amide bond in the lactam ring can be reversed (e.g., a lactam ring can be formed between the side chains of a Lys12 and a Glu16 or alternatively between a Glu 12 and a Lys16). In accordance with one embodiment a glucagon analog of SEQ ID NO: 45 is provided wherein at least one lactam ring is formed between the side chains of an amino acid pair selected from the group consisting of amino acid pairs 12 and 16, 16 and 20, 20 and 24 or 24 and 28. In one embodiment a glucagon/GLP-1 receptor co-agonist is provided wherein the co-agonist comprises a glucagon peptide analog of SEQ ID NO: 20 wherein the peptide comprises an intramolecular lactam bridge formed between amino acid positions 12 and 16 or between amino acid positions 16 and 20. In one embodiment a glucagon/GLP-1 receptor co-agonist is provided comprising the sequence of SEQ ID NO: 20, wherein an intramolecular lactam bridge is formed between amino acid positions 12 and 16, between amino acid positions 16 and 20, or between amino acid positions 20 and 24 and the amino acid at position 29 is glycine, wherein the sequence of SEQ ID NO: 29 is linked to the C-terminal amino acid of SEQ ID NO: 20. In a further embodiment the amino acid at position 28 is aspartic acid.

Intramolecular bridges other than a lactam bridge can be used to stabilize the alpha helix of the glucagon analog peptides. In one embodiment, the intramolecular bridge is a hydrophobic bridge. In this instance, the intramolecular bridge optionally is between the side chains of two amino acids that are part of the hydrophobic face of the alpha helix of the glucagon analog peptide. For example, one of the amino acids joined by the hydrophobic bridge can be the amino acid at position 10, 14, and 18.

In one specific aspect, olefin metathesis is used to cross-link one or two turns of the alpha helix of the glucagon peptide using an all-hydrocarbon cross-linking system. The glucagon peptide in this instance can comprise α-methylated amino acids bearing olefinic side chains of varying length and configured with either R or S stereochemistry at the i and i+4 or i+7 positions. For example, the olefinic side can can comprise $(CH_2)n$, wherein n is any integer between 1 to 6. In one embodiment, n is 3 for a cross-link length of 8 atoms. Suitable methods of forming such intramolecular bridges are described in the art. See, for example, Schafmeister et al., *J. Am. Chem. Soc.* 122: 5891-5892 (2000) and Walensky et al., *Science* 305: 1466-1470 (2004). Alternatively, the glucagon peptide can comprise O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In another specific aspect, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α,ω-diaminoalkane tethers, e.g., 1,4-diaminopropane and 1,5-diaminopentane) between two Glu residues at positions i and i+7 are used to stabilize the alpha helix of the glucagon peptide. Such tethers lead to the formation of a bridge 9-atoms or more in length, depending on the length of the diaminoalkane tether. Suitable methods of producing peptides cross-linked with such tethers are described in the art. See, for example, Phelan et al., *J. Am. Chem. Soc.* 119: 455-460 (1997).

In yet another embodiment of the invention, a disulfide bridge is used to cross-link one or two turns of the alpha helix of the glucagon peptide. Alternatively, a modified disulfide bridge in which one or both sulfur atoms are replaced by a methylene group resulting in an isosteric macrocyclization is used to stabilize the alpha helix of the glucagon peptide. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet another embodiment, the alpha helix of the glucagon peptide is stabilized via the binding of metal atom by two His residues or a His and Cys pair positioned at i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the glucagon peptide can alternatively be stabilized through other means of peptide cyclizing, which means are reviewed in Davies, *J. Peptide. Sci.* 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g. suberic acid (octanedioic acid), etc. can introduce a link between two functional groups of an amino acid side chain, such as a free amino, hydroxyl, thiol group, and combinations thereof.

In accordance with one embodiment, the alpha helix of the glucagon peptide is stabilized through the incorporation of hydrophobic amino acids at positions i and i+4. For instance, i can be Tyr and i+4 can be either Val or Leu; i can be Phe and i+4 can be Cys or Met; I can be Cys and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position.

In accordance with yet another embodiment of the invention, the glucagon peptide with enhanced GLP-1 activity comprises (a) one or more substitutions within amino acid positions 12-29 with an α,α-disubstituted amino acid and optionally, (b) a C-terminal amide. In some aspects, it is to be appreciated that such glucagon peptides specifically lack an intramolecular bridge, e.g., a covalent intramolecular bridge, that stabilizes the alpha-helix in the C-terminal portion of glucagon (around positions 12-29). In some embodiments, one, two, three, four or more of positions 16, 17, 18, 19, 20, 21, 24 or 29 of glucagon is substituted with an α,α-disubstituted amino acid, e.g., amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). For example, substitution of position 16 with AIB enhances GLP-1 activity, in the absence of an intramolecular bridge, e.g., a non-covalent intramolecular bridge (e.g., a salt bridge) or a covalent intramolecular bridge (e.g., a lactam). In some embodiments, one, two, three or more of positions 16, 20, 21 or 24 are substituted with AIB. Such a glucagon peptide may further comprise one or more of the other modifications described herein, including, but not limited to, acylation, alkylation, pegylation, deletion of 1-2 amino acids at the C-terminus, addition of and/or substitution with charged amino acids at the C-terminus, replacement of the C-terminal carboxylate with an amide, addition of a C-terminal extension, and conservative and/or non-conservative amino acid substitutions, such as substitution of Met at position 27 with Leu or Nle, substitution of Asp at position 15 with Glu (or like amino acid), substitution at position 1 and/or 2 with amino acids which achieve DPP-IV protease resistance, substitution of Ser at position 2 with Ala, substitution of Tyr at position 10 with Val or Phe, substitution of Lys at position 12 with Arg, substitution of Ser at position 16 with Thr or AIB, substitution of Gln at position 20 and/or 24 with Asp, Glu, or AIB, substitution of Ser at position 16 with Glu or Thr, Arg at position 18 with Ala, Gln at position 20 with Lys, Asp at position 21 with Glu, and Gln at position 24 with Asn or Cys. In some embodiments, the foregoing glucagon peptide comprises a Gln or Gly at position 29 or addition of a C-terminal extension, e.g., GGPSSGAPPPS (SEQ ID NO: 26) C-terminal to the amino acid at position 28. In a specific aspect, the glucagon peptide comprises one or more of an amide group in place of the C-terminal carboxylate, an acyl group, e.g., a C16 fatty acid, and a hydrophilic moiety, e.g., a polyethylene glycol (PEG).

Also, in another specific aspect, the glucagon peptide comprises the amino acid sequence of any of SEQ ID NOs: 1-25, 30-64, and 66-555 comprising no more than ten modifications relative to SEQ ID NO: 1 and comprising one or more amino acid substitutions with AIB at positions 16, 20, 21, and/or 24, wherein the peptide lacks an intramolecular bridge, e.g., a covalent intramolecular bridge, between the side chains of two amino acids of the peptide. Accordingly, in a more specific aspect, the glucagon peptide comprises the amino acid sequence of any of SEQ ID NOs: 556-561.

In accordance with some embodiments, the glucagon peptide lacking an intramolecular bridge comprises one or more substitutions within amino acid positions 12-29 with an α,α-disubstituted amino acid and an acyl or alkyl group covalently attached to the side chain of the amino acid at position 10 of the glucagon peptide. In specific embodiments, the acyl or alkyl group is not naturally occurring on an amino acid. In certain aspects, the acyl or alkyl group is non-native to the amion acid at position 10. In exemplary embodiments, the glucagon peptide lacking an intramolecular bridge comprises the amino acid sequence of any of SEQ ID NOs: 556-561 and an acyl or alkyl group covalently attached to the side chain of the amino acid at position 10 of the glucagon peptide. Such acylated or alkylated glucagon peptides lacking an intramolecular bridge exhibit enhanced activity at the GLP-1 and glucagon receptors as compared to the non-acylated counterpart peptides. Further enhancement in activity at the GLP-1 and glucagon receptors can be achieved by the acylated glucagon peptides lacking an intramolecular bridge by incorporating a spacer between the acyl or alkyl group and the side chain of the amino acid at position 10 of the peptide. Acylation and alkylation, with or without incorporating spacers, are further described herein.

Modification at Position 1

In accordance with one embodiment of the invention, the glucagon peptide with enhanced GLP-1 activity comprises (a) an amino acid substitution of His at position 1 with a large, aromatic amino acid and (b) an intramolecular bridge that stabilizes that alpha-helix in the C-terminal portion of the molecule (e.g. around positions 12-29). In a specific embodiment, the amino acid at position 1 is Tyr, Phe, Trp, amino-Phe, nitro-Phe, chloro-Phe, sulfo-Phe, 4-pyridyl-Ala, methyl-Tyr, or 3-amino Tyr. In a specific aspect, the intramolecular bridge is between the side chains of two amino acids that are separated by three intervening amino acids, i.e., between the side chains of amino acids i and i+4. In some embodiments, the intramolecular bridge is a lactam bridge. In a more specific embodiment of the invention, the glucagon peptide comprises a large, aromatic amino acid at position 1 and a lactam bridge between the amino acids at positions 16 and 20 of the peptide. Such a glucagon peptide may further comprise one or more (e.g., two, three, four, five or more) of the other modifications described herein. For example, the glucagon peptide can comprise an amide in place of the C-terminal carboxylate. Accordingly, in one embodiment, the glucagon peptide comprises that amino acid sequence of SEQ ID NO: 555.

Acylation

In accordance with one embodiment, the glucagon peptide comprises an acyl group, e.g., an acyl group which is non-native to a naturally-occurring amino acid. The acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the GLP-1 and glucagon receptors. As shown herein, acylated glucagon peptides do not exhibit decreased activity at the glucagon and GLP-1 receptors in comparison to the corresponding unacylated glucagon peptide. Rather, in some instances, acylated glucagon peptides actually exhibit increased activity at the GLP-1 and glucagon receptors. Accordingly, the potency of the acylated analogs is comparable to the unacylated versions of the glucagon co-agonist analogs, if not enhanced.

In accordance with one embodiment, the glucagon peptide is modified to comprise an acyl group which is attached to the glucagon peptide via an ester, thioester, or amide linkage for purposes of prolonging half-life in circulation and/or delaying the onset of and/or extending the duration of action and/or improving resistance to proteases such as DPP-IV.

Acylation can be carried out at any position within the glucagon peptide, including any of positions 1-29, a position within a C-terminal extension, or the C-terminal amino acid, provided that glucagon and/or GLP-1 activity is retained, if not enhanced. Nonlimiting examples include positions 5, 7, 10, 11, 12, 13, 14, 16, 17, 18, 19, 20, 21, 24, 27, 28, or 29. In specific embodiments, acylation occurs at position 10 of the glucagon peptide and the glucagon peptide lacks an intramolecular bridge, e.g., a covalent intramolecular bridge (e.g., a lactam bridge). Such acylated peptides lacking an intramolecular bridge demonstrate enhanced activity at the GLP-1 and glucagon receptors as compared to the corresponding non-acylated peptides lacking a covalent intramolecular bridge and in comparison to the corresponding peptides lacking an intramolecular bridge acylated at a position other than position 10. As shown herein, acylation at position 10 can even transform a glucagon analog having little activity at the glucagon receptor to a glucagon analog having activity at both the glucagon and GLP-1 receptors. Accordingly, the position at which acylation occurs can alter the overall activity profile of the glucagon analog.

Glucagon peptides may be acylated at the same amino acid position where a hydrophilic moiety is linked, or at a different amino acid position. Nonlimiting examples include acylation at position 10 and pegylation at one or more positions in the C-terminal portion of the glucagon peptide, e.g., position 24, 28 or 29, within a C-terminal extension, or at the C-terminus (e.g., through adding a C-terminal Cys).

The acyl group can be covalently linked directly to an amino acid of the glucagon peptide, or indirectly to an amino acid of the glucagon peptide via a spacer, wherein the spacer is positioned between the amino acid of the glucagon peptide and the acyl group.

In a specific aspect of the invention, the glucagon peptide is modified to comprise an acyl group by direct acylation of an amine, hydroxyl, or thiol of a side chain of an amino acid of the glucagon peptide. In some embodiments, the glucagon peptide is directly acylated through the side chain amine, hydroxyl, or thiol of an amino acid. In some embodiments, acylation is at position 10, 20, 24, or 29. In this regard, the acylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments of the invention, the direct acylation of the glucagon peptide occurs through the side chain amine, hydroxyl, or thiol of the amino acid at position 10.

In some embodiments, the amino acid comprising a side chain amine is an amino acid of Formula I:

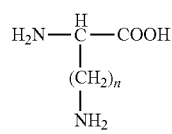

[Formula I]

wherein n = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

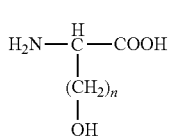

[Formula II]

wherein n = 1 to 4

In some exemplary embodiments, the amino acid of Formula II is the amino acid wherein n is 1 (Ser).

In yet other embodiments, the amino acid comprising a side chain thiol is an amino acid of Formula III:

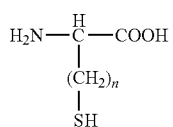

[Formula III]

wherein n = 1 to 4

In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In one embodiment of the invention, the acylated glucagon peptide comprises a spacer between the peptide and the acyl group. In some embodiments, the glucagon peptide is covalently bound to the spacer, which is covalently bound to the acyl group.

In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain NH₂, —OH, or —COOH (e.g., Lys, Orn, Ser, Asp, or Glu) is suitable. In this respect, the acylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu.

In the instance in which the side chain amine of the amino acid of the spacer is acylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be acylated, such that the glucagon peptide is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C12 to C18 fatty acyl group, e.g., C14 fatty acyl group, C16 fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms.

In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the spacer comprises an overall negative charge, e.g., comprises one or two negatively charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

In some exemplary embodiments, the glucagon peptide is modified to comprise an acyl group by acylation of an amine, hydroxyl, or thiol of a spacer, which spacer is attached to a side chain of an amino acid at position 10, 20, 24, or 29, or at the C-terminal amino acid of the glucagon peptide.

In yet more specific embodiments, the acyl group is attached to the amino acid at position 10 of the glucagon peptide and the length of the spacer and acyl group is 14 to 28 atoms. The amino acid at position 10, in some aspects, is an amino acid of Formula I, e.g., Lys, or a disubstituted amino acid related to Formula I. In more specific embodiments, the glucagon peptide lacks an intramolecular bridge, e.g., a covalent intramolecular bridge. The glucagon peptide, for example, can be a peptide comprising one or more alpha, alpha-disubstituted amino acids, e.g., AIB, for stabilizing the alpha helix of the peptide. Accordingly, the acylated glucagon peptide can comprise the amino acid sequence of any of SEQ ID NOs: 555-561 and 610-612, the AIB-containing peptides of Tables 20 and 28. As shown herein, such peptides comprising an acylated spacer covalently attached to the side chain of the amino acid at position 10 exhibit enhanced potency at both the GLP-1 and glucagon receptors.

Suitable methods of peptide acylation via amines, hydroxyls, and thiols are known in the art. See, for example, Example 19 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem.* "Chemical Modifications of Proteins: History and Applications" pages 1, 2-12 (1990); Hashimoto et al., *Pharmacuetical Res.* "Synthesis of Palmitoyl Derivatives of Insulin and their Biological Activity" Vol. 6, No: 2 pp. 171-176 (1989).

The acyl group of the acylated glucagon peptide can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid; C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In some embodiments of the invention, the glucagon peptide is modified to comprise an acyl group by acylation of a long chain alkane by the glucagon peptide. In specific aspects, the long chain alkane comprises an amine, hydroxyl, or thiol group (e.g. octadecylamine, tetradecanol, and hexadecanethiol) which reacts with a carboxyl group, or activated form thereof, of the glucagon peptide. The carboxyl group, or activated form thereof, of the glucagon peptide can be part of a side chain of an amino acid (e.g., glutamic acid, aspartic acid) of the glucagon peptide or can be part of the peptide backbone.

In certain embodiments, the glucagon peptide is modified to comprise an acyl group by acylation of the long chain alkane by a spacer which is attached to the glucagon peptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form of a carboxyl group" refers to a carboxyl group with the general formula R(C=O)X, wherein X is a leaving group and R is the glucagon peptide or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects of the invention, in which a long chain alkane is acylated by the glucagon peptide or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, an amine, hydroxyl, or thiol group of the glucagon peptide is acylated with a cholesterol acid. In a specific embodiment, the glucagon peptide is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the glucagon peptide comprises the structure:

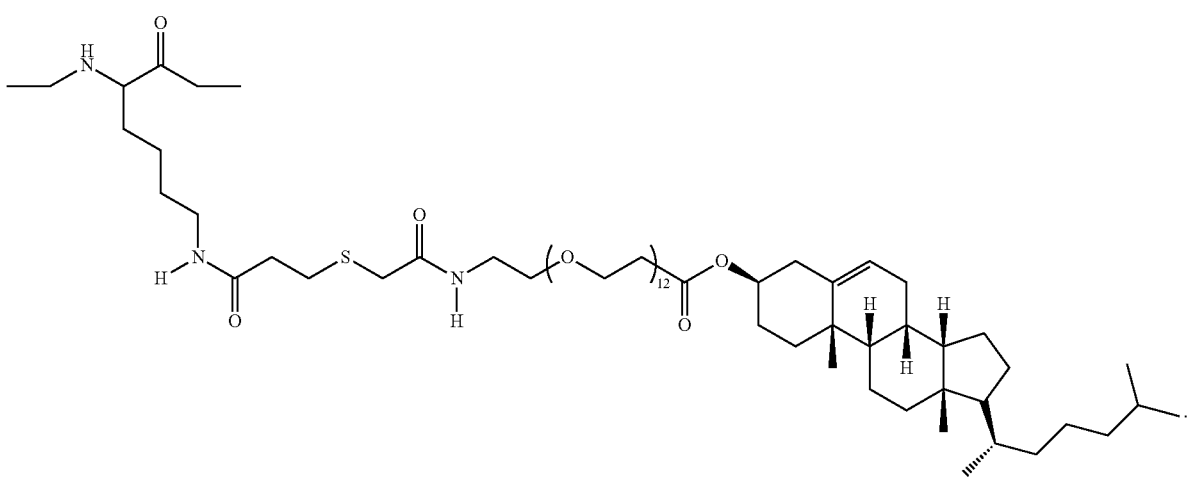

The acylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon peptide can comprise SEQ ID NO: 1, including any of the modifications described herein, in which at least one of the amino acids at position 10, 20, 24, and 29 comprise an acyl group and at least one of the amino acids at position 16, 17, 21, 24, or 29, a position within a C-terminal extension, or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the acyl group is attached to position 10, optionally via a spacer comprising Cys, Lys, Orn, homo-Cys, or Ac-Phe, and the hydrophilic moiety is incorporated at a Cys residue at position 24.

Alternatively, the acylated glucagon peptide can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In a specific aspect of the invention, the acylated glucagon peptide comprises the amino acid sequence of any of SEQ ID NOs: 534-544 and 546-549.

Alkylation

In accordance with some embodiments, the glucagon peptide is modified to comprise an alkyl group, e.g., an alkyl group which is not naturally-occurring on an amino acid (e.g., an alkyl group which is non-native to a naturally-occurring amino acid). Without being held to any particular theory, it is believed that alkylation of glucagon peptides will achieve similar, if not the same, effects as acylation of the glucagon peptides, e.g., a prolonged half-life in circulation, a delayed onset of action, an extended duration of action, an improved resistance to proteases, such as DPP-IV, and increased potency at the GLP-1 and glucagon receptors.

Alkylation can be carried out at any positions within the glucagon peptide, including any of positions 1-29, a position within a C-terminal extension, or the C-terminal amino acid, provided that the glucagon activity is retained. Nonlimiting examples include positions 5, 7, 10, 11, 12, 13, 14, 16, 17, 18, 19, 20, 21, 24, 27, 28, or 29. The alkyl group can be covalently linked directly to an amino acid of the glucagon peptide, or indirectly to an amino acid of the glucagon peptide via a spacer, wherein the spacer is positioned between the amino acid of the glucagon peptide and the alkyl group. Glucagon peptides may be alkylated at the same amino acid position where a hydrophilic moiety is linked, or at a different amino acid position. Nonlimiting examples include alkylation at position 10 and pegylation at one or more positions in the C-terminal portion of the glucagon peptide, e.g., position 24, 28 or 29, within a C-terminal extension, or at the C-terminus (e.g., through adding a C-terminal Cys).

In a specific aspect of the invention, the glucagon peptide is modified to comprise an alkyl group by direct alkylation of an amine, hydroxyl, or thiol of a side chain of an amino acid of the glucagon peptide. In some embodiments, alkylation is at position 10, 20, 24, or 29. In this regard, the alkylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or thiol. In some specific embodiments of the invention, the direct alkylation of the glucagon peptide occurs through the side chain amine, hydroxyl, or thiol of the amino acid at position 10.

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula His the amino acid wherein n is 1 (Ser).

In yet other embodiments, the amino acid comprising a side chain thiol is an amino acid of Formula III. In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

In one embodiment of the invention, the alkylated glucagon peptide comprises a spacer between the peptide and the alkyl group. In some embodiments, the glucagon peptide is covalently bound to the spacer, which is covalently bound to the alkyl group. In some exemplary embodiments, the glucagon peptide is modified to comprise an alkyl group by alkylation of an amine, hydroxyl, or thiol of a spacer, which spacer is attached to a side chain of an amino acid at position 10, 20, 24, or 29 of the glucagon peptide. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the glucagon peptide is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser.

When alkylation occurs through a thiol group of spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer is comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In some embodiments, the spacer is a hydrophobic bifunctional spacer. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydropholic bifunctional spacer comprises an amine group and a carboxylate. In other embodiments, the hydropholic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms)) in length. In more specific embodiments; the spacer is about 3 to 10 atoms (e.g., 6 to 10 atoms) in length and the alkyl is a C12 to C18 alkyl group, e.g., C14 alkyl group, C16 alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl is 17 to 28 (e.g., 19 to 26, 19 to 21) atoms.

In accordance with certain foregoing embodiments, the bifunctional spacer can be a synthetic or non-naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer can be composed of naturally-occurring and/or non-naturally occurring amino acids, including, for example, any of the amino acids taught herein. In some embodiments, the spacer comprises an overall negative charge, e.g., comprises one or two negatively charged amino acids. In some embodiments, the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

Suitable methods of peptide alkylation via amines, hydroxyls, and thiols are known in the art. For example, a Williamson ether synthesis can be used to form an ether linkage between a hydroxyl group of the glucagon peptide and the alkyl group. Also, a nucleophilic substitution reaction of the peptide with an alkyl halide can result in any of an ether, thioether, or amino linkage.

The alkyl group of the alkylated glucagon peptide can be of any size, e.g., any length carbon chain, and can be linear or branched. In some embodiments of the invention, the alkyl group is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

In some embodiments of the invention, the glucagon peptide is modified to comprise an alkyl group by reacting a nucleophilic, long chain alkane with the glucagon peptide, wherein the glucagon peptide comprises a leaving group suitable for nucleophilic substitution. In specific aspects, the nucleophilic group of the long chain alkane comprises an amine, hydroxyl, or thiol group (e.g. octadecylamine, tetradecanol, and hexadecanethiol). The leaving group of the glucagon peptide can be part of a side chain of an amino acid or can be part of the peptide backbone. Suitable leaving groups include, for example, N-hydroxysuccinimide, halogens, and sulfonate esters.

In certain embodiments, the glucagon peptide is modified to comprise an alkyl group by reacting the nucleophilic, long chain alkane with a spacer which is attached to the glucagon peptide, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group.

With regard to these aspects of the invention, in which a long chain alkane is alkylated by the glucagon peptide or the spacer, the long chain alkane may be of any size and can comprise any length of carbon chain. The long chain alkane can be linear or branched. In certain aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, alkylation can occur between the glucagon peptide and a cholesterol moiety. For example, the hydroxyl group of cholesterol can displace a leaving group on the long chain alkane to form a cholesterol-glucagon peptide product.

The alkylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon peptide can comprise SEQ ID NO: 1 or a modified amino acid sequence thereof comprising one or more of the amino acid modifications described herein, in which at least one of the amino acids at position 10, 20, 24, and 29 comprise an alkyl group and at least one of the amino acids at position 16, 17, 21, 24, and 29, a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10, optionally via a spacer comprising Cys, Lys, Orn, homo-Cys, or Ac-Phe, and the hydrophilic moiety is incorporated at a Cys residue at position 24.

Alternatively, the alkylated glucagon peptide can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

C-terminal Truncation

In some embodiments, the glucagon peptides described herein are further modified by truncation or deletion of one or two amino acids of the C-terminus of the glucagon peptide (i.e., position 29 and/or 28) without affecting activity and/or potency at the glucagon and GLP-1 receptors. In this regard, the glucagon peptide can comprise amino acids 1-27 or 1-28 of the native glucagon peptide (SEQ ID NO: 1), optionally with one or more modifications described herein.

In one embodiment, the truncated glucagon agonist peptide comprises SEQ ID NO: 550 or SEQ ID NO: 551. In another embodiment, the truncated glucagon agonist peptide comprises SEQ ID NO: 552 or SEQ ID NO: 553.

Charged C-terminal Residues

The solubility of the glucagon peptide of SEQ ID NO: 20 can be further improved, for example, by introducing one, two, three or more charged amino acid(s) to the C-terminal portion of glucagon peptide of SEQ ID NO: 20, preferably at a position C-terminal to position 27. Such a charged amino acid can be introduced by substituting a native amino acid with a charged amino acid, e.g. at positions 28 or 29, or alternatively by adding a charged amino acid, e.g. after position 27, 28 or 29. In exemplary embodiments, one, two, three or all of the charged amino acids are negatively charged. Alternatively, solubility can also be enhanced by covalently linking hydrophilic moieties, such as polyethylene glycol, to the peptide.

Exemplary Embodiments

In accordance with one embodiment, a glucagon analog is provided comprising the sequence of SEQ ID NO: 55, wherein said analog differs from SEQ ID NO: 55 by 1 to 3 amino acids, selected from positions 1, 2, 3, 5, 7, 10, 11, 13, 14, 17, 18, 19, 21, 24, 27, 28, and 29, wherein said glucagon peptide exhibits at least 20% of the activity of native GLP-1 at the GLP-1 receptor.

In accordance with one embodiment a glucagon/GLP-1 receptor co-agonist is provided comprising the sequence: NH$_2$-His-Ser-Gln-Gly-Thr-Phe-Thr-Ser-Asp-Tyr-Ser-Lys-Tyr-Leu-Xaa-Xaa-Arg-Arg-Ala-Xaa-Asp-Phe-Val-Xaa-Trp-Leu-Met-Xaa-Xaa-R (SEQ ID NO: 33) wherein the Xaa at position 15 is selected from the group of amino acids consisting of Asp, Glu, cysteic acid, homoglutamic acid and homocysteic acid, Xaa at position 16 is selected from the group of amino acids consisting of Ser, Glu, Gln, homoglutamic acid and homocysteic acid, the Xaa at position 20 is Gln or Lys, the Xaa at position 24 is Gln or Glu, the Xaa at position 28 is Asn, Lys or an acidic amino acid, the Xaa at position 29 is Thr, Gly or an acidic amino acid, and R is COOH or CONH$_2$, with the proviso that when position 16 is serine, position 20 is Lys, or alternatively when position 16 is serine the position 24 is Glu and either position 20 or position 28 is Lys. In one embodiment the glucagon/GLP-1 receptor co-agonist comprises the sequence of SEQ ID NO: 33 wherein the amino acid at position 28 is aspartic acid and the amino acid at position 29 is glutamic acid. In another embodiment the amino acid at position 28 is the native asparagine, the amino acid at position 29 is glycine and the amino acid sequence of SEQ ID NO: 29 or SEQ ID NO: 65 is covalently linked to the carboxy terminus of SEQ ID NO: 33.

In one embodiment a co-agonist is provided comprising the sequence of SEQ ID NO: 33 wherein an additional acidic amino acid added to the carboxy terminus of the peptide. In a further embodiment the carboxy terminal amino acid of the glucagon analog has an amide in place of the carboxylic acid group of the natural amino acid. In one embodiment the glucagon analog comprises a sequence selected from the group consisting of SEQ ID NO: 40, SEQ ID NO: 41, SEQ ID NO: 42, SEQ ID NO: 43 and SEQ ID NO: 44.

In accordance with one embodiment a glucagon peptide analog of SEQ ID NO: 33 is provided, wherein said analog differs from SEQ ID NO: 33 by 1 to 3 amino acids, selected from positions 1, 2, 3, 5, 7, 10, 11, 13, 14, 17, 18, 19, 21 and 27, with the proviso that when the amino acid at position 16 is serine, either position 20 is lysine, or a lactam bridge is formed between the amino acid at position 24 and either the amino acid at position 20 or position 28. In accordance with one embodiment the analog differs from SEQ ID NO: 33 by 1 to 3 amino acids selected from positions 1, 2, 3, 21 and 27. In one embodiment the glucagon peptide analog of SEQ ID NO: 33 differs from that sequence by 1 to 2 amino acids, or in one embodiment by a single amino acid, selected form positions 1, 2, 3, 5, 7, 10, 11, 13, 14, 17, 18, 19, 21 and 27, with the proviso that when the amino acid at position 16 is serine, either position 20 is lysine, or a lactam bridge is formed between the amino acid at position 24 and either the amino acid at position 20 or position 28.

In accordance with another embodiment a relatively selective GLP-1 receptor agonist is provided comprising the sequence NH2-His-Ser-Xaa-Gly-Thr-Phe-Thr-Ser-Asp-Tyr-Ser-Lys-Tyr-Leu-Xaa-Xaa-Arg-Arg-Ala-Xaa-Asp-Phe-Val-Xaa-Trp-Leu-Met-Xaa-Xaa-R (SEQ ID NO: 53) wherein the Xaa at position 3 is selected from the group of amino acids consisting of Glu, Orn or Nle, the Xaa at position 15 is selected from the group of amino acids consisting of Asp, Glu, cysteic acid, homoglutamic acid and homocysteic acid, Xaa at position 16 is selected from the group of amino acids consisting of Ser, Glu, Gln, homoglutamic acid and homocysteic acid, the Xaa at position 20 is Gln or Lys, the Xaa at position 24 is Gln or Glu, the Xaa at position 28 is Asn, Lys or an acidic amino acid, the Xaa at position 29 is Thr, Gly or an acidic amino acid, and R is COOH, CONH$_2$, SEQ ID NO: 26 or SEQ ID NO: 29, with the proviso that when position 16 is serine, position 20 is Lys, or alternatively when position 16 is serine the position 24 is Glu and either position 20 or position 28 is Lys. In one embodiment the amino acid at position 3 is glutamic acid. In one embodiment the acidic amino acid substituted at position 28 and/or 29 is aspartic acid or glutamic acid. In one embodiment the glucagon peptide, including a co-agonist peptide, comprises the sequence of SEQ ID NO: 33 further comprising an additional acidic amino acid added to the carboxy terminus of the peptide. In a further embodiment the carboxy terminal amino acid of the glucagon analog has an amide in place of the carboxylic acid group of the natural amino acid.

In accordance with one embodiment a glucagon/GLP-1 receptor co-agonist is provided comprising a modified glucagon peptide selected from the group consisting of: NH$_2$-His-Ser-Gln-Gly-Thr-Phe-Thr-Ser-Asp-Tyr-Ser-Lys-Tyr-Leu-Xaa-Xaa-Arg-Arg-Ala-Xaa-Asp-Phe-Val-Xaa-Trp-Leu-Met-Xaa-Xaa-R (SEQ ID NO: 34), wherein the Xaa at position 15 is selected from the group of amino acids consisting of Asp, Glu, cysteic acid, homoglutamic acid and homocysteic acid, Xaa at position 16 is selected from the group of amino acids consisting of Ser, Glu, Gln, homoglutamic acid and homocysteic acid, the Xaa at position 20 is Gln or Lys, the Xaa at position 24 is Gln or Glu and the Xaa at position 28 is Asn, Asp or Lys, R is COOH or CONH$_2$, the Xaa at position 29 is Thr or Gly, and R is COOH, CONH$_2$, SEQ ID NO: 26 or SEQ ID NO: 29, with the proviso that when position 16 is serine, position 20 is Lys, or alternatively when position 16 is serine the position 24 is Glu and either position 20 or position 28 is Lys. In one embodiment R is CONH$_2$, the Xaa at position 15 is Asp, the Xaa at position 16 is selected from the group of amino acids consisting of Glu, Gln, homoglutamic acid and homocysteic acid, the Xaas at positions 20 and 24 are each Gln the Xaa at position 28 is Asn or Asp and the Xaa at position 29 is Thr. In one embodiment the Xaas at positions 15 and 16 are each Glu, the Xaas at positions 20 and 24 are each Gln, the Xaa at position 28 is Asn or Asp, the Xaa at position 29 is Thr and R is CONH$_2$.

It has been reported that certain positions of the native glucagon peptide can be modified while retaining at least some of the activity of the parent peptide. Accordingly, applicants anticipate that one or more of the amino acids located at positions at positions 2, 5, 7, 10, 11, 12, 13, 14, 17, 18, 19, 20, 21, 24, 27, 28 or 29 of the peptide of SEQ ID NO: 11 can be substituted with an amino acid different from that present in the native glucagon peptide, and still retain activity at the glucagon receptor. In one embodiment the methionine residue present at position 27 of the native peptide is changed to leucine or norleucine to prevent oxidative degradation of the peptide. In another embodiment the amino acid at position 20 is substituted with Lys, Arg, Orn or Citrullene and/or position 21 is substituted with Glu, homoglutamic acid or homocysteic acid.

In one embodiment a glucagon analog of SEQ ID NO: 20 is provided wherein 1 to 6 amino acids, selected from positions 1, 2, 5, 7, 10, 11, 13, 14, 17, 18, 19, 21, 27, 28 or 29 of the analog differ from the corresponding amino acid of SEQ ID NO: 1, with the proviso that when the amino acid at position 16 is serine, position 20 is Lys, or alternatively when position 16 is serine the position 24 is Glu and either position 20 or position 28 is Lys. In accordance with another embodiment a glucagon analog of SEQ ID NO: 20 is provided wherein 1 to 3 amino acids selected from positions 1, 2, 5, 7, 10, 11, 13, 14, 17, 18, 19, 20, 21, 27, 28 or 29 of the analog differ from the corresponding amino acid of SEQ ID NO: 1. In another embodiment, a glucagon analog of SEQ ID NO: 8, SEQ ID NO: 9 or SEQ ID NO: 11 is provided wherein 1 to 2 amino acids selected from positions 1, 2, 5, 7, 10, 11, 13, 14, 17, 18, 19, 20 or 21 of the analog differ from the corresponding amino acid of SEQ ID NO: 1, and in a further embodiment the one to two differing amino acids represent conservative amino acid substitutions relative to the amino acid present in the native glucagon sequence (SEQ ID NO: 1). In one embodiment a glucagon peptide of SEQ ID NO: 12, SEQ ID NO: 13, SEQ ID NO: 14 or SEQ ID NO: 15 is provided wherein the glucagon peptide further comprises one, two or three amino acid substitutions at positions selected from positions 2, 5, 7, 10, 11, 13, 14, 17, 18, 19, 20, 21, 27 or 29.

In one embodiment the substitutions at positions 2, 5, 7, 10, 11, 13, 14, 16, 17, 18, 19, 20, 21, 27 or 29 are conservative amino acid substitutions.

In accordance with one embodiment a glucagon/GLP-1 receptor co-agonist is provided comprising a variant of the sequence of SEQ ID NO 33, wherein 1 to 10 amino acids selected from positions 16, 17, 18, 20, 21, 23, 24, 27, 28 and 29, respectively, of the variant differ from the corresponding amino acid of SEQ ID NO: 1. In accordance with one embodiment a variant of the sequence of SEQ ID NO 33 is provided wherein the variant differs from SEQ ID NO: 33 by one or more amino acid substitutions selected from the group consisting of Gln17, Ala18, Glu21, Ile23, Ala24, Val27 and Gly29. In accordance with one embodiment a glucagon/GLP-1 receptor co-agonist is provided comprising variants of the sequence of SEQ ID NO 33, wherein 1 to 2 amino acids selected from positions 17-26 of the variant differ from the corresponding amino acid of SEQ ID NO: 1. In accordance with one embodiment a variant of the sequence of SEQ ID NO 33 is provided wherein the variant differs from SEQ ID NO: 33 by an amino acid substitution selected from the group consisting of Gln17, Ala18, Glu21, Ile23 and Ala24. In accordance with one embodiment a variant of the sequence of SEQ ID NO 33 is provided wherein the variant differs from SEQ ID NO: 33 by an amino acid substitution at position 18 wherein the substituted amino acid is selected from the group consisting of Ala, Ser, Thr, and Gly. In accordance with one embodiment a variant of the sequence of SEQ ID NO 33 is provided wherein the variant differs from SEQ ID NO: 33 by an amino acid substitution of Ala at position 18. Such variations are encompassed by SEQ ID NO: 55. In another embodiment a glucagon/GLP-1 receptor co-agonist is provided comprising variants of the sequence of SEQ ID NO 33, wherein 1 to 2 amino acids selected from positions 17-22 of the variant differ from the corresponding amino acid of SEQ ID NO: 1, and in a further embodiment a variant of SEQ ID NO 33 is provided wherein the variant differs from SEQ ID NO: 33 by for 2 amino acid substitutions at positions 20 and 21. In accordance with one embodiment a glucagon/GLP-1 receptor co-agonist is provided comprising the sequence: NH2-His-Ser-Gln-Gly-Thr-Phe-Thr-Ser-Asp-Tyr-Ser-Lys-Tyr-Leu-Xaa-Xaa-Arg-Arg-Ala-Xaa-Xaa-Phe-Val-Xaa-Trp-Leu-Met-Xaa-Xaa-R (SEQ ID NO: 51), wherein the Xaa at position 15 is Asp, Glu, cysteic acid, homoglutamic acid or homocysteic acid, the Xaa at position 16 is Ser, Glu, Gln, homoglutamic acid or homocysteic acid, the Xaa at position 20 is Gln, Lys, Arg, Orn or citrulline, the Xaa at position 21 is Asp, Glu, homoglutamic acid or homocysteic acid, the Xaa at position 24 is Gln or Glu, the Xaa at position 28 is Asn, Lys or an acidic amino acid, the Xaa at position 29 is Thr or an acid amino acid and R is COOH or CONH$_2$. In one embodiment R is CONH$_2$. In accordance with one embodiment a glucagon/GLP-1 receptor co-agonist is provided comprising a variant of SEQ ID NO: 11, SEQ ID NO: 12, SEQ ID NO: 13, SEQ ID NO: 14, SEQ ID NO: 15, SEQ ID NO: 47, SEQ ID NO: 48 or SEQ ID NO: 49, wherein the variant differs from said sequence by an amino acid substitution at position 20. In one embodiment the amino acid substitution is selected form the group consisting of Lys, Arg, Orn or citrulline for position 20.

In one embodiment a glucagon agonist is provided comprising an analog peptide of SEQ ID NO: 34 wherein the analog differs from SEQ ID NO: 34 by having an amino acid other than serine at position 2. In one embodiment the serine residue is substituted with aminoisobutyric acid, D-alanine, and in one embodiment the serine residue is substituted with aminoisobutyric acid. Such modifications suppresses cleavage by dipeptidyl peptidase IV while retaining the inherent potency of the parent compound (e.g. at least 75, 80, 85; 90, 95% or more of the potency of the parent compound). In one embodiment the solubility of the analog is increased, for example, by introducing one, two, three or more charged amino acid(s) to the C-terminal portion of native glucagon, preferably at a position C-terminal to position 27. In exemplary embodiments, one, two, three or all of the charged amino acids are negatively charged. In another embodiment the analog further comprises an acidic amino acid substituted for the native amino acid at position 28 or 29 or an acidic amino acid added to the carboxy terminus of the peptide of SEQ ID NO: 34.

In one embodiment the glucagon analogs disclosed herein are further modified at position 1 or 2 to reduce susceptibility to cleavage by dipeptidyl peptidase IV. In one embodiment a glucagon analog of SEQ ID NO: 9, SEQ ID NO: 11, SEQ ID NO: 12, SEQ ID NO: 13, SEQ ID NO: 14 or SEQ ID NO: 15 is provided wherein the analog differs from the parent molecule by a substitution at position 2 and exhibits reduced susceptibility (i.e., resistance) to cleavage by dipeptidyl peptidase IV. More particularly, in one embodiment position 2 of the analog peptide is substituted with an amino acid selected from the group consisting of D-serine, D-alanine, valine, amino n-butyric acid, glycine, N-methyl serine and aminoisobutyric acid. In one embodiment position 2 of the analog peptide is substituted with an amino acid selected from the group consisting of D-serine, D-alanine, glycine, N-methyl serine and aminoisobutyric acid. In another embodiment position 2 of the analog peptide is substituted with an amino acid selected from the group consisting of D-serine, glycine, N-methyl serine and aminoisobutyric acid. In one embodiment the glucagon peptide comprises the sequence of SEQ ID NO: 21 or SEQ ID NO: 22.

In one embodiment a glucagon analog of SEQ ID NO: 9, SEQ ID NO: 11, SEQ ID NO: 12, SEQ ID NO: 13, SEQ ID NO: 14 or SEQ ID NO: 15 is provided wherein the analog differs from the parent molecule by a substitution at position 1 and exhibits reduced susceptibility (i.e., resistance) to cleavage by dipeptidyl peptidase IV. More particularly, position 1 of the analog peptide is substituted with an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. In another embodiment a glucagon agonist is provided comprising an analog peptide of SEQ ID NO: 34 wherein the analog differs from SEQ ID NO: 34 by having an amino acid other than histidine at position 1. In one embodiment the solubility of the analog is increased, for example, by introducing one, two, three or more charged amino acid(s) to the C-terminal portion of native glucagon, preferably at a position C-terminal to position 27. In exemplary embodiments, one, two, three or all of the charged amino acids are negatively charged. In another embodiment the analog further comprises an acidic amino acid substituted for the native amino acid at position 28 or 29 or an acidic amino acid added to the carboxy terminus of the peptide of SEQ ID NO: 34. In one embodiment the acidic amino acid is aspartic acid or glutamic acid.

In one embodiment the glucagon/GLP-1 receptor co-agonist comprises a sequence of SEQ ID NO: 20 further comprising an additional carboxy terminal extension of one amino acid or a peptide selected from the group consisting of SEQ ID NO: 26, SEQ ID NO: 27 and SEQ ID NO: 28. In the embodiment wherein a single amino acid is added to the carboxy terminus of SEQ ID NO: 20, the amino acid is typically selected from one of the 20 common amino acids, and in one embodiment the additional carboxy terminus amino acid has an amide group in place of the carboxylic acid of the native amino acid. In one embodiment the additional amino acid is selected from the group consisting of glutamic acid, aspartic acid and glycine.

In an alternative embodiment a glucagon/GLP-1 receptor co-agonist is provided wherein the peptide comprises at least one lactam ring formed between the side chain of a glutamic acid residue and a lysine residue, wherein the glutamic acid residue and a lysine residue are separated by three amino acids. In one embodiment the carboxy terminal amino acid of the lactam bearing glucagon peptide has an amide group in place of the carboxylic acid of the native amino acid. More particularly, in one embodiment a glucagon and GLP-1 co-agonist is provided comprising a modified glucagon peptide selected from the group consisting of:

```
                                        (SEQ ID NO: 66)
NH2-His-Ser-Gln-Gly-Thr-Phe-Thr-Ser-Asp-Tyr-Ser-
Lys-Tyr-Leu-Asp-Glu-Arg-Arg-Ala-Gln-Asp-Phe-Val-
Gln-Trp-Leu-Met-Xaa-Xaa-R (SEQ ID NO: 67)
NH2-His-Ser-Gln-Gly-Thr-Phe-Thr-Ser-Asp-Tyr-Ser-
Lys-Tyr-Leu-Asp-Glu-Arg-Arg-Ala-Lys-Asp-Phe-Val-
Gln-Trp-Leu-Met-Xaa-Xaa-R (SEQ ID NO: 68)
NH2-His-Ser-Gln-Gly-Thr-Phe-Thr-Ser-Asp-Tyr-Ser-
Lys-Tyr-Leu-Asp-Ser-Arg-Arg-Ala-Lys-Asp-Phe-Val-
Glu-Trp-Leu-Met-Xaa-Xaa-R (SEQ ID NO: 69)
NH2-His-Ser-Gln-Gly-Thr-Phe-Thr-Ser-Asp-Tyr-Ser-
Lys-Tyr-Leu-Asp-Ser-Arg-Arg-Ala-Gln-Asp-Phe-Val-
Glu-Trp-Leu-Met-Lys-Xaa-R (SEQ ID NO: 16)
NH2-His-Ser-Gln-Gly-Thr-Phe-Thr-Ser-Asp-Tyr-Ser-
Lys-Tyr-Leu-Asp-Glu-Arg-Arg-Ala-Lys-Asp-Phe-Val-
Glu-Trp-Leu-Met-Asn-Thr-R (SEQ ID NO: 17)
NH2-His-Ser-Gln-Gly-Thr-Phe-Thr-Ser-Asp-Tyr-Ser-
Lys-Tyr-Leu-Asp-Glu-Arg-Arg-Ala-Gln-Asp-Phe-Val-
Glu-Trp-Leu-Met-Lys-Thr-R (SEQ ID NO: 18)
NH2-His-Ser-Gln-Gly-Thr-Phe-Thr-Ser-Asp-Tyr-Ser-
Lys-Tyr-Leu-Asp-Glu-Arg-Arg-Ala-Lys-Asp-Phe-Val-
Glu-Trp-Leu-Met-Lys-Thr-R
``` wherein Xaa at position 28=Asp, or Asn, the Xaa at position 29 is Thr or Gly, R is selected from the group consisting of COOH, CONH$_2$, glutamic acid, aspartic acid, glycine, SEQ ID NO: 26, SEQ ID NO: 27 and SEQ ID NO: 28, and a lactam bridge is formed between Lys at position 12 and Glu at position 16 for SEQ ID NO: 66, between Glu at position 16 and Lys at position 20 for SEQ ID NO: 67, between Lys at position 20 and Glu at position 24 for SEQ ID NO: 68, between Glu at position 24 and Lys at position 28 for SEQ ID NO: 69, between Lys at position 12 and Glu at position 16 and between Lys at position 20 and Glu at position 24 for SEQ ID NO: 16, between Lys at position 12 and Glu at position 16 and between Glu at position 24 and Lys at position 28 for SEQ ID NO: 17 and between Glu at position 16 and Lys at position 20 and between Glu at position 24 and Lys at position 28 for SEQ ID NO: 18. In one embodiment R is selected from the group consisting of COOH, CONH$_2$, glutamic acid, aspartic acid, glycine, the amino acid at position 28 is Asn, and the amino acid at position 29 is threonine. In one embodiment R is CONH$_2$, the amino acid at position 28 is Asn and the amino acid at position 29 is threonine. In another embodiment R is selected from the group consisting of SEQ ID NO: 26, SEQ ID NO: 29 and SEQ ID NO: 65 and the amino acid at position 29 is glycine.

In a further embodiment the glucagon/GLP-1 receptor co-agonist is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, wherein the peptide further comprises an additional carboxy terminal extension of one amino acid or a peptide selected from the group consisting of SEQ ID NO: 26, SEQ ID NO: 27 and SEQ ID NO: 28. In one embodiment the terminal extension comprises the sequence of SEQ ID NO: 26, SEQ ID NO: 29 or SEQ ID NO: 65 and the glucagon peptide comprises the sequence of SEQ ID NO: 55. In one embodiment the glucagon/GLP-1 receptor co-agonist comprises the sequence of SEQ ID NO: 33 wherein the amino acid at position 16 is glutamic acid, the amino acid at position 20 is lysine, the amino acid at position 28 is asparagine and the amino acid sequence of SEQ ID No: 26 or SEQ ID NO: 29 is linked to the carboxy terminus of SEQ ID NO: 33.

In the embodiment wherein a single amino acid is added to the carboxy terminus of SEQ ID NO: 20, the amino acid is typically selected from one of the 20 common amino acids, and in one embodiment the amino acid has an amide group in place of the carboxylic acid of the native amino acid. In one embodiment the additional amino acid is selected from the group consisting of glutamic acid and aspartic acid and glycine. In the embodiments wherein the glucagon agonist analog further comprises a carboxy terminal extension, the carboxy terminal amino acid of the extension, in one embodiment, ends in an amide group or an ester group rather than a carboxylic acid.

In another embodiment the glucagon/GLP-1 receptor co-agonist comprises the sequence: $NH_2$-His-Ser-Gln-Gly-Thr-Phe-Thr-Ser-Asp-Tyr-Ser-Lys-Tyr-Leu-Asp-Glu-Arg-Arg-Ala-Gln-Asp-Phe-Val-Gln-Trp-Leu-Met-Asn-Thr-Xaa-$CONH_2$ (SEQ ID NO: 19), wherein the Xaa at position 30 represents any amino acid. In one embodiment Xaa is selected from one of the 20 common amino acids, and in one embodiment the amino acid is glutamic acid, aspartic acid or glycine. The solubility of this peptide can be further improved by covalently linking a PEG chain to the side chain of amino acid at position 17, 21, 24 or 30 of SEQ ID NO: 19. In a further embodiment the peptide comprises an additional carboxy terminal extension of a peptide selected from the group consisting of SEQ ID NO: 26, SEQ ID NO: 27 and SEQ ID NO: 28. In accordance with one embodiment the glucagon/GLP-1 receptor co-agonist comprises the sequence of SEQ ID NO: 30, SEQ ID NO: 31 and SEQ ID NO: 32.

Additional site specific modifications internal to the glucagon sequence of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 64 can be made to yield a set of glucagon agonists that possess variable degrees of GLP-1 agonism. Accordingly, peptides that possess virtually identical in vitro potency at each receptor have been prepared and characterized. Similarly, peptides with tenfold selectively enhanced potency at each of the two receptors have been identified and characterized. As noted above substitution of the serine residue at position 16 with glutamic acid enhances the potency of native glucagon at both the Glucagon and GLP-1 receptors, but maintains approximately a tenfold selectivity for the glucagon receptor. In addition by substituting the native glutamine at position 3 with glutamic acid (SEQ ID NO: 22) generates a glucagon analog that exhibits approximately a tenfold selectivity for the GLP-1 receptor.

The solubility of the glucagon/GLP-1 co-agonist peptides can be further enhanced in aqueous solutions at physiological pH, while retaining the high biological activity relative to native glucagon by the introduction of hydrophilic groups at positions 16, 17, 21, and 24 of the peptide, or by the addition of a single modified amino acid (i.e., an amino acid modified to comprise a hydrophilic group) at the carboxy terminus of the glucagon/GLP-1 co-agonist peptide. In accordance with one embodiment the hydrophilic group comprises a polyethylene (PEG) chain. More particularly, in one embodiment the glucagon peptide comprises the sequence of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 wherein a PEG chain is covalently linked to the side chain of an amino acids at position 16, 17, 21, 24, 29 or the C-terminal amino acid of the glucagon peptide, with the proviso that when the peptide comprises SEQ ID NO: 10, SEQ ID NO: 11, SEQ ID NO: 12 or SEQ ID NO: 13 the polyethylene glycol chain is covalently bound to an amino acid residue at position 17, 21 or 24, when the peptide comprises SEQ ID NO: 14 or SEQ ID NO: 15 the polyethylene glycol chain is covalently bound to an amino acid residue at position 16, 17 or 21, and when the peptide comprises SEQ ID NO: 16, SEQ ID NO: 17 or SEQ ID NO: 18 the polyethylene glycol chain is covalently bound to an amino acid residue at position 17 or 21.

In one embodiment the glucagon peptide comprises the sequence of SEQ ID NO: 11, SEQ ID NO: 12 or SEQ ID NO: 13, wherein a PEG chain is covalently linked to the side chain of an amino acids at position 17, 21, 24, or the C-terminal amino acid of the glucagon peptide, and the carboxy terminal amino acid of the peptide has an amide group in place of the carboxylic acid group of the native amino acid. In one embodiment the glucagon/GLP-1 receptor co-agonist peptide comprises a sequence selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, wherein a PEG chain is covalently linked to the side chain of an amino acid at position 17, 21 or 24 of SEQ ID NO: 12, SEQ ID NO: 13 and SEQ ID NO: 19, or at position 16, 17 or 21 of SEQ ID NO 14 and SEQ ID NO: 15 or at position 17 or 21 of SEQ ID NO: 16, SEQ ID NO: 17 and SEQ ID NO: 18 of the glucagon peptide. In another embodiment the glucagon/GLP-1 receptor co-agonist peptide comprises the sequence of SEQ ID NO: 11 or SEQ ID NO: 19, wherein a PEG chain is covalently linked to the side chain of an amino acids at position 17, 21 or 24 or the C-terminal amino acid of the glucagon peptide.

In accordance with one embodiment, and subject to the proviso limitations described in the preceding paragraphs, the glucagon co-agonist peptide is modified to contain one or more amino acid substitution at positions 16, 17, 21, 24, or 29 or the C-terminal amino acid, wherein the native amino acid is substituted with an amino acid having a side chain suitable for crosslinking with hydrophilic moieties, including for example, PEG. The native peptide can be substituted with a naturally occurring amino acid or a synthetic (non-naturally occurring) amino acid. Synthetic or non-naturally occurring amino acids refer to amino acids that do not naturally occur in vivo but which, nevertheless, can be incorporated into the peptide structures described herein. Alternatively, the amino acid having a side chain suitable for crosslinking with hydrophilic moieties, including for example, PEG, can be added to the carboxy terminus of any of the glucagon analogs disclosed herein. In accordance with one embodiment an amino acid substitution is made in the glucagon/GLP-1 receptor co-agonist peptide at a position selected from the group consisting of 16, 17, 21, 24, or 29 replacing the native amino acid with an amino acid selected from the group consisting of lysine, cysteine, ornithine, homocysteine and acetyl phenylalanine, wherein the substituting amino acid further comprises a PEG chain covalently bound to the side chain of the amino acid. In one embodiment a glucagon peptide selected form the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19 is further modified to comprise a PEG chain is covalently linked to the side chain of an amino acid at position 17 or 21 of the glucagon peptide. In one embodiment the pegylated glucagon/GLP-1 receptor co-agonist further comprises the sequence of SEQ ID NO: 26, SEQ ID NO: 27 or SEQ ID NO: 29.

In another embodiment the glucagon peptide comprises the sequence of SEQ ID NO: 55 or SEQ ID NO: 56, further comprising a C-terminal extension of SEQ ID NO: 26, SEQ ID NO: 29 or SEQ ID NO: 65 linked to the C-terminal amino acid of SEQ ID NO: 55 or SEQ ID NO: 56, and optionally further comprising a PEG chain covalently linked to the side chain of an amino acids at position 17, 18, 21, 24 or 29 or the C-terminal amino acid of the peptide. In another embodiment the glucagon peptide comprises the sequence of SEQ ID NO: 55 or SEQ ID NO: 56, wherein a PEG chain is covalently linked to the side chain of an amino acids at position 21 or 24 of the glucagon peptide and the peptide further comprises a C-terminal extension of SEQ ID NO: 26, or SEQ ID NO: 29.

In another embodiment the glucagon peptide comprises the sequence of SEQ ID NO: 55, or SEQ ID NO: 33 or SEQ ID NO: 34, wherein an additional amino acid is added to the carboxy terminus of SEQ ID NO: 33 or SEQ ID NO: 34, and a PEG chain is covalently linked to the side chain of the added amino acid. In a further embodiment, the pegylated glucagon analog further comprises a C-terminal extension of SEQ ID NO: 26 or SEQ ID NO: 29 linked to the C-terminal amino acid of SEQ ID NO: 33 or SEQ ID NO: 34. In another embodiment the glucagon peptide comprises the sequence of SEQ ID NO: 19, wherein a PEG chain is covalently linked to the side chain of the amino acid at position 30 of the glucagon peptide and the peptide further comprises a C-terminal extension of SEQ ID NO: 26 or SEQ ID NO: 29 linked to the C-terminal amino acid of SEQ ID NO: 19.

The polyethylene glycol chain may be in the form of a straight chain or it may be branched. In accordance with one embodiment the polyethylene glycol chain has an average molecular weight selected from the range of about 500 to about 10,000 Daltons. In one embodiment the polyethylene glycol chain has an average molecular weight selected from the range of about 1,000 to about 5,000 Daltons. In an alternative embodiment the polyethylene glycol chain has an average molecular weight selected from the range of about 10,000 to about 20,000 Daltons. In accordance with one embodiment the pegylated glucagon peptide comprises two or more polyethylene chains covalently bound to the glucagon peptide wherein the total molecular weight of the glucagon chains is about 1,000 to about 5,000 Daltons. In one embodiment the pegylated glucagon agonist comprises a peptide consisting of SEQ ID NO: 5 or a glucagon agonist analog of SEQ ID NO: 5, wherein a PEG chain is covalently linked to the amino acid residue at position 21 and at position 24, and wherein the combined molecular weight of the two PEG chains is about 1,000 to about 5,000 Daltons.

In certain exemplary embodiments, the glucagon peptide comprises the amino acid sequence of SEQ ID NO: 1 with up to ten amino acid modifications and comprises an amino acid at position 10 which is acylated or alkylated. In some embodiments, the amino acid at position 10 is acylated or alkylated with a C4 to C30 fatty acid. In certain aspects, the amino acid at position 10 comprises an acyl group or an alkyl group which is non-native to a naturally-occurring amino acid.

In certain embodiments, the glucagon peptide comprising an amino acid at position 10 which is acylated or alkylated comprises a stabilized alpha helix. Accordingly, in certain aspects, the glucagon peptide comprises an acyl or alkyl group as described herein and an intramolecular bridge, e.g., a covalent intramolecular bridge (e.g., a lactam bridge) between the side chains of an amino acid at position i and an amino acid at position i+4, wherein i is 12, 16, 20, or 24. Alternatively or additionally, the glucagon peptide comprises an acyl or alkyl group as described herein and one, two, three or more of positions 16, 20, 21 and/or 24 of the glucagon peptide are substituted with an α,α-disubstituted amino acid, e.g., MB. In some instances, the non-native glucagon peptide comprises Glu at position 16 and Lys at position 20, wherein optionally a lactam bridge lnkes the Glu and the Lys, and, optionally, the glucagon peptide further comprises one or more modifications selected from the group consisting of: Gln at position 17, Ala at position 18, Glu at position 21, Ile at position 23, and Ala at position 24.

Also, in any of the embodiments, wherein the glucagon peptide comprises an amino acid at position 10 which is acylated or alkylated, the glucagon peptide can further comprise a C-terminal amide in lieu of the C-terminal alpha carboxylate.

In some embodiments, the glucagon peptide comprising an acyl or alkyl group as described herein further comprises an amino acid substitution at position 1, at position 2, or at positions 1 and 2, wherein the amino acid substitution(s) achieve DPP-IV protease resistance. For example, the His at position 1 may be substituted with an amino acid selected from the group consisting of: D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. Alternatively or additionally, the Ser at position 2 may be substituted with an amino acid selected from the group consisting of: D-serine, alanine, D-alanine, valine, glycine, N-methyl serine, N-methyl alanine, and amino isobutyric acid.

The glucagon peptide comprising the amino acid at position 10 which is acylated or alkylated as described herein can comprise any amino acid sequence which is substantially related to SEQ ID NO: 1. For instance, the glucagon peptide comprises SEQ ID NO: 1 with up to 10 amino acid modifications (e.g., 0, 1, 2, 3, 4, 5, 6, 7, 8, 9, 10 modifications). In certain embodiments, the amino acid sequence of the acylated or alkylated glucagon peptide is greater than 25% identical to SEQ ID NO: 1 (e.g., greater than 30%, 35%, 40%, 50%, 60%, 70% 75%, 80%, 85%, 90%, 95%, 96%, 97%, 98%, 99%, or nearly 100% identical to SEQ ID NO: 1). In certain specific embodiments, the glucagon peptide is one which comprises SEQ ID NOs: 55 with an amino acid at position 10 acylated or alkylated as described herein. The glucagon peptide can be any of SEQ ID NOs: 55, 55 with 1 or 2 amino acid modifications, 2-4, 9-18, 20, 23-25, 33, 40-44, 53, 56, 61, 62, 64, 66-514, and 534.

The acyl or alkyl group of these embodiments may be any acyl or alkyl group described herein. For example, the acyl group may be a C4 to C30 (e.g., C8 to C24) fatty acyl group and the alkyl group may be a C4 to C30 (e.g., C8 to C24) alkyl group.

The amino acid to which the acyl or alkyl group is attached may be any of the amino acids described herein, e.g., an amino acid of any of Formula I (e.g., Lys), Formula II, and Formula III.

In some embodiments, the acyl group or alkyl group is directly attached to the amino acid at position 10. In some embodiments, the acyl or alkyl group is attached to the amino acid at position 10 via a spacer, such as, for example, a spacer which is 3 to 10 atoms in length, e.g., an amino acid or dipeptide. Suitable spacers for purposes of attaching an acyl or alkyl group are described herein.

Uses

As described in detail in the Examples, the glucagon agonists of the present invention have enhanced biophysical stability and aqueous solubility while demonstrating enhanced bioactivity relative to the native peptide. Accordingly, the glucagon agonists of the present invention are believed to be suitable for any use that has previously been described for the native glucagon peptide. Accordingly, the modified glucagon peptides described herein can be used to treat hypoglycemia or to increase blood glucose level, to induce temporary paralysis of the gut for radiological uses, or treat other metabolic diseases that result from low blood levels of glucagon. The glucagon peptides described herein also are expected to be used to reduce or maintain body weight, or to treat hyperglycemia, or to reduce blood glucose level, or to normalize blood glucose level.

The glucagon peptides of the invention may be administered alone or in combination with other anti-diabetic or anti-obesity agents. Anti-diabetic agents known in the art or under investigation include insulin, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to XENICAL (Orlistat) or Cetilistat (also known as ATL-962), or GT 389-255.

One aspect of the present disclosure is directed to a preformulated aqueous solution of the presently disclosed glucagon agonist for use in treating hypoglycemia. The improved stability and solubility of the agonist compositions described herein allow for the preparation of pre-formulated aqueous solutions of glucagon for rapid administration and treatment of hypoglycemia. In one embodiment a solution comprising a pegylated glucagon agonist is provided for administration to a patient suffering from hypoglycemia, wherein the total molecular weight of the PEG chains linked to the pegylated glucagon agonist is between about 500 to about 5,000 Daltons. In one embodiment the pegylated glucagon agonist comprises a peptide selected from the group consisting of SEQ ID NO: 23, SEQ ID NO: 24, and SEQ ID NO: 25, and glucagon agonist analogs of SEQ ID NO: 23, SEQ ID NO: 24, and SEQ ID NO: 25, or a pegylated lactam derivative of glucagon comprising the sequence of SEQ ID NO: 20, wherein the side chain of an amino acid residue of said glucagon peptide is covalently bound to the polyethylene glycol chain.

The treatment methods in accordance with the present invention, including but not limited to treatment of hypoglycemia, may comprise the steps of administering the presently disclosed glucagon agonists to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the glucagon composition is prepackaged in a syringe. In another embodiment, the composition is prepackaged in an inhaler or other aerosolized drug delivery device.

Surprisingly, applicants have discovered that pegylated glucagon peptides can be prepared that retain the parent peptide's bioactivity and specificity. However, increasing the length of the PEG chain, or attaching multiple PEG chains to the peptide, such that the total molecular weight of the linked PEG is greater than 5,000 Daltons, begins to delay the time action of the modified glucagon. In accordance with one embodiment, a glucagon peptide of SEQ ID NO: 23, SEQ ID NO: 24, and SEQ ID NO: 25, or a glucagon agonist analog thereof, or a pegylated lactam derivative of glucagon comprising the sequence of SEQ ID NO: 20 is provided wherein the peptide comprises one or more polyethylene glycol chains, wherein the total molecular weight of the linked PEG is greater than 5,000 Daltons, and in one embodiment is greater than 10,000 Daltons, but less than 40,000 Daltons. Such modified glucagon peptides have a delayed or prolonged time of activity but without loss of the bioactivity. Accordingly, such compounds can be administered to extend the effect of the administered glucagon peptide.

Glucagon peptides that have been modified to be covalently bound to a PEG chain having a molecular weight of greater than 10,000 Daltons can be administered in conjunction with insulin to buffer the actions of insulin and help to maintain stable blood glucose levels in diabetics. The modified glucagon peptides of the present disclosure can be co-administered with insulin as a single composition, simultaneously administered as separate solutions, or alternatively, the insulin and the modified glucagon peptide can be administered at different time relative to one another. In one embodiment the composition comprising insulin and the composition comprising the modified glucagon peptide are administered within 12 hours of one another. The exact ratio of the modified glucagon peptide relative to the administered insulin will be dependent in part on determining the glucagon levels of the patient, and can be determined through routine experimentation.

In accordance with one embodiment a composition is provided comprising insulin and a modified glucagon peptide selected from the group consisting of SEQ ID NO: 2, SEQ ID NO: 3, SEQ ID NO: 4, SEQ ID NO: 5 and glucagon agonist analogs thereof, wherein the modified glucagon peptide further comprises a polyethylene glycol chain covalently bound to an amino acid side chain at position 17, 21, 24 or 21 and 24. In one embodiment the composition is an aqueous solution comprising insulin and the glucagon analog. In embodiments where the glucagon peptide comprises the sequence of SEQ ID NO: 24 or SEQ ID NO: 25 the PEG chain is covalently bound at position 21 or 24 of the glucagon peptide. In one embodiment the polyethylene glycol chain has a molecular weight of about 10,000 to about 40,000.

In accordance with one embodiment the modified glucagon peptides disclosed herein are used to induce temporary paralysis of the intestinal tract. This method has utility for radiological purposes and comprises the step of administering an effective amount of a pharmaceutical composition comprising a pegylated glucagon peptide, a glucagon peptide comprising a c-terminal extension or a dimer of such peptides. In one embodiment the glucagon peptide comprises a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 SEQ ID NO: 14 and SEQ ID NO: 15. In one embodiment the glucagon peptide further comprises a PEG chain, of about 1,000 to 40,000 Daltons is covalently bound to an amino acid residue at position 21 or 24. In one embodiment the glucagon peptide is selected from the group consisting of SEQ ID NO: 10, SEQ ID NO: 11, SEQ ID NO: 12, SEQ ID NO: 13, SEQ ID NO: 14 and SEQ ID NO: 15. In one embodiment the PEG chain has a molecular weight of about 500 to about 5,000 Daltons.

In a further embodiment the composition used to induce temporary paralysis of the intestinal tract comprises a first modified glucagon peptide and a second modified glucagon peptide. The first modified peptide comprises a sequence selected from the group consisting of SEQ ID NO: 23, SEQ ID NO: 24 and SEQ ID NO: 25, optionally linked to a PEG chain of about 500 to about 5,000 Daltons, and the second peptide comprises a sequence selected from the group consisting of SEQ ID NO: 23, SEQ ID NO: 24 and SEQ ID NO: 25, covalently linked to a PEG chain of about 10,000 to about 40,000 Daltons. In this embodiment the PEG chain of each peptide is covalently bound to an amino acid residue at either position 17, 21 or 24 of the respective peptide, and independent of one another.

Oxyntomodulin, a naturally occurring digestive hormone found in the small intestine, has been reported to cause weight loss when administered to rats or humans (see Diabetes 2005; 54:2390-2395). Oxyntomodulin is a 37 amino acid peptide that contains the 29 amino acid sequence of glucagon (i.e., SEQ ID NO: 1) followed by an 8 amino acid carboxy terminal extension of SEQ ID NO: 27 (KRNRNNIA). Accordingly, applicants believe that the bioactivity of oxyntomodulin can be retained (i.e., appetite suppression and induced weight loss/weight maintenance), while improving the solubility and stability of the compound and improving the pharmacokinetics, by substituting the glucagon peptide portion of oxyntomodulin with the modified glucagon peptides disclosed herein. In addition applicants also believe that a truncated Oxyntomodulin molecule comprising a glucagon peptide of the invention, having the terminal four amino acids of oxyntomodulin removed will also be effective in suppressing appetite and inducing weight loss/weight maintenance.

Accordingly, the present invention also encompasses the modified glucagon peptides of the present invention that have a carboxy terminal extension of SEQ ID NO: 27 (KRNRNNIA) or SEQ ID NO: 28. These compounds can be administered to individuals to induce weight loss or prevent weight gain. In accordance with one embodiment a glucagon agonist analog of SEQ ID NO: 33 or SEQ ID NO: 20, further comprising the amino acid sequence of SEQ ID NO: 27 (KRNRNNIA) or SEQ ID NO: 28 linked to amino acid 29 of the glucagon peptide, is administered to individuals to induce weight loss or prevent weight gain. More particularly, the glucagon peptide comprises a sequence selected from the group consisting of SEQ ID NO: 10, SEQ ID NO: 12, SEQ ID NO: 13 SEQ ID NO: 14 and SEQ ID NO: 15, further comprising the amino acid sequence of SEQ ID NO: 27 (KRNRNNIA) or SEQ ID NO: 28 linked to amino acid 29 of the glucagon peptide.

Exendin-4, is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivity of glucagon. In one embodiment the terminal ten amino acids of Exendin-4 (i.e., the sequence of SEQ ID NO: 26 (GPSSGAPPPS)) are linked to the carboxy terminus of a glucagon peptide of the present disclosure. These fusion proteins are anticipated to have pharmacological activity for suppressing appetite and inducing weight loss/weight maintenance. In accordance with one embodiment a glucagon agonist analog of SEQ ID NO: 33 or SEQ ID NO: 20, further comprising the amino acid sequence of SEQ ID NO: 26 (GPSSGAPPPS) or SEQ ID NO: 29 linked to amino acid 29 of the glucagon peptide, is administered to individuals to induce weight loss or prevent weight gain. More particularly, the glucagon peptide comprises a sequence selected from the group consisting of SEQ ID NO: 10, SEQ ID NO: 12, SEQ ID NO: 13 SEQ ID NO: 14, SEQ ID NO: 15, SEQ ID NO: 16, SEQ ID NO: 17, SEQ ID NO: 18, SEQ ID NO: 66, SEQ ID NO: 67, SEQ ID NO: 68, SEQ ID NO: 69, SEQ ID NO: 55 and SEQ ID NO: 56 further comprising the amino acid sequence of SEQ ID NO: 26 (GPSSGAPPPS) or SEQ ID NO: 29 linked to amino acid 29 of the glucagon peptide. In one embodiment the administered glucagon peptide analog comprises the sequence of SEQ ID NO: 64.

Multimers

The present disclosure also encompasses multimers of the modified glucagon peptides disclosed herein. Two or more of the modified glucagon peptides can be linked together using standard linking agents and procedures known to those skilled in the art. For example, dimers can be formed between two modified glucagon peptides through the use of bifunctional thiol crosslinkers and bi-functional amine crosslinkers, particularly for the glucagon peptides that have been substituted with cysteine, lysine ornithine, homocysteine or acetyl phenylalanine residues (e.g. SEQ ID NO: 3 and SEQ ID NO: 4). The dimer can be a homodimer or alternatively can be a heterodimer. In certain embodiments, the linker connecting the two (or more) glucagon peptides is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects of the invention, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

In one embodiment the dimer comprises a homodimer of a glucagon fusion peptide wherein the glucagon peptide portion comprises SEQ ID NO: 11 or SEQ ID NO: 20 and an amino acid sequence of SEQ ID NO: 26 (GPSSGAPPPS), SEQ ID NO: 27 (KRNRNNIA) or SEQ ID NO: 28 (KRNR) linked to amino acid 29 of the glucagon peptide. In another embodiment the dimer comprises a homodimer of a glucagon agonist analog of SEQ ID NO: 11, wherein the glucagon peptide further comprises a polyethylene glycol chain covalently bound to position 21 or 24 of the glucagon peptide.

In accordance with one embodiment a dimer is provided comprising a first glucagon peptide bound to a second glucagon peptide via a linker, wherein the first glucagon peptide comprises a peptide selected from the group consisting of SEQ ID NO: 8, SEQ ID NO: 9, SEQ ID NO: 10 and SEQ ID NO: 11 and the second glucagon peptide comprises SEQ ID NO: 20. In accordance with another embodiment a dimer is provided comprising a first glucagon peptide bound to a second glucagon peptide via a linker, wherein said first glucagon peptide comprises a sequence selected from the group consisting of SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11 and the second glucagon peptide comprise SEQ ID NO: 11, and pharmaceutically acceptable salts of said glucagon polypeptides. In accordance with another embodiment a dimer is provided comprising a first glucagon peptide bound to a second glucagon peptide via a linker, wherein said first glucagon peptide is selected from the group consisting of SEQ ID NO: 11, SEQ ID NO: 12, SEQ ID NO: 13 SEQ ID NO: 14, SEQ ID NO: 15, SEQ ID NO: 16, SEQ ID NO: 17 and SEQ ID NO: 18 and the second glucagon peptide is independently selected from the group consisting of SEQ ID NO: 11, SEQ ID NO: 12, SEQ ID NO: 13 SEQ ID NO: 14, SEQ ID NO: 15, SEQ ID NO: 16, SEQ ID NO: 17 and SEQ ID NO: 18, and pharmaceutically acceptable salts of said glucagon polypeptides. In one embodiment the first glucagon peptide is selected from the group consisting of SEQ ID NO: 20 and the second glucagon peptide is independently selected from the group consisting of SEQ ID NO: 8, SEQ ID NO: 9 and SEQ ID NO: 11. In one embodiment the dimer is formed between two peptides wherein each peptide comprises the amino acid sequence of SEQ ID NO: 11.

Kits

The modified glucagon peptides of the present invention can be provided in accordance with one embodiment as part of a kit. In one embodiment a kit for administering a glucagon agonist to a patient in need thereof is provided wherein the kit comprises a modified glucagon peptide selected from the group consisting of 1) a glucagon peptide comprising the sequence of SEQ ID NO: 20, SEQ ID NO: 9, SEQ ID NO: 10 or SEQ ID NO:11; 2) a glucagon fusion peptide comprising a glucagon agonist analog of SEQ ID NO: 11, SEQ ID NO: 20 or SEQ ID NO: 55, and an amino acid sequence of SEQ ID NO: 26 (GPSSGAPPPS), SEQ ID NO: 27 (KRNRNNIA) or SEQ ID NO: 28 (KRNR) linked to amino acid 29 of the glucagon peptide; and 3) a pegylated glucagon peptide of SEQ ID NO: 11 or SEQ ID NO: 51, further comprising an amino acid sequence of SEQ ID NO: 26 (GPSSGAPPPS), SEQ ID NO: 27 (KRNRNNIA) or SEQ ID NO: 28 (KRNR) linked to amino acid 29 of the glucagon peptide, wherein the PEG chain covalently bound to position 17, 21 or 24 has a molecular weight of about 500 to about 40,000 Daltons. In one embodiment the kit comprise a glucagon/GLP-1 co-agonist wherein the peptide comprises a sequence selected from the group consisting of SEQ ID NO: 11, SEQ ID NO: 12, SEQ ID NO: 13 SEQ ID NO: 14, SEQ ID NO: 15, SEQ ID NO: 16, SEQ ID NO: 17 and SEQ ID NO: 18.

In one embodiment the kit is provided with a device for administering the glucagon composition to a patient, e.g. syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the glucagon peptide in a lyophilized form or in an aqueous solution. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the sterile glucagon composition is prepackaged within the syringe.

Pharmaceutical Formulations

In accordance with one embodiment a pharmaceutical composition is provided wherein the composition comprises a glucadon peptide of the present disclosure, or pharmaceutically acceptable salt thereof, and a pharmaceutically acceptable carrier. The pharmaceutical composition can comprise any pharmaceutically acceptable ingredient, including, for example, acidifying agents, additives, adsorbents, aerosol propellants, air displacement agents, alkalizing agents, anti-caking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edetate, disodium edetate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

The pharmaceutical formulations disclosed herein may be designed to be short-acting, fast-releasing, long-acting, or sustained-releasing as described below. The pharmaceutical formulations may also be formulated for immediate release, controlled release or for slow release. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capabale of buffering at the desired pH such as, for example, phosphate buffers (e.g. PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g. at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Position 3 Modification

Any of the glucagon peptides, including glucagon analogs, glucagon agonist analogs, glucagon co-agonists, and glucagon/GLP-1 co-agonist molecules, described herein may be modified to contain a modification at position 3, e.g., Gln substituted with Glu, to produce a peptide with high selectivity, e.g., tenfold selectivity, for the GLP-1 receptor as compared to the selectivity for the glucagon receptor.

Any of the glucagon peptides, including glucagon analogs, glucagon agonist analogs, glucagon co-agonists, and glucagon/GLP-1 co-agonist molecules, described herein may be modified to contain a modification at position 3, e.g., Gln substituted with a glutamine analog (e.g. Dab(Ac)), without a substantial loss of activity at the glucagon receptor, and in some cases, with an enhancement of glucagon receptor activity.

Preparation Methods

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXAMPLES

General Synthesis Protocol

Glucagon analogs were synthesized using HBTU-activated "Fast Boc" single coupling starting from 0.2 mmole of Boc Thr(OBzl)Pam resin on a modified Applied Biosystem 430 A peptide synthesizer. Boc amino acids and HBTU were obtained from Midwest Biotech (Fishers, Ind.). Side chain protecting groups used were: Arg(Tos), Asn(Xan), Asp(OcHex), Cys(pMeBzl), His(Bom), Lys(2Cl-Z), Ser(OBzl), Thr(OBzl), Tyr(2Br-Z), and Trp(CHO). The side-chain protecting group on the N-terminal His was Boc.

Each completed peptidyl resin was treated with a solution of 20% piperidine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-maleimido)

Typically, the glucagon Cys analog is dissolved in phosphate buffered saline (5-10 mg/ml) and 0.01M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated analogs.

Example 1

Synthesis of Glucagon $Cys^{17}$(1-29) and Similar MonoCys Analogs 0.2 mmole Boc Thr(OBzl) Pam resin (SynChem Inc) in a 60 ml reaction vessel and the following sequence was entered and run on a modified Applied Biosystems 430A Peptide Synthesizer using FastBoc HBTU-activated single couplings.

HSQGTFTSDYSKYLDSCRAQDFVQWLMNT    (SEQ ID NO: 35)

The following side chain protecting groups were used: Arg(Tos), Asp(OcHex), Asn(Xan), Cys(pMeBzl), Glu(OcHex), His(Boc), Lys(2Cl-Z), Ser(Bzl), Thr(Bzl), Trp(CHO), and Tyr(Br-Z). The completed peptidyl resin was treated with 20% piperidine/dimethylformamide to remove the Trp formyl protection then transferred to an HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] with a small sample of the cleavage extract. The remaining extract was loaded onto a 2.2×25 cm Kromasil C18 preparative reverse phase column and an acetonitrile gradient was run using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min.

The fractions containing the purest product (48-52) were combined frozen, and lyophilized to give 30.1 mg. An HPLC analysis of the product demonstrated a purity of >90% and MALDI mass spectral analysis demonstrated the desired mass of 3429.7. Glucagon $Cys^{21}$, Glucagon $Cys^{24}$, and Glucagon $Cys^{29}$ were similarly prepared.

Example 2

Synthesis of Glucagon-Cex and Other C-Terminal Extended Analogs.

285 mg (0.2 mmole) methoxybenzhydrylamine resin (Midwest Biotech) was placed in a 60 ml reaction vessel and the following sequence was entered and run on a modified Applied Biosystems 430A peptide synthesizer using FastBoc HBTU-activated single couplings.

(SEQ ID NO: 36)
HSQGTFTSDYSKYLDSRRAQDFVQWLMNTGPSSGAPPPS

The following side chain protecting groups were used: Arg (Tos), Asp(OcHex), Asn(Xan), Cys(pMeBzl), Glu(OcHex), His(Boc), Lys(2Cl-Z), Ser(Bzl), Thr(Bzl), Trp(CHO), and Tyr(Br-Z). The completed peptidyl resin was treated with 20% piperidine/dimethylformamide to remove the Trp formyl protection then transferred to HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 mL/min, 45 C, 214 nm, A buffer of 0.1% TFA, B buffer of 0.1% TFA/90% ACN, gradient=10% B to 80% B over 10 min.] on an aliquot of the cleavage extract. The extract was loaded onto a 2.2×25 cm Kromasil C18 preparative reverse phase column and an acetonitrile gradient was run for elution using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min. Fractions 58-65 were combined, frozen and lyophilized to give 198.1 mg.

HPLC analysis of the product showed a purity of greater than 95%. MALDI mass spectral analysis showed the presence of the desired theoretical mass of 4316.7 with the product as a C-terminal amide. Oxyntomodulin and oxyntomodulin-KRNR were similarly prepared as the C-terminal carboxylic acids starting with the appropriately loaded PAM-resin.

Example 3

Glucagon $Cys^{17}$ Mal-PEG-5K 15.1 mg of Glucagon $Cys^{17}$(1-29) and 27.3 mg methoxy poly(ethyleneglycol) maleimide avg. M.W.5000 (mPEG-Mal-5000,Nektar Therapeutics) were dissolved in 3.5 ml phosphate buffered saline (PBS) and 0.5 ml 0.01M ethylenediamine tetraacetic acid (EDTA) was added. The reaction was stirred at room temperature and the progress of the reaction was monitored by HPLC analysis [0.46×5 cm Zorbax C8, 1 ml/min,45 C, 214 nm (0.5 A), A=0.1% TFA, B=0.1% TFA/90% ACN, gradient=10% B to 80% B over 10 min.].

After 5 hours, the reaction mixture was loaded onto 2.2×25 cm Kromasil C18 preparastive reverse phase column. An acetonitrile gradient was run on a Pharmacia FPLC while monitoring the UV wavelength at 214 nm and collecting 5 min fractions. A=0.1% TFA, B=0.1% TFA/50% acetonitrile, gradient=30% B to 100% B over 450 min. The fractions corresponding to the product were combined, frozen and lyophilized to give 25.9 mg.

This product was analyzed on HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] which showed a purity of aprox. 90%. MALDI (matrix assisted laser desorption ionization) mass spectral analysis showed a broad mass range (typical of PEG derivatives) of 8700 to 9500. This shows an addition to the mass of the starting glucagon peptide (3429) of approximately 5,000 a.m.u.

Example 4

Glucagon $Cys^{21}$ Mal-PEG-5K 21.6 mg of Glucagon $Cys^{21}$(1-29) and 24 mg mPEG-MAL-5000 (Nektar Therapeutics) were dissolved in 3.5 ml phosphate buffered saline (PBS) and 0.5 ml 0.01-Methylene diamine tetraacetic acid (EDTA) was added. The reaction was stirred at room temp. After 2 hrs, another 12.7 mg of mPEG-MAL-5000 was added. After 8 hrs, the reaction mixture was loaded onto a 2.2×25 cm Vydac C18 preparative reverse phase column and an acetonitrile gradient was run on a Pharmacia FPLC at 4 ml/min while collecting 5 min fractions. A=0.1% TFA, B=0.1% TFA/50% ACN. Gradient=20% to 80% B over 450 min.

The fractions corresponding to the appearance of product were combined frozen and lyophilized to give 34 mg. Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a homogeneous product that was different than starting glucagon peptide. MALDI (matrix assisted laser desorption ionization) mass spectral analysis showed a broad mass range (typical of PEG analogs) of 8700 to 9700. This shows an addition to the mass of the starting glucagon peptide (3470) of approximately 5,000 a.m.u.

Example 5

Glucagon $Cys^{24}$ Mal-PEG-5K 20.1 mg Glucagon $C^{24}$(1-29) and 39.5 mg mPEG-Mal-5000 (Nektar Therapeutics) were dissolved in 3.5 ml PBS with stirring and 0.5 ml 0.01M EDTA was added. The reaction was stirred at room temp for 7 hrs, then another 40 mg of mPEG-Mal-5000 was added. After approximately 15 hr, the reaction mixture was loaded onto a 2.2×25 cm Vydac C18 preparative reverse phase column and an acetonitrile gradient was run using a Pharmacia FPLC. 5 min. fractions were collected while monitoring the UV at 214 nm (2.0 A). A buffer=0.1% TFA, B buffer=0.1% TFA/50% ACN, gradient=30% B to 100% B over 450 min. The fractions corresponding to product were combined, frozen and lyophilized to give 45.8 mg. MALDI mass spectral analysis showed a typical PEG broad signal with a maximum at 9175.2 which is approximately 5,000 a.m.u. more than Glucagon $C^{24}$ (3457.8).

Example 6

Glucagon $Cys^{24}$ Mal-PEG-20K 25.7 mg of Glucagon $Cys^{24}$(1-29) and 40.7 mg mPEG-Mal-20K (Nektar Therapeutics) were dissolved in 3.5 ml PBS with stirring at room temp. and 0.5 ml 0.01 M EDTA was added. After 6 hrs, the ratio of starting material to product was aprox. 60:40 as determined by HPLC. Another 25.1 mg of mPEG-Mal-20K was added and the reaction allowed to stir another 16 hrs. The product ratio had not significantly improved, so the reaction mixture was loaded onto a 2.2×25 cm Kromasil C18 preparative reverse phase column and purified on a Pharmacia FPLC using a gradient of 30% B to 100% B over 450 min. A buffer=0.1% TFA, B buffer=0.1% TFA/50% ACN, flow=4 ml/min, and 5 min fractions were collected while monitoring the UV at 214 nm (2.0 A). The fractions containing homogeneous product were combined, frozen and lyophilized to give 25.7 mg. Purity as determined by analytical HPLC was ~90%. A MALDI mass spectral analysis showed a broad peak from 23,000 to 27,000 which is approximately 20,000 a.m.u. more than starting Glucagon $C^{24}$ (3457.8).

Example 7

Glucagon Cys[29] Mal-PEG-5K 20.0 mg of Glucagon Cys[29](1-29) and 24.7 mg mPEG-Mal-5000 (Nektar Therapeutics) were dissolved in 3.5 ml PBS with stirring at room temperature and 0.5 ml 0.01M EDTA was added. After 4 hr, another 15.6 mg of mPEG-Mal-5000 was added to drive the reaction to completion. After 8 hrs, the reaction mixture was loaded onto a 2.2×25 cm Vydac C18 preparative reverse phase column and an acetonitrile gradient was run on a Pharmacia FPLC system. 5 min fractions were collected while monitoring the UV at 214 nm (2.0 A). A=0.1% TFA, B=0.1% TFA/50% ACN. Fractions 75-97 were combined frozen and lyophilized to give 40.0 mg of product that is different than recovered starting material on HPLC (fractions 58-63). Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a purity greater than 95%.

MALDI mass spectral analysis showed the presence of a PEG component with a mass range of 8,000 to 10,000 (maximum at 9025.3) which is 5,540 a.m.u. greater than starting material (3484.8).

Example 8

Glucagon Cys[24] (2-butyrolactone)

To 24.7 mg of Glucagon Cys[24](1-29) was added 4 ml 0.05M ammonium bicarbonate/50% acetonitrile and 5.5 ul of a solution of 2-bromo-4-hydroxybutyric acid-γ-lactone (100 ul in 900 ul acetonitrile). After 3 hrs of stirring at room temperature, another 105 ul of lactone solution was added to the reaction mixture which was stirred another 15 hrs. The reaction mixture was diluted to 10 ml with 10% aqueous acetic acid and was loaded onto a 2.2×25 cm Kromasil C18 preparative reverse phase column. An acetonitrile gradient (20% B to 80% B over 450 min) was run on a Pharmacia FPLC while collecting 5 min fractions and monitoring the UV at 214 nm (2.0 A). Flow=4 mL/min, A=0.1% TFA, B=0.1% TFA/50% ACN. Fractions 74-77 were combined frozen and lyophilized to give 7.5 mg. HPLC analysis showed a purity of 95% and MALDI mass spect analysis showed a mass of 3540.7 or 84 mass units more than starting material. This result is consistent with the addition of a single butyrolactone moiety.

Example 9

Glucagon Cys[24](S-carboxymethyl)

18.1 mg of Glucagon Cys[24](1-29) was dissolved in 9.4 ml 0.1M sodium phosphate buffer (pH=9.2) and 0.6 ml bromoacetic acid solution (1.3 mg/ml in acetonitrile) was added. The reaction was stirred at room temperature and the reaction progress was followed by analytical HPLC. After 1 hr another 0.1 ml bromoacetic acid solution was added. The reaction was stirred another 60 min. then acidified with aqueous acetic acid and was loaded onto a 2.2×25 cm Kromasil C18 preparative reverse phase column for purification. An acetonitrile gradient was run on a Pharmacia FPLC (flow=4 ml/min) while collecting 5 min fractions and monitoring the UV at 214 nm (2.0 A). A=0.1% TFA, B=0.1% TFA/50% ACN. Fractions 26-29 were combined frozen and lyophilized to give several mg of product. Analytical HPLC showed a purity of 90% and MALDI mass spectral analysis confirmed a mass of 3515 for the desired product.

SEQ ID NO: 38

Molecular Weight = 3515.87
Exact Mass = 3512
Molecular Formula = C153H224N42O50S2

Example 10

Glucagon Cys[24] maleimido,PEG-3.4K-dimer 16 mg Glucagon Cys[24] and 1.02 mg Mal-PEG-Mal-3400, poly(ethyleneglycol)-bis-maleimide avg. M.W. 3400, (Nektar Therapeutics) were dissolved in 3.5 phosphate buffered saline and 0.5 ml 0.01M EDTA and the reaction was stirred at room temperature. After 16 hrs, another 16 mg of Glucagon Cys[24] was added and the stirring continued. After approximately 40 hrs, the reaction mixture was loaded onto a Pharmcia PepRPC 16/10 column and an acetonitrile gradient was run on a Pharmacia FPLC while collecting 2 min fractions and monitoring the UV at 214 nm (2.0 A). Flow=2 ml/min, A=0.1% TFA, B=0.1% TFA/50% ACN. Fractions 69-74 were combined frozen and lyophilized to give 10.4 mg. Analytical HPLC showed a purity of 90% and MALDI mass spectral analysis shows a component in the 9500-11,000 range which is consistent with the desired dimer.

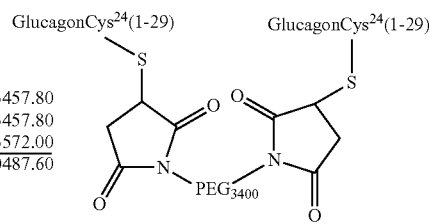

Example 11

Synthesis of Glucagon Lactams 285 mg (0.2 mmole) methoxybenzhydrylamine resin (Midwest Biotech) was added to a 60 mL reaction vessels and the following sequence was assembled on a modified Applied Biosystems 430A peptide synthesizer using Boc DEPBT-activated single couplings.

```
                      (12-16 Lactam; SEQ ID NO: 12)
HSQGTFTSDYSKYLDERRAQDFVQWLMNT-NH2
```

The following side chain protecting groups were used: Arg(Tos), Asp(OcHx), Asn(Xan), Glu(OFm), His(BOM), Lys(Fmoc), Ser(Bzl), Thr(Bzl), Trp(CHO), Tyr(Br-Z). Lys (Cl-Z) was used at position 12 if lactams were constructed from 16-20, 20-24, or 24-28. The completed peptidyl resin was treated with 20% piperidine/dimethylformamide for one hour with rotation to remove the Trp formyl group as well as the Fmoc and OFm protection from Lys12 and Glu16. Upon confirmation of removal by a positive ninhydrin test, the resin was washed with dimethylformamide, followed by dichloromethane and than again with dimethylformamide. The resin was treated with 520 mg (1 mmole) Benzotriazole-1-yl-oxy-tris-pyrrolidino-phosphonium hexafluorophosphate (PyBOP) in dimethylformamide and diisopropylethylamine (DIEA). The reaction proceeded for 8-10 hours and the cyclization was confirmed by a negative ninhydrin reaction. The resin was washed with dimethylformamide, followed by dichloromethane and subsequently treated with trifluoroacetic acid for 10 minutes. The removal of the Boc group was confirmed by a positive ninhydrin reaction. The resin was washed with dimethylformamide and dichloromethane and dried before being transferred to a hydrofluoric acid (HF) reaction vessel. 500 µL p-cresol was added along with a magnetic stir bar. The vessel was attached to the HF apparatus (Peninsula Labs), cooled in a dry ice/methanol bath, evacuated, and approximately 10 mL of liquid hydrofluoric acid was condensed into the vessel. The reaction was stirred for 1 hour to in an ice bath and the HF was subsequently removed in vacuo. The residue was suspended in ethyl ether; the solids were filtered, washed with ether, and the peptide was solubilized with 150 mL 20% acetonitrile/1% acetic acid.

An analytical HPLC analysis of the crude solubilized peptide was conducted under the following conditions [4.6×30 mm Xterra C8, 1.50 mL/min, 220 nm, A buffer 0.1% TFA/10% ACN, B buffer 0.1% TFA/100% ACN, gradient 5-95% B over 15 minutes]. The extract was diluted twofold with water and loaded onto a 2.2×25 cm Vydac C4 preparative reverse phase column and eluted using an acetonitrile gradient on a Waters HPLC system (A buffer of 0.1% TFA/10% ACN, B buffer of 0.1% TFA/10% CAN and a gradient of 0-100% B over 120 minutes at a flow of 15.00 ml/min. HPLC analysis of the purified peptide demonstrated greater than 95% purity and electrospray ionization mass spectral analysis confirmed a mass of 3506 Da for the 12-16 lactam. Lactams from 16-20, 20-24, and 24-28 were prepared similarly.

Example 12

Glucagon Solubility Assays:

A solution (1 mg/ml or 3 mg/ml) of glucagon (or an analog) is prepared in 0.01N HCl. 100 ul of stock solution is diluted to 1 ml with 0.01 N HCl and the UV absorbance (276 nm) is determined. The pH of the remaining stock solution is adjusted to pH7 using 200-250 ul 0.1M $Na_2HPO_4$ (pH9.2). The solution is allowed to stand overnight at 4° C. then centrifuged. 100 ul of supernatant is then diluted to 1 ml with 0.01 N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Results are shown in Table 1 wherein Glucagon-Cex represents wild type glucagon (SEQ ID NO: 1) plus a carboxy terminal addition of SEQ ID NO: 26 and Glucagon-Cex $R^{12}$ represents SEQ ID NO: 39.

TABLE 1

Solubility date for glucagon analogs

| Analog | Percent Soluble |
|---|---|
| Glucagon | 16 |
| Glucagon-Cex, R12 | 104 |
| Glucagon-Cex | 87 |
| Oxyntomodulin | 104 |
| Glucagon, Cys17PEG5K | 94 |
| Glucagon, Cys21PEG5K | 105 |
| Glucagon, Cys24PEG5K | 133 |

Example 13

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (3-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following: % Specific Binding=((Bound-NSB)/(Total bound−NSB))× 100. $IC_{50}$ values were determined by using Origin software (OriginLab, Northampton, Mass.).

Example 14

Functional Assay-cAMP Synthesis

The ability of glucagon analogs to induce cAMP was measured in a firefly luciferase-based reporter assay. HEK293 cells co-transfected with either glucagon- or GLP-1 receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass. Results are shown in FIGS. 3-9 and in Tables 2 through 10.

TABLE 2 cAMP Induction by Glucagon Analogs with C-Terminus Extension

| | cAMP Induction | | | |
|---|---|---|---|---|
| | Glucagon Receptor | | GLP-1 Receptor | |
| Peptide | $EC_{50}$, nM | N* | $EC_{50}$, nM | N* |
| Glucagon | 0.22 ± 0.09 | 14 | 3.85 ± 1.64 | 10 |
| GLP-1 | 2214.00 ± 182.43 | 2 | 0.04 ± 0.01 | 14 |
| Glucagon Cex | 0.25 ± 0.15 | 6 | 2.75 ± 2.03 | 7 |
| Oxyntomodulin | 3.25 ± 1.65 | 5 | 2.53 ± 1.74 | 5 |
| Oxyntomodulin KRNR | 2.77 ± 1.74 | 4 | 3.21 ± 0.49 | 2 |
| Glucagon R12 | 0.41 ± 0.17 | 6 | 0.48 ± 0.11 | 5 |
| Glucagon R12 Cex | 0.35 ± 0.23 | 10 | 1.25 ± 0.63 | 10 |
| Glucagon R12 K20 | 0.84 ± 0.40 | 5 | 0.82 ± 0.49 | 5 |
| Glucagon R12 K24 | 1.00 ± 0.39 | 4 | 1.25 ± 0.97 | 5 |
| Glucagon R12 K29 | 0.81 ± 0.49 | 5 | 0.41 ± 0.24 | 6 |
| Glucagon Amide | 0.26 ± 0.15 | 3 | 1.90 ± 0.35 | 2 |
| Oxyntomodulin C24 | 2.54 ± 0.63 | 2 | 5.27 ± 0.26 | 2 |
| Oxyntomodulin C24 PEG 20K | 0.97 ± 0.04 | 1 | 1.29 ± 0.11 | 1 |

*number of experiments

TABLE 3 cAMP Induction by Pegylated Glucagon Analogs

| | cAMP Induction | | | |
|---|---|---|---|---|
| | Glucagon Receptor | | GLP-1 Receptor | |
| Peptide | $EC_{50}$, nM | N* | $EC_{50}$, nM | N* |
| Glucagon | 0.33 ± 0.23 | 18 | 12.71 ± 3.74 | 2 |
| Glucagon C17 PEG 5K | 0.82 ± 0.15 | 4 | 55.86 ± 1.13 | 2 |
| Glucagon C21 PEG 5K | 0.37 ± 0.16 | 6 | 11.52 ± 3.68 | 2 |
| Glucagon C24 PEG 5K | 0.22 ± 0.10 | 12 | 13.65 ± 2.95 | 4 |
| Glucagon C29 PEG 5K | 0.96 ± 0.07 | 2 | 12.71 ± 3.74 | 2 |
| Glucagon C24 PEG 5K | 0.08 ± 0.05 | 3 | Not determined | |
| Glucagon C24 Dimer | 0.10 ± 0.05 | 3 | Not determined | |
| GLP-1 | >1000 | | 0.05 ± 0.02 | 4 |

*-number of experiments

TABLE 4 cAMP Induction by E16 Glucagon Analogs
Percent Potency Relative to Native Ligand

| Peptide | GRec | GLP-1Rec |
|---|---|---|
| E16 Gluc-NH2 | 187.2 | 17.8 |
| Glucagon | 100.0 | 0.8 |
| Gluc-NH2 | 43.2 | 4.0 |
| NLeu3, E16 Gluc-NH2 | 7.6 | 20.6 |
| E3, E16 Gluc-NH2 | 1.6 | 28.8 |
| Orn3, E16 Gluc-NH2 | 0.5 | 0.1 |
| GLP-1 | <0.1 | 100 |

TABLE 5 cAMP Induction by E16 Glucagon Analogs
Percent Potency Relative to Native Ligand

| Peptide | GRec | GLP-1Rec |
|---|---|---|
| E16 Gluc-NH2 | 187.2 | 17.8 |
| E15, E16 Gluc-NH2 | 147.0 | 9.2 |
| E16, K20 Gluc-NH2 | 130.1 | 41.5 |
| Gluc-NH2 | 43.2 | 4.0 |

TABLE 6

EC50 values for cAMP Induction by E16 Glucagon Analogs

| | Glucagon Receptor | | | GLP-1 Receptor | | |
|---|---|---|---|---|---|---|
| Peptide | EC50 (nM) | StDev | n | EC50 (nM) | StDev | n |
| Glucagon | 0.28 | 0.14 | 10 | 4.51 | N/A | 1 |
| Glucagon-NH2 | 0.53 | 0.33 | 8 | 1.82 | 0.96 | 5 |
| E16 Gluc-NH2 | 0.07 | 0.07 | 10 | 0.16 | 0.14 | 10 |
| E16, G30 Gluc-NH2 | 0.41 | 0.36 | 5 | 0.24 | 0.10 | 5 |
| E16, G30 Gluc-Cex | 0.51 | 0.46 | 5 | 1.19 | 0.86 | 5 |
| GLP-1 | 2214 | N/A | 1 | 0.03 | 0.02 | 9 |

TABLE 7

EC50 values for cAMP Induction by E16 Glucagon Analogs

| | Glucagon Receptor EC50 | | | GLP-1 Receptor EC50 | | |
|---|---|---|---|---|---|---|
| Peptide | (nM) | StDev | n | (nM) | StDev | n |
| E16 Glucagon NH2 | 0.07 | 0.07 | 10 | 0.16 | 0.14 | 10 |
| hCSO$_3$16 Glucagon-NH2 | 0.25 | 0.12 | 2 | 0.19 | 0.02 | 2 |
| hE16 Glucagon-NH2 | 0.17 | 0.08 | 2 | 0.25 | 0.03 | 2 |
| H16 Glucagon-NH2 | 0.45 | 0.3 | 2 | 0.38 | 0.11 | 2 |
| Q16 Glucagon-NH2 | 0.22 | 0.1 | 2 | 0.39 | 0.08 | 2 |
| D16 Glucagon-NH2 | 0.56 | 0.15 | 2 | 0.93 | 0.28 | 2 |
| (S16) Glucagon-NH2 | 0.53 | 0.33 | 8 | 1.82 | 0.96 | 5 |

TABLE 8

EC50 values for cAMP Induction by E16 Glucagon Analogs

| | Glucagon Receptor | | | GLP-1 Receptor | | |
|---|---|---|---|---|---|---|
| Peptide | EC50 (nM) | StD | n | EC50 (nM) | StDev | n |
| E16 Glucagon NH2 | 0.07 | 0.07 | 10 | 0.16 | 0.14 | 10 |
| T16 Glucagon NH2 | 0.10 | 0.02 | 3 | 1.99 | 0.48 | 3 |
| G16 Glucagon NH2 | 0.10 | 0.01 | 3 | 2.46 | 0.60 | 3 |
| Glucagon NH2 | 0.53 | 0.33 | 4 | 1.82 | 0.96 | 5 |
| GLP-1 | 2214 | N/A | 1 | 0.03 | 0.02 | 9 |

E16 Gluc NH$_2$ was 4-fold more potent at the glucagon receptor relative to G16-COOH and T16 Gluc NH$_2$, when the compounds were tested side by side.

TABLE 9 cAMP Induction by E16/Lactam Glucagon Analogs
Percent Potency Relative to Native Ligand

| Peptide | GRec | GLP-1Rec |
|---|---|---|
| E24K28 Gluc-NH2 Lac | 196.4 | 12.5 |
| E16K20 Gluc-NH2 Lac | 180.8 | 63.0 |
| K12E16 Gluc-NH2 Lac | 154.2 | 63.3 |
| K20E24 Gluc-NH2 Lac | 120.2 | 8.1 |
| E16 Gluc-NH2 | 187.2 | 17.8 |
| E16, K20 Gluc-NH2 | 130.1 | 41.5 |
| Glucagon | 100.0 | 0.8 |
| Gluc-NH2 | 43.2 | 4.0 |

TABLE 10 cAMP Induction by GLP-1 17-26 Glucagon Analogs

| Peptide | Glucagon Receptor EC50(nM) | StD | GLP-1 Receptor EC50(nM) | StD |
|---|---|---|---|---|
| GLP-1 | | | 0.023 | 0.002 |
| Gluc-NH2 | 0.159 | 0.023 | | |
| E16 GLP-1 | | | 0.009 | 0.000 |
| E16 Glucagon-NH2 | 0.072 | 0.007 | | |
| E16 GLP(17-26)Glu(27-29)-NH2 | 0.076 | 0.004 | 0.014 | 0.001 |
| E16 GLP(17-29)-NH2 | 0.46 | 0.023 | 0.010 | 0.000 |
| E16 GLP(17-29)-NH2 E24, K28 | 0.23 | 0.020 | 0.007 | |
| E16 GLP(17-29)-NH2 E24, K28 Lactam | 0.16 | 0.017 | 0.007 | 0.000 |

Example 15

Stability Assay for Glucagon Cys-maleimido PEG Analogs

Each glucagon analog was dissolved in water or PBS and an initial HPLC analysis was conducted. After adjusting the pH (4, 5, 6, 7), the samples were incubated over a specified time period at 37° C. and re-analyzed by HPLC to determine the integrity of the peptide. The concentration of the specific peptide of interest was determined and the percent remaining intact was calculated relative to the initial analysis. Results for Glucagon $Cys^{21}$-maleimidoPEG$_{5K}$ are shown in FIGS. 1 and 2.

Example 16

The following glucagon peptides are constructed generally as described above in Examples 1-11:
In all of the following sequences, "a" means a C-terminal amide.

```
                                      (SEQ ID NO: 70)
HSQGT FTSDY SKYLD ERRAQ DFVQW LMNTa (SEQ ID NO: 71)
HSQGT FTSDY SKYLD ERRAK DFVQW LMNTa (lactam @ 16-20; SEQ ID NO: 72)
HSQGT FTSDY SKYLD ERRAK DFVQW LMNTa (lactam @ 12-16; SEQ ID NO: 73)
HSQGT FTSDY SKYLD ERRAQ DFVQW LMNTa (lactam @ 12-16; SEQ ID NO: 74)
HSQGT FTSDY SKYLD ERRAK DFVQW LMNTa (lactam @ 16-20; SEQ ID NO: 75)
HSQGT FTSDY SKYLD KRRAE DFVQW LMNTa (SEQ ID NO: 76)
HSQGT FTSDY SKYLD ERAAK DFVQW LMNTa (lactam @ 16-20; SEQ ID NO: 77)
HSQGT FTSDY SKYLD ERAAK DFVQW LMNTa (lactam @ 12-16; SEQ ID NO: 78)
HSQGT FTSDY SKYLD ERAAQ DFVQW LMNTa (lactam @ 12-16; SEQ ID NO: 79)
HSQGT FTSDY SKYLD ERAAK DFVQW LMNTa (lactam @ 16-20; SEQ ID NO: 80)
HSQGT FTSDY SKYLD KRAAE DFVQW LMNTa (SEQ ID NO: 81)
HSQGT FTSDY SKYLD EQAAK EFIAW LMNTa (lactam @ 12-16; SEQ ID NO: 82)
HSQGT FTSDY SKYLD EQAAK EFIAW LMNTa (lactam @ 16-20; SEQ ID NO: 83)
HSQGT FTSDY SKYLD EQAAK EFIAW LMNTa (SEQ ID NO: 84)
HSQGT FTSDY SKYLD EQAAK EFIAW LVKGa (lactam @ 12-16; SEQ ID NO: 85)
HSQGT FTSDY SKYLD EQAAK EFIAW LVKGa (lactam @ 16-20; SEQ ID NO: 86)
HSQGT FTSDY SKYLD EQAAK EFIAW LVKGa (SEQ ID NO: 87)
X1SQGT FTSDY SKYLD ERRAQ DFVQW LMNTa (SEQ ID NO: 88)
X1SQGT FTSDY SKYLD ERRAK DFVQW LMNTa (lactam @ 16-20; SEQ ID NO: 89)
X1SQGT FTSDY SKYLD ERRAK DFVQW LMNTa (lactam @ 12-16; SEQ ID NO: 90)
X1SQGT FTSDY SKYLD ERRAQ DFVQW LMNTa (lactam @ 12-16; SEQ ID NO: 91)
X1SQGT FTSDY SKYLD ERRAK DFVQW LMNTa (lactam @ 16-20; SEQ ID NO: 92)
X1SQGT FTSDY SKYLD KRRAE DFVQW LMNTa (SEQ ID NO: 93)
X1SQGT FTSDY SKYLD ERAAK DFVQW LMNTa (lactam @ 16-20; SEQ ID NO: 94)
X1SQGT FTSDY SKYLD ERAAK DFVQW LMNTa (lactam @ 12-16; SEQ ID NO: 95)
X1SQGT FTSDY SKYLD ERAAQ DFVQW LMNTa (lactam @ 12-16; SEQ ID NO: 96)
X1SQGT FTSDY SKYLD ERAAK DFVQW LMNTa (lactam @ 16-20; SEQ ID NO: 97)
X1SQGT FTSDY SKYLD KRAAE DFVQW LMNTa (SEQ ID NO: 98)
X1SQGT FTSDY SKYLD EQAAK EFIAW LMNTa (lactam @ 12-16; SEQ ID NO: 99)
X1SQGT FTSDY SKYLD EQAAK EFIAW LMNTa (lactam @ 16-20; SEQ ID NO: 100)
X1SQGT FTSDY SKYLD EQAAK EFIAW LMNTa (SEQ ID NO: 101)
X1SQGT FTSDY SKYLD EQAAK EFIAW LVKGa (lactam @ 12-16; SEQ ID NO: 102)
X1SQGT FTSDY SKYLD EQAAK EFIAW LVKGa
```

(lactam @ 16-20; SEQ ID NO: 103)
X1SQGT FTSDY SKYLD EQAAK EFIAW LVKGa
Wherein in the preceding sequences,
X1 = (Des-amino)His (SEQ ID NO: 104)
HX2QGT FTSDY SKYLD ERRAQ DFVQW LMNTa (SEQ ID NO: 105)
HX2QGT FTSDY SKYLD ERRAK DFVQW LMNTa (lactam @ 16-20; SEQ ID NO: 106)
HX2QGT FTSDY SKYLD ERRAK DFVQW LMNTa (lactam @ 12-16; SEQ ID NO: 107)
HX2QGT FTSDY SKYLD ERRAQ DFVQW LMNTa (lactam @ 12-16; SEQ ID NO: 108)
HX2QGT FTSDY SKYLD ERRAK DFVQW LMNTa (lactam @ 16-20; SEQ ID NO: 109)
HX2QGT FTSDY SKYLD KRRAE DFVQW LMNTa (SEQ ID NO: 110)
HX2QGT FTSDY SKYLD ERAAK DFVQW LMNTa (lactam @ 16-20; SEQ ID NO: 111)
HX2QGT FTSDY SKYLD ERAAK DFVQW LMNTa (lactam @ 12-16; SEQ ID NO: 112)
HX2QGT FTSDY SKYLD ERAAQ DFVQW LMNTa (lactam @ 12-16; SEQ ID NO: 113)
HX2QGT FTSDY SKYLD ERAAK DFVQW LMNTa (lactam @ 16-20; SEQ ID NO: 114)
HX2QGT FTSDY SKYLD KRAAE DFVQW LMNTa (SEQ ID NO: 115)
HX2QGT FTSDY SKYLD EQAAK EFIAW LMNTa (lactam @ 12-16; SEQ ID NO: 116)
HX2QGT FTSDY SKYLD EQAAK EFIAW LMNTa (lactam @ 16-20; SEQ ID NO: 117)
HX2QGT FTSDY SKYLD EQAAK EFIAW LMNTa (SEQ ID NO: 118)
HX2QGT FTSDY SKYLD EQAAK EFIAW LVKGa (lactam @ 12-16; SEQ ID NO: 119)
HX2QGT FTSDY SKYLD EQAAK EFIAW LVKGa (lactam @ 16-20; SEQ ID NO: 120)
HX2QGT FTSDY SKYLD EQAAK EFIAW LVKGa
Wherein in the preceding sequences
X2 = Aminoisobutyric acid (SEQ ID NO: 121)
HX2QGT FTSDY SKYLD ERRAQ DFVQW LMNTa (SEQ ID NO: 122)
HX2QGT FTSDY SKYLD ERRAK DFVQW LMNTa (lactam @ 16-20; SEQ ID NO: 123)
HX2QGT FTSDY SKYLD ERRAK DFVQW LMNTa (lactam @ 12-16; SEQ ID NO: 124)
HX2QGT FTSDY SKYLD ERRAQ DFVQW LMNTa (lactam @ 12-16; SEQ ID NO: 125)
HX2QGT FTSDY SKYLD ERRAK DFVQW LMNTa (lactam @ 16-20; SEQ ID NO: 126)
HX2QGT FTSDY SKYLD KRRAE DFVQW LMNTa (SEQ ID NO: 127)
HX2QGT FTSDY SKYLD ERAAK DFVQW LMNTa (lactam @ 16-20; SEQ ID NO: 128)
HX2QGT FTSDY SKYLD ERAAK DFVQW LMNTa (lactam @ 12-16; SEQ ID NO: 129)
HX2QGT FTSDY SKYLD ERAAQ DFVQW LMNTa (lactam @ 12-16; SEQ ID NO: 130)
HX2QGT FTSDY SKYLD ERAAK DFVQW LMNTa (lactam @ 16-20; SEQ ID NO: 131)
HX2QGT FTSDY SKYLD KRAAE DFVQW LMNTa (SEQ ID NO: 132)
HX2QGT FTSDY SKYLD EQAAK EFIAW LMNTa (lactam @ 12-16; SEQ ID NO: 133)
HX2QGT FTSDY SKYLD EQAAK EFIAW LMNTa (lactam @ 16-20; SEQ ID NO: 134)
HX2QGT FTSDY SKYLD EQAAK EFIAW LMNTa (SEQ ID NO: 135)
HX2QGT FTSDY SKYLD EQAAK EFIAW LVKGa (lactam @ 12-16; SEQ ID NO: 136)
HX2QGT FTSDY SKYLD EQAAK EFIAW LVKGa (lactam @ 16-20; SEQ ID NO: 137)
HX2QGT FTSDY SKYLD EQAAK EFIAW LVKGa
Wherein in the preceding sequences
X2 = (D-Ala)

(SEQ ID NO: 138)
HSEGT FTSDY SKYLD ERRAQ DFVQW LMNTa (SEQ ID NO: 139)
HSEGT FTSDY SKYLD ERRAK DFVQW LMNTa (lactam @ 16-20; SEQ ID NO: 140)
HSEGT FTSDY SKYLD ERRAK DFVQW LMNTa (lactam @ 12-16; SEQ ID NO: 141)
HSEGT FTSDY SKYLD ERRAQ DFVQW LMNTa (lactam @ 12-16; SEQ ID NO: 142)
HSEGT FTSDY SKYLD ERRAK DFVQW LMNTa (lactam @ 16-20; SEQ ID NO: 143)
HSEGT FTSDY SKYLD KRRAE DFVQW LMNTa (SEQ ID NO: 144)
HSEGT FTSDY SKYLD ERAAK DFVQW LMNTa (lactam @ 16-20; SEQ ID NO: 145)
HSEGT FTSDY SKYLD ERAAK DFVQW LMNTa (lactam @ 12-16; SEQ ID NO: 146)
HSEGT FTSDY SKYLD ERAAQ DFVQW LMNTa (lactam @ 12-16; SEQ ID NO: 147)
HSEGT FTSDY SKYLD ERAAK DFVQW LMNTa (lactam @ 16-20; SEQ ID NO: 148)
HSEGT FTSDY SKYLD KRAAE DFVQW LMNTa (SEQ ID NO: 149)
HSEGT FTSDY SKYLD EQAAK EFIAW LMNTa (lactam @ 12-16; SEQ ID NO: 150)
HSEGT FTSDY SKYLD EQAAK EFIAW LMNTa (lactam @ 16-20; SEQ ID NO: 151)
HSEGT FTSDY SKYLD EQAAK EFIAW LMNTa (SEQ ID NO: 152)
HSEGT FTSDY SKYLD EQAAK EFIAW LVKGa (lactam @ 12-16; SEQ ID NO: 153)
HSEGT FTSDY SKYLD EQAAK EFIAW LVKGa

```
                                               (SEQ ID NO: 154)
HSEGT FTSDY SKYLD EQAAK EFIAW LVKGa (SEQ ID NO: 155)
X1SEGT FTSDY SKYLD ERRAQ DFVQW LMNTa (SEQ ID NO: 156)
X1SEGT FTSDY SKYLD ERRAK DFVQW LMNTa (lactam @ 16-20; SEQ ID NO: 157)
X1SEGT FTSDY SKYLD ERRAK DFVQW LMNTa (lactam @ 12-16; SEQ ID NO: 158)
X1SEGT FTSDY SKYLD ERRAQ DFVQW LMNTa (lactam @ 12-16; SEQ ID NO: 159)
X1SEGT FTSDY SKYLD ERRAK DFVQW LMNTa (lactam @ 16-20; SEQ ID NO: 160)
X1SEGT FTSDY SKYLD KRRAE DFVQW LMNTa (SEQ ID NO: 161)
X1SEGT FTSDY SKYLD ERAAK DFVQW LMNTa (lactam @ 16-20; SEQ ID NO: 162)
X1SEGT FTSDY SKYLD ERAAK DFVQW LMNTa (lactam @ 12-16; SEQ ID NO: 163)
X1SEGT FTSDY SKYLD ERAAQ DFVQW LMNTa (lactam @ 12-16; SEQ ID NO: 164)
X1SEGT FTSDY SKYLD ERAAK DFVQW LMNTa (lactam @ 16-20; SEQ ID NO: 165)
X1SEGT FTSDY SKYLD KRAAE DFVQW LMNTa (SEQ ID NO: 166)
X1SEGT FTSDY SKYLD EQAAK EFIAW LMNTa (lactam @ 12-16; SEQ ID NO: 167)
X1SEGT FTSDY SKYLD EQAAK EFIAW LMNTa (lactam @ 16-20; SEQ ID NO: 168)
X1SEGT FTSDY SKYLD EQAAK EFIAW LMNTa (SEQ ID NO: 169)
X1SEGT FTSDY SKYLD EQAAK EFIAW LVKGa (lactam @ 12-16; SEQ ID NO: 170)
X1SEGT FTSDY SKYLD EQAAK EFIAW LVKGa (lactam @ 16-20; SEQ ID NO: 171)
X1SEGT FTSDY SKYLD EQAAK EFIAW LVKGa
Wherein in the preceding sequences
X1 = (Des-amino)His (SEQ ID NO: 172)
HX2EGT FTSDY SKYLD ERRAQ DFVQW LMNTa (SEQ ID NO: 173)
HX2EGT FTSDY SKYLD ERRAK DFVQW LMNTa (lactam @ 16-20; SEQ ID NO: 174)
HX2EGT FTSDY SKYLD ERRAK DFVQW LMNTa (lactam @ 12-16; SEQ ID NO: 175)
HX2EGT FTSDY SKYLD ERRAQ DFVQW LMNTa (lactam @ 12-16; SEQ ID NO: 176)
HX2EGT FTSDY SKYLD ERRAK DFVQW LMNTa (lactam @ 16-20; SEQ ID NO: 177)
HX2EGT FTSDY SKYLD KRRAE DFVQW LMNTa (SEQ ID NO: 178)
HX2EGT FTSDY SKYLD ERAAK DFVQW LMNTa (lactam @ 16-20; SEQ ID NO: 179)
HX2EGT FTSDY SKYLD ERAAK DFVQW LMNTa (lactam @ 12-16; SEQ ID NO: 180)
HX2EGT FTSDY SKYLD ERAAQ DFVQW LMNTa (lactam @ 12-16; SEQ ID NO: 181)
HX2EGT FTSDY SKYLD ERAAK DFVQW LMNTa (lactam @ 16-20; SEQ ID NO: 182)
HX2EGT FTSDY SKYLD KRAAE DFVQW LMNTa (SEQ ID NO: 183)
HX2EGT FTSDY SKYLD EQAAK EFIAW LMNTa (lactam @ 12-16; SEQ ID NO: 184)
HX2EGT FTSDY SKYLD EQAAK EFIAW LMNTa (lactam @ 16-20; SEQ ID NO: 185)
HX2EGT FTSDY SKYLD EQAAK EFIAW LMNTa (SEQ ID NO: 186)
HX2EGT FTSDY SKYLD EQAAK EFIAW LVKGa (lactam @ 12-16; SEQ ID NO: 187)
HX2EGT FTSDY SKYLD EQAAK EFIAW LVKGa (lactam @ 16-20; SEQ ID NO: 188)
HX2EGT FTSDY SKYLD EQAAK EFIAW LVKGa
Wherein in the preceding sequences
X2 = Aminoisobutyric acid (SEQ ID NO: 189)
HX2EGT FTSDY SKYLD ERRAQ DFVQW LMNTa (SEQ ID NO: 190)
HX2EGT FTSDY SKYLD ERRAK DFVQW LMNTa (lactam @ 16-20; SEQ ID NO: 191)
HX2EGT FTSDY SKYLD ERRAK DFVQW LMNTa (lactam @ 12-16; SEQ ID NO: 192)
HX2EGT FTSDY SKYLD ERRAQ DFVQW LMNTa (lactam @ 12-16; SEQ ID NO: 193)
HX2EGT FTSDY SKYLD ERRAK DFVQW LMNTa (lactam @ 16-20; SEQ ID NO: 194)
HX2EGT FTSDY SKYLD KRRAE DFVQW LMNTa (SEQ ID NO: 195)
HX2EGT FTSDY SKYLD ERAAK DFVQW LMNTa (lactam @ 16-20; SEQ ID NO: 196)
HX2EGT FTSDY SKYLD ERAAK DFVQW LMNTa (lactam @ 12-16; SEQ ID NO: 197)
HX2EGT FTSDY SKYLD ERAAQ DFVQW LMNTa (lactam @ 12-16; SEQ ID NO: 198)
HX2EGT FTSDY SKYLD ERAAK DFVQW LMNTa (lactam @ 16-20; SEQ ID NO: 199)
HX2EGT FTSDY SKYLD KRAAE DFVQW LMNTa (SEQ ID NO: 200)
HX2EGT FTSDY SKYLD EQAAK EFIAW LMNTa (lactam @ 12-16; SEQ ID NO: 201)
HX2EGT FTSDY SKYLD EQAAK EFIAW LMNTa (lactam @ 16-20; SEQ ID NO: 202)
HX2EGT FTSDY SKYLD EQAAK EFIAW LMNTa (SEQ ID NO: 203)
HX2EGT FTSDY SKYLD EQAAK EFIAW LVKGa (lactam @ 12-16; SEQ ID NO: 204)
HX2EGT FTSDY SKYLD EQAAK EFIAW LVKGa (lactam @ 16-20; SEQ ID NO: 205)
HX2EGT FTSDY SKYLD EQAAK EFIAW LVKGa
Wherein in the preceding sequences
X2 = (D-Ala)
```

```
                                            (SEQ ID NO: 206)
HSQGT FTSDY SKYLD ERRAQ DFVC*W LMNTa (SEQ ID NO: 207)
HSQGT FTSDY SKYLD ERRAK DFVC*W LMNTa (lactam @ 16-20; SEQ ID NO: 208)
HSQGT FTSDY SKYLD ERRAK DFVC*W LMNTa (lactam @ 12-16; SEQ ID NO: 209)
HSQGT FTSDY SKYLD ERRAQ DFVC*W LMNTa (lactam @ 12-16; SEQ ID NO: 210)
HSQGT FTSDY SKYLD ERRAK DFVC*W LMNTa (lactam @ 16-20; SEQ ID NO: 211)
HSQGT FTSDY SKYLD KRRAE DFVC*W LMNTa (SEQ ID NO: 212)
HSQGT FTSDY SKYLD ERAAK DFVC*W LMNTa (lactam @ 16-20; SEQ ID NO: 213)
HSQGT FTSDY SKYLD ERAAK DFVC*W LMNTa (lactam @ 12-16; SEQ ID NO: 214)
HSQGT FTSDY SKYLD ERAAQ DFVC*W LMNTa (lactam @ 12-16; SEQ ID NO: 215)
HSQGT FTSDY SKYLD ERAAK DFVC*W LMNTa (lactam @ 16-20; SEQ ID NO: 216)
HSQGT FTSDY SKYLD KRAAE DFVC*W LMNTa (SEQ ID NO: 217)
HSQGT FTSDY SKYLD EQAAK EFIC*W LMNTa (lactam @ 12-16; SEQ ID NO: 218)
HSQGT FTSDY SKYLD EQAAK EFIC*W LMNTa (lactam @ 16-20; SEQ ID NO: 219)
HSQGT FTSDY SKYLD EQAAK EFIC*W LMNTa (SEQ ID NO: 220)
HSQGT FTSDY SKYLD EQAAK EFIC*W LVKGa (lactam @ 12-16; SEQ ID NO: 221)
HSQGT FTSDY SKYLD EQAAK EFIC*W LVKGa (lactam @ 16-20; SEQ ID NO: 222)
HSQGT FTSDY SKYLD EQAAK EFIC*W LVKGa (SEQ ID NO: 223)
X1SQGT FTSDY SKYLD ERRAQ DFVC*W LMNTa (SEQ ID NO: 224)
X1SQGT FTSDY SKYLD ERRAK DFVC*W LMNTa (lactam @ 16-20; SEQ ID NO: 225)
X1SQGT FTSDY SKYLD ERRAK DFVC*W LMNTa (lactam @ 12-16; SEQ ID NO: 226)
X1SQGT FTSDY SKYLD ERRAQ DFVC*W LMNTa (lactam @ 12-16; SEQ ID NO: 227)
X1SQGT FTSDY SKYLD ERRAK DFVC*W LMNTa (lactam @ 16-20; SEQ ID NO: 228)
X1SQGT FTSDY SKYLD KRRAE DFVC*W LMNTa (SEQ ID NO: 229)
X1SQGT FTSDY SKYLD ERAAK DFVC*W LMNTa (lactam @ 16-20; SEQ ID NO: 230)
X1SQGT FTSDY SKYLD ERAAK DFVC*W LMNTa (lactam @ 12-16; SEQ ID NO: 231)
X1SQGT FTSDY SKYLD ERAAQ DFVC*W LMNTa (lactam @ 12-16; SEQ ID NO: 232)
X1SQGT FTSDY SKYLD ERAAK DFVC*W LMNTa (lactam @ 16-20; SEQ ID NO: 233)
X1SQGT FTSDY SKYLD KRAAE DFVC*W LMNTa (SEQ ID NO: 234)
X1SQGT FTSDY SKYLD EQAAK EFIC*W LMNTa (lactam @ 12-16; SEQ ID NO: 235)
X1SQGT FTSDY SKYLD EQAAK EFIC*W LMNTa (lactam @ 16-20; SEQ ID NO: 236)
X1SQGT FTSDY SKYLD EQAAK EFIC*W LMNTa (SEQ ID NO: 237)
X1SQGT FTSDY SKYLD EQAAK EFIC*W LVKGa (lactam @ 12-16; SEQ ID NO: 238)
X1SQGT FTSDY SKYLD EQAAK EFIC*W LVKGa (lactam @ 16-20; SEQ ID NO: 239)
X1SQGT FTSDY SKYLD EQAAK EFIC*W LVKGa
Wherein in the preceding sequences
X1 = (Des-amino)His; and wherein the C* is a
Cys, or a Cys attached to a hydrophilic
polymer, or alternatively the C* is a Cys
attached to a polyethylene glycol of about
20 kD average weight, or alternatively the
C* is a Cys attached to a polyethylene
glycol of about 40 kD average weight.

(SEQ ID NO: 240)
HX2QGT FTSDY SKYLD ERRAQ DFVC*W LMNTa (SEQ ID NO: 241)
HX2QGT FTSDY SKYLD ERRAK DFVC*W LMNTa (lactam @ 16-20; SEQ ID NO: 242)
HX2QGT FTSDY SKYLD ERRAK DFVC*W LMNTa (lactam @ 12-16; SEQ ID NO: 243)
HX2QGT FTSDY SKYLD ERRAQ DFVC*W LMNTa (lactam @ 12-16; SEQ ID NO: 244)
HX2QGT FTSDY SKYLD ERRAK DFVC*W LMNTa (lactam @ 16-20; SEQ ID NO: 245)
HX2QGT FTSDY SKYLD KRRAE DFVC*W LMNTa (SEQ ID NO: 246)
HX2QGT FTSDY SKYLD ERAAK DFVC*W LMNTa (lactam @ 16-20; SEQ ID NO: 247)
HX2QGT FTSDY SKYLD ERAAK DFVC*W LMNTa (lactam @ 12-16; SEQ ID NO: 248)
HX2QGT FTSDY SKYLD ERAAQ DFVC*W LMNTa (lactam @ 12-16; SEQ ID NO: 249)
HX2QGT FTSDY SKYLD ERAAK DFVC*W LMNTa (lactam @ 16-20; SEQ ID NO: 250)
HX2QGT FTSDY SKYLD KRAAE DFVC*W LMNTa (SEQ ID NO: 251)
HX2QGT FTSDY SKYLD EQAAK EFIC*W LMNTa (lactam @ 12-16; SEQ ID NO: 252)
HX2QGT FTSDY SKYLD EQAAK EFIC*W LMNTa (lactam @ 16-20; SEQ ID NO: 253)
HX2QGT FTSDY SKYLD EQAAK EFIC*W LMNTa (SEQ ID NO: 254)
HX2QGT FTSDY SKYLD EQAAK EFIC*W LVKGa (lactam @ 12-16; SEQ ID NO: 255)
HX2QGT FTSDY SKYLD EQAAK EFIC*W LVKGa (lactam @ 16-20; SEQ ID NO: 256)
HX2QGT FTSDY SKYLD EQAAK EFIC*W LVKGa
Wherein in the preceding sequences
```

X2 = Aminoisobutyric acid; and wherein the C* is a Cys, or a Cys attached to a hydrophilic polymer, or alternatively the C* is a Cys attached to a polyethylene glycol of about 20 kD average weight, or alternatively the C* is a Cys attached to a polyethylene glycol of about 40 kD average weight.

(SEQ ID NO: 257)
HX2QGT FTSDY SKYLD ERRAQ DFVC*W LMNTa (SEQ ID NO: 258)
HX2QGT FTSDY SKYLD ERRAK DFVC*W LMNTa (lactam @ 16-20; SEQ ID NO: 259)
HX2QGT FTSDY SKYLD ERRAK DFVC*W LMNTa (lactam @ 12-16; SEQ ID NO: 260)
HX2QGT FTSDY SKYLD ERRAQ DFVC*W LMNTa (lactam @ 12-16; SEQ ID NO: 261)
HX2QGT FTSDY SKYLD ERRAK DFVC*W LMNTa (lactam @ 16-20; SEQ ID NO: 262)
HX2QGT FTSDY SKYLD KRRAE DFVC*W LMNTa (SEQ ID NO: 263)
HX2QGT FTSDY SKYLD ERAAK DFVC*W LMNTa (lactam @ 16-20; SEQ ID NO: 264)
HX2QGT FTSDY SKYLD ERAAK DFVC*W LMNTa (lactam @ 12-16; SEQ ID NO: 265)
HX2QGT FTSDY SKYLD ERAAQ DFVC*W LMNTa (lactam @ 12-16; SEQ ID NO: 266)
HX2QGT FTSDY SKYLD ERAAK DFVC*W LMNTa (lactam @ 16-20; SEQ ID NO: 267)
HX2QGT FTSDY SKYLD KRAAE DFVC*W LMNTa (SEQ ID NO: 268)
HX2QGT FTSDY SKYLD EQAAK EFIC*W LMNTa (lactam @ 12-16; SEQ ID NO: 269)
HX2QGT FTSDY SKYLD EQAAK EFIC*W LMNTa (lactam @ 16-20; SEQ ID NO: 270)
HX2QGT FTSDY SKYLD EQAAK EFIC*W LMNTa (SEQ ID NO: 271)
HX2QGT FTSDY SKYLD EQAAK EFIC*W LVKGa (lactam @ 12-16; SEQ ID NO: 272)
HX2QGT FTSDY SKYLD EQAAK EFIC*W LVKGa (lactam @ 16-20; SEQ ID NO: 273)
HX2QGT FTSDY SKYLD EQAAK EFIC*W LVKGa
Wherein in the preceding sequences X2 = (D-Ala); and wherein the C* is a Cys, or a Cys attached to a hydrophilic polymer, or alternatively the C* is a Cys attached to a polyethylene glycol of about 20 kD average weight, or alternatively the C* is a Cys attached to a polyethylene glycol of about 40 kD average weight.

(SEQ ID NO: 274)
HSEGT FTSDY SKYLD ERRAQ DFVC*W LMNTa (SEQ ID NO: 275)
HSEGT FTSDY SKYLD ERRAK DFVC*W LMNTa (lactam @ 16-20; SEQ ID NO: 276)
HSEGT FTSDY SKYLD ERRAK DFVC*W LMNTa (lactam @ 12-16; SEQ ID NO: 277)
HSEGT FTSDY SKYLD ERRAQ DFVC*W LMNTa (lactam @ 12-16; SEQ ID NO: 278)
HSEGT FTSDY SKYLD ERRAK DFVC*W LMNTa (lactam @ 16-20; SEQ ID NO: 279)
HSEGT FTSDY SKYLD KRRAE DFVC*W LMNTa (SEQ ID NO: 280)
HSEGT FTSDY SKYLD ERAAK DFVC*W LMNTa (lactam @ 16-20; SEQ ID NO: 281)
HSEGT FTSDY SKYLD ERAAK DFVC*W LMNTa (lactam @ 12-16; SEQ ID NO: 282)
HSEGT FTSDY SKYLD ERAAQ DFVC*W LMNTa (lactam @ 12-16; SEQ ID NO: 283)
HSEGT FTSDY SKYLD ERAAK DFVC*W LMNTa (lactam @ 16-20; SEQ ID NO: 284)
HSEGT FTSDY SKYLD KRAAE DFVC*W LMNTa (SEQ ID NO: 285)
HSEGT FTSDY SKYLD EQAAK EFIC*W LMNTa (lactam @ 12-16; SEQ ID NO: 286)
HSEGT FTSDY SKYLD EQAAK EFIC*W LMNTa (lactam @ 16-20; SEQ ID NO: 287)
HSEGT FTSDY SKYLD EQAAK EFIC*W LMNTa (SEQ ID NO: 288)
HSEGT FTSDY SKYLD EQAAK EFIC*W LVKGa (lactam @ 12-16; SEQ ID NO: 289)
HSEGT FTSDY SKYLD EQAAK EFIC*W LVKGa (lactam @ 16-20; SEQ ID NO: 290)
HSEGT FTSDY SKYLD EQAAK EFIC*W LVKGa (SEQ ID NO: 291)
X1SEGT FTSDY SKYLD ERRAQ DFVC*W LMNTa (SEQ ID NO: 292)
X1SEGT FTSDY SKYLD ERRAK DFVC*W LMNTa (lactam @ 16-20; SEQ ID NO: 293)
X1SEGT FTSDY SKYLD ERRAK DFVC*W LMNTa (lactam @ 12-16; SEQ ID NO: 294)
X1SEGT FTSDY SKYLD ERRAQ DFVC*W LMNTa (lactam @ 12-16; SEQ ID NO: 295)
X1SEGT FTSDY SKYLD ERRAK DFVC*W LMNTa (lactam @ 16-20; SEQ ID NO: 296)
X1SEGT FTSDY SKYLD KRRAE DFVC*W LMNTa (SEQ ID NO: 297)
X1SEGT FTSDY SKYLD ERAAK DFVC*W LMNTa (lactam @ 16-20; SEQ ID NO: 298)
X1SEGT FTSDY SKYLD ERAAK DFVC*W LMNTa (lactam @ 12-16; SEQ ID NO: 299)
X1SEGT FTSDY SKYLD ERAAQ DFVC*W LMNTa (lactam @ 12-16; SEQ ID NO: 300)
X1SEGT FTSDY SKYLD ERAAK DFVC*W LMNTa (lactam @ 16-20; SEQ ID NO: 301)
X1SEGT FTSDY SKYLD KRAAE DFVC*W LMNTa (SEQ ID NO: 302)
X1SEGT FTSDY SKYLD EQAAK EFIC*W LMNTa (lactam @ 12-16; SEQ ID NO: 303)
X1SEGT FTSDY SKYLD EQAAK EFIC*W LMNTa (lactam @ 16-20; SEQ ID NO: 304)
X1SEGT FTSDY SKYLD EQAAK EFIC*W LMNTa -continued (SEQ ID NO: 305)
X1SEGT FTSDY SKYLD EQAAK EFIC*W LVKGa (lactam @ 12-16; SEQ ID NO: 306)
X1SEGT FTSDY SKYLD EQAAK EFIC*W LVKGa (lactam @ 16-20; SEQ ID NO: 307)
X1SEGT FTSDY SKYLD EQAAK EFIC*W LVKGa Wherein in the preceding sequences X1 = (Des-amino)His; and wherein the C* is a Cys, or a Cys attached to a hydrophilic polymer, or alternatively the C* is a Cys attached to a polyethylene glycol of about 20 kD average weight, or alternatively the C* is a Cys attached to a polyethylene glycol of about 40 kD average weight.

(SEQ ID NO: 308)
HX2EGT FTSDY SKYLD ERRAQ DFVC*W LMNTa (SEQ ID NO: 309)
HX2EGT FTSDY SKYLD ERRAK DFVC*W LMNTa (lactam @ 16-20; SEQ ID NO: 310)
HX2EGT FTSDY SKYLD ERRAK DFVC*W LMNTa (lactam @ 12-16; SEQ ID NO: 311)
HX2EGT FTSDY SKYLD ERRAQ DFVC*W LMNTa (lactam @ 12-16; SEQ ID NO: 312)
HX2EGT FTSDY SKYLD ERRAK DFVC*W LMNTa (lactam @ 16-20; SEQ ID NO: 313)
HX2EGT FTSDY SKYLD KRRAE DFVC*W LMNTa (SEQ ID NO: 314)
HX2EGT FTSDY SKYLD ERAAK DFVC*W LMNTa (lactam @ 16-20; SEQ ID NO: 315)
HX2EGT FTSDY SKYLD ERAAK DFVC*W LMNTa (lactam @ 12-16; SEQ ID NO: 316)
HX2EGT FTSDY SKYLD ERAAQ DFVC*W LMNTa (lactam @ 12-16; SEQ ID NO: 317)
HX2EGT FTSDY SKYLD ERAAK DFVC*W LMNTa (lactam @ 16-20; SEQ ID NO: 318)
HX2EGT FTSDY SKYLD KRAAE DFVC*W LMNTa (SEQ ID NO: 319)
HX2EGT FTSDY SKYLD EQAAK EFIC*W LMNTa (lactam @ 12-16; SEQ ID NO: 320)
HX2EGT FTSDY SKYLD EQAAK EFIC*W LMNTa (lactam @ 16-20; SEQ ID NO: 321)
HX2EGT FTSDY SKYLD EQAAK EFIC*W LMNTa (SEQ ID NO: 322)
HX2EGT FTSDY SKYLD EQAAK EFIC*W LVKGa (lactam @ 12-16; SEQ ID NO: 323)
HX2EGT FTSDY SKYLD EQAAK EFIC*W LVKGa (lactam @ 16-20; SEQ ID NO: 324)
HX2EGT FTSDY SKYLD EQAAK EFIC*W LVKGa Wherein in the preceding sequences X2 = Aminoisobutyric acid; and wherein the C* is a Cys, or a Cys attached to a hydrophilic polymer, or alternatively the C* is a Cys attached to a polyethylene glycol of about 20 kD average weight, or alternatively the C* is a Cys attached to a polyethylene glycol of about 40 kD average weight.

(SEQ ID NO: 325)
HX2EGT FTSDY SKYLD ERRAQ DFVC*W LMNTa (SEQ ID NO: 326)
HX2EGT FTSDY SKYLD ERRAK DFVC*W LMNTa (lactam @ 16-20; SEQ ID NO: 327)
HX2EGT FTSDY SKYLD ERRAK DFVC*W LMNTa (lactam @ 12-16; SEQ ID NO: 328)
HX2EGT FTSDY SKYLD ERRAQ DFVC*W LMNTa (lactam @ 12-16; SEQ ID NO: 329)
HX2EGT FTSDY SKYLD ERRAK DFVC*W LMNTa (lactam @ 16-20; SEQ ID NO: 330)
HX2EGT FTSDY SKYLD KRRAE DFVC*W LMNTa (SEQ ID NO: 331)
HX2EGT FTSDY SKYLD ERAAK DFVC*W LMNTa (lactam @ 16-20; SEQ ID NO: 332)
HX2EGT FTSDY SKYLD ERAAK DFVC*W LMNTa (lactam @ 12-16; SEQ ID NO: 333)
HX2EGT FTSDY SKYLD ERAAQ DFVC*W LMNTa (lactam @ 12-16; SEQ ID NO: 334)
HX2EGT FTSDY SKYLD ERAAK DFVC*W LMNTa (lactam @ 16-20; SEQ ID NO: 335)
HX2EGT FTSDY SKYLD KRAAE DFVC*W LMNTa (SEQ ID NO: 336)
HX2EGT FTSDY SKYLD EQAAK EFIC*W LMNTa (lactam @ 12-16; SEQ ID NO: 337)
HX2EGT FTSDY SKYLD EQAAK EFIC*W LMNTa (lactam @ 16-20; SEQ ID NO: 338)
HX2EGT FTSDY SKYLD EQAAK EFIC*W LMNTa (SEQ ID NO: 339)
HX2EGT FTSDY SKYLD EQAAK EFIC*W LVKGa (lactam @ 12-16; SEQ ID NO: 340)
HX2EGT FTSDY SKYLD EQAAK EFIC*W LVKGa (lactam @ 16-20; SEQ ID NO: 341)
HX2EGT FTSDY SKYLD EQAAK EFIC*W LVKGa Wherein in the preceding sequences X2 = (D-Ala); and wherein the C* is a Cys, or a Cys attached to a hydrophilic polymer, or alternatively the C* is a Cys attached to a polyethylene glycol of about 20 kD average weight, or alternatively the C* is a Cys attached to a polyethylene glycol of about 40 kD average weight.

(SEQ ID NO: 342)
HSQGT FTSDY SKYLD C*RRAK DFVQW LMNTa (SEQ ID NO: 343)
HSQGT FTSDY SKYLD C*RAAK DFVQW LMNTa (SEQ ID NO: 344)
HSQGT FTSDY SKYLD C*QAAK EFIAW LMNTa (SEQ ID NO: 345)
HSQGT FTSDY SKYLD C*QAAK EFIAW LVKGa (SEQ ID NO: 346)
X1SQGT FTSDY SKYLD C*RRAK DFVQW LMNTa (SEQ ID NO: 347)
X1SQGT FTSDY SKYLD C*RAAK DFVQW LMNTa (SEQ ID NO: 348)
X1SQGT FTSDY SKYLD C*QAAK EFIAW LMNTa (SEQ ID NO: 349)
X1SQGT FTSDY SKYLD C*QAAK EFIAW LVKGa

Wherein X1 = (Des-amino)His; and wherein the C* is a Cys, or a Cys attached to a
hydrophilic polymer, or alternatively the
C* is a Cys attached to a polyethylene
glycol of about 20 kD average weight, or
alternatively the C* is a Cys attached
to a polyethylene glycol of about 40 kD
average weight.

(SEQ ID NO: 350)
HX2QGT FTSDY SKYLD C*RRAK DFVQW LMNTa (SEQ ID NO: 351)
HX2QGT FTSDY SKYLD C*RAAK DFVQW LMNTa (SEQ ID NO: 352)
HX2QGT FTSDY SKYLD C*QAAK EFIAW LMNTa (SEQ ID NO: 353)
HX2QGT FTSDY SKYLD C*QAAK EFIAW LVKGa
Wherein X2 = Aminoisobutyric acid; and
wherein the C* is a Cys, or a Cys
attached to a hydrophilic polymer, or
alternatively the C* is a Cys attached
to a polyethylene glycol of about 20 kD
average weight, or alternatively the C*
is a Cys attached to a polyethylene
glycol of about 40 kD average weight.

(SEQ ID NO: 354)
HX2QGT FTSDY SKYLD C*RRAK DFVQW LMNTa (SEQ ID NO: 355)
HX2QGT FTSDY SKYLD C*RAAK DFVQW LMNTa (SEQ ID NO: 356)
HX2QGT FTSDY SKYLD C*QAAK EFIAW LMNTa (SEQ ID NO: 357)
HX2QGT FTSDY SKYLD C*QAAK EFIAW LVKGa
Wherein X2 = (D-Ala); and wherein the C* is
a Cys, or a Cys attached to a hydrophilic
polymer, or alternatively the C* is a Cys
attached to a polyethylene glycol of about
20 kD average weight, or alternatively the
C* is a Cys attached to a polyethylene
glycol of about 40 kD average weight.

(SEQ ID NO: 358)
HSEGT FTSDY SKYLD C*RRAK DFVQW LMNTa (SEQ ID NO: 359)
HSEGT FTSDY SKYLD C*RAAK DFVQW LMNTa (SEQ ID NO: 360)
HSEGT FTSDY SKYLD C*QAAK EFIAW LMNTa (SEQ ID NO: 361)
HSEGT FTSDY SKYLD C*QAAK EFIAW LVKGa (SEQ ID NO: 362)
X1SEGT FTSDY SKYLD C*RRAK DFVQW LMNTa (SEQ ID NO: 363)
X1SEGT FTSDY SKYLD C*RAAK DFVQW LMNTa (SEQ ID NO: 364)
X1SEGT FTSDY SKYLD C*QAAK EFIAW LMNTa (SEQ ID NO: 365)
X1SEGT FTSDY SKYLD C*QAAK EFIAW LVKGa
Wherein X1 = (Des-amino)His; and wherein the
C* is a Cys, or a Cys attached to a hydro-
philic polymer, or alternatively the C* is a
Cys attached to a polyethylene glycol of
about 20 kD average weight, or alternatively
the C* is a Cys attached to a polyethylene
glycol of about 40 kD average weight.

(SEQ ID NO: 366)
HX2EGT FTSDY SKYLD C*RRAK DFVQW LMNTa (SEQ ID NO: 367)
HX2EGT FTSDY SKYLD C*RAAK DFVQW LMNTa (SEQ ID NO: 368)
HX2EGT FTSDY SKYLD C*QAAK EFIAW LMNTa (SEQ ID NO: 369)
HX2EGT FTSDY SKYLD C*QAAK EFIAW LVKGa
Wherein X2 = (D-Ala); and wherein the C* is
a Cys, or a Cys attached to a hydrophilic
polymer, or alternatively the C* is a Cys
attached to a polyethylene glycol of about
20 kD average weight, or alternatively the
C* is a Cys attached to a polyethylene
glycol of about 40 kD average weight.

(SEQ ID NO: 370)
HX2EGT FTSDY SKYLD C*RRAK DFVQW LMNTa (SEQ ID NO: 371)
HX2EGT FTSDY SKYLD C*RAAK DFVQW LMNTa (SEQ ID NO: 372)
HX2EGT FTSDY SKYLD C*QAAK EFIAW LMNTa (SEQ ID NO: 373)
HX2EGT FTSDY SKYLD C*QAAK EFIAW LVKGa
Wherein X2 = (D-Ala); and wherein the C* is
a Cys, or a Cys attached to a hydrophilic
polymer, or alternatively the C* is a Cys
attached to a polyethylene glycol of about
20 kD average weight, or alternatively the
C* is a Cys attached to a polyethylene
glycol of about 40 kD average weight.

(SEQ ID NO: 374)
HSQGT FTSDY SKYLD ERRAQ DFVQW LMDTa (SEQ ID NO: 375)
HSQGT FTSDY SKYLD ERRAK DFVQW LMDTa (lactam @ 16-20; SEQ ID NO: 376)
HSQGT FTSDY SKYLD ERRAK DFVQW LMDTa (lactam @ 12-16; SEQ ID NO: 377)
HSQGT FTSDY SKYLD ERRAQ DFVQW LMDTa (lactam @ 12-16; SEQ ID NO: 378)
HSQGT FTSDY SKYLD ERRAK DFVQW LMDTa (lactam @ 16-20; SEQ ID NO: 379)
HSQGT FTSDY SKYLD KRRAE DFVQW LMDTa (SEQ ID NO: 380)
HSQGT FTSDY SKYLD ERAAK DFVQW LMDTa (lactam @ 16-20; SEQ ID NO: 381)
HSQGT FTSDY SKYLD ERAAK DFVQW LMDTa (lactam @ 12-16; SEQ ID NO: 382)
HSQGT FTSDY SKYLD ERAAQ DFVQW LMDTa (lactam @ 12-16; SEQ ID NO: 383)
HSQGT FTSDY SKYLD ERAAK DFVQW LMDTa (lactam @ 16-20; SEQ ID NO: 384)
HSQGT FTSDY SKYLD KRAAE DFVQW LMDTa (SEQ ID NO: 385)
HSQGT FTSDY SKYLD EQAAK EFIAW LMDTa (lactam @ 12-16; SEQ ID NO: 386)
HSQGT FTSDY SKYLD EQAAK EFIAW LMDTa (lactam @ 16-20; SEQ ID NO: 387)
HSQGT FTSDY SKYLD EQAAK EFIAW LMDTa (SEQ ID NO: 388)
X1SQGT FTSDY SKYLD ERRAQ DFVQW LMDTa

```
                                    (SEQ ID NO: 389)
X1SQGT FTSDY SKYLD ERRAK DFVQW LMDTa (lactam @ 16-20; SEQ ID NO: 390)
X1SQGT FTSDY SKYLD ERRAK DFVQW LMDTa (lactam @ 12-16; SEQ ID NO: 391)
X1SQGT FTSDY SKYLD ERRAQ DFVQW LMDTa (lactam @ 12-16; SEQ ID NO: 392)
X1SQGT FTSDY SKYLD ERRAK DFVQW LMDTa (lactam @ 16-20; SEQ ID NO: 393)
X1SQGT FTSDY SKYLD KRRAE DFVQW LMDTa (SEQ ID NO: 394)
X1SQGT FTSDY SKYLD ERAAK DFVQW LMDTa (lactam @ 16-20; SEQ ID NO: 395)
X1SQGT FTSDY SKYLD ERAAK DFVQW LMDTa (lactam @ 12-16; SEQ ID NO: 396)
X1SQGT FTSDY SKYLD ERAAQ DFVQW LMDTa (lactam @ 12-16; SEQ ID NO: 397)
X1SQGT FTSDY SKYLD ERAAK DFVQW LMDTa (lactam @ 16-20; SEQ ID NO: 398)
X1SQGT FTSDY SKYLD KRAAE DFVQW LMDTa (SEQ ID NO: 399)
X1SQGT FTSDY SKYLD EQAAK EFIAW LMDTa (lactam @ 12-16; SEQ ID NO: 400)
X1SQGT FTSDY SKYLD EQAAK EFIAW LMDTa (lactam @ 16-20; SEQ ID NO: 401)
X1SQGT FTSDY SKYLD EQAAK EFIAW LMDTa
Wherein in the preceding sequences
X1 = (Des-amino)His (SEQ ID NO: 402)
HX2QGT FTSDY SKYLD ERRAQ DFVQW LMDTa (SEQ ID NO: 403)
HX2QGT FTSDY SKYLD ERRAK DFVQW LMDTa (lactam @ 16-20; SEQ ID NO: 404)
HX2QGT FTSDY SKYLD ERRAK DFVQW LMDTa (lactam @ 12-16; SEQ ID NO: 405)
HX2QGT FTSDY SKYLD ERRAQ DFVQW LMDTa (lactam @ 12-16; SEQ ID NO: 406)
HX2QGT FTSDY SKYLD ERRAK DFVQW LMDTa (lactam @ 16-20; SEQ ID NO: 407)
HX2QGT FTSDY SKYLD KRRAE DFVQW LMDTa (SEQ ID NO: 408)
HX2QGT FTSDY SKYLD ERAAK DFVQW LMDTa (lactam @ 16-20; SEQ ID NO: 409)
HX2QGT FTSDY SKYLD ERAAK DFVQW LMDTa (lactam @ 12-16; SEQ ID NO: 410)
HX2QGT FTSDY SKYLD ERAAQ DFVQW LMDTa (lactam @ 12-16; SEQ ID NO: 411)
HX2QGT FTSDY SKYLD ERAAK DFVQW LMDTa (lactam @ 16-20; SEQ ID NO: 412)
HX2QGT FTSDY SKYLD KRAAE DFVQW LMDTa (SEQ ID NO: 413)
HX2QGT FTSDY SKYLD EQAAK EFIAW LMDTa (lactam @ 12-16; SEQ ID NO: 414)
HX2QGT FTSDY SKYLD EQAAK EFIAW LMDTa (lactam @ 16-20; SEQ ID NO: 415)
HX2QGT FTSDY SKYLD EQAAK EFIAW LMDTa
Wherein in the preceding sequences
X2 = Aminoisobutyric acid (SEQ ID NO: 416)
HX2QGT FTSDY SKYLD ERRAQ DFVQW LMDTa (SEQ ID NO: 417)
HX2QGT FTSDY SKYLD ERRAK DFVQW LMDTa (lactam @ 16-20; SEQ ID NO: 418)
HX2QGT FTSDY SKYLD ERRAK DFVQW LMDTa (lactam @ 12-16; SEQ ID NO: 419)
HX2QGT FTSDY SKYLD ERRAQ DFVQW LMDTa (lactam @ 12-16; SEQ ID NO: 420)
HX2QGT FTSDY SKYLD ERRAK DFVQW LMDTa (lactam @ 16-20; SEQ ID NO: 421)
HX2QGT FTSDY SKYLD KRRAE DFVQW LMDTa (SEQ ID NO: 422)
HX2QGT FTSDY SKYLD ERAAK DFVQW LMDTa (lactam @ 16-20; SEQ ID NO: 423)
HX2QGT FTSDY SKYLD ERAAK DFVQW LMDTa (lactam @ 12-16; SEQ ID NO: 424)
HX2QGT FTSDY SKYLD ERAAQ DFVQW LMDTa (lactam @ 12-16; SEQ ID NO: 425)
HX2QGT FTSDY SKYLD ERAAK DFVQW LMDTa (lactam @ 16-20; SEQ ID NO: 426)
HX2QGT FTSDY SKYLD KRAAE DFVQW LMDTa (SEQ ID NO: 427)
HX2QGT FTSDY SKYLD EQAAK EFIAW LMDTa (lactam @ 12-16; SEQ ID NO: 428)
HX2QGT FTSDY SKYLD EQAAK EFIAW LMDTa (lactam @ 16-20; SEQ ID NO: 429)
HX2QGT FTSDY SKYLD EQAAK EFIAW LMDTa
Wherein in the preceding sequences
X2 = (D-Ala)

(SEQ ID NO: 430)
HSEGT FTSDY SKYLD ERRAQ DFVQW LMDTa (SEQ ID NO: 431)
HSEGT FTSDY SKYLD ERRAK DFVQW LMDTa (lactam @ 16-20; SEQ ID NO: 432)
HSEGT FTSDY SKYLD ERRAK DFVQW LMDTa (lactam @ 12-16; SEQ ID NO: 433)
HSEGT FTSDY SKYLD ERRAQ DFVQW LMDTa (lactam @ 12-16; SEQ ID NO: 434)
HSEGT FTSDY SKYLD ERRAK DFVQW LMDTa (lactam @ 16-20; SEQ ID NO: 435)
HSEGT FTSDY SKYLD KRRAE DFVQW LMDTa (SEQ ID NO: 436)
HSEGT FTSDY SKYLD ERAAK DFVQW LMDTa (lactam @ 16-20; SEQ ID NO: 437)
HSEGT FTSDY SKYLD ERAAK DFVQW LMDTa (lactam @ 12-16; SEQ ID NO: 438)
HSEGT FTSDY SKYLD ERAAQ DFVQW LMDTa (lactam @ 12-16; SEQ ID NO: 439)
HSEGT FTSDY SKYLD ERAAK DFVQW LMDTa (lactam @ 16-20; SEQ ID NO: 440)
HSEGT FTSDY SKYLD KRAAE DFVQW LMDTa
```

```
                                      (SEQ ID NO: 441)
HSEGT FTSDY SKYLD EQAAK EFIAW LMDTa (lactam @ 12-16; SEQ ID NO: 442)
HSEGT FTSDY SKYLD EQAAK EFIAW LMDTa (lactam @ 16-20; SEQ ID NO: 443)
HSEGT FTSDY SKYLD EQAAK EFIAW LMDTa (SEQ ID NO: 444)
X1SEGT FTSDY SKYLD ERRAQ DFVQW LMDTa (SEQ ID NO: 445)
X1SEGT FTSDY SKYLD ERRAK DFVQW LMDTa (lactam @ 16-20; SEQ ID NO: 446)
X1SEGT FTSDY SKYLD ERRAK DFVQW LMDTa (lactam @ 12-16; SEQ ID NO: 447)
X1SEGT FTSDY SKYLD ERRAQ DFVQW LMDTa (lactam @ 12-16; SEQ ID NO: 448)
X1SEGT FTSDY SKYLD ERRAK DFVQW LMDTa (lactam @ 16-20; SEQ ID NO: 449)
X1SEGT FTSDY SKYLD KRRAE DFVQW LMDTa (SEQ ID NO: 450)
X1SEGT FTSDY SKYLD ERAAK DFVQW LMDTa (lactam @ 16-20; SEQ ID NO: 451)
X1SEGT FTSDY SKYLD ERAAK DFVQW LMDTa (lactam @ 12-16; SEQ ID NO: 452)
X1SEGT FTSDY SKYLD ERAAQ DFVQW LMDTa (lactam @ 12-16; SEQ ID NO: 453)
X1SEGT FTSDY SKYLD ERAAK DFVQW LMDTa (lactam @ 16-20; SEQ ID NO: 454)
X1SEGT FTSDY SKYLD KRAAE DFVQW LMDTa (SEQ ID NO: 455)
X1SEGT FTSDY SKYLD EQAAK EFIAW LMDTa (lactam @ 12-16; SEQ ID NO: 456)
X1SEGT FTSDY SKYLD EQAAK EFIAW LMDTa (lactam @ 16-20; SEQ ID NO: 457)
X1SEGT FTSDY SKYLD EQAAK EFIAW LMDTa
Wherein in the preceding sequences
X1 = (Des-amino)His (SEQ ID NO: 458)
HX2EGT FTSDY SKYLD ERRAQ DFVQW LMDTa (SEQ ID NO: 459)
HX2EGT FTSDY SKYLD ERRAK DFVQW LMDTa (lactam @ 16-20; SEQ ID NO: 460)
HX2EGT FTSDY SKYLD ERRAK DFVQW LMDTa (lactam @ 12-16; SEQ ID NO: 461)
HX2EGT FTSDY SKYLD ERRAQ DFVQW LMDTa (lactam @ 12-16; SEQ ID NO: 462)
HX2EGT FTSDY SKYLD ERRAK DFVQW LMDTa (lactam @ 16-20; SEQ ID NO: 463)
HX2EGT FTSDY SKYLD KRRAE DFVQW LMDTa (SEQ ID NO: 464)
HX2EGT FTSDY SKYLD ERAAK DFVQW LMDTa (lactam @ 16-20; SEQ ID NO: 465)
HX2EGT FTSDY SKYLD ERAAK DFVQW LMDTa (lactam @ 12-16; SEQ ID NO: 466)
HX2EGT FTSDY SKYLD ERAAQ DFVQW LMDTa (lactam @ 12-16; SEQ ID NO: 467)
HX2EGT FTSDY SKYLD ERAAK DFVQW LMDTa (lactam @ 16-20; SEQ ID NO: 468)
HX2EGT FTSDY SKYLD KRAAE DFVQW LMDTa (SEQ ID NO: 469)
HX2EGT FTSDY SKYLD EQAAK EFIAW LMDTa (lactam @ 12-16; SEQ ID NO: 470)
HX2EGT FTSDY SKYLD EQAAK EFIAW LMDTa (lactam @ 16-20; SEQ ID NO: 471)
HX2EGT FTSDY SKYLD EQAAK EFIAW LMDTa
Wherein in the preceding sequences
X2 = Aminoisobutyric acid (SEQ ID NO: 472)
HX2EGT FTSDY SKYLD ERRAQ DFVQW LMDTa (SEQ ID NO: 473)
HX2EGT FTSDY SKYLD ERRAK DFVQW LMDTa (lactam @ 16-20; SEQ ID NO: 474)
HX2EGT FTSDY SKYLD ERRAK DFVQW LMDTa (lactam @ 12-16; SEQ ID NO: 475)
HX2EGT FTSDY SKYLD ERRAQ DFVQW LMDTa (lactam @ 12-16; SEQ ID NO: 476)
HX2EGT FTSDY SKYLD ERRAK DFVQW LMDTa (lactam @ 16-20; SEQ ID NO: 477)
HX2EGT FTSDY SKYLD KRAAE DFVQW LMDTa (SEQ ID NO: 478)
HX2EGT FTSDY SKYLD ERAAK DFVQW LMDTa (lactam @ 16-20; SEQ ID NO: 479)
HX2EGT FTSDY SKYLD ERAAK DFVQW LMDTa (lactam @ 12-16; SEQ ID NO: 480)
HX2EGT FTSDY SKYLD ERAAQ DFVQW LMDTa (lactam @ 12-16; SEQ ID NO: 481)
HX2EGT FTSDY SKYLD ERAAK DFVQW LMDTa (lactam @ 16-20; SEQ ID NO: 482)
HX2EGT FTSDY SKYLD KRAAE DFVQW LMDTa (SEQ ID NO: 483)
HX2EGT FTSDY SKYLD EQAAK EFIAW LMDTa (lactam @ 12-16; SEQ ID NO: 484)
HX2EGT FTSDY SKYLD EQAAK EFIAW LMDTa (lactam @ 16-20; SEQ ID NO: 485)
HX2EGT FTSDY SKYLD EQAAK EFIAW LMDTa
Wherein in the preceding sequences
X2 = (D-Ala)
```

The following glucagon peptides with a GLP-1/glucagon activity ratio of about 5 or more are also constructed generally as described above in Examples 1-11. Generally, in these peptides, AIB at position 2 provides DPP IV resistance but also significantly reduces glucagon activity.

```
                                      (SEQ ID NO: 486)
HX2QGT FTSDY SKYLD EQAAK EFIC*W LMNTa (SEQ ID NO: 487)
HX2QGT FTSDY SKYLD EQAAK EFIAW LMNC*a (SEQ ID NO: 488)
HX2QGT FTSDY SKYLD EQAAK EFIAW LMNGG PSSGA
PPPSC*a (lactam @ 16-20; SEQ ID NO: 489)
HX2QGT FTSDY SKYLD EQAAK EFIAW LMNGG PSSGA
PPPSC*a
```

```
                                              (SEQ ID NO: 490)
HX2QGT FTSDY SKYLD EQAAK EFIC*W LMNGG PSSGA
PPPSa (lactam @ 16-20; SEQ ID NO: 491)
HX2QGT FTSDY SKYLD EQAAK EFIC*W LMNGG PSSGA
PPPSa
Wherein in the preceding sequences X2 = AIB,
and wherein the C* is a Cys, or a Cys at-
tached to a hydrophilic polymer, or alter-
natively the C* is a Cys attached to a poly-
ethylene glycol of about 20 kD average
weight, or alternatively the C* is a Cys
attached to a polyethylene glycol of about
40 kD average weight.

(SEQ ID NO: 492)
HX2QGT FTSDY SKYLD ERAAK DFVC*W LMNTa (SEQ ID NO: 493)
HX2QGT FTSDY SKYLD ERAAK DFVQW LMNC*a (SEQ ID NO: 494)
HX2QGT FTSDY SKYLD ERAAK DFVQW LMNGG PSSGA
PPPSC*a (lactam @ 16-20; SEQ ID NO: 495)
HX2QGT FTSDY SKYLD ERAAK DFVQW LMNGG PSSGA
PPPSC*a (SEQ ID NO: 496)
HX2QGT FTSDY SKYLD ERAAK DFVC*W LMNGG PSSGA
PPPSa (lactam @ 16-20; SEQ ID NO: 497)
HX2QGT FTSDY SKYLD ERAAK DFVC*W LMNGG PSSGA
PPPSa (SEQ ID NO: 498)
HX2QGT FTSDY SKYLD ERRAK DFVC*W LMNTa (SEQ ID NO: 499)
HX2QGT FTSDY SKYLD ERRAK DFVQW LMNC*a (SEQ ID NO: 500)
HX2QGT FTSDY SKYLD ERRAK DFVQW LMNGG PSSGA
PPPSC*a (lactam @ 16-20; SEQ ID NO: 501)
HX2QGT FTSDY SKYLD ERRAK DFVQW LMNGG PSSGA
PPPSC*a (SEQ ID NO: 502)
HX2QGT FTSDY SKYLD ERRAK DFVC*W LMNGG PSSGA
PPPSa (lactam @ 16-20; SEQ ID NO: 503)
HX2QGT FTSDY SKYLD ERRAK DFVC*W LMNGG PSSGA
PPPSa
Wherein in the preceding sequences X2 = AIB,
and wherein the C* is a Cys, or a Cys at-
tached to a hydrophilic polymer, or alter-
natively the C* is a Cys attached to a poly-
ethylene glycol of about 20 kD average
weight, or alternatively the C* is a Cys
attached to a polyethylene glycol of about
40 kD average weight.

The following glucagon peptides which are GLP-
1/glucagon co-agonists are also constructed
generally as described above in Examples 1-11.
Formation of a lactam bridge between amino
acids 16 and 20 restores the reduction in
glucagon activity caused by the substitution
at position 2.

(lactam @ 16-20; SEQ ID NO: 504)
HX2QGT FTSDY SKYLD EQAAK EFIC*W LMNTa
Wherein in the preceding sequence X2 = AIB,
and wherein the C* is a Cys, or a Cys at-
tached to a hydrophilic polymer, or alter-
natively the C* is a Cys attached to a poly-
ethylene glycol of about 20 kD average
weight, or alternatively the C* is a Cys
attached to a polyethylene glycol of about
40 kD average weight.

(lactam @ 16-20; SEQ ID NO: 505)
X1SQGT FTSDY SKYLD EQAAK EFIC*W LMNTa (lactam @ 16-20; SEQ ID NO: 506)
X1SQGT FTSDY SKYLD EQAAK EFIAW LMNC*a (lactam @ 16-20; SEQ ID NO: 507)
X1SQGT FTSDY SKYLD EQAAK EFIAW LMNGG PSSGA
PPPSC*a (lactam @ 16-20; SEQ ID NO: 508)
X1SQGT FTSDY SKYLD ERRAK DFVQW LMNGG PSSGA
PPPSC*a (lactam @ 16-20; SEQ ID NO: 509)
X1SQGT FTSDY SKYLD EQAAK EFIC*W LMNGG PSSGA
PPPSa (lactam @ 16-20; SEQ ID NO: 510)
X1SQGT FTSDY SKYLD ERRAK DFVC*W LMNTa (lactam @ 16-20; SEQ ID NO: 511)
HX2QGT FTSDY SKYLD ERRAK DFVC*W LMNTa (lactam @ 16-20; SEQ ID NO: 512)
X1SQGT FTSDY SKYLD ERRAK DFVQW LMNC*a (lactam @ 16-20; SEQ ID NO: 513)
X1SQGT FTSDY SKYLD ERRAK DFVC*W LMNGG PSSGA
PPPSa
Wherein in the preceding sequences X1 = DMIA
(alpha, alpha-dimethyl imidiazole acetic acid),
and wherein the C* is a Cys, or a Cys at-
tached to a hydrophilic polymer, or alter-
natively the C* is a Cys attached to a poly-
ethylene glycol of about 20 kD average weight,
or alternatively the C* is a Cys attached to
to a polyethylene glycol of about 40 kD
average weight.

(optionally with lactam @ 16-20;
                                              SEQ ID NO: 514)
HSQGT FTSDY SKYLD EQAAK EFIC*W LMNTa
Wherein the C* is a Cys, or a Cys attached to
a hydrophilic polymer, or alternatively the C*
is a Cys attached to a polyethylene glycol of
about 20 kD average weight, or alternatively
the C* is a Cys attached to a polyethylene
glycol of about 40 kD average weight.

(lactam @ 16-20; SEQ ID NO: 517)
HX2QGT FTSDY SKYLD ERRAK DFVC*W LMNTa (lactam @ 16-20; SEQ ID NO: 528)
HX2QGT FTSDY SKYLD ERRAK DFVC*W LMNTa (SEQ ID NO: 531)
HX2QGT FTSDY SKYLD ERRAK EFIC*W LMNGG PSSGA
PPPSC*a (SEQ ID NO: 532)
HX2QGT FTSDY SKYLD EQAAK EFIAW LMNGG PSSGA
PPPSC*C*a (SEQ ID NO: 533)
HX2QGT FTSDY SKYLD EQAAK EFIC*W LMNGG PSSGA
PPPSa
Wherein in the preceding sequence X2 = AIB,
and wherein the C* is a Cys, or a Cys attached
to a hydrophilic polymer, or alternatively the
C* is a Cys attached to a polyethylene glycol
of about 20 kD average weight, or alternatively
the C* is a Cys attached to a polyethylene
glycol of about 40 kD average weight.
```

(SEQ ID NO: 518)
HSQGT FTSDYSKYLD EQAAK EFIC*W LMNTa (SEQ ID NO: 519)
X1SQGT FTSDYSKYLD EQAAK EFIC*W LMNTa (SEQ ID NO: 520)
X1SQGT FTSDYSKYLD EQAAK EFIAW LMNC*a (SEQ ID NO: 529)
X1SQGT FTSDY SKYLD ERRAK DFVC*W LMNGG PSSGA
PPPSa (SEQ ID NO: 530)
X1SQGT FTSDY SKYLD ERRAK DFVC*W LMNTa
Wherein in the preceding sequences X1 = DMIA
(alpha, alpha-dimethyl imidiazole acetic acid),
and wherein the C* is a Cys, or a Cys at-
tached to a hydrophilic polymer, or alter-
natively the C* is a Cys attached to a poly-
ethylene glycol of about 20 kD average weight,
or alternatively the C* is a Cys attached
to a polyethylene glycol of about
40 kD average weight.

(SEQ ID NO: 521)
HSQGT FTSDYSKYLD SRRAQ DFVQW LMNTGPSSGAPPPSa (SEQ ID NO: 522)
HSQGT FTSDYSKYLD SRRAQ DFVQW LMNGGPSSGAPPPSa (SEQ ID NO: 523)
HSQGT FTSDYSKYLD SRRAQ DFVQW LMKGGPSSGAPPPSa (SEQ ID NO: 524)
HSQGT FTSDYSKYLD SRRAQ DFVQW LVKGGPSSGAPPPSa (SEQ ID NO: 525)
HSQGT FTSDYSKYLD SRRAQ DFVQW LMDGGPSSGAPPPSa (SEQ ID NO: 526)
HSQGT FTSDYSKYLD ERRAK DFVQW LMDGGPSSGAPPPSa (SEQ ID NO: 527)
HAEGT FTSDV SSYLE GQAAK EFIAW LVKGGa (SEQ ID NO: 61)
X1X2QGT FTSDY SKYLD ERX5AK DFVX3W LMNX4
wherein
X1 = His, D-histidine, desaminohistidine,
hydroxyl-histidine, acetyl-histidine, homo-
histidine or alpha, alpha-dimethyl imidiazole
acetic acid (DMIA) N-methyl histidine, alpha-
methyl histidine, or imidazole acetic acid, X2 = Ser, D-serine, Ala, Val, glycine, N-methyl
serine or aminoisobutyric acid (AIB), N-methyl
alanine and D-alanine.

X3 = Ala, Gln or Cys-PEG

X4 = Thr-CONH2 or Cys-PEG or (SEQ ID NO: 515)
GGPSSGAPPPS
or (SEQ ID NO: 516)
GGPSSGAPPPSC-PEG
Provided that when X3 is Cys-PEG, X4 is not
Cys-PEG or (SEQ ID NO: 516)
GGPSSGAPPPSC-PEG,
and when X2 = Ser, X1 is not His.

X5 = Ala or Arg (SEQ ID NO: 62)
X1X2QGT FTSDY SKYLD EQ X5AK EFI X3W LMNX4 wherein
X1 = His, D-histidine, desaminohistidine,
hydroxyl-histidine, acetyl-histidine, homo-
histidine or alpha, alpha-dimethyl imidiazole
acetic acid (DMIA), N-methyl histidine, alpha-
methyl histidine, or imidazole acetic acid X2 = Ser, D-serine, Ala, Val, glycine, N-methyl
serine or aminoisobutyric acid (AIB), N-methyl
alanine and D-alanine.

X3 = Ala, Gln or Cys-PEG

X4 = Thr-CONH2 or Cys-PEG or (SEQ ID NO: 515)
GGPSSGAPPPS
or (SEQ ID NO: 516)
GGPSSGAPPPSC-PEG
Provided that when X3 is Cys-PEG, X4 is not
Cys-PEG or (SEQ ID NO: 516)
GGPSSGAPPPSC-PEG,
and when X2 = Ser, X1 is not His.

X5 = Ala or Arg (SEQ ID NO: 554)
HSEGT FTSDY SKYLD EQAAK EFIAW LXNTa,
wherein X at position 27 is Norleucine,
wherein the amino acid at position 29 is
amidated Any of the preceding sequences can include additional modifications, e.g., 1, 2, 3, 4 or 5 modifications that do not destroy activity, including but not limited to W10 or R20 substitutions that can be used to enhance potency. Any of the preceding sequences can also be produced without the modifications that confer DPP IV resistance, i.e., in which the native His is at position 1 and the native Ser is at position 2. In addition, any of the preceding compounds may optionally be linked to a conjugate, such as a heterologous polypeptide, an immunoglobulin or a portion thereof (e.g. Fc region), a targeting agent, a diagnostic label, or a diagnostic or therapeutic agent.

Example 17

The following glucagon peptides modified to comprise the c-terminal extension of SEQ ID NO: 26 linked to the carboxy terminus of the glucagon peptide were constructed generally as described above in Examples 1-11 and assayed for activity at the GLP-1 and glucagon receptors using the in vitro assay described in Example 14.

Table 11 represents the activity of various glucagon analogs at the glucagon and GLP-1 receptors. The data shows that for glucagon analogs comprising the c-terminal extension of SEQ ID NO: 26, amino acid substitutions at positions 16, 20, 28 and 29 can impact the analogs activity at the GLP-1 receptor.

TABLE 11

Glucagon-Cex Structure Activity Relationship

| Glucagon Peptide | Glucagon Receptor EC50 (nM) | Glucagon Receptor Relative Potency (%) | GLP-1 Receptor EC50 (nM) | GLP-1 Receptor Relative Potency (%) |
|---|---|---|---|---|
| -MNT$^{29}$ (SEQ ID NO: 1) | 0.086 | 100 | | |
| -MNTG$^{30}$ PSSGAPPPS (SEQ ID NO: 521) | 0.14 | 61 | 1.19 | 2 |
| -MNGG$^{30}$ PSSGAPPPS (SEQ ID NO: 522) | 0.28 | 30 | 0.31 | 8 |
| -MKGG$^{30}$ PSSGAPPPS (SEQ ID NO: 523) | 0.61 | 14 | 0.80 | 3 |
| -VKGG$^{30}$ PSSGAPPPS (SEQ ID NO: 524) | 1.16 | 7 | 0.21 | 12 |
| -MDGG$^{30}$ PSSGAPPPS (SEQ ID NO: 525) | 0.12 | 72 | 0.13 | 19 |
| E16K$^{20}$-MDGG$^{30}$ PSSGAPPPS (SEQ ID NO: 526) | 0.22 | 39 | 0.020 | 125 |
| GLP-1-VKGG$^{30}$ (SEQ ID NO: 527) | | | 0.025 | 100 |

Example 18

Table 12 represents in vitro data accumulated for various glucagon peptides comparing their relative activities at the glucagon and GLP-1 receptors.

TABLE 12

COMPARISON OF AGONISTS AND CO-AGONISTS w/ and w/o PEG

| CONTROLS | % Potency Relative to Native GR | % Potency Relative to Native GL-1R |
|---|---|---|
| Glucagon | 100 | 0.78 |
| GLP-1 | <0.01 | 100 |

| | Parent w/o PEG % Potency Relative to Native | | Parent w/PEG % Potency Relative to Native | |
|---|---|---|---|---|
| | GR | GLP-1R | GR | GLP-1R |
| AGONISTS | | | | |
| Chimera A1B2, Cys24 (SEQ ID NO: 486) | 15.4 | 160.6 | 2.6 | 82.5 |
| Chimera A1B2, Cys29 (SEQ ID NO: 487) | 20.1 | 124.6 | 5.6 | 54.3 |
| Chimera A1B2, Gly29, 30 Cys40 Cex (SEQ ID NO: 488) | 2.2 | 359.1 | 0.3 | 68.8 |
| Chimera A1B2, Gly29, 30 Cys40 Cex Lactam (SEQ ID NO: 489) | 14.2 | 169.6 | 3.2 | 63.6 |
| Chimera A1B2, Gly29, 30 Cys24 Cex (SEQ ID NO: 490) | 2.5 | 457.8 | 0.2 | 95.4 |
| Chimera A1B2, Gly29, 30 Cys24 Cex Lactam (SEQ ID NO: 491) | 25.2 | 381.5 | 1.4 | 96.4 |
| E16, K20A1B2, A18 Cys24 (SEQ ID NO: 492) | — | — | 1.1 | 73.5 |
| E16, K20A1B2, A18 Gly29, 30 Cys 24 (SEQ ID NO: 496) | — | — | 0.1 | 88.5 |
| CO-AGONISTS | | | | |
| Chimera DMIA1, Cys24 Lactam (SEQ ID NO: 505) | 160.7 | 82.5 | 19.1 | 12.5 |
| Chimera A1B2, Cys24 Lactam (SEQ ID NO: 504) | 114.2 | 230.4 | 9.2 | 38.0 |

TABLE 12-continued

COMPARISON OF AGONISTS AND CO-AGONISTS w/ and w/o PEG

| | | | | |
|---|---|---|---|---|
| Chimera DMIA1, Cys29 Lactam (SEQ ID NO: 506) | — | — | — | — |
| Chimera DMIA1, Gly29, 30 Cys40 Cex Lactam (SEQ ID NO: 507) | — | — | — | — |
| E16, K20 DMIA1, Gly29, 30 Cys40 Cex Lactam (SEQ ID NO: 508) | — | — | — | — |
| Chimera DMIA1, Gly29, 30 Cys24 Cex Lactam (SEQ ID NO: 509) | — | — | — | — |
| E16, K20 DMIA1, Cys24 Lactam (SEQ ID NO: 510) | — | — | 64.1 | 9.3 |
| E16, K20 AIB2, Cys24 Lactam (SEQ ID NO: 517) | 108.3 | 96.9 | 15.8 | 31.0 |
| Chimera Cys24 (SEQ ID NO: 518) | — | — | 19.8 | 29.3 |
| E16, K20 DMIA1, Gly29, 30 Cys24 Cex Lactam (SEQ ID NO: 513) | 116.0 | 78.3 | 12.6 | 11.3 |
| Chimera DMIA1, Cys29 (SEQ ID NO: 520) | — | — | 5.3 | 27.3 |
| Chimera DMIA1, Cys24 (SEQ ID NO: 519) | 28.9 | 64.5 | 6.9 | 19.3 |

Example 19

Acylated and/or PEGylated peptides were prepared as follows. Peptides were synthesized on a solid support resin using either a CS Bio 4886 Peptide Synthesizer or Applied Biosystems 430A Peptide Synthesizer. In situ neutralization chemistry was used as described by Schnolzer et al., *Int. J. Peptide Protein Res.* 40: 180-193 (1992). For acylated peptides, the target amino acid residue to be acylated (e.g., position ten) was substituted with an N ε-FMOC lysine residue. Treatment of the completed N-terminally BOC protected peptide with 20% piperidine in DMF for 30 minutes removed FMOC/formyl groups. Coupling to the free c-amino Lys residue was achieved by coupling a ten-fold molar excess of either an FMOC-protected spacer amino acid (ex. FMOC-(N—BOC)-Tryptophan-OH) or acyl chain (ex. C17-COOH) and PyBOP or DEPBT coupling reagent in DMF/DIEA. Subsequent removal of the spacer amino acid's FMOC group is followed by repetition of coupling with an acyl chain. Final treatment with 100% TFA resulted in removal of any side chain protecting groups and the N-terminal BOC group. Peptide resins were neutralized with 5% DIEA/DMF, dried, and then cleaved from the support using HF/p-cresol, 95:5, at 0° C. for one hour. Following ether extraction, a 5% HOAc solution was used to solvate the crude peptide. A sample of the solution was then verified to contain the correct molecular weight peptide by ESI-MS. Correct peptides were purified by RP-HPLC using a linear gradient of 10% CH3CN/0.1% TFA to 0.1% TFA in 100% CH3CN. A Vydac C18 22 mm×250 mm protein column was used for the purification. Acylated peptide analogs generally completed elution by a buffer ratio of 20:80. Portions were pooled together and checked for purity on an analytical RP-HPLC. Pure fractions were lyophilized yielding white, solid peptides. Yields typically ranged from 10 mg to 100 mg depending on the synthesis.

If a peptide comprises a lactam bridge and target residues to be acylated, acylation is carried out as described above upon addition of that amino acid to the peptide backbone.

For peptide pegylation, 40 kDa methoxy poly(ethylene glycol) maleimido-propionamide (Chirotech Technology Ltd.) was reacted with a molar equivalent of peptide in 7M Urea, 50 mM Tris-HCl buffer using the minimal amount of solvent needed to dissolve both peptide and PEG into a clear solution (generally less than 2 mL for a reaction using 2-3 mg peptide). Vigorous stirring at room temperature commenced for 4-6 hours and the reaction analyzed by analytical RP-HPLC. PEGylated products appeared distinctly from the starting material with decreased retention times. Purification was performed on a Vydac C4 column with conditions similar to those used for the initial peptide purification. Elution occurred around buffer ratios of 50:50. Fractions of pure PEGylated peptide were found and lyophilized. Yields were above 50%, varying per reaction.

Peptides were assayed for biological activity, by co-transfecting HEK293 cells with either the glucagon receptor (GLUR) or GLP-1 receptor (GLP-1R) and a luciferase gene linked to a cAMP responsive element. The transfected cells were serum deprived by culturing for 16 hours in DMEM supplemented with 0.25% Bovine Growth Serum and then incubated for 5 hours with serial dilutions of the selected analogs and either Glucagon or GLP-1 as standards, respectively. Peptide absorbance readings were obtained from UV Absorbance measurements at 280 nm on a Genesys 6 Spectrophotometer (Thermo Electron Corporation). Beer's Law was used to calculate solution concentrations based on the number of tryptophan and tyrosine residues in each analog. At the end of the incubation, 100 μL LucLite luminescence substrate reagent was added to each well, the plate sealed and shaken, and placed into a Wallac Trilux luminescence counter for cAMP detection. Effective 50% concentrations (EC50) were calculated using Origin software (OriginLab, Northampton, Mass.).

Acylated glucagon-based co-agonist peptides were prepared. In vitro results for a selection of these peptides are shown in Table 13. Although the unacylated peptide, like native glucagon, was insoluble in phosphate-buffered saline solutions at 1 mg/mL concentrations, acylation was observed to enhance solubility of the peptide at neutral pH.

TABLE 13

Receptor Activation Curves and nM EC$_{50}$ values for Acylated Peptides

| Peptide | GLP-1 Receptor | N | Glucagon Receptor | N |
|---|---|---|---|---|
| GLP-1 | 0.04 | 15 | >100 | 3 |
| E16 K20-glucagon-NH2 | 0.21 | 9 | 0.18 | 10 |
| E16 K20-glucagon-NH2 with $K^{10}$—$C_{16}$ | 0.09 | 8 | 0.40 | 8 |
| E16 K20-glucagon-NH2 with $K^{10}$—W—$C_{16}$ | 0.05 | 8 | 0.14 | 8 |
| E16 K20-glucagon-NH2 with $K^{10}$—$C_{18}$ | 0.03 | 8 | 0.12 | 8 |
| E16 K20-glucagon-NH2 with $K^{10}$—W—$C_{18}$ | 0.04 | 11 | 0.05 | 12 |
| Glucagon | 7.42 | 6 | 0.07 | 17 |

All four acylated peptides exhibited increased potency at the GLP-1 receptor. Inclusion of the tryptophan spacer provided better potency at the glucagon receptor. An acyl chain length of C18 is slightly preferred.

While acylation can extend the half-life of a peptide to 5 hours or more, PEGylation with repeats in tens of kDa ranges can do even more. Peptides comprising both types of modifications were prepared. These peptides are expected to exhibit extended half-life in circulation, as well as resistance to DPP-IV and other proteases. In vitro results for a selection of these peptides are shown in Table 14.

TABLE 14

Receptor Activation Curves and nM $EC_{50}$ values for Acylated, PEGylated Peptides

| Peptide | GLP-1 Receptor | N | Glucagon Receptor | N |
|---|---|---|---|---|
| GLP-1 | 0.04 | 15 | >100 | 3 |
| E16 K20-glucagon-NH2 (SEQ ID NO: 545) | 0.21 | 9 | 0.18 | 10 |
| E16 K20-glucagon-NH2 with $K^{10}$—W—$C_{16}$ and $C^{24}$-40K PEG (SEQ ID NO: 546) | 0.23 | 13 | 0.52 | 13 |
| E16 K20-glucagon-NH2 with $K^{10}$—W—$C_{18}$ and $C^{24}$-40K PEG (SEQ ID NO: 547) | 0.15 | 12 | 0.84 | 13 |
| E16 K20-glucagon-NH2 with $K^{10}$—W—$C_{18}$ and $C^{24}$-40K PEG (SEQ ID NO: 548) | 1.64 | 3 | 1.30 | 5 |
| Glucagon (SEQ ID NO: 1) | 7.42 | 6 | 0.07 | 17 |

Two of the three peptides retained their high potency at both the GLP-1 and glucagon receptors, with an EC50 of less than 1 nM. The $K^{10}$-W—$C_{18}$ acylated and PEGylated peptide exhibited about ten-fold potency losses at both receptors. This series of peptides shows that the position ten acylation is compatible with a PEGylation in the C-terminal portion of the glucagon peptide, e.g. position 24, 28 or 29, within a C-terminal extension, or at the C-terminus (e.g., through adding a C-terminal Cys).

Example 20

Various acylated glucagon co-agonist peptides were made as essentially described in Example 19 and tested for in vivo activity. Specifically, Peptide A (SEQ ID NO:1 modified to contain AIB at position 2, Glu at position 16, Gln at position 17, Ala at position 18, Lys at position 20, Glu at position 21, Ile at position 23, Cys at position 24, which Cys is bonded to a 40K PEG, and C-terminal amide) was further modified to comprise a Lys at position 10. The Lys10 was acylated with a C8 fatty acid chain, a C14 fatty acid chain, a C16 fatty acid chain, or a C18 fatty acid chain.

Activity at the GLP-1 receptor of each of the acylated peptides was assayed as described in Example 14 and compared to the activity of GLP-1(7-37)acid (SEQ ID NO: 50) as a control. The EC50 of each of the acylated peptides at the GLP-1 receptor shown in Table 15 is similar to the EC50 of the GLP-1 peptide.

TABLE 15

| | GLP-1 Receptor Activation Potency $EC_{50}$ (nM) |
|---|---|
| GLP-1 | 0.0222 ± 0.0002 |
| Peptide A $K^{10}$—$C_8$ | 0.0174 ± 0.0004 |

TABLE 15-continued

| | GLP-1 Receptor Activation Potency $EC_{50}$ (nM) |
|---|---|
| Peptide A $K^{10}$—$C_{14}$ | 0.0168 ± 0.0004 |
| Peptide A $K^{10}$—$C_{16}$ | 0.0127 ± 0.0003 |
| Peptide A $K^{10}$—$C_{18}$ | 0.0118 ± 0.0002 |

The peptides were then tested in vivo by subcutaneously injecting diet-induced obesity (DIO) mice with various acylated and non-acylated peptides, or vehicle alone, QW (70 nmol/kg/week) for 2 weeks. 6 mice per group with initial average body weight of 44 g were tested. Body weight, body composition, food intake, and blood glucose levels were determined periodically.

As shown in FIG. 11, the acylated peptides are able to cause weight loss to a similar extent than the non-acylated peptide. As shown in FIG. 11, between about 7 and 12% weight loss is achieved within the first 3 days of treatment with the acylated peptides. As shown in FIG. 12, the acylated peptides caused a decrease in food intake. Furthermore, as shown in FIG. 13, the ad libitum blood glucose levels of the acylated peptides were reduced after 1 day of treatment.

Example 21

The following acylated glucagon co-agonist peptides were made as essentially described in Example 19.
(A) "Chimera-2 Aib2 Lys10-C18 Cys24(40K)": native glucagon amino acid sequence (SEQ ID NO: 1) comprising the following modifications: Glu at position 16, Gln at position 17, Ala at position 18, Lys at position 20, Glu at position 21, Ile at position 23, and Ala at position 24, and a C-terminal amide ("Chimera 2"), further modified with AIB at position 2, a Lys10 acylated with a C18 fatty acid and a Cys at position 24 pegylated with a 40K PEG group;
(B) "Chimera-2 Aib2 Lys 10-C16 Cys24(40K)": Chimera 2 further modified with AIB at position 2, a Lys10 acylated with a C16 fatty acid and a Cys24 pegylated with a 40K PEG group;
(C) "Glucagon Lys10-C18 E16 K20 Cys24(40K)": native glucagon amino acid sequence (SEQ ID NO: 1) comprising the following modifications: Glu at position 16, Lys at position 20, and C-terminal amide ("E16K20-glucagon-NH2") was further modified with a Lys10 acylated with a C18 fatty acid and a Cys24 pegylated with a 40K PEG group;
(D) "Glucagon Lys10-TrpC16 E16 K20 Cys24(40K)": E16K20-glucagon-NH2 was further modified with Lys 10 linked to a Trp spacer which was acylated with a C16 fatty acid;
(E) "Glucagon Lys10-TrpC18 E16 K20 Cys24(40K)": E16K20-glucagon-NH2 was further modified with Lys 10 linked to a Trp spacer which was acylated with a C18 fatty acid.

The acylated glucagon co-agonist peptides were tested for their activities at the Glucagon and GLP-1 receptors generally as described in Example 14. The EC50 at each of the glucagon receptor and the GLP-1 receptor in comparison to controls (GLP-1 (7-37) OH (amino acids 7-37 of GLP-1), Glucagon (1-29)OH (SEQ ID NO: 1), and Chimera 2 Cys24 (40K) (Chimera 2 with a 40K PEG on Cys 24)) are as shown in Table 16.

TABLE 16

| | EC50 at Glucagon Receptor (nM) | EC50 at GLP-1 Receptor (nM) |
|---|---|---|
| GLP-1 (7-37) OH | >1000.00 | 0.04 |
| Glucagon (1-29) OH | 0.07 | 7.5 |
| Chimera 2 Cys24 (40K) | 2.83 | 0.04 |
| Chimera-2 Aib2 Lys10-C18 Cys24 (40K) | 8.55 | 0.14 |
| Chimera-2 Aib2 Lys10-C16 Cys24 (40K) | 17.41 | 0.05 |
| Glucagon Lys10-C18 E16 K20 Cys24 (40K) | 0.84 | 0.15 |
| Glucagon Lys10-TrpC16 E16 K20 Cys24 (40K) | 0.54 | 0.23 |
| Glucagon Lys10-TrpC18 E16 K20 Cys24 (40K) | 1.29 | 1.64 |

Example 22

The following acylated glucagon co-agonist peptides were made as essentially described in Example 19:

(A) Peptide A: native glucagon amino acid sequence (SEQ ID NO: 0.1) comprising the following modifications: Glu at position 16, Lys at position 20, and C-terminal amide ("E16K20-glucagon-NH2");

(B) Peptide B: E16K20-glucagon-NH2 further comprising a Lys10 acylated with a C16 fatty acid;

(C) Peptide C: E16K20-glucagon-NH2 further comprising a Lys 10 acylated with a C18 fatty acid;

(D) Peptide D: E16K20-glucagon-NH2 further comprising a Lys10 linked to a Glu (a spacer residue) acylated with a C16 fatty acid;

(E) Peptide E: E16K20-glucagon-NH2 further comprising a Lys10 linked to a Trp (a spacer residue) acylated with a C18 fatty acid.

The activity of the peptides were assayed generally according to Example 14 and the EC50 at each of the glucagon receptor and the GLP-1 receptor are shown in Table 17.

TABLE 17

| | $EC_{50}$ at Glucagon Receptor (nM) | $EC_{50}$ at GLP-1 Receptor (nM) |
|---|---|---|
| GLP-1 OH | >1000 | 0.037 |
| Glucagon (1-29) OH (SEQ ID NO: 1) | 0.098 | 10 |
| Peptide A | 0.203 | 0.188 |
| Peptide B | 0.236 | 0.125 |
| Peptide C | 0.086 | 0.032 |
| Peptide D | 0.062 | 0.056 |
| Peptide E | 0.044 | 0.031 |

Example 23

A glucagon co-agonist peptide was made comprising the amino acid sequence of SEQ ID NO: 1 with the following modifications: Glu at position 16, Gln at position 17, Ala at position 18, Lys at position 20, Glu at position 21, Ile at position 23, Ala at position 24, Val at position 27, Lys at position 28 and C-terminal amide ("Chimera 1"). C-terminally truncated versions of Chimera 1 were made by deleting the amino acid at position 29 of Chimera 1 ("Chi 1 (1-28)"), or by deleting amino acids at both positions 28 and 29 of Chimera 1 ("Chi 1 (1-27)").

A glucagon peptide comprising the amino acid sequence of SEQ ID NO: 1 with the following modifications: Glu at position 16, C-terminal amide ("E16 Gluc-NH2") was also C-terminally truncated, by deleting either the amino acid at position 29 ("E16 GlucNH2 (1-28)") or by deleting amino acids at both positions 28 and 29 ("E16 GlucNH2 (1-27)").

The activity at the glucagon receptor and the GLP-1 receptor of the truncated peptides, as well as the non-truncated peptides, were assayed for functional activity generally according to Example 14. Deletion of amino acids at positions 28 and 29 of the E16 GlucNH2 peptide or the Chimera 1 peptide did not significantly impact the activity of the peptide at the glucagon receptor. Deletion of amino acids at positions 28 and 29 of E16 GlucNH2 did not appreciably change the potency of the peptide at the GLP-1 receptor. Deletion of amino acids at positions 28 and 29 of Chimera 1 did not impact its activity at the GLP-1 receptor.

Deletion of the amino acid at position 29 of either the Chimera 1 peptide or the E16 GlucNH$_2$ peptide did not significantly impact the activity at either the glucagon receptor or the GLP-1 receptor.

Example 24

Diet-induced obesity (DIO) mice were injected intraperitoneally at the −15 min time point with 0.2, 2, 20, or 70 nmol/kg of one of the following:

(A) vehicle only, (B) native glucagon amino acid sequence (SEQ ID NO: 1) comprising the following modifications: Glu at position 16, Gln at position 17, Ala at position 18, Lys at position 20, Glu at position 21, Ile at position 23, and Ala at position 24, and a C-terminal amide ("Chimera 2") further modified to comprise AIB at position 2 and Cys at position 24, which Cys is pegylated with a 40K PEG ("Chimera-2-AIB$^2$ Cys$^{24}$-40 kD"), (C) Chimera 2 further modified to comprise AIB at position 2, Lys at position 10, which Lys is acylated with a C8 fatty acid, and Cys at position 24, which Cys is pegylated with a 40K PEG ("Chimera-2 AIB$^2$K$^{10}$-C8 Cys$^{24}$-40 kD"), or (D) Chimera 2 further modified to comprise AIB at position 2, Lys at position 10, which Lys is acylated with a C16 fatty acid, and Cys at position 24, which Cys is pegylated with a 40K PEG ("Chimera-2 AIB$^2$ K$^{10}$-C16 Cys$^{24}$-40 kD").

A saline solution comprising 25% (v/v) glucose was injected at a dose of 1.5 g/kg of body weight at the 0 min time point. Blood glucose levels were measured at the −15, 0, 15, 30, 60, and 120 min time points.

FIGS. 15-17 show the blood glucose levels (mg/dL) of mice injected with 2, 20, and 70 nmol/kg, respectively, at the indicated time points. For all doses tested, Chimera-2 AIB$^2$K$^{10}$-C8 Cys$^{24}$-40 kD demonstrated the greatest ability to lower blood glucose in the mice. As shown in FIG. 17, this peptide had similar activity as Chimera-2-AIB$^2$ Cys$^{24}$-40 kD.

Example 25

DIO mice were injected intraperitoneally at the −24 hr time point with 70 nmol/kg of one of the following:

(A) vehicle only, (B) Chimera-2-AIB$^2$ Cys$^{24}$-40 kD, as described above in Example 24, (C) Chimera-2 AIB$^2$ K$^{10}$-C8 Cys$^{24}$-40 kD, as described above in Example 24, or (D) Chimera-2 AIB$^2$ K$^{10}$-C16 Cys$^{24}$-40 kD, as described above in Example 24.

A saline solution comprising 25% (v/v) glucose was injected at a dose of 1.5 g/kg of body weight at the 0 min time point. Blood glucose levels were measured at the 0, 15, 30, 60, and 120 min time points.

FIG. 18 demonstrates the blood glucose levels (mg/dL) of the mice at the indicated time points. All three peptides demonstrate significant activity at lowering blood glucose in the mice.

Example 26

DIO mice were injected intraperitoneally with vehicle only or 15 or 70 nmol/kg of one of the following:

(A) Chimera-2-AIB$^2$ Cys$^{24}$-40 kD, as described above in Example 24, (B) Chimera-2 AIB$^2$ K$^{10}$-C8 Cys$^{24}$-40 kD, as described above in Example 24, or (C) Chimera-2 AIB$^2$K$^{10}$-C16 Cys$^{24}$-40 kD, as described above in Example 24.

Body weight was measured before injection and at 1, 3, 5, and 7 days post-injection.

FIG. 19 demonstrates the % change of body weight for each group of mice. At both doses tested, Chimera-2 AIB$^2$ Cys$^{24}$-40 kD and Chimera-2-AIB$^2$ Cys$^{24}$-40 kD demonstrate comparable ability to lower body weight. At the higher dose tested, Chimera-2 AIB$^2$ K$^{10}$-C16 Cys$^{24}$-40 kD demonstrates significant ability to lower body weight Example 27

A peptide of SEQ ID NO: 555, comprising a Tyrosine at position 1 and a lactam bridge between E16 and K20, (and an amide in place of the C-terminal carboxylate) was synthesized as essentially described above and tested in vitro for activity at GLP-1 and glucagon receptors by Example 14. The EC50 of the peptide at each receptor is shown in Table 18.

TABLE 18

| Receptor | EC$_{50}$ (nM) | Std. Dev | Relative Activity |
| --- | --- | --- | --- |
| Glucagon | 0.044 | 0.151 | 343.18% |
| GLP-1 | 0.062 | 0.062 | 100.00% |

Relative activity is activity relative to the native hormone of the indicated receptor.

Based on these data, it was determined that the peptide of SEQ ID NOs: 555 was an exemplary glucagon/GLP-1 co-agonist peptide.

Example 28

A peptide of SEQ ID NO: 1 (Glucagon(1-29)), a peptide of SEQ ID NO: 1 with an amide replacing the C-terminal carboxylate (Glucagon (1-29a)), and a peptide of SEQ ID NO: 1 with AIB at each of positions 2 and 16 and an amide replacing the C-terminal carboxylate (Glucagon(1-29a) Aib$^2$ Aib$^{16}$) were synthesized as essentially described above. These peptides were then tested in vitro for activity at the GLP-1 receptor and glucagon receptors by the methods described in Example 14. The EC50 of each peptide are shown in Table 19.

TABLE 19

| | Glucagon Receptor | | GLP-1 Receptor | |
| --- | --- | --- | --- | --- |
| Peptide | EC$_{50}$ (nM) | SD | EC$_{50}$ (nM) | SD |
| Glucagon(1-29) | 0.04 | 0.01 | 3.65 | 0.21 |
| Glucagon(1-29a) Aib$^2$ Aib$^{16}$ | 0.09 | 0.02 | 0.10 | 0.01 |
| Glucagon(1-29a) | ND | ND | 0.50 | 0.05 |
| GLP-1(1-31)OH | ND | ND | 0.03 | 0.00 |

SD = standard deviation

Example 29

The following peptides were synthesized as essentially described above:

(1) Glucagon(1-29), as described in Example 28, (2) Glucagon(1-29a) Aib$^2$ Aib$^{16}$ (as described in Example 28) with a Cys at position 24 and a Lys at position 10 covalently bonded to a Trp comprising a C16 fatty acid ("Glucagon (1-29a) Aib$^2$ Lys$^{10}$-Trp-C16 Aib$^{16}$ Cys$^{24}$")

(3) Glucagon (1-29a) Aib$^2$ Lys$^{10}$-Trp-C16 Aib$^{16}$ Cys$^{24}$ in which the Cys comprises a 40 kD PEG group ("Glucagon (1-29a) Aib$^2$ Lys$^{10}$-Trp-C16 Aib$^{16}$ Cys$^{24}$-40 kD"), (4) Glucagon (1-29a) Aib$^2$ Lys$^{10}$-Trp-C16 Aib$^{16}$ Cys$^{24}$ comprising Aib at position 20 ("Glucagon (1-29a) Aib$^2$ Lys$^{10}$-Trp-C16 Aib$^{16}$ Aib$^{20}$ Cys$^{24}$), and (5) Glucagon (1-29a) Aib$^2$ Lys$^{10}$-Trp-C16 Aib$^{16}$ Aib$^{20}$ Cys$^{24}$ in which the Cys comprises a 40 kD PEG group ("Glucagon (1-29a) Aib$^2$ Lys$^{10}$-Trp-C16 Aib$^{16}$ Aib$^{20}$Cys$^{24}$-40 kD). These peptides were then tested in vitro for activity at the GLP-1 receptor and glucagon receptors by the methods of Example 14. The EC50 of each peptide are shown in Table 20.

TABLE 20

| | Glucagon Receptor | | GLP-1 Receptor | |
| --- | --- | --- | --- | --- |
| Peptide | EC$_{50}$ (nM) | SD | EC$_{50}$ (nM) | SD |
| Glucagon(1-29) | 0.04 | 0.01 | | |
| Glucagon (1-29a) Aib$^2$ Lys$^{10}$-Trp-C16 Aib$^{16}$ Cys$^{24}$ | 0.25 | 0.02 | 0.24 | 0.03 |
| Glucagon (1-29a) Aib$^2$ Lys$^{10}$-Trp-C16 Aib$^{16}$ Cys$^{24}$-40K | 0.29 | 0.03 | 0.19 | 0.02 |
| Glucagon (1-29a) Aib$^2$ Lys$^{10}$-Trp-C16 Aib$^{16}$ Aib$^{20}$ Cys$^{24}$ | 2.06 | 0.02 | 1.15 | 0.19 |
| Glucagon (1-29a) Aib$^2$ Lys$^{10}$-Trp-C16 Aib$^{16}$ Aib$^{20}$ Cys$^{24}$-40K | 2.37 | 0.24 | 0.60 | 0.06 |
| GLP-1(1-31)OH | | | 0.02 | 0.01 |

Example 30

The in vivo effects of acylated and pegylated glucagon peptides were tested in DIO mice. Specifically, 6 groups of DIO mice (8 mice per group), each group having an average initial body weight of 58 g, were injected intraperitoneally with 10, 20, 40, or 80 nmol/kg of an acylated and pegylated glucagon peptide or a vehicle control once a week for 2 weeks. The acylated and pegylated glucagon peptides used in the study were Chimera-2 AIB$^2$K$^{10}$-C8 Cys$^{24}$-40 kD (as described in Example 26) and Peptide A K$^{10}$-C$_{14}$ (as described in Example 20).

Changes in body weight of and food intake by the mice were measured 0, 1, 3, 5, 7, 8, 10, 12, and 14 days after injection. Blood glucose levels of the mice were monitored throughout the 14 days. Glucose tolerance tests were performed by injecting a 25% glucose in saline solution 1 hour or 24 hours after administration of the acylated or pegylated peptide and measuring blood glucose levels at −60, 0, 15, 30, 60, or 120 min after the glucose injection.

As shown in FIG. 20, the total body weight of mice injected with 40 or 80 nmol/kg of acylated and pegylated Peptide A $K^{10}$-$C_{14}$ was reduced as compared to mice injected with the vehicle control.

As shown in FIG. 21, the blood glucose levels of mice injected with 20, 40, or 80 nmol/kg Peptide A $K^{10}$-$C_{14}$ or with 20 nmol/kg Chimera-2 $AIB^2 K^{10}$-C8 $Cys^{24}$-40 kD in response to a glucose injection are lowered in comparison to vehicle control.

Example 31

Acylated glucagon analog peptides comprising or lacking a covalent intramolecular bridge were made by solid-phase synthesis and tested for in vitro activity at the glucagon and GLP-1 receptors. The EC50 (nM) at each receptor and the % activity of the peptide relative to the native peptide at the corresponding receptor is shown in Table 21.

TABLE 21

| Peptide Name | SEQ ID NO: | $EC_{50}$ at the GLP-1 receptor (nM) | % Activity of GLP-1 | $EC_{50}$ at the Glucagon receptor (nM) | % Activity of Glucagon |
|---|---|---|---|---|---|
| DMIA1, K10(C14), [E16/K20]-Gluc Amide | 607 | 0.050 | 30% | 0.027 | 203.7% |
| DMIA1, K10(C16), [E16/K20]-Gluc Amide | 608 | 0.015 | 100% | 0.014 | 392% |
| DMIA1, K10(C18), [E16/K20]-Gluc Amide | 609 | 0.011 | 136% | 0.13 | 42.3% |
| AIB2, AIB16, K10(C14) Gluc Amide | 610 | 0.024 | 33.3% | 0.044 | 77.3% |
| AIB2, AIB16, K10(C16) Gluc Amide | 611 | 0.011 | 72.3% | 0.020 | 170% |
| AIB2, AIB16, K10(C18) Gluc Amide | 612 | 0.009 | 88.9% | 0.016 | 212.5% |
| dS2, E16/K20, K10(C14) Gluc Amide | 613 | 0.128 | 6.3% | 0.155 | 21.9% |
| dS2, E16/K20, K10(C16) Gluc Amide | 614 | 0.041 | 19.5% | 0.076 | 44.7% |
| dS2, E16/K20, K10(C18) Gluc Amide | 615 | 0.025 | 60% | 0.028 | 196% |

Several glucagon analogs lacking a covalent intramolecular bridge and comprising an AIB at position 2, an MB at position 16, and a fatty acyl group attached via a spacer to a Lys residue at position 10 were made as essentially described herein. The acylated glucagon analogs differed by the type of spacer, the presence or absence of pegylation, and/or by the size of the acyl group. The acylated glucagon analogs were tested for in vitro activity at the glucagon receptor and the GLP-1 receptor as essentially described in Example 14. A summary of the structure and in vitro activity at the glucagon and GLP-1 receptors of each peptide is shown in Tables 22 and 23.

TABLE 22

Glucagon analog backbone amino acid sequence:
HXQGTFTSDKSKYLDXRRAQDFVQWLMNT-NH$_2$
wherein X = AIB
(SEQ ID NO: 562)

| Peptide Name | SEQ ID NO: | Spacer | Size of Fatty Acyl Group | $EC_{50}$ at Glucagon Receptor (nM) | $EC_{50}$ at GLP-1 Receptor (nM) |
|---|---|---|---|---|---|
| wt glucagon | 1 | n/a | n/a | 0.031 ± 0.014 | |
| wt GLP-1 | | n/a | n/a | | 0.036 ± 0.010 |
| 26 | 637 | None | None | 0.653 ± 0.285 | 0.475 ± 0.046 |
| 50 | 563 | None | C16 | 0.572 ± 0.084 | 0.291 ± 0.060 |
| 82 | 564 | Ala-Ala | C16 | 0.024 ± 0.001 | 0.108 ± 0.018 |
| 83 | 565 | γ-Glu-γ-Glu | C16 | 0.014 ± 0.002 | 0.043 ± 0.005 |
| 84 | 566 | β-Ala-β-Ala | C16 | 0.011 | 0.004 |
| 85 | 567 | 6-amino-hexanoic acid | C16 | 0.010 | 0.005 |
| 86 | 568 | Leu-Leu | C16 | 0.011 | 0.006 |
| 87 | 569 | Pro-Pro | C16 | 0.017 | 0.009 |
| 77* | 570 | None | C14 | 21.94 ± 14.47 | 1.458 ± 0.132 |
| 78* | 571 | γ-Glu-γ-Glu | C14 | 0.319 ± 0.091 | 0.103 ± 0.023 |
| 81* | 573 | Ala-Ala | C14 | 0.597 ± 0.175 | 0.271 ± 0.019 |
| 79* | 575 | Ala-Ala | C16 | 0.102 ± 0.011 | 0.055 ± 0.001 |
| 80* | 576 | γ-Glu-γ-Glu | C16 | 0.108 ± 0.028 | 0.042 ± 0.008 |

*indicates that the peptide comprised a Cys residue at position 24 (in place of Gln) which Cys was covalently attached to a 40 kDa PEG group.

TABLE 23

Glucagon analog backbone amino acid sequence:
HXQGTFTSDKSKYLDXRRAQDFVQWLMNT-NH$_2$
wherein X = AIB
(SEQ ID NO: 562)

| Peptide Name | SEQ ID NO: | Spacer | Size of Fatty Acyl Group | $EC_{50}$ at Glucagon Receptor (nM) | $EC_{50}$ at GLP-1 Receptor (nM) |
|---|---|---|---|---|---|
| wt glucagon | 1 | n/a | n/a | 0.008 ± 0.003 | |
| wt GLP-1 | | n/a | n/a | | 0.004 ± 0.001 |
| 77** | 616 | none | C14 | 0.144 ± 0.029 | 0.063 ± 0.012 |
| 78** | 617 | γ-Glu-γ-Glu | C14 | 0.009 ± 0.001 | 0.008 ± 0.001 |
| 81** | 618 | Ala-Ala | C14 | 0.027 ± 0.006 | 0.018 ± 0.001 |
| 80** | 619 | γ-Glu-γ-Glu | C16 | 0.006 ± 0.001 | 0.008 ± 0.001 |
| 79** | 620 | Ala-Ala | C16 | 0.010 ± 0.001 | 0.008 ± 0.001 |

**peptide comprising Cys at position 24 (in place of Gln) which Cys was not covalently attached to a PEG molecule As shown in Tables 22 and 23, the peptides comprising a fatty acyl group attached via a spacer significantly increased their potency as compared to peptides comprising a fatty acyl group attached directly to the peptide backbone.

Example 32

DIO mice (8 mice per group), each with an average body-weight of 48.7 g, were subcutaneously injected daily for seven days with vehicle only, with 30 nmol/kg or 100 nmol/kg of an acylated glucagon analog peptide, or with the long-acting GLP-1 analog, Liraglutide (Novo Nordisk, Denmark). The acylated glucagon analogs were as follows:

"(C16) Glucagon Amide" comprised the amino acid sequence of wild-type glucagon (SEQ ID NO: 1) with the Tyr at position 10 modified to an acylated Lys residue, wherein the acylated Lys comprised a C16 fatty acyl group, and the C-terminal carboxylate replaced with an amide group;

"γE-γE-C16 Glucagon Amide" comprised the same structure of C16 Glucagon Amide, except that the C16 fatty acyl group was attached to the Lys at position 10 through a gamma-Glu-gamma-Glu dipeptide spacer (see structure of acylated Lys below);

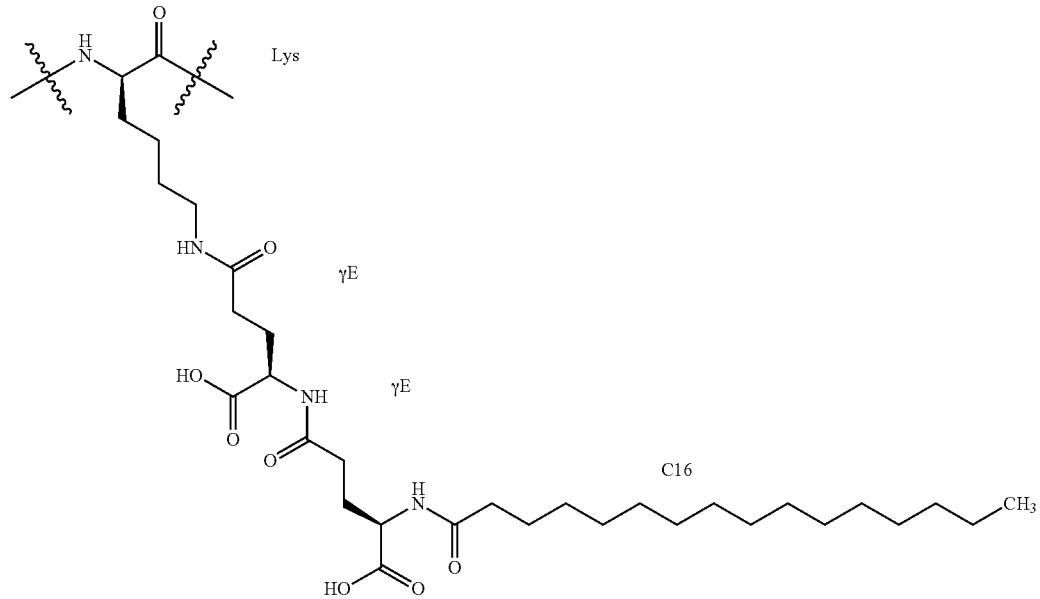

"AA-C16 Glucagon Amide" comprised the same structure of C16 Glucagon Amide, except that the C16 fatty acyl group was attached to the Lys at position 10 through an Ala-Ala dipeptide spacer; and "βAβA-C16 Glucagon Amide" comprised the same structure of C16 Glucagon Amide, except that the C16 fatty acyl group was attached to the Lys at position 10 through an β-Ala-β-Ala dipeptide spacer.

The body weight of the mice was monitored daily and the total change in body weight (%) is shown in FIG. 22. As shown in FIG. 22, most of the acylated glucagon peptides at each dose caused a reduction in body weight. While Liraglutide demonstrated an approximate 12% decrease in body weight, the glucagon analog peptide γE-γE-C16 Glucagon Amide exhibited the greatest ability to cause weight loss in mice at the matched dose. Even the lower dose of γE-γE-C16 Glucagon Amide caused a substantial decrease in body weight.

The fat mass of the mice was measured on Day 7 of the study. As shown in FIG. 23, the mice which were administered 100 nmol/kg γE-γE-C16 Glucagon Amide exhibited the lowest fat mass.

Blood glucose levels of the mice were also monitored during the course of the assay. As shown in FIG. 24, the glucagon analog peptide γE-γE-C16 Glucagon Amide at the higher dose worked as well as Liraglutide to decrease blood glucose levels in mice.

Example 33

Acylation of a glucagon analog peptide having GLP-1 activity was evaluated as follows. A non-acylated glucagon analog peptide comprising the structure of Chimera 2 with AIB at position 2 and Cys at position 24 (comprising a 40 kDa PEG molecule) was modified to comprise an acylated Lys residue at position 10. The non-acylated glucagon analog peptide comprised the amino acid sequence of SEQ ID NO: 580. The Lys at position 10 was acylated with a C8, C14, C16, or C18 fatty acyl group and the acylated peptides comprised the structures of SEQ ID NOs: 534-537, respectively. The in vitro activity at the GLP-1 receptor of the non-acylated peptide and acylated versions thereof were tested as essentially described herein. The EC50 at the GLP-1 receptor of each peptide is shown in Table 24.

TABLE 24

| Glucagon analog peptide sequence HXQGTFTSDYSKYLDEQAAKEFICWLMNT-NH$_2$, wherein X = AIB (SEQ ID NO: 580) | $EC_{50}$ (nM) | SD |
|---|---|---|
| GLP-1 | 0.026 | 0.003 |
| Non-acylated Glucagon analog peptide (SEQ ID NO: 580) | 0.095 | 0.015 |
| C$_8$ acylated Glucagon analog peptide (SEQ ID NO: 534) | 0.058 | 0.002 |
| C$_{14}$ acylated Glucagon analog peptide (SEQ ID NO: 535) | 0.044 | 0.005 |
| C$_{16}$ acylated Glucagon analog peptide (SEQ ID NO: 536) | 0.033 | 0.005 |
| C$_{18}$ acylated Glucagon analog peptide (SEQ ID NO: 537) | 0.011 | 0.001 |

Example 34

Glucagon analog peptides were made by solid-phase peptide synthesis as described herein and were acylated at either position 10 or 30 of the peptide. The peptides and their structure were as follows:

"Peptide dS2E16K20K30-C14 Gluc Amide" comprised the amino acid sequence HXQGTFTSDYSKYLDER-RAKDFVQWLMNTK-amide (SEQ ID NO: 581), wherein the X at position 2 is d-Ser, wherein the Lys at position 30 is acylated with a C14 fatty acyl group, and the C-terminal carboxylate is replaced with an amide;

"Peptide dS2K10(C14)E16K20-Gluc Amide" comprised the amino acid sequence HXQGTFTSDKSKYLDER-RAKDFVQWLMNT-amide (SEQ ID NO: 582); wherein the X at position 2 is d-Ser, wherein the Lys at position 10 is acylated with a C14 fatty acyl group, and the C-terminal carboxylate is replaced with an amide;

"Peptide dS2E16K20K30-C16 Gluc Amide" comprised the amino acid sequence HXQGTFTSDYSKYLDER-RAKDFVQWLMNTK-amide (SEQ ID NO: 583), wherein the X at position 2 is d-Ser, wherein the Lys at position 30 is acylated with a C16 fatty acyl group, and the C-terminal carboxylate is replaced with an amide;

"Peptide dS2K10(C16)E16K20-Gluc Amide" comprised the amino acid sequence HXQGTFTSDKSKYLDER-RAKDFVQWLMNT-amide (SEQ ID NO: 584); wherein the X at position 2 is d-Ser, wherein the Lys at position 10 is acylated with a C16 fatty acyl group, and the C-terminal carboxylate is replaced with an amide;

"Peptide Chimera 2-AIB2-K10-acylated" comprised the amino acid sequence HXQGTFTSDKSKYLD-EQAAKEFICWLMNT-amide (SEQ ID NO: 585); wherein the X at position 2 is AIB, the K at position 10 is acylated with a C18 fatty acyl group, Cys at position 24 comprises a 40 kDa PEG molecule, and the C-terminal carboxylate is replaced with an amide; and "Peptide Chimera 2-AIB2-K30-acylated" comprised the amino acid sequence HXQGTFTSDYSKYLD-EQAAKEFICWLMNTK-amide (SEQ ID NO: 586), wherein the X at position 2 is AIB, the K at position 10 is acylated with a C18 fatty acyl group, Cys at position 24 comprises a 40 kDa PEG molecule, and the C-terminal carboxylate is replaced with an amide.

The in vitro activity at the GLP-1 receptor and glucagon receptor of each peptide was tested as essentially described in Example 14. The results are shown in Table 25.

TABLE 25

| Peptide Name | Position at which acyl group is found | EC50 at the glucagon receptor (nM) | EC50 at the GLP-1 receptor (nM) |
| --- | --- | --- | --- |
| Peptide dS2E16K20K30-C14 Gluc Amide | 30 | 3.53 | 0.84 |
| Peptide dS2K10(C14)E16K20-Gluc Amide | 10 | 0.155 | 0.041 |
| Peptide dS2E16K20K30-C16 Gluc Amide | 30 | 4.89 | 3.05 |
| dS2K10(C16)E16K20-Gluc Amide | 10 | 0.076 | 0.041 |
| Peptide Chimera 2-AIB2-K10-acylated | 30 | N/A | 0.465 |
| Peptide Chimera 2-AIB2-K30-acylated | 10 | N/A | 0.007 |

Example 35

Solid-phase peptide synthesis was employed for the assembly of the sequence, XSQGTFTSDYSKYLDER-RAKDFVCWLMNT-NH$_2$, where X=DMIA (SEQ ID NO: 587). After selective deprotection of the Glu at position 16 and the Lys at position 20, the peptide was cyclized via a lactam bridge on resin. The crude peptide after cleavage was then purified by preparative RP-HPLC and characterized by MS (calc. for [M+H]: 3479.9. found 3480.9). PEGylation was conducted by mixing the peptide precursor and iodoacetyl-functioned 40 k Da PEG (NOF)(1:1) in 7 M urea/50 mM Tris buffer, pH 8.5, at room temperature for 45 minutes to form a covalent, thioether bond between the PEG and a Cys of the peptide, as shown below

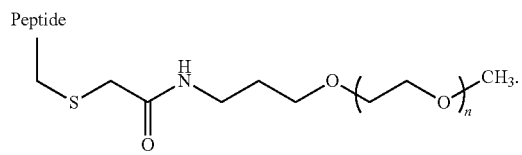

The PEGylated peptide was purified by preparative HPLC and the desired fractions were collected and lyophilized to yield a off-white powder. The product was confirmed by MALDI-TOF-MS (44000-46000, broad peak).

The in vitro activity at the GLP-1 receptor and glucagon receptor were tested as essentially described in Example 14. The EC50s at the GLP-1 receptor and glucagon receptor were 0.327 nM and 0.042 nM, respectively.

Example 36

Solid-phase peptide synthesis was employed for the preparation of the peptide precursor, HXEGTFTSDYSKYLD-EQAAKEFICWLMNT-NH$_2$, wherein X=AIB (SEQ ID NO: 589). The crude peptide was then purified by preparative RP-HPLC and characterized by MS (calc. for [M+H]: 3412.8. found 3413.9). PEGylation was conducted by mixing the peptide precursor and iodoacetyl-functioned 40 k Da PEG (NOF)(1:1) in 7 M urea/50 mM Tris buffer, pH 8.5, at room temperature for 45 minutes to form a covalent, thioether bond between the PEG and a Cys of the peptide, as shown below

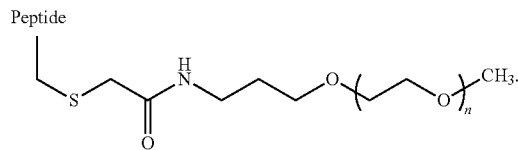

The PEGylated peptide was purified by preparative HPLC and the desired fractions were collected and lyophilized to yield a off-white powder. The product was confirmed by MALDI-TOF-MS (44000-46000, broad peak).

The in-vitro activity at the GLP-1 receptor and glucagon receptor were tested as essentially described in Example 14. The EC50s at the GLP-1 receptor and glucagon receptor were 0.027 nM and 33 nM, respectively.

Example 37

The following glucagon analog peptides comprising a backbone of Peptide J

```
                                      (SEQ ID NO: 591)
    HS-X-GTFTSDYSKYLDTRRAAEFVAWL(Nle)DE
``` or Peptide K

```
                                      (SEQ ID NO: 592)
    HS-X-GTFTSDYSKYLD(Aib)RRAADFVAWLMDE
``` with additional modification at position 3 were made by solid-phase peptide synthesis as essentially described herein. The peptides were tested for in vitro activity at the glucagon receptor as essentially described in Example 14. The EC50 (nM) of each peptide is shown in Table 26.

TABLE 26

| Peptide Backbone | Amino Acid at Position 3 | SEQ ID NO: | EC50 at Glucagon Receptor (nM) | % activity* |
|---|---|---|---|---|
| J | Q | 593 | 0.24 | 25% |
| J | C(Acm) | 594 | 0.18 | 33% |
| J | Dab(Ac) | 595 | 0.31 | 19% |
| J | Dap(urea) | 596 | 0.48 | 13% |
| J | Q(Me) | 597 | 0.48 | 13% |
| J | M(O) | 598 | 0.91 | 7% |
| J | Orn(Ac) | 599 | 0.92 | 7% |
| K | Q | 600 | 0.39 | 15% |
| K | Dab(Ac) | 601 | 0.07 | 86% |
| K | Q(Me) | 602 | 0.11 | 55% |

Q = glutamine;
C(Acm) = acetamidomethyl-cysteine;
Dab(Ac) = acetyldiaminobutanoic acid;
Dap(urea) = carbamoyldiaminopropanoic acid;
Q(Me) = methylglutamine;
M(O) = methionine-sulfoxide;
Orn(Ac) = acetylornithine.

As shown in Table 26, multiple amino acids could be placed at position 3 without a substantial loss of activity at the glucagon receptor, and, in some cases, the modification actually increased the activity, e.g., Dab(Ac) and Q(Me) on the Peptide K backbone.

Example 38

Glucagon analog peptides comprising Dab(Ac) at position 3 on various glucagon analog backbones were made as essentially described herein and the in vitro activity at the glucagon receptor was tested. The structures and activities of each peptide are shown in Table 27.

TABLE 27

| Amino acid sequence | SEQ ID NO: | EC50 (nm) at Glucagon Receptor | % activity* |
|---|---|---|---|
| Wildtype Glucagon | 1 | 0.026 | 100 |
| HSQGTFTSDYSKYLDSRRAQDFVQWLMDT | 642 | 0.015 | 173 |
| HSDab(Ac)GTFTSDYSKYLDAibRRAADFVAWLLDE | 603 | 0.069 | 37 |
| HSDab(Ac)GTFTSDYSKYLDAibRRAADFVAWLLDTGPSSGAPPPS amide | 604 | 0.023 | 113 |
| HSDab(Ac)GTFTSDYSKYLDAibRRASDFVSWLLDE | 605 | 0.048 | 54 |
| HSDab(Ac)GTFTSDYSKYLDAibRRATDFVTWLLDE | 606 | 0.057 | 46 |

Example 39

A first glucagon analog peptide (AIB2, AIB16, K10(C16) Gluc Amide) comprising SEQ ID NO: 1 with AIB at positions 2 and 16, Lys at position 10, wherein the Lys at position 10 was covalently attached to a C16 fatty acyl group, and an amide in place of the C-terminal carboxylate was made as essentially described herein. A second glucagon analog peptide (AIB2, AIB16, K10(C16), K30 Gluc Amide) having the same structure as the first glucagon analog peptide, except that a Lys was added to the C-terminus. The in vitro activity of the peptides was tested as essentially described in Example 14 and was additionally tested in a solution comprising 20% human plasma. The EC50 (nM) at each receptor for the peptides is shown in Table 28.

TABLE 28

| Amino acid sequence | SEQ ID NO: | EC50 (nm) at Glucagon Receptor | EC50 (nm) at Glucagon Receptor (20% human plasma) | EC50 (nm) at GLP-1 Receptor | EC50 (nm) at GLP-1 Receptor (20% human plasma) |
|---|---|---|---|---|---|
| Glucagon | 1 | 0.026 | 0.046 | | |
| GLP-1 | | | | 0.022 | 0.028 |
| AIB2, AIB16, K10(C16) Glucagon Amide | 563 | 0.052 | 0.023 | 0.026 | 0.014 |
| AIB2, AIB16, K10(C16), K30 Glucagon Amide | 622 | 0.761 | 0.313 | 0.031 | 0.017 |

Example 40

The discovery of leptin documented the existence of an endocrine system that regulates energy balance and body adiposity. It also recruited interest and investment in obesity research as a means to identify environmental and pharmacologic approaches to manage what has become a global epidemic of disease. Sufficiently efficacious and safe pharmacologic treatment for obesity has yet to emerge and surgery constitutes the only proven option to sustained weight loss. It is reported herein that the combinatorial efficacy of receptor agonism at two endocrine hormonal receptors to achieve potent satiety inducing and lipolytic effects in a single peptide of sustained duration of action. Two specific glucagon analogs with activity at the GLP1-R comparable to native GLP-1, but differing from each other in their level of glucagon receptor agonism were studied pharmacologically in rodent obesity models. Once weekly administration of these pegylated peptides selected from a series of high potency analogs with differential glucagon and GLP-1 activity normalized adiposity and glucose tolerance levels in diet induced obese mice (average body weight ca. 50 g) within a month. Body weight loss was a consequence of body fat loss resulting from decreased food intake and increased energy expenditure, which increased with the level of glucagon receptor agonism. These co-agonist compounds also normalized glucose and lipid metabolism including liver steatosis. Effects were dose dependent and successfully repeated in diet induced obese rats. These preclinical studies indicate that when full GLP-1 agonism is enhanced with an appropriate degree of glucagon receptor activation, body fat reduction can be substantially and safely accelerated. The findings shown herein establish a basis for clinical testing and suggest an attractive novel treatment option for the metabolic syndrome.

Example 41

The following materials and methods pertain to the experiments described in Examples 42 to 51.

Boc Peptide Synthesis and Cleavage.

Peptide syntheses were performed using 0.2 mmol 4-methylbenzhydrylamine (MBHA) resin (Midwest Biotech, Fishers, Ind.) on a modified Applied Biosystems 430A peptide synthesizer. Solid-phase peptide syntheses utilized in situ neutralization for Boc-chemistry (Schnolzer, M. et al., *International Journal of Peptide Research and Therapeutics*, 13:31-44 (2007)). Completed peptidyl-resins were treated with HF/p-cresol (10:0.5 v/v) at 0° C. for 1 h. HF was removed in vacuo and the deprotected peptide was precipitated and washed in diethyl ether. The peptide was dissolved in 20% acetonitrile/1% acetic acid and lyophilized. Most peptides were prepared by Boc chemistry. The following side chain protecting groups were used for Boc-amino acids (Midwest Biotech): Arg(Tos), Asp(OcHex), Asn(Xan), Glu(OcHex), His(BOM), Lys(2-Cl—Z), Ser(Bzl), Thr(Bzl), Trp(CHO), Tyr(Br—Z). Peptide molecular weights were confirmed by electrospray ionization or MALDI-TOF mass spectrometry and purified as described elsewhere.

Lactam Synthesis.

Cyclized peptides with i to i+4 lactam formation were synthesized on resin. Glu(OFm)—OH gamma ester (Peptides International, Louisville, Ky.) and Lys(Fmoc)—OH (Peptides International) were substituted for Glu(OcHex) and Lys(2-Cl—Z) at positions involved in lactam formation. The fully protected peptidyl-resin was treated with 20% piperidine in DMF for 45 minutes to remove Fmoc and OFm protecting groups. On resin, lactam formation was achieved after treatment with 5 equivalents of benzotriazole-1-yloxy-tris-pyrrolidino-phosphonium hexafluorophosphate (PyBOP) (Fluka) in DMF/DIEA for 5 h. Lactam formation was confirmed by ninhydrin analysis and mass reduction of 18 relative to the open form of the peptide.

Peptide Purification.

Following cleavage from the resin, crude peptide extracts were analyzed by analytical reverse-phase HPLC. Analytical separations were conducted in 0.1% TFA with an acetonitrile gradient on a Zorbax C8 column (0.46×5 cm). After analytical analysis, the crude extract was purified by semi-preparative chromatography in 0.1% TFA with an acetonitrile gradient on a Vydac C4 or C18 column (2.2×25 cm). Pegylated peptides were purified using the same conditions. Preparative fractions were analyzed for purity (>95%) by analytical reverse-phase HPLC utilizing the conditions listed for analytical separations. Peptide masses and purity were confirmed by electrospray ionization mass spectrometry (ESI-MS) or matrix-assisted laser desorption/ionization time-of-flight (MALDI-TOF) mass spectrometry. Pegylated peptides showed a broad mass range spanning 43400 by MALDI-TOF. Purified peptides were lyophilized and stored at 4° C.

Pegylation of Peptides.

Purified peptides were mixed at a 1:1 molar ratio with methoxy poly(ethylene glycol) maleimido-propionamide-40K (Chirotech Technology Ltd, Cambridge) in 7M urea/50 mM Tris, pH 8.0. Reaction progress was monitored by analytical reverse-phase HPLC and free peptide was consumed within 30 minutes. The reaction was quenched in 0.1% TFA, purified and characterized as described elsewhere.

Glucagon and GLP-I Receptor-Mediated cAMP Synthesis.

Each peptide analog was tested for its ability to stimulate cAMP production through the glucagon (Gcg) and GLP-1 receptors. HEK293 cells were co-transfected with the GcgR or GLP-1R cDNAs and a luciferase reporter gene-linked to a cAMP response element (CRE). Cells were serum deprived for 16 h by culturing in DMEM (Invitrogen, Carlsbad, Calif.) and supplemented with 0.25% Bovine Growth Serum (HyClone, Logan, Utah). Serial dilutions of Glucagon and GLP-1 analogs were added to 96-well poly-D-Lysine-coated plates (BD Biosciences, San Jose, Calif.) containing co-transfected HEK293 cells, and plates were incubated for 5 h at 37° C., 5% $CO_2$. Following incubation, an equivalent volume (100 µL) of LucLite luminescence substrate reagent (Perkin-Elmer, Wellesley, Mass.) was added to each well and the plate was shaken for 3 min at 800 rpm. The plate was incubated for 10 min in the dark and light output was quantified on a Micro-Beta1450 liquid scintillation counter (Perkin-Elmer, Wellesley, Mass.). Effective 50% concentrations (EC50) were calculated by Origin software (OriginLab, Northampton, Mass.).

Circular Dichroism Measurements.

Peptides were dissolved in 10 mM phosphate buffer pH 5.9 with increasing concentrations of TFE, and peptide concentrations were quantified. Each sample was diluted to 10 µM for CD measurements. CD data were collected on a JASCO J-715 circular dichroism spectropolarimeter with constant nitrogen stream and temperature control of the 1 mm path length cell set at 25° C. Spectral data were accumulated for 5 scans from 270-190 nm with a scan speed of 100 nm/min and 1 nm wavelength step. Solvent signal was subtracted and data were smoothed (Savitzky and Golay, *Anal. Chem.* 36:1627 (1964)); in the JASCO Spectra Manager software. Millidegree values obtained were converted to mean residue ellipticity with units of $deg \cdot cm^2 \cdot dmol^{-1}$. Calculated mean residue ellipticity values were input into DICHROWEB (Whitmore and Wallace, *Biopolymers* 89:392-400 (2008); Whitmore and Wallace, *Nucleic Acids Research* 32:W668-W673 (2004) to obtain percent helicity values.

Animals.

C57Bl/6 mice were obtained from Jackson Laboratories and fed a diabetogenic diet from Research Diets, a high sucrose diet with 58% kcal from fat. Mice were single or group-housed on a 12:12-h light-dark cycle at 22° C. with free access to food and water. All studies were approved by and performed according to the guidelines of the Institutional Animal Care and Use Committee of the University of Cincinnati.

Body Composition Measurements.

Whole body composition (fat and lean mass) was measured using NMR technology (EchoMRI, Houston, Tex.).

Energy Balance Physiology Measurements.

Energy intake and expenditure, as well as home-cage activity, were assessed by using a combined indirect calorimetry system (TSE Systems, Bad Homburg, Germany). Oxygen consumption and $CO_2$ production were measured every 45 min for a total of 120 h (including 12 h of adaptation) to determine the respiratory quotient and energy expenditure. Food and water intake and meal patterns were determined continuously for 120 h at the same time as the indirect calorimetry assessments by integration of scales into the sealed cage environment. Meals were defined as food intake events with a minimum duration of 60 s, and a break of 300 s between food intake events. Home-cage locomotor activity was determined using a multidimensional infrared light beam system with beams scanning the bottom and top levels of the cage, and activity being expressed as beam breaks. Stationary motor activity (fidgeting) was defined as consecutive breaks of one single light beam at cage-bottom level, ambulatory movement as breaks of any two different light beams at cage-bottom level, and rearing as simultaneous breaks of light beams on both cage-bottom and the top level.

Blood Parameters.

Blood was collected after a 6-h fast from tail veins using EDTA-coated Microvette tubes (Sarstedt, Nuremberg, Germany) and immediately chilled on ice. After 15 min of centrifugation at 3,000 g and 4° C., plasma was stored at −80° C. Plasma insulin was quantified by a radioimmunoassay from Linco (Sensitive Rat Insulin RIA; Linco Research, St. Charles, Mo.). Plasma TGs and cholesterol levels were measured by enzymatic assay kits (Thermo Electron, Waltham, Mass.). Samples were analyzed individually with the exception that pooled samples (0.25 ml) from 5 animals/group were subjected to fast-performance liquid chromatography (FPLC) gel filtration on two Superose 6 columns connected in series for lipoprotein separation. All assays were performed according to the manufacturer's instructions.

Glucose Tolerance Test.

For the determination of glucose tolerance, mice were subjected to 6 h of fasting and injected intraperitoneally (i.p.) with 2 g glucose/kg body wt (50% D-glucose (Sigma) in 0.9% saline) for the glucose tolerance test (GTT). Tail blood glucose levels (mg/dl) were measured by using a hand-held glucometer (TheraSense Freestyle) before (0 min) and at 15, 30, 60, 90, and 120 min after injection.

Western Blot of WAT HSI.

Adipose tissue was placed in a 1.5-ml microfuge tube and lysed in ice cold RIPA buffer (1×PBS, 1% Nonidet P40, 0.5% sodium doxycholate, 0.1% SDS with 50 mM NaF, 0.5 M phenylmethylsulfonyl fluoride, 0.1 mM Na Vanadate, 20 µg/ml Aprotinin, 10 µg/ml Leupeptin) using a tissue lyser (Retsch, Inc Newtown, Pa. Cat. # 85210) at 30 hz for 3 min. Samples were spun at 12,000 rpm for 15 min (4° C.) at which time the internatant was removed to a new tube and sonicated for 15 sec on ice. Samples were spun at 14,000 rpm for 10 min (4° C.) and the internatant was collected to a new tube. Samples were again spun at 19,000 rpm for 10 min (4° C.) and the internatant collected to a new tube. An aliquot of sample was then taken for protein assay. Samples were then boiled in 4×SDS/DTT buffer for 2 min. 50 µg of protein from cell lysate were subjected to SDS/PAGE on 9% (w/v) acrylamide resolving gels and transferred to Hybond ECL nictrocellulose membranes. Membranes were blocked and probed with primary antibodies of interest (HSL (4107)) from Cell Signaling; Phospho-HSL (ser 660) (4126) from Cell Signaling). After washing, primary antibody detection was performed using either HRP-conjugated anti-(rabbit IgG) or anti-(mouse IgG) (HRP-conjugated anti-rabbit and anti-mouse secondary antibodies were purchased from Bio-Rad (170-6515 & 170-6516)) and detected using enhanced chemiluminescence (Amersham Biosciences) and exposed to CL-Xposure film (Pierce).

Immunohistochemistry.

Paraffin embedded sections of white epididymal adipose tissue (5 µm) were stained with hematoxylin/eosin as described (Ogden, C. L. et al. *JAMA* 295:1549-1555 (2006)). For each individual mouse tissue block, adipocyte size of 100 cells from each of three different high-power fields was quantified as areal measurement using Image Pro Plus 5.1 software (Media Cybernetics, Bethesda, Md., USA).

Oil Red Staining.

To visualize lipid accumulation in liver tissue, 4-8 mm cross-sections of the livers that were harvested at sacrifice were stained with Oil Red 0 dye. Images at both 20× and 40× magnification were acquired using a [compound-lens] microscope.

Quantitative RT-PCR procedure.

Animals were sacrificed by decapitation in the fed state (1-4 h after the morning feeding) and various tissues were sampled, freeze-clamped, and stored at −80° C. for subsequent measurement of mRNA expression of PEPCK, G6P, and HPRT (housekeeping) by real-time quantitative PCR (icycler, BioRad).

Total RNA was extracted from frozen tissue samples using a RNeasy Lipid Tissue Kit (Qiagen, Ca# 74804) using the standard protocol. RNA concentrations and purity were determined by spectrophotometry using the Nanodrop. cDNA templates for RT-PCR were obtained using 2 µg of total RNA. Reverse transcription reaction was performed with 10×DNase I Reaction Buffer, DNase I, Amp Grade, 1 U/µl, depc-$H_2O$, 25 mM EDTA, 10 mM dNTP Mix, oligo(dT) 20 (50 µM), 5× First-Strand Buffer, 0.1 M DTT, RNaseOUT, and SuperScript 111 (Invitrogen).

The synthesized cDNAs were further amplified by PCR using the fluorescent dye SYBR green (BioRad, Ca# 1708882) containing a final concentration of 0.5 µM of forward and reverse primers. Product purity was confirmed by dissociation curves. No-template controls were included in all assays, yielding no consistent amplification. A standard curve was used to obtain the relative concentration of PEPCK or G6P, and the results were corrected according to the concentration of HPRT, used as housekeeping genes. The results are expressed as percent of vehicle, setting the mean of the vehicle group at 100% and then calculating each individual value of the 3 groups of animals studied.

Primer Sequences.

Primer sequences for PEPCK, G6P, and HPRT were taken from the NIH website and primers were generated by IDT DNA.

Reverse Transcription and Quantitative Real-Time RT-PCR.

CD68 mRNA expression was quantified by real-time RT-PCR as described (Nomiyama, T. et al. *Journal of Clinical Investigation* 117:2877-2888 (2007)). Briefly, upon sacrifice, 100 mg epididymal adipose tissue was homogenized in TRIZOL and total mRNA was reverse transcribed into cDNA. PCR reactions were performed using an iCycler (Bio-Rad) and SYBR Green I system (Bio-Rad). Each sample was analyzed in triplicate and normalized to values for TFIIB mRNA expression. Mouse primer sequences used were as follows:

```
                                      (SEQ ID NO: 638)
CD68, 5'-CAAGGTCCAGGGAGGTTGTG-3' (forward), (SEQ ID NO: 639)
5'-CCAAAGGTAAGCTGTCCATAAGGA-3' (reverse);
and (SEQ ID NO: 640)
TFIIB, 5'-CTCTCCCAAGAGTCACATGTCC, (SEQ ID NO: 641)
5'-CAATAACTCGGTCCCCTACAAC-3' (reverse).
```

Statistical Analyses.

Unless indicated otherwise, all statistical analyses were performed using GraphPad Prism one-way ANOVAs and column statistics. Stated P values are for one-way analysis of variance. All results are presented as means±SE. (Receptor activation data is ±S.D.).

Example 42

Two glucagon peptides, Peptides X and Y, comprising the amino acid sequence of SEQ ID NO: 1 with amino acid modifications were made as described herein. Both peptides comprised AIB at position 2, Glu at position 16, Gln at position 17, Ala at position 18, Lys at position 20, Glu at position 21, Ile at position 23, and Cys at position 24. Site-specific 40-kd pegylation was achieved at Cys at position 24 through reaction with a maleimide-functionalized linear peg to yield Peptide X-PEG and Y-PEG. Peptides Y and Y-PEG differed from Peptides X and X-PEG, respectively, in that a single side-chain lactam bridge was introduced in the middle of Peptide Y or Peptide Y-PEG to stabilize the secondary structure and enhance glucagon agonism. The two side chains of Glu at position 16 and Lys at position 20 were covalently coupled in the course of peptide assembly as a side-chain amide. This macrocyclization of the peptide represents a 21-atom lactam. Peptides X-PEG and Y-PEG were tested for solubility and were found to be soluble in physiological buffers at concentrations that exceed 25 mg/ml, and Peptides X-PEG and Y-PEG proved completely resistant to ex vivo incubation with plasma for periods of one week.

Example 43

The secondary conformation of peptides when solubilized in various concentrations of aqueous trifluoroethanol (TFE) was analyzed by circular dichroism (FIG. 25). Glucagon was the least helical peptide tested, and had calculated helicity of 10, 15 and 33% in TFE solutions of 0, 10 and 20%, respectively (Table 29). Under the same experimental conditions, GLP-1 had enhanced helicity of 14, 29 and 55%, demonstrating that these two peptides differ in primary as well as secondary structure. There were no significant changes in the helicity of Peptides X and Y when pegylated, despite the fact that the pegylated portions represent more than 90% of the molecule by mass (Table 29). In contrast, the apparent helicity of Peptide Y in phosphate buffer in the absence of TFE was approximately double that of Peptide X, from 17% to 36%. Consequently, the pegylated forms of these two chimeric peptides (Peptide X-PEG and Peptide Y-PEG) differed appreciably in secondary structure (FIG. 25) and the differences in biological properties are likely a function of these secondary structural differences.

TABLE 29

| Peptide | Percent Helicity | | |
|---|---|---|---|
| | 0% TFE | 10% TFE | 20% TFE |
| Glucagon | 10 | 15 | 33 |
| GLP-1 | 14 | 29 | 55 |
| Peptide X | 17 | 34 | 60 |
| Peptide X-PEG | 12 | 31 | — |
| Peptide Y | 36 | 35 | 64 |
| Peptide Y-PEG | 37 | 51 | — |

Example 44

The two peptides (Peptides X and Y) and their 40-kd pegylated derivatives (Peptides X-PEG and Y-PEG) were assessed for their ability to stimulate cAMP synthesis in cell-based CRE-luciferase reporter assays (FIG. 26). As shown in Table 30, native glucagon activated glucagon receptors half-maximally at an effective concentration (EC50) of 0.055±0.014 nM and the GLP-1 receptor (GLP-1R) at a much higher concentration, EC50 of 3.29±0.39 nM. In contrast, GLP-1 activated its receptor with an EC50 of 0.028±0.009 nM and proved highly specific in that interaction at the glucagon receptor (GcgR) occurred at an EC50 exceeding 1 μM. The dynamic range in specificity exhibited for the native ligands at their receptors is in excess of a million. The potency of Peptide X-PEG at GLP-1R was twice that of native GLP-1 and even more enhanced at GcgR in a relative sense. However, the GcgR activity was only approximately 10% that of native glucagon. The introduction of the lactam restored full glucagon agonism without a change at GLP-1R. Consequently, Peptide Y-PEG is a fully potent, nearly balanced co-agonist relative to the native ligands at the two respective receptors. PEGylation of each peptide reduced potency by as much as ten-fold at GcgR and five-fold at GLP-1R. The slightly enhanced loss in activity at GcgR may be a function of the greater relative importance of the C-terminal sequence to glucagon receptor interaction. The pegylated peptides (Peptides X-PEG and Y-PEG) were slightly less potent at GLP-1R than native GLP-1 but still had a subnanomolar EC50. Peptide X-PEG is seven-fold more selective than the lactam version of this peptide, i.e., Peptide Y-PEG, at the GLP-1R. Therefore, these two DPP-4-resistant peptides are suitable for sustained in vivo time-action experiments and well-matched for GLP-1R agonism, but differ in glucagon agonism.

TABLE 30

| Peptide | Glucagon Receptor | | | GLP-1 Receptor | | | Selectivity* |
|---|---|---|---|---|---|---|---|
| | EC50 (nM) | Standard Deviation | % activity of native glucagon | EC50 (nM) | Standard Deviation | % activity of native GLP-1 | |
| Glucagon | 0.055 | 0.014 | 100.00 | 3.293 | 0.389 | 0.86 | 0.009 |
| GLP-1 | >1000 | — | <0.008 | 0.028 | 0.009 | 100.00 | >12500 |
| Peptide X | 0.585 | 0.125 | 9.38 | 0.014 | 0.002 | 202.12 | 21.5 |
| Peptide X-PEG | 2.895 | 0.963 | 1.90 | 0.036 | 0.014 | 78.41 | 41.4 |
| Peptide Y | 0.055 | 0.011 | 99.51 | 0.013 | 0.005 | 219.78 | 2.21 |
| Peptide Y-PEG | 0.667 | 0.264 | 8.22 | 0.059 | 0.029 | 47.61 | 5.79 |

Example 45

The 40-kd pegylated peptides Peptides X-PEG and Y-PEG were used as single weekly subcutaneous (s.c) injections in diet-induced obese (D10) C57B6 mice. A single injection of 325 nmol/kg of Peptide Y-PEG decreased body weight over one week by 25.8%, from 50.9±1.4 g to 37.8±0.8 g (p<0.0001, n=8/group). Comparable administration of Peptide X-PEG was effective but considerably less potent, as the decrease in body weight was 9% (49.1±1.51 g to 44.68±1.38 g). Saline-injected control mice did not change their body weight (before: 50.61±1.32 g, after: 50.87±1.46 g; FIG. 27A). The body weight changes were a result of a decrease in fat mass (41.9% for the lactam peptide, 22.2% for open form, 2.3% for controls, p<0.001; FIG. 27B) and were paralleled by a significant decrease in average daily food intake (Peptide Y-PEG: 0.40±0.29 g/day, Peptide X-PEG: 1.83±0.81 g/day, saline: 2.70±0.78 g/day, p<0.0001, FIG. 27C). Blood glucose was significantly decreased for both peptides when compared to control, and slightly more so in Peptide Y-PEG (Peptide Y-PEG: −90.1 mg/dL, Peptide X-PEG: −79.6 mg/dL, control: −23.9 g,/dL, p=0.0433; FIG. 27D). The relative difference between the two peptides (Peptide X-PEG and Peptide Y-PEG) was not statistically significant.

Example 46

In a separate experiment, single s.c. injections of six different doses (0, 7, 14, 35, 70, 140 and 350 nmol/kg) of Peptide Y-PEG and Peptide X-PEG demonstrated linearly responsive, dose-dependent decreases in body weight and blood glucose (FIGS. 28A, 28B, 28C and 28D). This suggests that the observed effects are pharmacologically relevant with no apparent toxicity, other than the indirect effects of rapid, excessive loss in body weight. The magnitude of the effect was more prominent with Peptide Y-PEG and indicates that the additional element of glucagon agonism improves the potency of the peptide.

Example 47

In a separate experiment, weekly s.c. injections of 70 nmol/kg of Peptide Y-PEG or Peptide X-PEG decreased body weight of DIO mice by 28.1% and 20.1%, respectively (p<0.0001, n=7-8/group; FIG. 29A). The body weight changes were associated with a decrease in fat mass (−62.9% for Peptide Y-PEG, −52.2% for Peptide X-PEG, and 5.1% for controls, p<0.0001; FIG. 29B). Long-term effects of these lower doses on food intake (p=0.95; FIG. 29C) were less impressive than short-term effects with a higher dose (FIG. 27C). Energy expenditure was increased with Peptide Y-PEG (14.60±0.69 kcal/[kg*h]) and Peptide X-PEG (17.19±1.49 kcal/[kg*h]) compared to vehicle (12.71±0.45 kcal/[kg*h]), p=0.0187), whereas the respiratory quotient tended to be decreased (FIGS. 29D and 29E; 0.719±0.01 for Peptide Y-PEG, 0.725±0.01 for Peptide X-PEG, and 0.755±0.01 for vehicle, p=0.1028), indicating that increased thermogenesis and altered nutrient partitioning may explain the overall negative energy balance. Increased energy expenditure was not associated with a change in spontaneous physical activity induced thermogenesis (NEAT) since locomotor activity did not differ between treatment groups and controls (p=0.4281; FIG. 29F). Neither automated online monitoring of acute feeding nor chronic monitoring of food intake revealed any differences in caloric intake (automated p=0.667, chronic p=0.9484; FIG. 30A).

Blood glucose levels were markedly decreased over the treatment period starting at Day 3 after the first injection (mean decrease: Peptide Y-PEG −32%, Peptide X-PEG −24.5%, controls: −2.7%, p<0.0001; FIG. 29G). In response to an intraperitoneally (i.p.) glucose challenge on Day 3, blood glucose peaks (FIG. 29H) and profiles (AUC) (FIG. 30F) were markedly lower in the two treated groups (Peptide Y-PEG 14183±1072, Peptide X-PEG 13794±824.1) compared to the vehicle-treated controls (34125±3142, p<0.0001). After one month of treatment with Peptide Y-PEG or Peptide X-PEG, plasma insulin was lower in the treatment groups (1194 pg/ml, 1034 pg/ml, p=0.0244) compared to controls (2675 pg/ml), suggesting improved insulin sensitivity (FIG. 29I). Plasma C-peptide levels tended to be decreased after one month of treatment with Peptide Y-PEG or Peptide X-PEG (738.8 pg/ml, 624.7 pg/ml) versus vehicle (1077 pg/ml) (p=0.108) (FIG. 30G).

To determine if the principal phenomenon generalizes across species, both compounds were administered to diet-induced obese rats (mean weight 777.4+/−2.1 g, dose 70 nmol/kg/week, once-a-week injection, 3-week treatment). Peptide Y-PEG and Peptide X-PEG each decreased body weight (Peptide X-PEG: −11.15+/−0.88%; Peptide Y-PEG: −20.58+/−2.26%, vehicle: 1.09+/−0.56%) (p<0.0001) and fat mass of the DIO rats (Peptide X-PEG: −19.17+/−2.03%; Peptide Y-PEG: −33.76+−/−4.76%, vehicle: 0.65+/−1.20%; p<0.0001), confirming a species-independent applicability of this anti-obesity treatment approach.

Example 48

Chronic s.c. treatment over 27 days with Peptide X-PEG and Peptide Y-PEG decreased total cholesterol in DIO mice (106.9±6.3 mg/dL and 200.8±29.58 mg/dL, respectively) relative to vehicle (254.0 25.33 mg/dL, p=0.0441; FIG. 31A). In a separate experiment, DIO mice received 70 nmol/kg s.c. of Peptide X-PEG, Peptide Y-PEG or vehicle on Days 0 and 7 and were evaluated on Day 9. Peptide Y-PEG decreased plasma triglycerides, LDL cholesterol and total cholesterol (total cholesterol 63.0 2.49 mg/dL compared to vehicle 177.7±11.8 mg/dL) (p<0.0001), while potentially causing a switch from LDL to HDL cholesterol (FIG. 31B). Peptide X-PEG decreased both LDL and HDL cholesterol but had no significant effect on triglycerides (FIG. 31C). There was a significant decrease in leptin (3343±723.3 pg/ml for Peptide Y-PEG; 7308±2927 for Peptide X-PEG, and 18,642±6124 for vehicle; p=0.0426; FIG. 31D, 31E, 31F). Chronic treatment for 27 days also normalized liver lipid content while control DIO mice maintained significant liver steatosis (data not shown).

Example 49

One month treatment with Peptide X-PEG or Peptide Y-PEG resulted in increased phosphorylation of hormone sensitive lipase (HSL) in white adipose tissue (WAT) of DIO mice (Peptide X-PEG: 1.135±0.315; Peptide Y-PEG: 1.625±0.149; vehicle: 0.597±0.204; p=0.0369; FIG. 32B), implying a glucagon-specific direct effect on WAT lipolysis. Concomitant with the decrease in fat mass of mice treated for two weeks at a dose of 35 nmol/kg/week with the Peptide Y-PEG and Peptide X-PEG, there was a significant reduction of adipocyte size in epididymal adipose tissues when compared to control mice (data not shown). However, despite having decreased fat mass and smaller adipocytes, this short term treatment of two weeks with the Peptide Y-PEG and Peptide X-PEG was not associated with a significant reduction of adipose tissue macrophage content as quantified by real-time RT-PCR for CD68 (FIG. 33C). Uncoupling protein I (UCP1) levels in brown adipose tissue (BAT) were increased by Peptide X-PEG, but not by Peptide Y-PEG treatment (Peptide X-PEG 2.167±0.429, Peptide Y-PEG 1.287±0.1558, and vehicle 1.0±0.118; p=0.0264; FIG. 32A), consistent with a GLP-1-specific action on BAT resting thermogenesis. Hepatic gene expression reflective of hepatic gluconeogenesis was not affected by either Peptide X-PEG or Peptide Y-PEG (FIG. 30H and 30I). Histology indicated that pancreatic islets tended to be smaller following Peptide X-PEG treatment (data not shown).

Example 50

In order to dissect the contributions of the GLP-1R and the GcgR agonist components of Peptides X-PEG and Y-PEG, each was administered for one month to GLP-1 receptor knock out (GLP-1R−/−) mice maintained on high-fat diet. Peptide X-PEG caused a reduction of body weight (p>0.05; FIGS. 34A and 34B) and fat mass (p>0.05; FIG. 34C) compared to saline. Peptide Y-PEG caused a significant decrease in body weight (p=0.0025) and fat mass (p=0.0025) in the GLP-1R−/−mice (FIGS. 34A-34C). Peptide X-PEG had no effect on food intake in GLP-1R−/−mice, while Peptide Y-PEG suppressed food intake significantly (p=0.017) (FIG. 34D). Peptide Y-PEG (but not Peptide X-PEG) had a tendency to increase blood glucose in a glucose tolerance test in the absence of a functional GLP-1R (p=0.03) (FIGS. 34E and 34F), implying that the GLP-1 component of the co-agonist is needed to protect against glucagon-induced hyperglycemia.

Example 51

As an independent assessment of the effect of Peptides X-PEG and Y-PEG that can be attributable to glucagon agonism, two additional peptide agonists with comparable GLP-1R potency but markedly different GcgR activity were studied. The two peptides (Peptides U and V) are related to the Peptides X-PEG and Y-PEG. Peptides U and V comprised the amino acid sequence of SEQ ID NO: 1 with the following modifications: Glu at position 16, Gln at position 17, Ala at position 18, Lys at position 20, Glu at position 21, Ile at position 23, and Cys at position 24, but comprised a 20-kd pegylation at the Cys at position 24 and did not comprise AIB at position 2. Peptide V additionally comprised a substitution of Gln3 with Glu which selectively reduced glucagon agonism by more than ten-fold. Neither Peptide U nor Peptide V comprised a lactam bridge. Treatment of DIO mice each day for one week at 50 nmol/kg s.c. with Peptide V revealed a reduced effect on body weight lowering relative to the Peptide U (−9.09±0.80 vs. −13.71±0.92 g, respectively (p<0.0001; FIG. 35A).

Example 52

Glucagon peptides comprising a C16 fatty acyl group attached to a Lys residue via a γ-Glu spacer or a γ-Glu-γ-Glu dipeptide spacer, wherein the Lys residue is located at position 10 or at the C-terminus (at position 29), were made as essentially described herein. The peptides were tested for in vitro activities at the glucagon and GLP-1 receptors as described herein. The results are shown in Table 31.

TABLE 31

| Peptide | | | EC50 (nM) at | EC50 at |
|---|---|---|---|---|
| Acylated AA | Spacer | SEQ ID NO: | Glucagon Receptor | GLP-1 Receptor |
| Chi-2, d-Ser2 | Lys10 | γE | 643 | 0.011 | 0.0014 |
| Chi-2, d-Ser2 | Lys10 | γE-γE | 644 | 0.008 | 0.003 |
| Chi-2, AIB2 | Lys10 | γE | 645 | 0.025 | 0.0014 |
| Chi-2, AIB2 | Lys10 | γE-γE | 646 | 0.014 | 0.0018 |
| Chi-2, AIB2, E3 | Lys10 | None | 647 | 46.084 | 0.005 |
| Chi-2, AIB2, E3 | Lys10 | γE-γE | 648 | 2.922 | 0.004 |
| Chi-2, AIB2, I7 | Lys10 | γE | 649 | 0.014 | 0.024 (0.044*) |
| Chi-2, AIB2, I7 | Lys10 | γE-γE | 650 | 0.007 | 0.010 |
| DMIA1, E16/K20 lactam | Lys10 | γE | 651 | 0.019 | 0.006 |
| DMIA1, E16/K20 lactam | Lys10 | γE-γE | 652 | 0.014 | 0.004 |
| DMIA1, E16/K20 lactam | Lys29 | γE | 653 | 0.107 | 0.075 |
| DMIA1, E16/K20 lactam | Lys29 | γE-γE | 654 | 0.025 | 0.070 |
| AIB2, AIB16, A18, D28 | Lys10 | γE-γE | 655 | 0.003 | 0.004 |
| AIB2, AIB16, A18, D28 | Lys10 | γE | 656 | 0.006 | 0.004 |

Example 53

The peptides shown in Table 32 were made as essentially described herein:

TABLE 32

| Peptide Name | SEQ ID NO: | Sequence |
|---|---|---|
| Chimera-2 Aib2C24Mal40KPEG | 624 | H(Aib)QGTFTSDYSKYLDEQAAKEFICWLMNT-amide |
| Chimera-2 Aib2E16K20lactamC24Mal40KPEG | 625 | H(Aib)QGTFTSDYSKYLDEQAAKEFICWLMNT-amide |
| Glucagon Aib2E16K20lactamC24amideMal40KPEG | 626 | H(Aib)QGTFTSDYSKYLDERRAKDFVCWLMNT-amide lactam |
| Glucagon Dmia1E16K20lactamC24Mal40KPEG | 628 | (Dmia)SQGTFTSDYSKYLDERRAKDFVCWLMNT-amide lactam |
| Glucagon Dmia1E16K20lactamC24Mal40KPEG | 629 | (Dmia)SQGTFTSDYSKYLDERRAKDFVCWLMNT-OH lactam |
| Glucagon Dmia1E16K20lactamC24thioether40KPEG | 630 | (Dmia)SQGTFTSDYSKYLDERRAKDFVCWLMNT-amide lactam |
| Chimera2 Aib2E3C24-Thioether40K PEG | 631 | H(Aib)EGTFTSDYSKYLDEQAAKEFICWLMNT-amide |
| Glucagon DMIA1, E3, E15, E16, K20, C24-Peg | 632 | (Dmia)SEGTFTSDYSKYLEERRAKDFVC(PEG40K)WLMNT-amide |
| Glucagon Aib2Aib16C24K10(rErE-C14)C24PEG40K TE)amide | 633 | H(Aib)QGTFTSDK(rErE-C14)SKYLDAibRRAQDFVC(PEG40K TE)WLMNT-amide |
| Glucagon Aib2Aib16K10(AA-C14)C24PEG40K TE amide | 634 | H(Aib)QGTFTSDK(AA-C14)SKYLDAibRRAQDFVC(PEG40K TE)WLMNT-amide |
| Glucagon Aib2Aib16K10(AA-C16) amide | 635 | H(Aib)QGTFTSD K(AA-C16)SKYLDAibRRAQDFVQWLMNT amide |
| Glucagon Aib2Aib16K10(rErE-C16) amide | 636 | H(Aib)QGTFTSD K(rErE-C16)SKYLDAibRRAQDFVQWLMNT amide |

All peptides of Table 32 demonstrated potent in vitro activities at both the glucagon and GLP-1 receptors, except for the peptides of SEQ ID NOs: 624, 631, and 632

Peptides of Set A comprising the amino acid sequence of native glucagon (SEQ ID NO: 1) except for the changes outlined in Table 33 are made as essentially described herein.

TABLE 33

| DPP-IV Protection | Alpha Helix Stabilization | Position 3 | Back-bone* | C-Terminal Amide? |
|---|---|---|---|---|
| DMIA at position 1 | AIB at position 16 | Gln (wild-type) | Wild-type | yes |
| AIB at position 2 | AIB at position 16 | Gln (wild-type) | Wild-type | yes |
| d-Ser at position 2 | AIB at position 16 | Gln (wild-type) | Wild-type | yes |
| DMIA at position 1 | AIB at position 16 | Glu | Wild-type | yes |
| AIB at position 2 | AIB at position 16 | Glu | Wild-type | yes |
| d-Ser at position 2 | AIB at position 16 | Glu | Wild-type | yes |
| DMIA at position 1 | AIB at positions 16 and 20 | Gln (wild-type) | Wild-type | yes |
| AIB at position 2 | AIB at positions 16 and 20 | Gln (wild-type) | Wild-type | yes |
| d-Ser at position 2 | AIB at positions 16 and 20 | Gln (wild-type) | Wild-type | yes |
| DMIA at position 1 | AIB at positions 16 and 20 | Glu | Wild-type | yes |
| AIB at position 2 | AIB at positions 16 and 20 | Glu | Wild-type | yes |
| d-Ser at position 2 | AIB at positions 16 and 20 | Glu | Wild-type | yes |
| DMIA at position 1 | Glu at position 16 and Lys at position 20 | Gln (wild-type) | Wild-type | yes |
| AIB at position 2 | Glu at position 16 and Lys at position 20 | Gln (wild-type) | Wild-type | yes |
| d-Ser at position 2 | Glu at position 16 and Lys at position 20 | Gln (wild-type) | Wild-type | yes |
| DMIA at position 1 | Lactam bridge between side chains of Glu at position 16 and Lys at position 20 | Gln (wild-type) | Wild-type | yes |
| AIB at position 2 | Lactam bridge between side chains of Glu at position 16 and Lys at position 20 | Gln (wild-type) | Wild-type | yes |
| d-Ser at position 2 | Lactam bridge between side chains of Glu at position 16 and Lys at position 20 | Gln (wild-type) | Wild-type | yes |
| DMIA at position 1 | Glu at position 16 and Lys at position 20 | Glu | Wild-type | yes |
| AIB at position 2 | Glu at position 16 and Lys at position 20 | Glu | Wild-type | yes |
| d-Ser at position 2 | Glu at position 16 and Lys at position 20 | Glu | Wild-type | yes |
| DMIA at position 1 | Lactam bridge between side chains of Glu at position 16 and Lys at position 20 | Glu | Wild-type | yes |
| AIB at position 2 | Lactam bridge between side chains of Glu at position 16 and Lys at position 20 | Glu | Wild-type | yes |

TABLE 33-continued

| DPP-IV Protection | Alpha Helix Stabilization | Position 3 | Backbone* | C-Terminal Amide? |
|---|---|---|---|---|
| d-Ser at position 2 | Lactam bridge between side chains of Glu at position 16 and Lys at position 20 | Glu | Wild-type | yes |
| DMIA at position 1 | Glu at position 16 and Lys at position 20 | Gln | Chimera 2 | yes |
| AIB at position 2 | Glu at position 16 and Lys at position 20 | Gln | Chimera 2 | yes |
| d-Ser at position 2 | Glu at position 16 and Lys at position 20 | Gln | Chimera 2 | yes |
| DMIA at position 1 | Lactam bridge between side chains of Glu at position 16 and Lys at position 20 | Gln (wild-type) | Chimera 2 | yes |
| AIB at position 2 | Lactam bridge between side chains of Glu at position 16 and Lys at position 20 | Gln (wild-type) | Chimera 2 | yes |
| d-Ser at position 2 | Lactam bridge between side chains of Glu at position 16 and Lys at position 20 | Gln (wild-type) | Chimera 2 | yes |
| DMIA at position 1 | Glu at position 16 and Lys at position 20 | Glu | Chimera 2 | yes |
| AIB at position 2 | Glu at position 16 and Lys at position 20 | Glu | Chimera 2 | yes |
| d-Ser at position 2 | Glu at position 16 and Lys at position 20 | Glu | Chimera 2 | yes |
| DMIA at position 1 | Lactam bridge between side chains of Glu at position 16 and Lys at position 20 | Glu | Chimera 2 | yes |
| AIB at position 2 | Lactam bridge between side chains of Glu at position 16 and Lys at position 20 | Glu | Chimera 2 | yes |
| d-Ser at position 2 | Lactam bridge between side chains of Glu at position 16 and Lys at position 20 | Glu | Chimera 2 | yes |

*indicates amino acids at positions 17, 28, 21, and 23 as wild-type or as Chimera 2 (Gln at position 17, Ala at position 18, Glu at position 21, and Ile at position 23).

Peptides having the same structure as the peptides of Set A, except that the Met at position 27 is replaced with a Norleucine, are made as essentially described herein. These modified peptides are the peptides of Set B.

Peptides having the same structure as the peptides of Sets A and B, except that the Gln at position 24 is replaced with a Cys covalently attached to a 40 kDa PEG, are made as essentially described herein. These pegylated peptides form the peptides of Set C.

Peptides having the same structure as the peptides of Set A, B, or C, except that the Tyr at position 10 is replaced with a Lys covalently attached to a C8, C12, C14, C16, or C18 fatty acyl group, are made as essentially described herein. The peptides acylated with a C8 fatty acyl group form the peptides of Set D. The peptides acylated with a C12 fatty acyl group form the peptides of Set E. The peptides acylated with a C14 fatty acyl group form the peptides of Set F. The peptides acylated with a C16 fatty acyl group form the peptides of Set G. The peptides acylated with a C18 fatty acyl group form the peptides of Set H.

Peptides having the same structure as the peptides of Sets D through H, except that the fatty acyl group is attached to the Lys at position 10 via a spacer, are made as essentially described herein. The peptides comprising a γ-Glu-γ-Glu spacer form the peptides of Set I. The peptides comprising a γ-Glu spacer form the peptides of Set J. The peptides comprising an Ala-Ala spacer form the peptides of Set K. The peptides comprising a β-Ala-β-Ala spacer form the peptides of Set L.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A glucagon peptide comprising an amino acid at position 10 which is acylated or alkylated with a C4 to C30 fatty acid; and an α, α-disubstituted amino acid at position 16 of the glucagon peptide or an intramolecular bridge between the side chains of an amino acid at position i and an amino acid at position i+4, wherein i is 12, 16, 20, or 24, wherein the amino acid sequence of the glucagon peptide differs from SEQ ID NO: 1 by no more than ten amino acid modifications.

2. A glucagon peptide that differs from SEQ ID NO: 1 by no more than ten amino acid modifications, comprising an amino isobutyric acid (AIB) at position 16 and an acyl group or alkyl group covalently linked to the amino acid at position 10 of the glucagon peptide, wherein said glucagon peptide exhibits enhanced activity at the GLP-1 receptor as compared to native glucagon.

3. The glucagon peptide of claim 1 or 2, further comprising one or more modifications selected from the group consisting of: Gln at position 17, Ala at position 18, Glu at position 21, Ile at position 23, and Ala at position 24.

4. The glucagon peptide of claim 1 or 2, comprising a C-terminal amide.

5. The glucagon peptide of claim 1 or 2, comprising an amino acid substitution at position 1, position 2, or positions 1 and 2, wherein the amino acid substitution(s) achieve DPP-IV protease resistance.

6. The glucagon peptide of claim 5, wherein (i) the His at position 1 is substituted with an amino acid selected from the group consisting of: D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine, (ii) wherein the Ser at position 2 is substituted with an amino acid selected from the group consisting of: D-serine, alanine, D-alanine, valine, glycine, N-methyl serine, N-methyl alanine, and amino isobutyric acid, or (iii) both (i) and (ii).

7. The glucagon peptide of claim 1 or 2, wherein the amino acid at position 10 of the glucagon peptide is an amino acid of Formula I, Formula II, or Formula III.

8. The glucagon peptide of claim 7, wherein the amino acid of Formula I is Lys.

9. The glucagon peptide of claim 1 or 2, further comprising a spacer between the amino acid at position 10 of the glucagon peptide and the acyl group or alkyl group.

10. The glucagon peptide of claim 9, wherein the spacer is an amino acid or a dipeptide.

11. A conjugate, dimer, or fusion peptide comprising a glucagon peptide of claim 1 or 2.

12. A pharmaceutical composition comprising a glucagon peptide of claim 1 or 2, a dimer thereof, or a pharmaceutically acceptable salt thereof, and a pharmaceutically acceptable carrier.

13. A method of treating diabetes, said method comprising administering to a patient in need thereof an effective amount of a pharmaceutical composition of claim 12 wherein the glucagon peptide of the pharmaceutical composition activates the GLP-1 receptor.

14. A method of reducing weight gain or inducing weight loss, said method comprising administering to a patient in need thereof an effective amount of a pharmaceutical composition of claim 12.

15. The glucagon peptide of claim 1 or 2, comprising:
   (a) one, two, or three charged amino acids C-terminal to the amino acid at position 27;
   (b) an amino acid selected from the group consisting of glutamic acid, glutamine, homoglutamic acid, homocysteic acid, threonine and glycine, at position 16;
   (c) leucine or norleucine at position 27;
   (d) a hydrophilic moiety;
   (e) or a combination thereof.

16. The glucagon peptide of claim 15, wherein the amino acid at position 28 or 29 is substituted with a charged amino acid.

17. The glucagon peptide of claim 16, wherein the amino acid at position 28 is Asp, Asn, or Lys and the amino acid at position 29 is Gly or Thr.

18. The glucagon peptide of claim 15, comprising a charged amino acid after position 29.

19. The glucagon peptide of claim 1, wherein the C4 to C30 fatty acid is a C8 to C20 fatty acid.

20. The glucagon peptide of claim 19, wherein the acyl group is a C12 to C18 fatty acid.

* * * * *

SEQUENCE LISTING

<160> NUMBER OF SEQ ID NOS: 656

<210> SEQ ID NO 1
<211> LENGTH: 29
<212> TYPE: PRT
<213> ORGANISM: Homo sapiens

```
<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Glu, Gln, homoglutamic acid or homocysteic acid
<220> FEATURE:
<221> NAME/KEY: MOD_RES
<222> LOCATION: (17)..(17)
<223> OTHER INFORMATION: Arg, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 2

His Ser Gln Gly Thr Phe Thr Ser Asp Tyr Ser Lys Tyr Leu Asp Xaa
1               5                   10                  15

Xaa Arg Ala Gln Asp Phe Val Gln Trp Leu Xaa Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Glu, Gln, homoglutamic acid or homocysteic acid
<220> FEATURE:
<221> NAME/KEY: MOD_RES
<222> LOCATION: (21)..(21)
<223> OTHER INFORMATION: Asp, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 3

His Ser Gln Gly Thr Phe Thr Ser Asp Tyr Ser Lys Tyr Leu Asp Xaa
1               5                   10                  15

Arg Arg Ala Gln Xaa Phe Val Gln Trp Leu Xaa Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Glu, Gln, homoglutamic acid or homocysteic acid
<220> FEATURE:
<221> NAME/KEY: MOD_RES
```

```
<222> LOCATION: (24)..(24)
<223> OTHER INFORMATION: Gln, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 4

His Ser Gln Gly Thr Phe Thr Ser Asp Tyr Ser Lys Tyr Leu Asp Xaa
 1               5                  10                  15

Arg Arg Ala Gln Asp Phe Val Xaa Trp Leu Xaa Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Glu, Gln, homoglutamic acid or homocysteic acid
<220> FEATURE:
<221> NAME/KEY: MOD_RES
<222> LOCATION: (21)..(21)
<223> OTHER INFORMATION: Asp, Cys, Orn, homocysteine or acetyl
      phenylalanine
<220> FEATURE:
<221> NAME/KEY: MOD_RES
<222> LOCATION: (24)..(24)
<223> OTHER INFORMATION: Gln, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 5

His Ser Gln Gly Thr Phe Thr Ser Asp Tyr Ser Lys Tyr Leu Asp Xaa
 1               5                  10                  15

Arg Arg Ala Gln Xaa Phe Val Xaa Trp Leu Xaa Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (21)..(21)
<223> OTHER INFORMATION: Asp, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 6

His Ser Gln Gly Thr Phe Thr Ser Asp Tyr Ser Lys Tyr Leu Asp Glu
 1               5                  10                  15

Arg Arg Ala Gln Xaa Phe Val Gln Trp Leu Xaa Asn Thr
            20                  25

<210> SEQ ID NO 7
<211> LENGTH: 29
<212> TYPE: PRT
<213> ORGANISM: Artificial Sequence
```

```
<220> FEATURE:
<223> OTHER INFORMATION: Synthetic Glucagon Analogue
<220> FEATURE:
<221> NAME/KEY: MOD_RES
<222> LOCATION: (24)..(24)
<223> OTHER INFORMATION: Gln, Cys, Orn, homocysteine or acetyl
      phenylalanine
<220> FEATURE:
<221> NAME/KEY: MOD_RES
<222> LOCATION: (27)..(27)
<223> OTHER INFORMATION: Met, Leu or Nle

<400> SEQUENCE: 7

His Ser Gln Gly Thr Phe Thr Ser Asp Tyr Ser Lys Tyr Leu Asp Glu
1               5                   10                  15

Arg Arg Ala Gln Asp Phe Val Xaa Trp Leu Xaa Asn Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Glu, Gln, homoglutamic acid or homocysteic acid

<400> SEQUENCE: 8

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (27)..(27)
<223> OTHER INFORMATION: Met, Leu or Nle

<400> SEQUENCE: 9

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Asn Thr
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 10

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 11
<211> LENGTH: 29
<212> TYPE: PRT
```

```
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation

<400> SEQUENCE: 11

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (12)..(16)
<223> OTHER INFORMATION: Lactam ring between side chains at position 12
      and 16

<400> SEQUENCE: 12

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 13

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (22)..(24)
<223> OTHER INFORMATION: Lactam ring between side chains at positions 22
      and 24

<400> SEQUENCE: 14

His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Asn Thr
            20                  25

<210> SEQ ID NO 15
```

```
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (24)..(28)
<223> OTHER INFORMATION: Lactam ring formed between side chains at
      positions 24 and 28

<400> SEQUENCE: 15

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MISC_FEATURE
<222> LOCATION: (20)..(24)
<223> OTHER INFORMATION: Lactam ring between side chains at positions 20
      and 24

<400> SEQUENCE: 16

His Ser Gln Gly Thr Phe Thr Ser Asp Tyr Ser Lys Tyr Leu Asp Glu
1               5                   10                  15

Arg Arg Ala Lys Asp Phe Val Glu Trp Leu Met Asn Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MISC_FEATURE
<222> LOCATION: (24)..(28)
<223> OTHER INFORMATION: Lactam ring between side chains at positions 24
      and 28

<400> SEQUENCE: 17

His Ser Gln Gly Thr Phe Thr Ser Asp Tyr Ser Lys Tyr Leu Asp Glu
1               5                   10                  15

Arg Arg Ala Asp Asp Phe Val Glu Trp Leu Met Lys Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
```

-continued

```
<222> LOCATION: (16)..(20)
<223> OTHER INFORMATION: Lactam ring between side chains at positions 16
      and 20

<400> SEQUENCE: 18

His Ser Gln Gly Thr Phe Thr Ser Asp Tyr Ser Lys Tyr Leu Asp Glu
1               5                   10                  15

Arg Arg Ala Lys Asp Phe Val Glu Trp Leu Met Lys Thr
            20                  25

<210> SEQ ID NO 19
<211> LENGTH: 30
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (30)..(30)
<223> OTHER INFORMATION: Variable amino acid

<400> SEQUENCE: 19

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Xaa
            20                  25                  30

<210> SEQ ID NO 20
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln, Lys, Arg, Orn or Citrulline
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Asp or Lys
<220> FEATURE:
<221> NAME/KEY: MOD_RES
<222> LOCATION: (29)..(29)
<223> OTHER INFORMATION: Thr or Gly

<400> SEQUENCE: 20

His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Xaa Xaa
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
```

```
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser, Ala, Gly, N-methyl Ser or
      aminoisobutyric acid

<400> SEQUENCE: 21

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 22

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (17)..(17)
<223> OTHER INFORMATION: Cys-PEG
<220> FEATURE:
<221> NAME/KEY: MOD_RES
<222> LOCATION: (27)..(27)
<223> OTHER INFORMATION: Met, Leu or Nle

<400> SEQUENCE: 23

His Ser Gln Gly Thr Phe Thr Ser Asp Tyr Ser Lys Tyr Leu Asp Glu
1               5                   10                  15

Cys Arg Ala Gln Asp Phe Val Gln Trp Leu Xaa Asn Thr
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (21)..(21)
<223> OTHER INFORMATION: Cys-PEG
```

```
<220> FEATURE:
<221> NAME/KEY: MOD_RES
<222> LOCATION: (27)..(27)
<223> OTHER INFORMATION: Met, Leu or Nle

<400> SEQUENCE: 24

His Ser Gln Gly Thr Phe Thr Ser Asp Tyr Ser Lys Tyr Leu Asp Glu
1               5                   10                  15

Arg Arg Ala Gln Cys Phe Val Gln Trp Leu Xaa Asn Thr
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG
<220> FEATURE:
<221> NAME/KEY: MOD_RES
<222> LOCATION: (27)..(27)
<223> OTHER INFORMATION: Met, Leu or Nle

<400> SEQUENCE: 25

His Ser Gln Gly Thr Phe Thr Ser Asp Tyr Ser Lys Tyr Leu Asp Glu
1               5                   10                  15

Arg Arg Ala Gln Asp Phe Val Cys Trp Leu Xaa Asn Thr
            20                  25

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide fragment representing the
      carboxy terminal 10 amino acids Exendin-4

<400> SEQUENCE: 26

Gly Pro Ser Ser Gly Ala Pro Pro Pro Ser
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide fragment representing the
      carboxy terminal 8 amino acids of oxyntomodulin

<400> SEQUENCE: 27

Lys Arg Asn Arg Asn Asn Ile Ala
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Lys Arg Asn Arg
1
```

```
<210> SEQ ID NO 29
<211> LENGTH: 10
<212> TYPE: PRT
<213> ORGANISM: Artificial Sequence
<220> FEATURE:
<223> OTHER INFORMATION: Synthetic peptide fragment representing the
      carboxy terminal 10 amino acids of Exendin-4
<220> FEATURE:
<221> NAME/KEY: MISC_FEATURE
<223> OTHER INFORMATION: c-term amidation

<400> SEQUENCE: 29

Gly Pro Ser Ser Gly Ala Pro Pro Pro Ser
1               5                   10

<210> SEQ ID NO 30
<211> LENGTH: 39
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (27)..(27)
<223> OTHER INFORMATION: Met, Leu or Nle

<400> SEQUENCE: 30

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Asn Thr Gly Pro Ser
            20                  25                  30

Ser Gly Ala Pro Pro Pro Ser
        35

<210> SEQ ID NO 31
<211> LENGTH: 37
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (27)..(27)
<223> OTHER INFORMATION: Met, Leu or Nle

<400> SEQUENCE: 31

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Asn Thr Lys Arg Asn
            20                  25                  30

Arg Asn Asn Ile Ala
        35

<210> SEQ ID NO 32
<211> LENGTH: 33
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (27)..(27)
<223> OTHER INFORMATION: Met, Leu or Nle

<400> SEQUENCE: 32

His Ser Gln Gly Thr Phe Thr Ser Asp Tyr Ser Lys Tyr Leu Asp Glu
1               5                   10                  15
```

-continued

Arg Arg Ala Gln Asp Phe Val Gln Trp Leu Xaa Asn Thr Lys Arg Asn
            20                  25                  30

Arg

<210> SEQ ID NO 33
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (15)..(15)
<223> OTHER INFORMATION: Asp, Glu, homoglutamic acid, cysteic acid or
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Lys or an acidic amino acid
<220> FEATURE:
<221> NAME/KEY: MOD_RES
<222> LOCATION: (29)..(29)
<223> OTHER INFORMATION: Thr, Gly or an acidic amino acid

<400> SEQUENCE: 33

His Ser Gln Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (15)..(15)
<223> OTHER INFORMATION: Asp, Glu, cysteic acid, homoglutamic acid or
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Asp or Lys
<220> FEATURE:
<221> NAME/KEY: MOD_RES
<222> LOCATION: (29)..(29)

<223> OTHER INFORMATION: Thr or Gly

<400> SEQUENCE: 34

His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Xaa Xaa
            20                  25

<210> SEQ ID NO 35
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 35

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 36
<211> LENGTH: 39
<212> TYPE: PRT
<213> ORGANISM: Artificial Sequence
<220> FEATURE:
<223> OTHER INFORMATION: Synthetic Glucagon Analogue

<400> SEQUENCE: 36

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 37
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (24)..(24)
<223> OTHER INFORMATION: 2-butyrolactone bound through thiol group of
      Cys

<400> SEQUENCE: 37

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (24)..(24)
<223> OTHER INFORMATION: Carboxymethyl group bound through thiol group
      of Cys

<400> SEQUENCE: 38

```
His Ser Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr
            20                  25
```

<210> SEQ ID NO 39
<211> LENGTH: 39
<212> TYPE: PRT
<213> ORGANISM: Artificial Sequence
<220> FEATURE:
<223> OTHER INFORMATION: Synthetic Glucagon Analogue

<400> SEQUENCE: 39

```
His Ser Gln Gly Thr Phe Thr Ser Asp Tyr Ser Arg Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
            35
```

<210> SEQ ID NO 40
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MOD_RES
<222> LOCATION: (28)..(28)
<223> OTHER INFORMATION: Glu or Asp

<400> SEQUENCE: 40

```
His Ser Gln Gly Thr Phe Thr Ser Asp Tyr Ser Lys Tyr Leu Xaa Glu
1               5                   10                  15

Arg Arg Ala Gln Asp Phe Val Gln Trp Leu Met Xaa Thr
            20                  25
```

<210> SEQ ID NO 41
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation; lactam ring between side
      chains at positions 12 and 16
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MOD_RES
<222> LOCATION: (28)..(28)
<223> OTHER INFORMATION: Glu or Asp -continued

<400> SEQUENCE: 41

His Ser Gln Gly Thr Phe Thr Ser Asp Tyr Ser Lys Tyr Leu Xaa Glu
1               5                   10                  15

Arg Arg Ala Gln Asp Phe Val Gln Trp Leu Met Xaa Thr
            20                  25

<210> SEQ ID NO 42
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation; lactam ring between side
      chains at positions 16 and 20
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (28)..(28)
<223> OTHER INFORMATION: Glu or Asp

<400> SEQUENCE: 42

His Ser Gln Gly Thr Phe Thr Ser Asp Tyr Ser Lys Tyr Leu Xaa Glu
1               5                   10                  15

Arg Arg Ala Lys Asp Phe Val Gln Trp Leu Met Xaa Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MISC_FEATURE
<222> LOCATION: (20)..(24)
<223> OTHER INFORMATION: Lactam ring between side chains at positions 20
      and 24
<220> FEATURE:
<221> NAME/KEY: MOD_RES
<222> LOCATION: (28)..(28)
<223> OTHER INFORMATION: Glu or Asp

<400> SEQUENCE: 43

His Ser Gln Gly Thr Phe Thr Ser Asp Tyr Ser Lys Tyr Leu Xaa Ser
1               5                   10                  15

Arg Arg Ala Lys Asp Phe Val Glu Trp Leu Met Xaa Thr
            20                  25

<210> SEQ ID NO 44
<211> LENGTH: 29

```
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MISC_FEATURE
<222> LOCATION: (24)..(28)
<223> OTHER INFORMATION: Lactam ring between side chains at positions 24
      and 28
<220> FEATURE:
<221> NAME/KEY: MOD_RES
<222> LOCATION: (29)..(29)
<223> OTHER INFORMATION: Glu or Thr

<400> SEQUENCE: 44

His Ser Gln Gly Thr Phe Thr Ser Asp Tyr Ser Lys Tyr Leu Xaa Ser
1               5                   10                  15

Arg Arg Ala Gln Asp Phe Val Glu Trp Leu Met Lys Xaa
            20                  25

<210> SEQ ID NO 45
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (12)..(12)
<223> OTHER INFORMATION: Lys or Glu
<220> FEATURE:
<221> NAME/KEY: MOD_RES
<222> LOCATION: (15)..(15)
<223> OTHER INFORMATION: Asp, Glu, homoglutamic acid, cysteic acid or
      homocysteic acid
<220> FEATURE:
<221> NAME/KEY: MOD_RES
<222> LOCATION: (16)..(16)
<223> OTHER INFORMATION: Ser, Gln, Glu, Lys, homoglutamic acid, cysteic
      acid or homocysteic acid
<220> FEATURE:
<221> NAME/KEY: MOD_RES
<222> LOCATION: (20)..(20)
<223> OTHER INFORMATION: Gln, Glu or Lys
<220> FEATURE:
<221> NAME/KEY: MOD_RES
<222> LOCATION: (24)..(24)
<223> OTHER INFORMATION: Gln, Lys or Glu
<220> FEATURE:
<221> NAME/KEY: MOD_RES
<222> LOCATION: (28)..(28)
<223> OTHER INFORMATION: Asn, Lys or an acidic amino acid
<220> FEATURE:
<221> NAME/KEY: MOD_RES
<222> LOCATION: (29)..(29)
<223> OTHER INFORMATION: Thr, Gly or an acidic amino acid

<400> SEQUENCE: 45

His Ser Gln Gly Thr Phe Thr Ser Asp Tyr Ser Xaa Tyr Leu Xaa Xaa
1               5                   10                  15

Arg Arg Ala Xaa Asp Phe Val Xaa Trp Leu Met Xaa Xaa
            20                  25

<210> SEQ ID NO 46
<211> LENGTH: 29
<212> TYPE: PRT
<213> ORGANISM: Artificial Sequence
```

```
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (24)..(24)
<223> OTHER INFORMATION: Gln or Glu

<400> SEQUENCE: 46

His Ser Gln Gly Thr Phe Thr Ser Asp Tyr Ser Lys Tyr Leu Asp Xaa
1               5                   10                  15

Arg Arg Ala Xaa Asp Phe Val Xaa Trp Leu Met Asn Thr
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 47

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 48

His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Asn Thr
            20                  25

<210> SEQ ID NO 49
<211> LENGTH: 29
<212> TYPE: PRT
<213> ORGANISM: Artificial Sequence
<220> FEATURE:
<223> OTHER INFORMATION: Synthetic Glucagon Analogue

<400> SEQUENCE: 49

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Thr
            20                  25

<210> SEQ ID NO 50
<211> LENGTH: 31
<212> TYPE: PRT
<213> ORGANISM: Homo sapiens

<400> SEQUENCE: 50
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 51
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (15)..(15)
<223> OTHER INFORMATION: Asp, Glu, homoglutamic acid, cysteic acid or homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic acid
<220> FEATURE:
<221> NAME/KEY: MOD_RES
<222> LOCATION: (20)..(20)
<223> OTHER INFORMATION: Gln, Lys, Arg, Orn, or Citrulline
<220> FEATURE:
<221> NAME/KEY: MOD_RES
<222> LOCATION: (21)..(21)
<223> OTHER INFORMATION: Asp, Glu, homoglutamic acid, or homocysteic acid
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Lys or an acidic amino acid
<220> FEATURE:
<221> NAME/KEY: MOD_RES
<222> LOCATION: (29)..(29)
<223> OTHER INFORMATION: Thr, Gly or an acidic amino acid

<400> SEQUENCE: 51

```
His Ser Gln Gly Thr Phe Thr Ser Asp Tyr Ser Lys Tyr Leu Xaa Xaa
1               5                   10                  15

Arg Arg Ala Xaa Xaa Phe Val Xaa Trp Leu Met Xaa Xaa
            20                  25
```

<210> SEQ ID NO 52
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 52

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 53
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:

```
<221> NAME/KEY: MOD_RES
<222> LOCATION: (3)..(3)
<223> OTHER INFORMATION: Glu, Orn or Nle
<220> FEATURE:
<221> NAME/KEY: MOD_RES
<222> LOCATION: (15)..(15)
<223> OTHER INFORMATION: Asp, Glu, homoglutamic acid, cysteic acid or
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Lys or an acidic amino acid
<220> FEATURE:
<221> NAME/KEY: MOD_RES
<222> LOCATION: (29)..(29)
<223> OTHER INFORMATION: Thr or an acidic amino acid

<400> SEQUENCE: 53

His Ser Xaa Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Xaa
            20                  25

<210> SEQ ID NO 54
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (17)..(17)
<223> OTHER INFORMATION: Arg or Gln
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (21)..(21)
<223> OTHER INFORMATION: Asp or Glu
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (24)..(24)
<223> OTHER INFORMATION: Gln or Ala

<400> SEQUENCE: 54

His Ser Gln Gly Thr Phe Thr Ser Asp Tyr Ser Lys Tyr Leu Asp Glu
1               5                   10                  15

Xaa Xaa Ala Lys Xaa Phe Xaa Xaa Trp Leu Met Asn Thr
            20                  25

<210> SEQ ID NO 55
<211> LENGTH: 29
<212> TYPE: PRT
<213> ORGANISM: Artificial Sequence
<220> FEATURE:
```

```
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His or alpha, alpha-dimethyl imidiazole acetic
      acid (DMIA), N-methyl His, alpha-methyl His, or imidazole acetic
      acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser,
      aminoisobutyric acid (AIB) or N-methyl Ala
<220> FEATURE:
<221> NAME/KEY: MOD_RES
<222> LOCATION: (3)..(3)
<223> OTHER INFORMATION: Gln, Glu, Orn or Nle
<220> FEATURE:
<221> NAME/KEY: MOD_RES
<222> LOCATION: (10)..(10)
<223> OTHER INFORMATION: Tyr or Trp
<220> FEATURE:
<221> NAME/KEY: MOD_RES
<222> LOCATION: (12)..(12)
<223> OTHER INFORMATION: Lys, Citrulline, Orn or Arg
<220> FEATURE:
<221> NAME/KEY: MOD_RES
<222> LOCATION: (15)..(15)
<223> OTHER INFORMATION: Asp, Glu, cysteic acid, homoglutamic acid and
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (17)..(17)
<223> OTHER INFORMATION: Arg, Gln, Lys, Cys, Orn, homocysteine or acetyl
      phenylalanine
<220> FEATURE:
<221> NAME/KEY: MOD_RES
<222> LOCATION: (18)..(18)
<223> OTHER INFORMATION: Arg, Ala, Lys, Cys, Orn, homocysteine or acetyl
      phenylalanine
<220> FEATURE:
<221> NAME/KEY: MOD_RES
<222> LOCATION: (20)..(20)
<223> OTHER INFORMATION: Gln, Lys, Arg, Orn or Citrulline
<220> FEATURE:
<221> NAME/KEY: MOD_RES
<222> LOCATION: (21)..(21)
<223> OTHER INFORMATION: Gln, Glu, Asp, Lys, Cys, Orn, homocystein or
      acetyl phenylalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (24)..(24)
<223> OTHER INFORMATION: Ala, Gln, Glu, Lys, Cys, Orn, homocysteine or
      acetyl phenylalanine
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (28)..(28)
<223> OTHER INFORMATION: Asn, Arg, Citrulline, Orn, Lys or Asp
<220> FEATURE:
<221> NAME/KEY: MOD_RES
<222> LOCATION: (29)..(29)
<223> OTHER INFORMATION: Thr, Gly, Lys, Cys, Orn, homocysteine or
      acetyl phenylalanine

<400> SEQUENCE: 55

Xaa Xaa Xaa Gly Thr Phe Thr Ser Asp Xaa Ser Xaa Tyr Leu Xaa Xaa
```

```
1               5               10              15
Xaa Xaa Ala Xaa Xaa Phe Xaa Xaa Trp Leu Xaa Xaa Xaa
            20              25
```

<210> SEQ ID NO 56
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His, acetyl-His, homo-His, DMIA, N-methyl His, alpha-methyl His, or imidazole acetic acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser, AIB or N-methyl Ala
<220> FEATURE:
<221> NAME/KEY: MOD_RES
<222> LOCATION: (3)..(3)
<223> OTHER INFORMATION: Gln, Glu, Orn or Nle
<220> FEATURE:
<221> NAME/KEY: MOD_RES
<222> LOCATION: (15)..(15)
<223> OTHER INFORMATION: Asp, Glu, cysteic acid, homoglutamic acid and homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic acid
<220> FEATURE:
<221> NAME/KEY: MOD_RES
<222> LOCATION: (20)..(20)
<223> OTHER INFORMATION: Gln, Lys, Arg, Orn or Citrulline
<220> FEATURE:
<221> NAME/KEY: MOD_RES
<222> LOCATION: (21)..(21)
<223> OTHER INFORMATION: Gln, Glu, Asp, Cys, Orn, homocycstein or acetyl phenylalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (24)..(24)
<223> OTHER INFORMATION: Ala, Gln, Glu, Cys, Orn, homocycsteine or acetyl phenylalanine
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (28)..(28)
<223> OTHER INFORMATION: Asn, Lys or Asp
<220> FEATURE:
<221> NAME/KEY: MOD_RES
<222> LOCATION: (29)..(29)
<223> OTHER INFORMATION: Thr, Gly, Lys, Cys, Orn, homocycsteine or acetyl phenylalanine

<400> SEQUENCE: 56

```
Xaa Xaa Xaa Gly Thr Phe Thr Ser Asp Tyr Ser Lys Tyr Leu Xaa Xaa
1               5                   10                  15
Arg Arg Ala Xaa Xaa Phe Xaa Xaa Trp Leu Xaa Xaa Xaa
                20                  25
```

<210> SEQ ID NO 57
<211> LENGTH: 29

```
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl- His, homo-His, DMIA, N-methyl His, alpha-methyl His, or
      imidazole acetic acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser,
      AIB or N-methyl Ala
<220> FEATURE:
<221> NAME/KEY: MOD_RES
<222> LOCATION: (3)..(3)
<223> OTHER INFORMATION: Gln, Glu, Orn or Nle
<220> FEATURE:
<221> NAME/KEY: MISC_FEATURE
<222> LOCATION: (12)..(16)
<223> OTHER INFORMATION: Lactam ring between side changes at position 12
      and 16
<220> FEATURE:
<221> NAME/KEY: MOD_RES
<222> LOCATION: (15)..(15)
<223> OTHER INFORMATION: Asp, Glu, cysteic acid, homoglutamic acid and
      homocysteic acid
<220> FEATURE:
<221> NAME/KEY: MOD_RES
<222> LOCATION: (20)..(20)
<223> OTHER INFORMATION: Gln, Lys, Arg, Orn or Citrulline
<220> FEATURE:
<221> NAME/KEY: MOD_RES
<222> LOCATION: (21)..(21)
<223> OTHER INFORMATION: Gln, Glu, Asp, Cys, Orn, homocycsteine or
      acetyl phenylalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (24)..(24)
<223> OTHER INFORMATION: Ala, Gln, Glu, Lys, Cys, Orn, homocysteine or
      acetyl Phe
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (28)..(28)
<223> OTHER INFORMATION: Asn, Lys or Asp
<220> FEATURE:
<221> NAME/KEY: MOD_RES
<222> LOCATION: (29)..(29)
<223> OTHER INFORMATION: Thr, Gly, Lys, Cys, Orn, homocysteine or acetyl
      phenylalanine

<400> SEQUENCE: 57

Xaa Xaa Xaa Gly Thr Phe Thr Ser Asp Tyr Ser Lys Tyr Leu Xaa Glu
1               5                   10                  15

Arg Arg Ala Xaa Xaa Phe Xaa Xaa Trp Leu Xaa Xaa Xaa
            20                  25

<210> SEQ ID NO 58
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His, DMIA, N-methyl His, alpha-methyl His, or
```

```
            imidazole acetic acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser,
      AIB or N-methyl Ala
<220> FEATURE:
<221> NAME/KEY: MOD_RES
<222> LOCATION: (3)..(3)
<223> OTHER INFORMATION: Gln, Glu, Orn or Nle
<220> FEATURE:
<221> NAME/KEY: MOD_RES
<222> LOCATION: (15)..(15)
<223> OTHER INFORMATION: Asp, Glu, cysteic acid, homoglutamic acid or
      homocysteic acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (21)..(21)
<223> OTHER INFORMATION: Gln, Glu, Asp, Lys, Cys, Orn, homocysteine or
      acetyl phenylalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (24)..(24)
<223> OTHER INFORMATION: Ala, Gln, Glu, Lys, Cys, Orn, homocysteine or
      acetyl phenylalanine
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (28)..(28)
<223> OTHER INFORMATION: Asn, Lys or Asp
<220> FEATURE:
<221> NAME/KEY: MOD_RES
<222> LOCATION: (29)..(29)
<223> OTHER INFORMATION: Thr, Gly, Lys, Cys, Orn, homocysteine or acetyl
      phenylalanine

<400> SEQUENCE: 58

Xaa Xaa Xaa Gly Thr Phe Thr Ser Asp Tyr Ser Lys Tyr Leu Xaa Glu
1               5                   10                  15

Arg Arg Ala Lys Xaa Phe Xaa Xaa Trp Leu Xaa Xaa Xaa
            20                  25

<210> SEQ ID NO 59
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His, DMIA, N-methyl His, alpha-methyl His, or
      imidazole acetic acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser,
      AIB, or N-methyl Ala
<220> FEATURE:
<221> NAME/KEY: MOD_RES
<222> LOCATION: (3)..(3)
<223> OTHER INFORMATION: Gln, Glu, Orn or Nle
<220> FEATURE:
<221> NAME/KEY: MOD_RES
```

```
<222> LOCATION: (15)..(15)
<223> OTHER INFORMATION: Asp, Glu, cysteic acid, homoglutamic acid and
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MISC_FEATURE
<222> LOCATION: (20)..(24)
<223> OTHER INFORMATION: Lactam ring between side chains at position 20
      and 24
<220> FEATURE:
<221> NAME/KEY: MOD_RES
<222> LOCATION: (21)..(21)
<223> OTHER INFORMATION: Gln, Glu, Asp, Lys, Cys, Orn, homocysteine or
      acetyl phenyalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (28)..(28)
<223> OTHER INFORMATION: Asn, Lys or Asp
<220> FEATURE:
<221> NAME/KEY: MOD_RES
<222> LOCATION: (29)..(29)
<223> OTHER INFORMATION: Thr, Gly, Lys, Cys, Orn, homocysteine or acetyl
      pheylalanine

<400> SEQUENCE: 59

Xaa Xaa Xaa Gly Thr Phe Thr Ser Asp Tyr Ser Lys Tyr Leu Xaa Xaa
1               5                   10                  15

Arg Arg Ala Lys Xaa Phe Xaa Glu Trp Leu Xaa Xaa Xaa
            20                  25

<210> SEQ ID NO 60
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His, DMIA, N-methyl His, alpha-methyl His, or
      imidazole acetic acid
<220> FEATURE:
<221> NAME/KEY: MOD_RES
<222> LOCATION: (2)..(2)
<223> OTHER INFORMATION: Ser, D-Ser, Ala, D-Ala, Val, Gly, N-methyl Ser,
      AIB or N-methyl Ala
<220> FEATURE:
<221> NAME/KEY: MOD_RES
<222> LOCATION: (3)..(3)
<223> OTHER INFORMATION: Gln, Glu, Orn or  Nle
<220> FEATURE:
<221> NAME/KEY: MOD_RES
<222> LOCATION: (15)..(15)
<223> OTHER INFORMATION: Asp, Glu, cysteic acid, homoglutamic acid and
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln, Lys, Arg, Orn, or Citrulline
```

```
<220> FEATURE:
<221> NAME/KEY: MOD_RES
<222> LOCATION: (21)..(21)
<223> OTHER INFORMATION: Gln, Glu, Asp, Lys, Cys, Orn, homocysteine or
      acetyl phenylalanine
<220> FEATURE:
<221> NAME/KEY: MOD_RES
<222> LOCATION: (23)..(23)
<223> OTHER INFORMATION: Val or Ile
<220> FEATURE:
<221> NAME/KEY: MISC_FEATURE
<222> LOCATION: (24)..(28)
<223> OTHER INFORMATION: Lactam ring between side chains at position 24
      and 28
<220> FEATURE:
<221> NAME/KEY: MOD_RES
<222> LOCATION: (27)..(27)
<223> OTHER INFORMATION: Met, Leu or Nle
<220> FEATURE:
<221> NAME/KEY: MOD_RES
<222> LOCATION: (29)..(29)
<223> OTHER INFORMATION: Thr, Gly, Lys, Cys, Orn, homocysteine or acetyl
      phenylalanine

<400> SEQUENCE: 60

Xaa Xaa Xaa Gly Thr Phe Thr Ser Asp Tyr Ser Lys Tyr Leu Xaa Xaa
1               5                   10                  15

Arg Arg Ala Xaa Xaa Phe Xaa Glu Trp Leu Xaa Lys Xaa
            20                  25

<210> SEQ ID NO 61
<211> LENGTH: 40
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: positions 30 to 40 are present only if position
      29 is Gly; see specification as filed for detailed description of
      substitutions and preferred embodiments
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His, DMIA, N-methyl His, alpha-methyl His, or
      imidazole acetic acid
<220> FEATURE:
<221> NAME/KEY: MOD_RES
<222> LOCATION: (2)..(2)
<223> OTHER INFORMATION: Ser, D-Ser, Ala, Val, Gly, N-methyl Ser, Aib,
      N-methyl, Ala or D-Ala
<220> FEATURE:
<221> NAME/KEY: MOD_RES
<222> LOCATION: (18)..(18)
<223> OTHER INFORMATION: Ala or Arg
<220> FEATURE:
<221> NAME/KEY: MOD_RES
<222> LOCATION: (24)..(24)
<223> OTHER INFORMATION: Ala, Gln or Cys-PEG
<220> FEATURE:
<221> NAME/KEY: MOD_RES
<222> LOCATION: (29)..(29)
<223> OTHER INFORMATION: Thr-CONH2, Cys-PEG, or Gly
<220> FEATURE:
<221> NAME/KEY: MOD_RES
<222> LOCATION: (40)..(40)
<223> OTHER INFORMATION: Cys-PEG or not present

<400> SEQUENCE: 61

Xaa Xaa Gln Gly Thr Phe Thr Ser Asp Tyr Ser Lys Tyr Leu Asp Glu
1               5                   10                  15

Arg Xaa Ala Lys Asp Phe Val Xaa Trp Leu Met Asn Xaa Gly Pro Ser
            20                  25                  30
```

```
Ser Gly Ala Pro Pro Pro Ser Cys
        35                  40
```

<210> SEQ ID NO 62
<211> LENGTH: 40
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<223> OTHER INFORMATION: positions 30 to 40 are present only if position
      29 is Gly; see specification as filed for detailed description of
      substitutions and preferred embodiments
<220> FEATURE:
<221> NAME/KEY: MOD_RES
<222> LOCATION: (1)..(1)
<223> OTHER INFORMATION: His, D-His, (Des-amino)His, hydroxyl-His,
      acetyl-His, homo-His, DMIA, N-methyl His, alpha-methyl His, or
      imidazole acetic acid
<220> FEATURE:
<221> NAME/KEY: MOD_RES
<222> LOCATION: (2)..(2)
<223> OTHER INFORMATION: Ser, D-Ser, Ala, Val, Gly, N-methyl Ser, AIB0,
      N-methyl Ala, or D-Ala
<220> FEATURE:
<221> NAME/KEY: MOD_RES
<222> LOCATION: (18)..(18)
<223> OTHER INFORMATION: Ala or Arg
<220> FEATURE:
<221> NAME/KEY: MOD_RES
<222> LOCATION: (24)..(24)
<223> OTHER INFORMATION: Ala, Gln or Cys-PEG
<220> FEATURE:
<221> NAME/KEY: MOD_RES
<222> LOCATION: (29)..(29)
<223> OTHER INFORMATION: Thr-CONH2, Cys-PEG, or Gly
<220> FEATURE:
<221> NAME/KEY: MOD_RES
<222> LOCATION: (40)..(40)
<223> OTHER INFORMATION: Cys-PEG or not present

<400> SEQUENCE: 62

```
Xaa Xaa Gln Gly Thr Phe Thr Ser Asp Tyr Ser Lys Tyr Leu Asp Glu
1               5                   10                  15

Gln Xaa Ala Lys Glu Phe Ile Xaa Trp Leu Met Asn Xaa Gly Pro Ser
            20                  25                  30

Ser Gly Ala Pro Pro Pro Ser Cys
        35                  40
```

<210> SEQ ID NO 63
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (21)..(21)
<223> OTHER INFORMATION: Asp, Lys, Cys, Orn, homocysteine or acetyl
      phealanine
<220> FEATURE:
<221> NAME/KEY: MOD_RES
<222> LOCATION: (24)..(24)
<223> OTHER INFORMATION: Gln, Lys, Cys, Orn, homocysteine or acetyl
      phealanine

```
<220> FEATURE:
<221> NAME/KEY: MOD_RES
<222> LOCATION: (27)..(27)
<223> OTHER INFORMATION: Met, Leu or Nle

<400> SEQUENCE: 63

His Ser Gln Gly Thr Phe Thr Ser Asp Tyr Ser Lys Tyr Leu Asp Xaa
1               5                   10                  15

Arg Arg Ala Xaa Xaa Phe Val Xaa Trp Leu Xaa Asn Thr
            20                  25

<210> SEQ ID NO 64
<211> LENGTH: 38
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MOD_RES
<222> LOCATION: (15)..(15)
<223> OTHER INFORMATION: Asp, Glu, homoglutamic acid, cysteic acid or
      homocysteic acid
<220> FEATURE:
<221> NAME/KEY: MOD_RES
<222> LOCATION: (16)..(16)
<223> OTHER INFORMATION: Ser, Glu, Gln, homoglutamic acid or homocysteic
      acid
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (24)..(24)
<223> OTHER INFORMATION: Gln or Glu
<220> FEATURE:
<221> NAME/KEY: MOD_RES
<222> LOCATION: (28)..(28)
<223> OTHER INFORMATION: Asn, Lys or Asp

<400> SEQUENCE: 64

His Ser Gln Gly Thr Phe Thr Ser Asp Tyr Ser Lys Tyr Leu Xaa Xaa
1               5                   10                  15

Arg Arg Ala Xaa Asp Phe Val Xaa Trp Leu Met Xaa Gly Gly Pro Ser
            20                  25                  30

Ser Gly Pro Pro Pro Ser
        35

<210> SEQ ID NO 65
<211> LENGTH: 11
<212> TYPE: PRT
<213> ORGANISM: Artificial Sequence
<220> FEATURE:
<223> OTHER INFORMATION: Synthetic peptide fragment representing the
      carboxy terminal 10 amino acids of Exendin-4
<220> FEATURE:
<221> NAME/KEY: MOD_RES
<222> LOCATION: (11)..(11)
<223> OTHER INFORMATION: Cys-PEG

<400> SEQUENCE: 65

Gly Pro Ser Ser Gly Ala Pro Pro Pro Ser Cys
1               5                   10

<210> SEQ ID NO 66
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
```

```
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (28)..(28)
<223> OTHER INFORMATION: Asp or Asn
<220> FEATURE:
<221> NAME/KEY: MOD_RES
<222> LOCATION: (29)..(29)
<223> OTHER INFORMATION: Thr or Gly

<400> SEQUENCE: 66

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Xaa Xaa
            20                  25

<210> SEQ ID NO 67
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (28)..(28)
<223> OTHER INFORMATION: Asp or Asn
<220> FEATURE:
<221> NAME/KEY: MOD_RES
<222> LOCATION: (29)..(29)
<223> OTHER INFORMATION: Thr or Gly

<400> SEQUENCE: 67

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Xaa Xaa
            20                  25

<210> SEQ ID NO 68
<211> LENGTH: 29
<212> TYPE: PRT
<213> ORGANISM: Artificial Sequence
<220> FEATURE:
<223> OTHER INFORMATION: Synthetic Glucagon Analogue
<220> FEATURE:
<221> NAME/KEY: MISC_FEATURE
<222> LOCATION: (20)..(24)
<223> OTHER INFORMATION: Lactam ring between side chains at positions 20
      and 24
<220> FEATURE:
<221> NAME/KEY: MOD_RES
<222> LOCATION: (28)..(28)
<223> OTHER INFORMATION: Asp or Asn
<220> FEATURE:
<221> NAME/KEY: MOD_RES
<222> LOCATION: (29)..(29)
<223> OTHER INFORMATION: Thr or Gly

<400> SEQUENCE: 68

His Ser Gln Gly Thr Phe Thr Ser Asp Tyr Ser Lys Tyr Leu Asp Ser
1               5                   10                  15

Arg Arg Ala Lys Asp Phe Val Glu Trp Leu Met Xaa Xaa
            20                  25
```

```
<210> SEQ ID NO 69
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (24)..(28)
<223> OTHER INFORMATION: Lactam ring between side chains at positions 24
      and 28
<220> FEATURE:
<221> NAME/KEY: MOD_RES
<222> LOCATION: (29)..(29)
<223> OTHER INFORMATION: Thr or Gly

<400> SEQUENCE: 69

His Ser Gln Gly Thr Phe Thr Ser Asp Tyr Ser Lys Tyr Leu Asp Ser
1               5                   10                  15

Arg Arg Ala Gln Asp Phe Val Glu Trp Leu Met Lys Xaa
            20                  25

<210> SEQ ID NO 70
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 70

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 71
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 71

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 72
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 72
```

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 73
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 73

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 74
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 74

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 75
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 75

His Ser Gln Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 76

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 76

His Ser Gln Gly Thr Phe Thr Ser Asp Tyr Ser Lys Tyr Leu Asp Glu
1               5                   10                  15
Arg Ala Ala Lys Asp Phe Val Gln Trp Leu Met Asn Thr
            20                  25

<210> SEQ ID NO 77
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 77

His Ser Gln Gly Thr Phe Thr Ser Asp Tyr Ser Lys Tyr Leu Asp Glu
1               5                   10                  15
Arg Ala Ala Lys Asp Phe Val Gln Trp Leu Met Asn Thr
            20                  25

<210> SEQ ID NO 78
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 78

His Ser Gln Gly Thr Phe Thr Ser Asp Tyr Ser Lys Tyr Leu Asp Glu
1               5                   10                  15
Arg Ala Ala Gln Asp Phe Val Gln Trp Leu Met Asn Thr
            20                  25

<210> SEQ ID NO 79
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
```

<400> SEQUENCE: 79

His Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 80
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 80

His Ser Gln Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 81
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation

<400> SEQUENCE: 81

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 82
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 82

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 83
<211> LENGTH: 29
<212> TYPE: PRT

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 83

His Ser Gln Gly Thr Phe Thr Ser Asp Tyr Ser Lys Tyr Leu Asp Glu
1               5                   10                  15
Gln Ala Ala Lys Glu Phe Ile Ala Trp Leu Met Asn Thr
            20                  25

<210> SEQ ID NO 84
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation

<400> SEQUENCE: 84

His Ser Gln Gly Thr Phe Thr Ser Asp Tyr Ser Lys Tyr Leu Asp Glu
1               5                   10                  15
Gln Ala Ala Lys Glu Phe Ile Ala Trp Leu Val Lys Gly
            20                  25

<210> SEQ ID NO 85
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 85

His Ser Gln Gly Thr Phe Thr Ser Asp Tyr Ser Lys Tyr Leu Asp Glu
1               5                   10                  15
Gln Ala Ala Lys Glu Phe Ile Ala Trp Leu Val Lys Gly
            20                  25

<210> SEQ ID NO 86
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 86

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 87

Xaa Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 88
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 88

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 89
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 89

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

```
<210> SEQ ID NO 90
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 90

Xaa Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 91
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 91

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 92
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 92

Xaa Ser Gln Gly Thr Phe Thr Ser Asp Tyr Ser Lys Tyr Leu Asp Lys
```

```
                1               5                  10                  15
Arg Arg Ala Glu Asp Phe Val Gln Trp Leu Met Asn Thr
                20                  25

<210> SEQ ID NO 93
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (29)..(29)
<223> OTHER INFORMATION: c-term amidation

<400> SEQUENCE: 93

Xaa Ser Gln Gly Thr Phe Thr Ser Asp Tyr Ser Lys Tyr Leu Asp Glu
1               5                  10                  15
Arg Ala Ala Lys Asp Phe Val Gln Trp Leu Met Asn Thr
                20                  25

<210> SEQ ID NO 94
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 94

Xaa Ser Gln Gly Thr Phe Thr Ser Asp Tyr Ser Lys Tyr Leu Asp Glu
1               5                  10                  15
Arg Ala Ala Lys Asp Phe Val Gln Trp Leu Met Asn Thr
                20                  25

<210> SEQ ID NO 95
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 95

Xaa Ser Gln Gly Thr Phe Thr Ser Asp Tyr Ser Lys Tyr Leu Asp Glu
```

```
1               5                  10                  15

Arg Ala Ala Gln Asp Phe Val Gln Trp Leu Met Asn Thr
            20                  25

<210> SEQ ID NO 96
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 96

Xaa Ser Gln Gly Thr Phe Thr Ser Asp Tyr Ser Lys Tyr Leu Asp Glu
1               5                  10                  15

Arg Ala Ala Lys Asp Phe Val Gln Trp Leu Met Asn Thr
            20                  25

<210> SEQ ID NO 97
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 97

Xaa Ser Gln Gly Thr Phe Thr Ser Asp Tyr Ser Lys Tyr Leu Asp Lys
1               5                  10                  15

Arg Ala Ala Glu Asp Phe Val Gln Trp Leu Met Asn Thr
            20                  25

<210> SEQ ID NO 98
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
```

<400> SEQUENCE: 98

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 99
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 99

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 100
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 100

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 101
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 101

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 102
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 102

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 103
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 103

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 104
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (29)..(29)
<223> OTHER INFORMATION: c-term amidation

```
<400> SEQUENCE: 104

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 105
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 105

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 106
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 106

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 107
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
```

```
<222> LOCATION: (12)..(16)
<223> OTHER INFORMATION: Lactam ring between side chains at positions 12
      and 16

<400> SEQUENCE: 107

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 108
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisebutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 108

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 109
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 109

His Xaa Gln Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 110
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
```

```
<222> LOCATION: (2)..(2)
<223> OTHER INFORMATION: Aminoisobutyric acid

<400> SEQUENCE: 110

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 111
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 111

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 112
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 112

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Met Asn Thr
            20                  25

<210> SEQ ID NO 113
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
```

<223> OTHER INFORMATION: Aminoisobutryic acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 113

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 114
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 114

His Xaa Gln Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 115
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 115

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 116
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

```
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 116

His Xaa Gln Gly Thr Phe Thr Ser Asp Tyr Ser Lys Tyr Leu Asp Glu
1               5                  10                  15

Gln Ala Ala Lys Glu Phe Ile Ala Trp Leu Met Asn Thr
            20                  25

<210> SEQ ID NO 117
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 117

His Xaa Gln Gly Thr Phe Thr Ser Asp Tyr Ser Lys Tyr Leu Asp Glu
1               5                  10                  15

Gln Ala Ala Lys Glu Phe Ile Ala Trp Leu Met Asn Thr
            20                  25

<210> SEQ ID NO 118
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 118

His Xaa Gln Gly Thr Phe Thr Ser Asp Tyr Ser Lys Tyr Leu Asp Glu
1               5                  10                  15

Gln Ala Ala Lys Glu Phe Ile Ala Trp Leu Val Lys Gly
            20                  25

<210> SEQ ID NO 119
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
```

```
<221> NAME/KEY: MISC_FEATURE
<222> LOCATION: (12)..(16)
<223> OTHER INFORMATION: Lactam ring between side chains at positions 12
      and 16

<400> SEQUENCE: 119

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 120
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 120

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 121
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 121

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 122
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 122
```

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 123
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 123

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 124
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 124

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 125
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)

<223> OTHER INFORMATION: Lactam ring between side chains at positions 12
      and 16

<400> SEQUENCE: 125

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 126
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 126

His Xaa Gln Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 127
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 127

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 128
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 128

His Xaa Gln Gly Thr Phe Thr Ser Asp Tyr Ser Lys Tyr Leu Asp Glu
1               5                   10                  15
Arg Ala Ala Lys Asp Phe Val Gln Trp Leu Met Asn Thr
            20                  25

<210> SEQ ID NO 129
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 129

His Xaa Gln Gly Thr Phe Thr Ser Asp Tyr Ser Lys Tyr Leu Asp Glu
1               5                   10                  15
Arg Ala Ala Gln Asp Phe Val Gln Trp Leu Met Asn Thr
            20                  25

<210> SEQ ID NO 130
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 130

His Xaa Gln Gly Thr Phe Thr Ser Asp Tyr Ser Lys Tyr Leu Asp Glu
1               5                   10                  15
Arg Ala Ala Lys Asp Phe Val Gln Trp Leu Met Asn Thr
            20                  25

<210> SEQ ID NO 131
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

```
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 131

His Xaa Gln Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 132
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 132

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 133
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 133

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 134
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
```

```
<221> NAME/KEY: MISC_FEATURE
<222> LOCATION: (16)..(20)
<223> OTHER INFORMATION: Lactam ring between side chains at positions 16
      and 20

<400> SEQUENCE: 134

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 135
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 135

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 136
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 136

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 137
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
```

<222> LOCATION: (16)..(20)
<223> OTHER INFORMATION: Lactam ring between side chains at positions 16
      and 20

<400> SEQUENCE: 137

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 138
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

<400> SEQUENCE: 138

His Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 139
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

<400> SEQUENCE: 139

His Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 140
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 140

His Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 141
<211> LENGTH: 29
<212> TYPE: PRT
<213> ORGANISM: Artificial Sequence
<220> FEATURE:

<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 141

His Ser Glu Gly Thr Phe Thr Ser Asp Tyr Ser Lys Tyr Leu Asp Glu
1               5                   10                  15
Arg Arg Ala Gln Asp Phe Val Gln Trp Leu Met Asn Thr
            20                  25

<210> SEQ ID NO 142
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 142

His Ser Glu Gly Thr Phe Thr Ser Asp Tyr Ser Lys Tyr Leu Asp Glu
1               5                   10                  15
Arg Arg Ala Lys Asp Phe Val Gln Trp Leu Met Asn Thr
            20                  25

<210> SEQ ID NO 143
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 143

His Ser Glu Gly Thr Phe Thr Ser Asp Tyr Ser Lys Tyr Leu Asp Lys
1               5                   10                  15
Arg Arg Ala Glu Asp Phe Val Gln Trp Leu Met Asn Thr
            20                  25

<210> SEQ ID NO 144
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

<400> SEQUENCE: 144

His Ser Glu Gly Thr Phe Thr Ser Asp Tyr Ser Lys Tyr Leu Asp Glu

```
                1               5                  10                  15
Arg Ala Ala Lys Asp Phe Val Gln Trp Leu Met Asn Thr
            20                  25
```

<210> SEQ ID NO 145
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 145

```
His Ser Glu Gly Thr Phe Thr Ser Asp Tyr Ser Lys Tyr Leu Asp Glu
1               5                  10                  15

Arg Ala Ala Lys Asp Phe Val Gln Trp Leu Met Asn Thr
            20                  25
```

<210> SEQ ID NO 146
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 146

```
His Ser Glu Gly Thr Phe Thr Ser Asp Tyr Ser Lys Tyr Leu Asp Glu
1               5                  10                  15

Arg Ala Ala Gln Asp Phe Val Gln Trp Leu Met Asn Thr
            20                  25
```

<210> SEQ ID NO 147
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 147

```
His Ser Glu Gly Thr Phe Thr Ser Asp Tyr Ser Lys Tyr Leu Asp Glu
1               5                  10                  15

Arg Ala Ala Lys Asp Phe Val Gln Trp Leu Met Asn Thr
            20                  25
```

<210> SEQ ID NO 148
<211> LENGTH: 29

```
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 148

His Ser Glu Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 149
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

<400> SEQUENCE: 149

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 150
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 150

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 151
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
```

<400> SEQUENCE: 151

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 152
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

<400> SEQUENCE: 152

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 153
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 153

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 154
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 154

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 155
<211> LENGTH: 29
<212> TYPE: PRT
<213> ORGANISM: Artificial Sequence

```
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 155

Xaa Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 156
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 156

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 157
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 157

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 158
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 158

Xaa Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 159
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 159

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 160
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 160

Xaa Ser Glu Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 161
<211> LENGTH: 29
<212> TYPE: PRT
<213> ORGANISM: Artificial Sequence
<220> FEATURE:
<223> OTHER INFORMATION: glucagon analog
```

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 161

Xaa Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 162
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 162

Xaa Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 163
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 163

Xaa Ser Glu Gly Thr Phe Thr Ser Asp Tyr Ser Lys Tyr Leu Asp Glu
1               5                   10                  15

Arg Ala Ala Gln Asp Phe Val Gln Trp Leu Met Asn Thr
            20                  25

<210> SEQ ID NO 164
<211> LENGTH: 29
<212> TYPE: PRT
<213> ORGANISM: Artificial Sequence
<220> FEATURE:
<223> OTHER INFORMATION: glucagon analog
<220> FEATURE:
```

<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 164

Xaa Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 165
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 165

Xaa Ser Glu Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 166
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 166

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 167
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 167

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 168
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 168

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 169
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 169

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 170
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation

```
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 170

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 171
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 171

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 172
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 172

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 173
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (2)..(2)
<223> OTHER INFORMATION: Aminoisobutyric acid

<400> SEQUENCE: 173

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 174
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 174

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 175
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 175

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 176
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
```

```
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 176

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 177
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 177

His Xaa Glu Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 178
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 178

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 179
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
```

-continued

```
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 179

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 180
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 180

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Met Asn Thr
            20                  25

<210> SEQ ID NO 181
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 181

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 182
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
```

```
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 182

His Xaa Glu Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 183
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 183

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 184
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 184

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 185
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
```

```
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 185

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 186
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 186

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 187
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 187

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 188
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 188

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 189
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 189

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 190
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 190

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 191
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
```

<223> OTHER INFORMATION: Lactam ring between side chains at positions 16
      and 20

<400> SEQUENCE: 191

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 192
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 192

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25

<210> SEQ ID NO 193
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 193

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 194
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)

```
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 194

His Xaa Glu Gly Thr Phe Thr Ser Asp Tyr Ser Lys Tyr Leu Asp Lys
1               5                   10                  15

Arg Arg Ala Glu Asp Phe Val Gln Trp Leu Met Asn Thr
            20                  25

<210> SEQ ID NO 195
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 195

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 196
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 196

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 197
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
```

```
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 197

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Met Asn Thr
            20                  25

<210> SEQ ID NO 198
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 198

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asn Thr
            20                  25

<210> SEQ ID NO 199
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 199

His Xaa Glu Gly Thr Phe Thr Ser Asp Tyr Ser Lys Tyr Leu Asp Lys
1               5                   10                  15

Arg Ala Ala Glu Asp Phe Val Gln Trp Leu Met Asn Thr
            20                  25

<210> SEQ ID NO 200
<211> LENGTH: 29
<212> TYPE: PRT
<213> ORGANISM: Artificial Sequence
```

```
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 200

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 201
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 201

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 202
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 202

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Met Asn Thr
            20                  25

<210> SEQ ID NO 203
<211> LENGTH: 29
<212> TYPE: PRT
<213> ORGANISM: Artificial Sequence
<220> FEATURE:
```

```
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 203

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 204
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 204

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 205
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: Lactam ring between side chains at positions 16
      and 20
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: c-term amidation

<400> SEQUENCE: 205

His Xaa Glu Gly Thr Phe Thr Ser Asp Tyr Ser Lys Tyr Leu Asp Glu
1               5                   10                  15

Gln Ala Ala Lys Glu Phe Ile Ala Trp Leu Val Lys Gly
            20                  25

<210> SEQ ID NO 206
<211> LENGTH: 29
<212> TYPE: PRT
<213> ORGANISM: Artificial Sequence
<220> FEATURE:
<223> OTHER INFORMATION: glucagon analog
```

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 206

His Ser Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 207
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 207

His Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 208
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 208

His Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 209
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
```

<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 209

His Ser Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 210
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 210

His Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 211
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 211

His Ser Gln Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 212
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 212

His Ser Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 213
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 213

His Ser Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 214
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 214

His Ser Gln Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 215
<211> LENGTH: 29
<212> TYPE: PRT
<213> ORGANISM: Artificial Sequence

```
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 215

His Ser Gln Gly Thr Phe Thr Ser Asp Tyr Ser Lys Tyr Leu Asp Glu
1               5                   10                  15
Arg Ala Ala Lys Asp Phe Val Cys Trp Leu Met Asn Thr
            20                  25

<210> SEQ ID NO 216
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 216

His Ser Gln Gly Thr Phe Thr Ser Asp Tyr Ser Lys Tyr Leu Asp Lys
1               5                   10                  15
Arg Ala Ala Glu Asp Phe Val Cys Trp Leu Met Asn Thr
            20                  25

<210> SEQ ID NO 217
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 217

His Ser Gln Gly Thr Phe Thr Ser Asp Tyr Ser Lys Tyr Leu Asp Glu
1               5                   10                  15
Gln Ala Ala Lys Glu Phe Ile Cys Trp Leu Met Asn Thr
            20                  25

<210> SEQ ID NO 218
<211> LENGTH: 29
<212> TYPE: PRT
<213> ORGANISM: Artificial Sequence
<220> FEATURE:
```

<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 218

His Ser Gln Gly Thr Phe Thr Ser Asp Tyr Ser Lys Tyr Leu Asp Glu
1               5                   10                  15
Gln Ala Ala Lys Glu Phe Ile Cys Trp Leu Met Asn Thr
            20                  25

<210> SEQ ID NO 219
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 219

His Ser Gln Gly Thr Phe Thr Ser Asp Tyr Ser Lys Tyr Leu Asp Glu
1               5                   10                  15
Gln Ala Ala Lys Glu Phe Ile Cys Trp Leu Met Asn Thr
            20                  25

<210> SEQ ID NO 220
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 220

His Ser Gln Gly Thr Phe Thr Ser Asp Tyr Ser Lys Tyr Leu Asp Glu
1               5                   10                  15
Gln Ala Ala Lys Glu Phe Ile Cys Trp Leu Val Lys Gly
            20                  25

<210> SEQ ID NO 221
<211> LENGTH: 29
<212> TYPE: PRT
<213> ORGANISM: Artificial Sequence
<220> FEATURE:
<223> OTHER INFORMATION: glucagon analog

```
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 221

His Ser Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 222
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 222

His Ser Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 223
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 223

Xaa Ser Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 224
<211> LENGTH: 29
<212> TYPE: PRT
```

```
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 224

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 225
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 225

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 226
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 226
```

```
Xaa Ser Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 227
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 227

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 228
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 228

Xaa Ser Gln Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 229
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
```

```
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 229

Xaa Ser Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 230
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 230

Xaa Ser Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 231
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation; lactam ring between side
      chains at positions 12 and 16
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 231

Xaa Ser Gln Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 232
```

```
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 232

Xaa Ser Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 233
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 233

Xaa Ser Gln Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 234
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG
```

<400> SEQUENCE: 234

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 235
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 235

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 236
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 236

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 237
<211> LENGTH: 29
<212> TYPE: PRT
<213> ORGANISM: Artificial Sequence
<220> FEATURE:
<223> OTHER INFORMATION: glucagon analog

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 237

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 238
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 238

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 239
<211> LENGTH: 29
<212> TYPE: PRT
<213> ORGANISM: Artificial Sequence
<220> FEATURE:
<223> OTHER INFORMATION: glucagon analog
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 239

Xaa Ser Gln Gly Thr Phe Thr Ser Asp Tyr Ser Lys Tyr Leu Asp Glu
1               5                   10                  15
```

```
Gln Ala Ala Lys Glu Phe Ile Cys Trp Leu Val Lys Gly
            20                  25

<210> SEQ ID NO 240
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 240

His Xaa Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 241
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 241

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 242
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
```

<223> OTHER INFORMATION: Cys-PEG

<400> SEQUENCE: 242

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 243
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 243

His Xaa Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 244
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 244

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 245
<211> LENGTH: 29
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring side chains at positions 16 and 20
<220> FEATURE:
<221> NAME/KEY: MOD_RES
<222> LOCATION: (24)..(24)
<223> OTHER INFORMATION: Cys-PEG

<400> SEQUENCE: 245

His Xaa Gln Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 246
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 246

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 247
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 247

His Xaa Gln Gly Thr Phe Thr Ser Asp Tyr Ser Lys Tyr Leu Asp Glu
1               5                   10                  15
```

```
Arg Ala Ala Lys Asp Phe Val Cys Trp Leu Met Asn Thr
            20                  25

<210> SEQ ID NO 248
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 248

His Xaa Gln Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 249
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 249

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 250
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
```

```
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 250

His Xaa Gln Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 251
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 251

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 252
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 252

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 253
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
```

-continued

<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 253

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 254
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 254

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 255
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 255

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 256

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 256

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 257
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 257

His Xaa Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 258
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 258

His Xaa Gln Gly Thr Phe Thr Ser Asp Tyr Ser Lys Tyr Leu Asp Glu
1               5                   10                  15
```

Arg Arg Ala Lys Asp Phe Val Cys Trp Leu Met Asn Thr
            20                  25

<210> SEQ ID NO 259
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 259

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 260
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 260

His Xaa Gln Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 261
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation; lactam ring between side
      chains at positions 12 and 16
<220> FEATURE:

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 261

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 262
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 262

His Xaa Gln Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 263
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 263

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 264
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 264

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 265
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 265

His Xaa Gln Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 266
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
```

```
<222> LOCATION: (24)..(24)
<223> OTHER INFORMATION: Cys-PEG

<400> SEQUENCE: 266

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 267
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 267

His Xaa Gln Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 268
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 268

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 269
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
```

```
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 269

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 270
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 270

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 271
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 271

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25
```

<210> SEQ ID NO 272
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12 and 16
<220> FEATURE:
<221> NAME/KEY: MOD_RES
<222> LOCATION: (24)..(24)
<223> OTHER INFORMATION: Cys-PEG

<400> SEQUENCE: 272

His Xaa Gln Gly Thr Phe Thr Ser Asp Tyr Ser Lys Tyr Leu Asp Glu
 1               5                  10                  15

Gln Ala Ala Lys Glu Phe Ile Cys Trp Leu Val Lys Gly
            20                  25

<210> SEQ ID NO 273
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16 and 20
<220> FEATURE:
<221> NAME/KEY: MOD_RES
<222> LOCATION: (24)..(24)
<223> OTHER INFORMATION: Cys-PEG

<400> SEQUENCE: 273

His Xaa Gln Gly Thr Phe Thr Ser Asp Tyr Ser Lys Tyr Leu Asp Glu
 1               5                  10                  15

Gln Ala Ala Lys Glu Phe Ile Cys Trp Leu Val Lys Gly
            20                  25

<210> SEQ ID NO 274
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

```
<400> SEQUENCE: 274

His Ser Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 275
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 275

His Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 276
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 276

His Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 277
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 277
```

His Ser Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 278
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 278

His Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 279
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 279

His Ser Glu Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 280
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 280

```
His Ser Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 281
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 281

His Ser Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 282
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 282

His Ser Glu Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 283
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
```

<223> OTHER INFORMATION: Cys-PEG

<400> SEQUENCE: 283

His Ser Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 284
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 284

His Ser Glu Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 285
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 285

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 286
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 286

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 287
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chain at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 287

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 288
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 288

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 289
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

```
<400> SEQUENCE: 289

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 290
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 290

His Ser Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 291
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 291

Xaa Ser Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 292
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
```

<223> OTHER INFORMATION: Cys-PEG

<400> SEQUENCE: 292

Xaa Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 293
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 293

Xaa Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 294
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 294

Xaa Ser Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 295
<211> LENGTH: 29
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 295

Xaa Ser Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 296
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 296

Xaa Ser Glu Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 297
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 297

Xaa Ser Glu Gly Thr Phe Thr Ser Asp Tyr Ser Lys Tyr Leu Asp Glu
```

```
1               5                  10                 15
Arg Ala Ala Lys Asp Phe Val Cys Trp Leu Met Asn Thr
            20                  25

<210> SEQ ID NO 298
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 298

Xaa Ser Glu Gly Thr Phe Thr Ser Asp Tyr Ser Lys Tyr Leu Asp Glu
1               5                  10                 15

Arg Ala Ala Lys Asp Phe Val Cys Trp Leu Met Asn Thr
            20                  25

<210> SEQ ID NO 299
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 299

Xaa Ser Glu Gly Thr Phe Thr Ser Asp Tyr Ser Lys Tyr Leu Asp Glu
1               5                  10                 15

Arg Ala Ala Gln Asp Phe Val Cys Trp Leu Met Asn Thr
            20                  25

<210> SEQ ID NO 300
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 300

Xaa Ser Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 301
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 301

Xaa Ser Glu Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 302
<211> LENGTH: 29
<212> TYPE: PRT
<213> ORGANISM: Artificial Sequencce
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (24)..(24)
<223> OTHER INFORMATION: Cys-PEG

<400> SEQUENCE: 302

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Met Asn Thr
            20                  25
```

```
<210> SEQ ID NO 303
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 303

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Met Asn Thr
            20                  25

<210> SEQ ID NO 304
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 304

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Met Asn Thr
            20                  25

<210> SEQ ID NO 305
<211> LENGTH: 29
<212> TYPE: PRT
<213> ORGANISM: Artificial Sequencce
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (des-amino)His
<220> FEATURE:
<221> NAME/KEY: MOD_RES
```

```
<222> LOCATION: (24)..(24)
<223> OTHER INFORMATION: Cys-PEG

<400> SEQUENCE: 305

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Val Lys Gly
            20                  25

<210> SEQ ID NO 306
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 306

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Val Lys Gly
            20                  25

<210> SEQ ID NO 307
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 307

Xaa Ser Glu Gly Thr Phe Thr Ser Asp Tyr Ser Lys Tyr Leu Asp Glu
1               5                   10                  15

Gln Ala Ala Lys Gly Phe Ile Cys Trp Leu Val Lys Gly
            20                  25

<210> SEQ ID NO 308
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 308

His Xaa Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 309
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 309

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 310
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 310

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25
```

<210> SEQ ID NO 311
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chain at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 311

His Xaa Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 312
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 312

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 313
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:

```
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 313

His Xaa Glu Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 314
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 314

His Xaa Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 315
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 315

His Xaa Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 316
<211> LENGTH: 29
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 316

His Xaa Glu Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 317
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 317

His Xaa Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 318
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
```

```
<221> NAME/KEY: MOD_RES
<222> LOCATION: (24)..(24)
<223> OTHER INFORMATION: Cys-PEG

<400> SEQUENCE: 318

His Xaa Glu Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 319
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 319

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 320
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 320

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 321
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at position 16
      and 20
<220> FEATURE:
<221> NAME/KEY: MOD_RES
<222> LOCATION: (24)..(24)
<223> OTHER INFORMATION: Cys-PEG

<400> SEQUENCE: 321

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 322
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 322

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 323
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 323

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
```

```
<210> SEQ ID NO 324
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at position 16
      and 20
<220> FEATURE:
<221> NAME/KEY: MOD_RES
<222> LOCATION: (24)..(24)
<223> OTHER INFORMATION: Cys-PEG

<400> SEQUENCE: 324

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 325
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 325

His Xaa Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 326
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG
```

<400> SEQUENCE: 326

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 327
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 327

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 328
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam between side chains at positions 12 and
      16
<220> FEATURE:
<221> NAME/KEY: MOD_RES
<222> LOCATION: (24)..(24)
<223> OTHER INFORMATION: Cys-PEG

<400> SEQUENCE: 328

His Xaa Glu Gly Thr Phe Thr Ser Asp Tyr Ser Lys Tyr Leu Asp Glu
1               5                   10                  15

Arg Arg Ala Gln Asp Phe Val Cys Trp Leu Met Asn Thr
            20                  25

<210> SEQ ID NO 329
<211> LENGTH: 29
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 329

His Xaa Glu Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 330
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 330

His Xaa Glu Gly Thr Phe Thr Ser Asp Tyr Ser Lys Tyr Leu Asp Lys
1               5                   10                  15

Arg Arg Ala Glu Asp Phe Val Cys Trp Leu Met Asn Thr
            20                  25

<210> SEQ ID NO 331
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 331

His Xaa Glu Gly Thr Phe Thr Ser Asp Tyr Ser Lys Tyr Leu Asp Glu
1               5                   10                  15
```

Arg Ala Ala Lys Asp Phe Val Cys Trp Leu Met Asn Thr
            20                  25

<210> SEQ ID NO 332
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 332

His Xaa Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 333
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 333

His Xaa Glu Gly Thr Phe Thr Ser Asp Tyr Ser Lys Tyr Leu Asp Glu
1               5                   10                  15

Arg Ala Ala Gln Asp Phe Val Cys Trp Leu Met Asn Thr
            20                  25

<210> SEQ ID NO 334
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)

<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 334

His Xaa Glu Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 335
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 335

His Xaa Glu Gly Thr Phe Thr Ser Asp Tyr Ser Lys Tyr Leu Asp Lys
1               5                   10                  15

Arg Ala Ala Glu Asp Phe Val Cys Trp Leu Met Asn Thr
            20                  25

<210> SEQ ID NO 336
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG

<400> SEQUENCE: 336

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 337

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 337

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 338
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam right between side chains at positions
      16 and 20
<220> FEATURE:
<221> NAME/KEY: MOD_RES
<222> LOCATION: (24)..(24)
<223> OTHER INFORMATION: Cys-PEG

<400> SEQUENCE: 338

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 339
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (24)..(24)
<223> OTHER INFORMATION: Cys-PEG
```

<400> SEQUENCE: 339

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 340
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16
<220> FEATURE:
<221> NAME/KEY: MOD_RES
<222> LOCATION: (24)..(24)
<223> OTHER INFORMATION: Cys-PEG

<400> SEQUENCE: 340

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 341
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 341

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Val Lys Gly
            20                  25

<210> SEQ ID NO 342
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 342

His Ser Gln Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 343
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 343

His Ser Gln Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 344
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 344

His Ser Gln Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 345
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 345

His Ser Gln Gly Thr Phe Thr Ser Asp Tyr Ser Lys Tyr Leu Asp Cys
```

```
1               5                   10                  15
Gln Ala Ala Lys Glu Phe Ile Ala Trp Leu Val Lys Gly
            20                  25
```

<210> SEQ ID NO 346
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 346

```
Xaa Ser Gln Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25
```

<210> SEQ ID NO 347
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 347

```
Xaa Ser Gln Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25
```

<210> SEQ ID NO 348
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 348

-continued

Xaa Ser Gln Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 349
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 349

Xaa Ser Gln Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 350
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 350

Xaa Ser Gln Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 351
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (16)..(16)
<223> OTHER INFORMATION: Cys-PEG

<400> SEQUENCE: 351

```
His Xaa Gln Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
                20                  25
```

<210> SEQ ID NO 352
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (16)..(16)
<223> OTHER INFORMATION: Cys-PEG

<400> SEQUENCE: 352

```
His Xaa Gln Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
                20                  25
```

<210> SEQ ID NO 353
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (16)..(16)
<223> OTHER INFORMATION: Cys-PEG

<400> SEQUENCE: 353

```
His Xaa Gln Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
                20                  25
```

<210> SEQ ID NO 354
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG -continued

```
<400> SEQUENCE: 354

His Xaa Gln Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 355
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 355

His Xaa Gln Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 356
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 356

His Xaa Gln Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 357
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG
```

<400> SEQUENCE: 357

His Xaa Gln Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 358
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 358

His Ser Glu Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 359
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 359

His Ser Glu Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 360
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 360

His Ser Glu Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 361

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Cys-PEG

<400> SEQUENCE: 361

His Ser Glu Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 362
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 362

Xaa Ser Glu Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 363
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 363

Xaa Ser Glu Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 364
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 364

Xaa Ser Glu Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 365
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MOD_RES
<222> LOCATION: (16)..(16)
<223> OTHER INFORMATION: Cys-PEG

<400> SEQUENCE: 365

Xaa Ser Glu Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 366
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 366

His Xaa Glu Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 367
<211> LENGTH: 29
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 367

His Xaa Glu Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 368
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 368

His Xaa Glu Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 369
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 369

His Xaa Glu Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 370
<211> LENGTH: 29

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 370

His Xaa Glu Gly Thr Phe Thr Ser Asp Tyr Ser Lys Tyr Leu Asp Cys
1               5                   10                  15

Arg Arg Ala Lys Asp Phe Val Gln Trp Leu Met Asn Thr
            20                  25

<210> SEQ ID NO 371
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 371

His Xaa Glu Gly Thr Phe Thr Ser Asp Tyr Ser Lys Tyr Leu Asp Cys
1               5                   10                  15

Arg Ala Ala Lys Asp Phe Val Gln Trp Leu Met Asn Thr
            20                  25

<210> SEQ ID NO 372
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 372

His Xaa Glu Gly Thr Phe Thr Ser Asp Tyr Ser Lys Tyr Leu Asp Cys
1               5                   10                  15

Gln Ala Ala Lys Glu Phe Ile Ala Trp Leu Met Asn Thr
            20                  25

<210> SEQ ID NO 373
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (16)..(16)
<223> OTHER INFORMATION: Cys-PEG

<400> SEQUENCE: 373

His Xaa Glu Gly Thr Phe Thr Ser Asp Tyr Ser Lys Tyr Leu Asp Cys
1               5                   10                  15

Gln Ala Ala Lys Glu Phe Ile Ala Trp Leu Val Lys Gly
            20                  25

<210> SEQ ID NO 374
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 374

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 375
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 375

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 376
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 376
```

```
His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 377
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 377

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 378
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 378

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 379
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 379

His Ser Gln Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25
```

```
<210> SEQ ID NO 380
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 380

His Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 381
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation; lactam ring between side
      chains at positions 16 and 20

<400> SEQUENCE: 381

His Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 382
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 382

His Ser Gln Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 383
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 383
```

His Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 384
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 384

His Ser Gln Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 385
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 385

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 386
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 386

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 387
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 387

His Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 388
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 388

Xaa Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 389
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 389

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 390
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
```

<223> OTHER INFORMATION: Lactam ring between side chains at positions 16
      and 20

<400> SEQUENCE: 390

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 391
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 391

Xaa Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 392
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 392

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 393
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 393

Xaa Ser Gln Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 394
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 394

Xaa Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 395
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 395

Xaa Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 396
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 396

```
Xaa Ser Gln Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 397
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 397

Xaa Ser Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 398
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 398

Xaa Ser Gln Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 399
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 399

Xaa Ser Gln Gly Thr Phe Thr Ser Asp Tyr Ser Lys Tyr Leu Asp Glu
```

```
                1               5                  10                  15
Gln Ala Ala Lys Glu Phe Ile Ala Trp Leu Met Asp Thr
            20                  25

<210> SEQ ID NO 400
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 400

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 401
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 401

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 402
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 402

His Xaa Gln Gly Thr Phe Thr Ser Asp Tyr Ser Lys Tyr Leu Asp Glu
1               5                   10                  15
```

```
Arg Arg Ala Gln Asp Phe Val Gln Trp Leu Met Asp Thr
            20                  25

<210> SEQ ID NO 403
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 403

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 404
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 404

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 405
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 405

His Xaa Gln Gly Thr Phe Thr Ser Asp Tyr Ser Lys Tyr Leu Asp Glu
1               5                   10                  15
```

-continued

Arg Arg Ala Gln Asp Phe Val Gln Trp Leu Met Asp Thr
            20                  25

<210> SEQ ID NO 406
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 406

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 407
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 407

His Xaa Gln Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 408
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (2)..(2)
<223> OTHER INFORMATION: c-term amidation

<400> SEQUENCE: 408

His Xaa Gln Gly Thr Phe Thr Ser Asp Tyr Ser Lys Tyr Leu Asp Glu
1               5                   10                  15

```
Arg Ala Ala Lys Asp Phe Val Gln Trp Leu Met Asp Thr
            20                  25
```

<210> SEQ ID NO 409
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 409

```
His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25
```

<210> SEQ ID NO 410
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 410

```
His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25
```

<210> SEQ ID NO 411
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 411

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 412
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 16
      and 20

<400> SEQUENCE: 412

His Xaa Gln Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 413
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 413

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 414
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 414

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 415
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 415

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 416
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 416

His Xaa Gln Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 417
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 417

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 418
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 418

His Xaa Gln Gly Thr Phe Thr Ser Asp Tyr Ser Lys Tyr Leu Asp Glu
1               5                   10                  15
Arg Arg Ala Lys Asp Phe Val Gln Trp Leu Met Asp Thr
            20                  25

<210> SEQ ID NO 419
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 419

His Xaa Gln Gly Thr Phe Thr Ser Asp Tyr Ser Lys Tyr Leu Asp Glu
1               5                   10                  15
Arg Arg Ala Gln Asp Phe Val Gln Trp Leu Met Asp Thr
            20                  25

<210> SEQ ID NO 420
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 420

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 421
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 421

His Xaa Gln Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 422
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 422

His Xaa Gln Gly Thr Phe Thr Ser Asp Tyr Ser Lys Tyr Leu Asp Glu
1               5                   10                  15

Arg Ala Lys Asp Phe Val Gln Trp Leu Met Asp Thr
            20                  25

<210> SEQ ID NO 423
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 423

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 424
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 424

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 425
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 425

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 426
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 426

His Xaa Gln Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 427
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 427

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 428
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 428

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 429
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 429

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 430
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 430

His Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 431
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 431

His Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 432
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 432

His Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 433
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE

```
<222> LOCATION: (16)..(16)
<223> OTHER INFORMATION: Lactam ring between side chains at positions 12
      and 16

<400> SEQUENCE: 433

His Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 434
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions
      12 and 16

<400> SEQUENCE: 434

His Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 435
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 435

His Ser Glu Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 436
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 436

His Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25
```

<210> SEQ ID NO 437
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<223> OTHER INFORMATION: Lactam ring between side chains at positions 16 and 20

<400> SEQUENCE: 437

His Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 438
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 438

His Ser Glu Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 439
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 439

His Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 440
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

```
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 440

His Ser Glu Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 441
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 441

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 442
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 442

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 443
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 443

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25
```

<210> SEQ ID NO 444
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 444

Xaa Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 445
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 445

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 446
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 446

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 447
<211> LENGTH: 29
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<223> OTHER INFORMATION: Lactam ring between side chains at positions 12
      and 16
<220> FEATURE:
<221> NAME/KEY: MOD_RES
<222> LOCATION: (1)..(1)
<223> OTHER INFORMATION: (Des-amino)His

<400> SEQUENCE: 447

Xaa Ser Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 448
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 448

Xaa Ser Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 449
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 449

Xaa Ser Glu Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 450
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 450

Xaa Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 451
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 451

Xaa Ser Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 452
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: C-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 452

Xaa Ser Glu Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 453
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 453

Xaa Ser Glu Gly Thr Phe Thr Ser Asp Tyr Ser Lys Tyr Leu Asp Glu
1               5                   10                  15
Arg Ala Ala Lys Asp Phe Val Gln Trp Leu Met Asp Thr
            20                  25

<210> SEQ ID NO 454
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 454

Xaa Ser Glu Gly Thr Phe Thr Ser Asp Tyr Ser Lys Tyr Leu Asp Lys
1               5                   10                  15
Arg Ala Ala Glu Asp Phe Val Gln Trp Leu Met Asp Thr
            20                  25

<210> SEQ ID NO 455
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His

<400> SEQUENCE: 455

Xaa Ser Glu Gly Thr Phe Thr Ser Asp Tyr Ser Lys Tyr Leu Asp Glu
1               5                   10                  15
Gln Ala Ala Lys Glu Phe Ile Ala Trp Leu Met Asp Thr
            20                  25

<210> SEQ ID NO 456
<211> LENGTH: 29
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (12)..(16)
<223> OTHER INFORMATION: Lactam ring between side chains at positions 12 and 16

<400> SEQUENCE: 456

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 457
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: (Des-amino)His
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 457

Xaa Ser Glu Gly Thr Phe Thr Ser Asp Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 458
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 458

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 459
<211> LENGTH: 29
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 459

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 460
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 460

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 461
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 461

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 462
<211> LENGTH: 29
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 462

His Xaa Glu Gly Thr Phe Thr Ser Asp Tyr Ser Lys Tyr Leu Asp Glu
1               5                  10                  15

Arg Arg Ala Lys Asp Phe Val Gln Trp Leu Met Asp Thr
            20                  25

<210> SEQ ID NO 463
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 463

His Xaa Glu Gly Thr Phe Thr Ser Asp Tyr Ser Lys Tyr Leu Asp Lys
1               5                  10                  15

Arg Arg Ala Glu Asp Phe Val Gln Trp Leu Met Asp Thr
            20                  25

<210> SEQ ID NO 464
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 464

His Xaa Glu Gly Thr Phe Thr Ser Asp Tyr Ser Lys Tyr Leu Asp Glu
1               5                  10                  15

Arg Ala Ala Lys Asp Phe Val Gln Trp Leu Met Asp Thr
            20                  25

<210> SEQ ID NO 465
<211> LENGTH: 29
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 465

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 466
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at postions 12
      and 16

<400> SEQUENCE: 466

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 467
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 467

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 468
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 16
      and 20

<400> SEQUENCE: 468

His Xaa Glu Gly Thr Phe Thr Ser Asp Tyr Ser Lys Tyr Leu Asp Lys
1               5                   10                  15
Arg Ala Ala Glu Asp Phe Val Gln Trp Leu Met Asp Thr
            20                  25

<210> SEQ ID NO 469
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid

<400> SEQUENCE: 469

His Xaa Glu Gly Thr Phe Thr Ser Asp Tyr Ser Lys Tyr Leu Asp Glu
1               5                   10                  15
Gln Ala Ala Lys Glu Phe Ile Ala Trp Leu Met Asp Thr
            20                  25

<210> SEQ ID NO 470
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 470

His Xaa Glu Gly Thr Phe Thr Ser Asp Tyr Ser Lys Tyr Leu Asp Glu
1               5                   10                  15
Gln Ala Ala Lys Glu Phe Ile Ala Trp Leu Met Asp Thr
            20                  25

<210> SEQ ID NO 471
<211> LENGTH: 29
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 471

His Xaa Glu Gly Thr Phe Thr Ser Asp Tyr Ser Lys Tyr Leu Asp Glu
1               5                   10                  15
Gln Ala Ala Lys Glu Phe Ile Ala Trp Leu Met Asp Thr
            20                  25

<210> SEQ ID NO 472
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 472

His Xaa Glu Gly Thr Phe Thr Ser Asp Tyr Ser Lys Tyr Leu Asp Glu
1               5                   10                  15
Arg Arg Ala Gln Asp Phe Val Gln Trp Leu Met Asp Thr
            20                  25

<210> SEQ ID NO 473
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 473

His Xaa Glu Gly Thr Phe Thr Ser Asp Tyr Ser Lys Tyr Leu Asp Glu
1               5                   10                  15
Arg Arg Ala Lys Asp Phe Val Gln Trp Leu Met Asp Thr
            20                  25

<210> SEQ ID NO 474
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

```
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 474

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 475
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 475

His Xaa Glu Gly Thr Phe Thr Ser Asp Tyr Ser Lys Tyr Leu Asp Glu
1               5                   10                  15

Arg Arg Ala Gln Asp Phe Val Gln Trp Leu Met Asp Thr
            20                  25

<210> SEQ ID NO 476
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 476

His Xaa Glu Gly Thr Phe Thr Ser Asp Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 477
<211> LENGTH: 29
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 477

His Xaa Glu Gly Thr Phe Thr Ser Asp Tyr Ser Lys Tyr Leu Asp Lys
1               5                   10                  15

Arg Arg Ala Glu Asp Phe Val Gln Trp Leu Met Asp Thr
            20                  25

<210> SEQ ID NO 478
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 478

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 479
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16 and 20

<400> SEQUENCE: 479

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 480
<211> LENGTH: 29
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 480

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Met Asp Thr
            20                  25

<210> SEQ ID NO 481
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 481

His Xaa Glu Gly Thr Phe Thr Ser Asp Tyr Ser Lys Tyr Leu Asp Glu
1               5                   10                  15

Arg Ala Ala Lys Asp Phe Val Gln Trp Leu Met Asp Thr
            20                  25

<210> SEQ ID NO 482
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 482

His Xaa Glu Gly Thr Phe Thr Ser Asp Tyr Ser Lys Tyr Leu Asp Lys
1               5                   10                  15

Arg Ala Ala Glu Asp Phe Val Gln Trp Leu Met Asp Thr
            20                  25

<210> SEQ ID NO 483
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala

<400> SEQUENCE: 483

His Xaa Glu Gly Thr Phe Thr Ser Asp Tyr Ser Lys Tyr Leu Asp Glu
 1               5                  10                  15

Gln Ala Ala Lys Glu Phe Ile Ala Trp Leu Met Asp Thr
            20                  25

<210> SEQ ID NO 484
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (12)..(16)
<223> OTHER INFORMATION: Lactam ring between side chains at positions 12
      and 16

<400> SEQUENCE: 484

His Xaa Glu Gly Thr Phe Thr Ser Asp Tyr Ser Lys Tyr Leu Asp Glu
 1               5                  10                  15

Gln Ala Ala Lys Glu Phe Ile Ala Trp Leu Met Asp Thr
            20                  25

<210> SEQ ID NO 485
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ala
<220> FEATURE:
<221> NAME/KEY: MISC_FEATURE
<222> LOCATION: (16)..(20)
<223> OTHER INFORMATION: Lactam ring between side chains at positions 16
      and 20

<400> SEQUENCE: 485

His Xaa Glu Gly Thr Phe Thr Ser Asp Tyr Ser Lys Tyr Leu Asp Glu
 1               5                  10                  15

Gln Ala Ala Lys Glu Phe Ile Ala Trp Leu Met Asp Thr
            20                  25

<210> SEQ ID NO 486
<211> LENGTH: 29
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 486

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 487
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (29)..(29)
<223> OTHER INFORMATION: Cys-PEG

<400> SEQUENCE: 487

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Cys
            20                  25

<210> SEQ ID NO 488
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (40)..(40)
<223> OTHER INFORMATION: Cys-PEG

<400> SEQUENCE: 488

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser Cys
            35                  40
```

```
<210> SEQ ID NO 489
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (40)..(40)
<223> OTHER INFORMATION: Cys-PEG

<400> SEQUENCE: 489

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser Cys
        35                  40

<210> SEQ ID NO 490
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 490

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser
        35

<210> SEQ ID NO 491
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
```

```
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 491

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser
        35

<210> SEQ ID NO 492
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 492

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Thr
            20                  25

<210> SEQ ID NO 493
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 493

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Cys
            20                  25

<210> SEQ ID NO 494
<211> LENGTH: 40
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 494

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Gly Gly Pro Ser
            20                  25                  30

Ser Gly Ala Pro Pro Pro Ser Cys
        35                  40

<210> SEQ ID NO 495
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (40)..(40)
<223> OTHER INFORMATION: Cys-PEG

<400> SEQUENCE: 495

His Xaa Gln Gly Thr Phe Thr Ser Asp Tyr Ser Lys Tyr Leu Asp Glu
1               5                   10                  15

Arg Ala Ala Lys Asp Phe Val Gln Trp Leu Met Asn Gly Gly Pro Ser
            20                  25                  30

Ser Gly Ala Pro Pro Pro Ser Cys
        35                  40

<210> SEQ ID NO 496
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 496

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Gly Gly Pro Ser
            20                  25                  30

Ser Gly Ala Pro Pro Pro Ser
        35

<210> SEQ ID NO 497
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
    and 20
<220> FEATURE:
<221> NAME/KEY: MOD_RES
<222> LOCATION: (24)..(24)
<223> OTHER INFORMATION: Cys-PEG

<400> SEQUENCE: 497

His Xaa Gln Gly Thr Phe Thr Ser Asp Tyr Ser Lys Tyr Leu Asp Glu
1               5                   10                  15

Arg Ala Ala Lys Asp Phe Val Cys Trp Leu Met Asn Gly Gly Pro Ser
            20                  25                  30

Ser Gly Ala Pro Pro Pro Ser
        35

<210> SEQ ID NO 498
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 498

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr Ala
            20                  25                  30

<210> SEQ ID NO 499
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 499

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Cys
            20                  25

<210> SEQ ID NO 500
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (40)..(40)
<223> OTHER INFORMATION: Cys-PEG

<400> SEQUENCE: 500

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Gly Gly Pro Ser
            20                  25                  30

Ser Gly Ala Pro Pro Pro Ser Cys
        35                  40

<210> SEQ ID NO 501
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (40)..(40)
<223> OTHER INFORMATION: Cys-PEG

<400> SEQUENCE: 501

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Gly Gly Pro Ser
            20                  25                  30
```

Ser Gly Ala Pro Pro Ser Cys
        35                  40

<210> SEQ ID NO 502
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 502

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Gly Gly Pro Ser
            20                  25                  30

Ser Gly Ala Pro Pro Pro Ser
        35

<210> SEQ ID NO 503
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 503

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Gly Gly Pro Ser
            20                  25                  30

Ser Gly Ala Pro Pro Pro Ser
        35

<210> SEQ ID NO 504
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES

```
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 504

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 505
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha-Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 505

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 506
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha-Dimethly Imidiazole Acetic Acid
<220> FEATURE:
<221> NAME/KEY: MOD_RES
<222> LOCATION: (1)..(1)
<223> OTHER INFORMATION: Alpha, Alpha-Dimethly Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (29)..(29)
<223> OTHER INFORMATION: Cys-PEG
```

<400> SEQUENCE: 506

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Cys
            20                  25

<210> SEQ ID NO 507
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (40)..(40)
<223> OTHER INFORMATION: Cys-PEG

<400> SEQUENCE: 507

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser Cys
        35                  40

<210> SEQ ID NO 508
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (40)..(40)
<223> OTHER INFORMATION: Cys-PEG

<400> SEQUENCE: 508

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Gly Gly Pro Ser
            20                  25                  30

Ser Gly Ala Pro Pro Pro Ser Cys
        35                  40

<210> SEQ ID NO 509

```
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 509

Xaa Ser Gln Gly Thr Phe Thr Ser Asp Tyr Ser Lys Tyr Leu Asp Glu
1               5                   10                  15
Gln Ala Ala Lys Glu Phe Ile Cys Trp Leu Met Asn Gly Gly Pro Ser
            20                  25                  30
Ser Gly Ala Pro Pro Pro Ser
        35

<210> SEQ ID NO 510
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 510

His Xaa Gln Gly Thr Phe Thr Ser Asp Tyr Ser Lys Tyr Leu Asp Glu
1               5                   10                  15
Arg Arg Ala Lys Asp Phe Val Cys Trp Leu Met Asn Thr
            20                  25

<210> SEQ ID NO 511
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (2)..(2)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 511

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 512
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (29)..(29)
<223> OTHER INFORMATION: Cys-PEG

<400> SEQUENCE: 512

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Cys
            20                  25

<210> SEQ ID NO 513
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 513

Xaa Ser Gln Gly Thr Phe Thr Ser Asp Tyr Ser Lys Tyr Leu Asp Glu
```

```
                1               5                  10                  15
Arg Arg Ala Lys Asp Phe Val Cys Trp Leu Met Asn Gly Gly Pro Ser
                20                  25                  30

Ser Gly Ala Pro Pro Ser
        35

<210> SEQ ID NO 514
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 514

His Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
                20                  25

<210> SEQ ID NO 515
<211> LENGTH: 11
<212> TYPE: PRT
<213> ORGANISM: Artificial Sequence
<220> FEATURE:
<223> OTHER INFORMATION: Synthetic peptide

<400> SEQUENCE: 515

Gly Gly Pro Ser Ser Gly Ala Pro Pro Ser
1               5                   10

<210> SEQ ID NO 516
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: Cys-PEG

<400> SEQUENCE: 516

Gly Gly Pro Ser Ser Gly Ala Pro Pro Ser Cys
1               5                   10

<210> SEQ ID NO 517
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
```

```
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 517

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 518
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (24)..(24)
<223> OTHER INFORMATION: Cys-PEG

<400> SEQUENCE: 518

His Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 519
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethly Imidiazole Acetic Acid
<220> FEATURE:
<221> NAME/KEY: MOD_RES
<222> LOCATION: (24)..(24)
<223> OTHER INFORMATION: Cys-PEG

<400> SEQUENCE: 519

Xaa Ser Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 520
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
```

<222> LOCATION: (1)..(1)
<223> OTHER INFORMATION: Alpha, Alpha Dimethyl Imidiazole Acetic Acid
<220> FEATURE:
<221> NAME/KEY: MOD_RES
<222> LOCATION: (29)..(29)
<223> OTHER INFORMATION: Cys-PEG

<400> SEQUENCE: 520

Xaa Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Cys
            20                  25

<210> SEQ ID NO 521
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 521

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 522
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 522

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Gly Gly Pro Ser
            20                  25                  30

Ser Gly Ala Pro Pro Pro Ser
        35

<210> SEQ ID NO 523
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 523

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Lys Gly Gly Pro Ser
            20                  25                  30

Ser Gly Ala Pro Pro Pro Ser
        35

<210> SEQ ID NO 524
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 524

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Val Lys Gly Gly Pro Ser
            20                  25                  30

Ser Gly Ala Pro Pro Pro Ser
        35

<210> SEQ ID NO 525
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 525

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Gly Gly Pro Ser
            20                  25                  30

Ser Gly Ala Pro Pro Pro Ser
        35

<210> SEQ ID NO 526
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 526

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asp Gly Gly Pro Ser
            20                  25                  30

Ser Gly Ala Pro Pro Pro Ser
        35

<210> SEQ ID NO 527
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation

<400> SEQUENCE: 527

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 528
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Lactam ring between side chains at positions 16
      and 20
<220> FEATURE:
<221> NAME/KEY: MOD_RES
<222> LOCATION: (24)..(24)
<223> OTHER INFORMATION: Cys-PEG

<400> SEQUENCE: 528

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 529
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Alpha, Alpha Dimethyl Imidiazole Acetic Acid
<220> FEATURE:
<221> NAME/KEY: MOD_RES
<222> LOCATION: (24)..(24)
<223> OTHER INFORMATION: Cys-PEG

<400> SEQUENCE: 529

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Gly Gly Pro Ser
            20                  25                  30

Ser Gly Ala Pro Pro Pro Ser
        35

<210> SEQ ID NO 530
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES

```
<222> LOCATION: (1)..(1)
<223> OTHER INFORMATION: Alpha, Alpha Dimethyl Imidiazole Acetic Acid
<220> FEATURE:
<221> NAME/KEY: MOD_RES
<222> LOCATION: (24)..(24)
<223> OTHER INFORMATION: Cys-PEG

<400> SEQUENCE: 530

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 531
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG
<220> FEATURE:
<221> NAME/KEY: MOD_RES
<222> LOCATION: (40)..(40)
<223> OTHER INFORMATION: Cys-PEG

<400> SEQUENCE: 531

His Xaa Gln Gly Thr Phe Thr Ser Asp Tyr Ser Lys Tyr Leu Asp Glu
1               5                   10                  15

Arg Arg Ala Lys Glu Phe Ile Cys Trp Leu Met Asn Gly Gly Pro Ser
            20                  25                  30

Ser Gly Ala Pro Pro Pro Ser Cys
        35                  40

<210> SEQ ID NO 532
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (40)..(40)
<223> OTHER INFORMATION: Cys-PEG
<220> FEATURE:
<221> NAME/KEY: MOD_RES
<222> LOCATION: (41)..(41)
<223> OTHER INFORMATION: Cys-PEG

<400> SEQUENCE: 532

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30
```

Ser Gly Ala Pro Pro Ser Cys Cys
        35                  40

<210> SEQ ID NO 533
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG
<220> FEATURE:
<221> NAME/KEY: MISC_FEATURE
<222> LOCATION: (24)..(24)
<223> OTHER INFORMATION: c-term amidation

<400> SEQUENCE: 533

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser
        35

<210> SEQ ID NO 534
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 AIB2 K10-C8 Cys 24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (10)..(10)
<223> OTHER INFORMATION: Acylated with C8 fatty acid
<220> FEATURE:
<221> NAME/KEY: MOD_RES
<222> LOCATION: (24)..(24)
<223> OTHER INFORMATION: Cys-PEG

<400> SEQUENCE: 534

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Met Asn Thr
            20                  25

<210> SEQ ID NO 535
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 AIB2 K10-C14 Cys 24-40K
<220> FEATURE:
<221> NAME/KEY: MISC_FEATURE

```
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (10)..(10)
<223> OTHER INFORMATION: Acylated with C14 fatty acid
<220> FEATURE:
<221> NAME/KEY: MOD_RES
<222> LOCATION: (24)..(24)
<223> OTHER INFORMATION: Cys-PEG

<400> SEQUENCE: 535

His Xaa Gln Gly Thr Phe Thr Ser Asp Lys Ser Lys Tyr Leu Asp Glu
 1               5                  10                  15

Gln Ala Ala Lys Glu Phe Ile Cys Trp Leu Met Asn Thr
            20                  25

<210> SEQ ID NO 536
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 AIB2 K10-C16 Cys24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (10)..(10)
<223> OTHER INFORMATION: Acylated with C16 fatty acid
<220> FEATURE:
<221> NAME/KEY: MOD_RES
<222> LOCATION: (24)..(24)
<223> OTHER INFORMATION: Cys-PEG

<400> SEQUENCE: 536

His Xaa Gln Gly Thr Phe Thr Ser Asp Lys Ser Lys Tyr Leu Asp Glu
 1               5                  10                  15

Gln Ala Ala Lys Glu Phe Ile Cys Trp Leu Met Asn Thr
            20                  25

<210> SEQ ID NO 537
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 AIB2 K10-C18 Cys24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (10)..(10)
<223> OTHER INFORMATION: Acylated with C18 fatty acid
<220> FEATURE:
<221> NAME/KEY: MOD_RES
<222> LOCATION: (24)..(24)
```

```
<223> OTHER INFORMATION: Cys-PEG

<400> SEQUENCE: 537

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Met Asn Thr
            20                  25

<210> SEQ ID NO 538
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 K10-C18 Cys24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Acylated with C18 fatty acid
<220> FEATURE:
<221> NAME/KEY: MOD_RES
<222> LOCATION: (24)..(24)
<223> OTHER INFORMATION: Cys-PEG

<400> SEQUENCE: 538

His Ser Gln Gly Thr Phe Thr Ser Asp Lys Ser Lys Tyr Leu Asp Glu
1               5                   10                  15

Gln Ala Ala Lys Glu Phe Ile Cys Trp Leu Met Asn Thr
            20                  25

<210> SEQ ID NO 539
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C18 Cys24-40K
<220> FEATURE:
<221> NAME/KEY: MOD_RES
<222> LOCATION: (10)..(10)
<223> OTHER INFORMATION: Acylated with C18 fatty acid
<220> FEATURE:
<221> NAME/KEY: MOD_RES
<222> LOCATION: (24)..(24)
<223> OTHER INFORMATION: Cys-PEG

<400> SEQUENCE: 539

His Ser Gln Gly Thr Phe Thr Ser Asp Lys Ser Lys Tyr Leu Asp Glu
1               5                   10                  15

Arg Arg Ala Lys Asp Phe Val Cys Trp Leu Met Asn Thr
            20                  25

<210> SEQ ID NO 540
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-W-C18
<220> FEATURE:
<221> NAME/KEY: MISC_FEATURE
<223> OTHER INFORMATION: c-term amidation
```

```
-continued

<220> FEATURE:
<221> NAME/KEY: MOD_RES
<222> LOCATION: (10)..(10)
<223> OTHER INFORMATION: Covalently bound to Trp residue comprising a
      C18 fatty acid

<400> SEQUENCE: 540

His Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 541
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-W-C16 Cys24-40K
<220> FEATURE:
<221> NAME/KEY: MOD_RES
<222> LOCATION: (10)..(10)
<223> OTHER INFORMATION: Covalently bound to Trp residue comprising a
      C16 fatty acid
<220> FEATURE:
<221> NAME/KEY: MOD_RES
<222> LOCATION: (24)..(24)
<223> OTHER INFORMATION: Cys-PEG

<400> SEQUENCE: 541

His Ser Gln Gly Thr Phe Thr Ser Asp Lys Ser Lys Tyr Leu Asp Glu
1               5                   10                  15

Arg Arg Ala Lys Asp Phe Val Cys Trp Leu Met Asn Thr
            20                  25

<210> SEQ ID NO 542
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C16
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to C16 fatty acid

<400> SEQUENCE: 542

His Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 543
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C16
<220> FEATURE:
<221> NAME/KEY: MISC_FEATURE
```

```
<223> OTHER INFORMATION: c-term amidation
<220> FEATURE:
<221> NAME/KEY: MOD_RES
<222> LOCATION: (10)..(10)
<223> OTHER INFORMATION: Covalently bound to Trp residue comprising a
      C16 fatty acid

<400> SEQUENCE: 543

His Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 544
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C18
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to C18 fatty acid

<400> SEQUENCE: 544

His Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 545
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20
<220> FEATURE:
<221> NAME/KEY: MISC_FEATURE
<223> OTHER INFORMATION: c-term amidation

<400> SEQUENCE: 545

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 546
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-W-C16 Cys 24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to Trp residue comprising C16
```

```
                    fatty acid
<220> FEATURE:
<221> NAME/KEY: MOD_RES
<222> LOCATION: (24)..(24)
<223> OTHER INFORMATION: Cys-PEG

<400> SEQUENCE: 546

His Ser Gln Gly Thr Phe Thr Ser Asp Lys Ser Lys Tyr Leu Asp Glu
1               5                   10                  15

Arg Arg Ala Lys Asp Phe Val Cys Trp Leu Met Asn Thr
            20                  25

<210> SEQ ID NO 547
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C18 Cys24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to C18 fatty acid
<220> FEATURE:
<221> NAME/KEY: MOD_RES
<222> LOCATION: (24)..(24)
<223> OTHER INFORMATION: Cys-PEG

<400> SEQUENCE: 547

His Ser Gln Gly Thr Phe Thr Ser Asp Lys Ser Lys Tyr Leu Asp Glu
1               5                   10                  15

Arg Arg Ala Lys Asp Phe Val Cys Trp Leu Met Asn Thr
            20                  25

<210> SEQ ID NO 548
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C18 Cys24-40K
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to Trp residue comprising a
      C18 fatty acid
<220> FEATURE:
<221> NAME/KEY: MOD_RES
<222> LOCATION: (24)..(24)
<223> OTHER INFORMATION: Cys-PEG

<400> SEQUENCE: 548

His Ser Gln Gly Thr Phe Thr Ser Asp Lys Ser Lys Tyr Leu Asp Glu
1               5                   10                  15

Arg Arg Ala Lys Asp Phe Val Cys Trp Leu Met Asn Thr
            20                  25

<210> SEQ ID NO 549
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Glucagon E16 K20 K10-C16 amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Covalently bound to Glu residue comprising a
      C16 fatty acid
<220> FEATURE:
<221> NAME/KEY: MOD_RES
<222> LOCATION: (24)..(24)
<223> OTHER INFORMATION: Cys-PEG

<400> SEQUENCE: 549

His Ser Gln Gly Thr Phe Thr Ser Asp Lys Ser Lys Tyr Leu Asp Glu
1               5                   10                  15
Arg Arg Ala Gln Asp Phe Val Cys Trp Leu Met Asn Thr
            20                  25

<210> SEQ ID NO 550
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 truncated by one amino acid

<400> SEQUENCE: 550

His Ser Gln Gly Thr Phe Thr Ser Asp Tyr Ser Lys Tyr Leu Asp Glu
1               5                   10                  15
Gln Ala Ala Lys Glu Phe Ile Ala Trp Leu Met Asn
            20                  25

<210> SEQ ID NO 551
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 truncated by two amino acids

<400> SEQUENCE: 551

His Ser Gln Gly Thr Phe Thr Ser Asp Tyr Ser Lys Tyr Leu Asp Glu
1               5                   10                  15
Gln Ala Ala Lys Glu Phe Ile Ala Trp Leu Met
            20                  25

<210> SEQ ID NO 552
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: aa 1-28, E16 K20 C-terminal amide
<220> FEATURE:
<221> NAME/KEY: MISC_FEATURE
<223> OTHER INFORMATION: c-term amidation

<400> SEQUENCE: 552
```

```
His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn
            20                  25

<210> SEQ ID NO 553
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: aa 1-27 E16 K20 C-terminal amide
<220> FEATURE:
<221> NAME/KEY: MISC_FEATURE
<223> OTHER INFORMATION: c-term amidation

<400> SEQUENCE: 553

His Ser Gln Gly Thr Phe Thr Ser Asp Tyr Ser Lys Tyr Leu Asp Glu
1               5                   10                  15

Arg Arg Ala Lys Asp Phe Val Gln Trp Lys Met
            20                  25

<210> SEQ ID NO 554
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (27)..(27)
<223> OTHER INFORMATION: Norleucine

<400> SEQUENCE: 554

His Ser Glu Gly Thr Phe Thr Ser Asp Tyr Ser Lys Tyr Leu Asp Glu
1               5                   10                  15

Gln Ala Ala Lys Glu Phe Ile Ala Trp Leu Xaa Asn Thr
            20                  25

<210> SEQ ID NO 555
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-138
<220> FEATURE:
<221> NAME/KEY: MISC_FEATURE
<222> LOCATION: (16)..(20)
<223> OTHER INFORMATION: Lactam bridging side chains at positions 16 and
      20

<400> SEQUENCE: 555

Tyr Ser Gln Gly Thr Phe Thr Ser Asp Tyr Ser Lys Tyr Leu Asp Glu
1               5                   10                  15

Gln Ala Ala Lys Glu Phe Val Asn Trp Leu Met Asn Gly Gly Pro Ser
            20                  25                  30

Ser Gly Ala Pro Pro Pro Ser
        35

<210> SEQ ID NO 556
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2 with AIB at 16
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (16)..(16)
<223> OTHER INFORMATION: Aminoisobutyric acid

<400> SEQUENCE: 556

His Ser Gln Gly Thr Phe Thr Ser Asp Tyr Ser Lys Tyr Leu Asp Xaa
1               5                   10                  15
Gln Ala Ala Lys Glu Phe Ile Ala Trp Leu Met Asn Thr
            20                  25

<210> SEQ ID NO 557
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (16)..(16)
<223> OTHER INFORMATION: Aminoisobutyric acid

<400> SEQUENCE: 557

His Xaa Gln Gly Thr Phe Thr Ser Asp Tyr Ser Lys Tyr Leu Asp Xaa
1               5                   10                  15
Arg Arg Ala Gln Asp Phe Val Gln Trp Leu Met Asn Thr
            20                  25

<210> SEQ ID NO 558
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (10)..(10)
<223> OTHER INFORMATION: Covalently bound to Trp residue comprising a
      C16 fatty acid
<220> FEATURE:
<221> NAME/KEY: MOD_RES
<222> LOCATION: (16)..(16)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 558
```

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 559
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutric Acid
<220> FEATURE:
<221> NAME/KEY: MISC_FEATURE
<222> LOCATION: (10)..(10)
<223> OTHER INFORMATION: Covalently bound to Trp residue comprising a
      C16 fatty acid
<220> FEATURE:
<221> NAME/KEY: MOD_RES
<222> LOCATION: (16)..(16)
<223> OTHER INFORMATION: Aminoisobutric Acid

<400> SEQUENCE: 559

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 560
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (10)..(10)
<223> OTHER INFORMATION: Covalently bound to Trp residue comprising a
      C16 fatty acid
<220> FEATURE:
<221> NAME/KEY: MOD_RES
<222> LOCATION: (16)..(16)
<223> OTHER INFORMATION: Aminoisobutyric acid
<220> FEATURE:
<221> NAME/KEY: MOD_RES
<222> LOCATION: (20)..(20)
<223> OTHER INFORMATION: Aminoisobutyric acid
<220> FEATURE:
<221> NAME/KEY: MOD_RES
<222> LOCATION: (24)..(24)
<223> OTHER INFORMATION: Cys-PEG

<400> SEQUENCE: 560

His Xaa Gln Gly Thr Phe Thr Ser Asp Lys Ser Lys Tyr Leu Asp Xaa
1               5                   10                  15

Arg Arg Ala Xaa Asp Phe Val Cys Trp Leu Met Asn Thr
            20                  25

```
<210> SEQ ID NO 561
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (10)..(10)
<223> OTHER INFORMATION: Covalently bound to Trp residue comprising a
      C16 fatty acid
<220> FEATURE:
<221> NAME/KEY: MOD_RES
<222> LOCATION: (16)..(16)
<223> OTHER INFORMATION: Aminoisobutyric acid
<220> FEATURE:
<221> NAME/KEY: MOD_RES
<222> LOCATION: (20)..(20)
<223> OTHER INFORMATION: Aminoisobutyric acid

<400> SEQUENCE: 561

His Xaa Gln Gly Thr Phe Thr Ser Asp Lys Ser Lys Tyr Leu Asp Xaa
1               5                   10                  15

Arg Arg Ala Xaa Asp Phe Val Cys Trp Leu Met Asn Thr
            20                  25

<210> SEQ ID NO 562
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (16)..(16)
<223> OTHER INFORMATION: Aminoisobutyric acid

<400> SEQUENCE: 562

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 563
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 50
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
```

```
<221> NAME/KEY: MOD_RES
<222> LOCATION: (10)..(10)
<223> OTHER INFORMATION: Acylated with a C16 fatty acyl group
<220> FEATURE:
<221> NAME/KEY: MOD_RES
<222> LOCATION: (16)..(16)
<223> OTHER INFORMATION: Aminoisobutyric Acid

<400> SEQUENCE: 563

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 564
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 82
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Acylated with a C16 fatty acyl group via
      Ala-Ala spacer
<220> FEATURE:
<221> NAME/KEY: MOD_RES
<222> LOCATION: (16)..(16)
<223> OTHER INFORMATION: Aminoisobutyric Acid

<400> SEQUENCE: 564

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 565
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 83
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Aminoisobutryic Acid

<400> SEQUENCE: 565
```

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 566
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 84
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      beta-Ala-beta-Ala spacer
<220> FEATURE:
<221> NAME/KEY: MOD_RES
<222> LOCATION: (16)..(16)
<223> OTHER INFORMATION: Aminoisobutryic Acid

<400> SEQUENCE: 566

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 567
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 85
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      6-aminohexanoic acid spacer
<220> FEATURE:
<221> NAME/KEY: MOD_RES
<222> LOCATION: (16)..(16)
<223> OTHER INFORMATION: Aminoisobutryic Acid

<400> SEQUENCE: 567

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 568
<211> LENGTH: 29
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 86
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      Leu-Leu spacer
<220> FEATURE:
<221> NAME/KEY: MOD_RES
<222> LOCATION: (16)..(16)
<223> OTHER INFORMATION: Aminoisobutryic Acid

<400> SEQUENCE: 568

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 569
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 87
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      Pro-Pro spacer
<220> FEATURE:
<221> NAME/KEY: MOD_RES
<222> LOCATION: (16)..(16)
<223> OTHER INFORMATION: Aminoisobutryic Acid

<400> SEQUENCE: 569

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 570
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 77*
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Acylated with a C14 fatty acyl group
<220> FEATURE:
<221> NAME/KEY: MOD_RES
<222> LOCATION: (16)..(16)
<223> OTHER INFORMATION: Aminoisobutyric Acid
<220> FEATURE:
<221> NAME/KEY: MOD_RES
<222> LOCATION: (24)..(24)
<223> OTHER INFORMATION: Pegylated

<400> SEQUENCE: 570

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 571
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 78*
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Acylated with a C14 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Aminoisobutyric Acid
<220> FEATURE:
<221> NAME/KEY: MOD_RES
<222> LOCATION: (24)..(24)
<223> OTHER INFORMATION: Pegylated

<400> SEQUENCE: 571

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 572
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 78
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
```

```
<220> FEATURE:
<221> NAME/KEY: MOD_RES
<222> LOCATION: (10)..(10)
<223> OTHER INFORMATION: Acylated with a C14 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Aminoisobutryic Acid

<400> SEQUENCE: 572

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 573
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 81*
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C14 fatty acyl group via
      Ala-Ala spacer
<220> FEATURE:
<221> NAME/KEY: MOD_RES
<222> LOCATION: (16)..(16)
<223> OTHER INFORMATION: Aminoisobutryic Acid
<220> FEATURE:
<221> NAME/KEY: MOD_RES
<222> LOCATION: (24)..(24)
<223> OTHER INFORMATION: Pegylated

<400> SEQUENCE: 573

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 574
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 81
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C14 fatty acyl group via
      Ala-Ala spacer
<220> FEATURE:
```

```
<221> NAME/KEY: MOD_RES
<222> LOCATION: (16)..(16)
<223> OTHER INFORMATION: Aminoisobutryic Acid

<400> SEQUENCE: 574

His Xaa Gln Gly Thr Phe Thr Ser Asp Lys Ser Lys Tyr Leu Asp Xaa
1               5                   10                  15
Arg Arg Ala Gln Asp Phe Val Gln Trp Leu Met Asn Thr
            20                  25

<210> SEQ ID NO 575
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 79*
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic acid
<220> FEATURE:
<221> NAME/KEY: MOD_RES
<222> LOCATION: (10)..(10)
<223> OTHER INFORMATION: Acylated with a C16 fatty acyl group via
      Ala-Ala spacer
<220> FEATURE:
<221> NAME/KEY: MOD_RES
<222> LOCATION: (16)..(16)
<223> OTHER INFORMATION: Aminoisobutryic acid
<220> FEATURE:
<221> NAME/KEY: MOD_RES
<222> LOCATION: (24)..(24)
<223> OTHER INFORMATION: Pegylated

<400> SEQUENCE: 575

His Xaa Gln Gly Thr Phe Thr Ser Asp Lys Ser Lys Tyr Leu Asp Xaa
1               5                   10                  15
Arg Arg Ala Gln Asp Phe Val Cys Trp Leu Met Asn Thr
            20                  25

<210> SEQ ID NO 576
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide 80*
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Aminoisobutryic Acid
<220> FEATURE:
<221> NAME/KEY: MOD_RES
<222> LOCATION: (24)..(24)
```

```
<223> OTHER INFORMATION: Pegylated

<400> SEQUENCE: 576

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 577
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: gamma-Glu-gamma-Glu C16 Glucagon Amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Acylated with a C16 fatty acyl group

<400> SEQUENCE: 577

His Ser Gln Gly Thr Phe Thr Ser Asp Lys Ser Lys Tyr Leu Asp Ser
1               5                   10                  15

Arg Arg Ala Gln Asp Phe Val Gln Trp Leu Met Asn Thr
            20                  25

<210> SEQ ID NO 578
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MISC_FEATURE
<223> OTHER INFORMATION: gamma-Glu-gamma-Glu-C16 Glucagon Amide
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer

<400> SEQUENCE: 578

His Ser Gln Gly Thr Phe Thr Ser Asp Lys Ser Lys Tyr Leu Asp Ser
1               5                   10                  15

Arg Arg Ala Gln Asp Phe Val Gln Trp Leu Met Asn Thr
            20                  25

<210> SEQ ID NO 579
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AA-C16 Glucagon Amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (10)..(10)
<223> OTHER INFORMATION: Acylated with a C16 fatty acyl group via
```

-continued

Ala-Ala spacer

<400> SEQUENCE: 579

His Ser Gln Gly Thr Phe Thr Ser Asp Lys Ser Lys Tyr Leu Asp Ser
1               5                   10                  15

Arg Arg Ala Gln Asp Phe Val Gln Trp Leu Met Asn Thr
            20                  25

<210> SEQ ID NO 580
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera 2, AIB2, Lys10, Cys24-PEG
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (24)..(24)
<223> OTHER INFORMATION: Pegylated

<400> SEQUENCE: 580

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Met Asn Thr
            20                  25

<210> SEQ ID NO 581
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide dS2E16K20K30-C14 Gluc Amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (30)..(30)
<223> OTHER INFORMATION: Acylated with a C14 fatty acyl group

<400> SEQUENCE: 581

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 582
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide dS2K10(C14)E16K20-Gluc Amide

```
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C14 fatty acyl group

<400> SEQUENCE: 582

His Xaa Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 583
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide dS2E16K20K30-C16 Gluc Amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (30)..(30)
<223> OTHER INFORMATION: Acylated with a C16 fatty acyl group

<400> SEQUENCE: 583

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 584
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide dS2K10(C16)E16K20-Gluc Amide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group

<400> SEQUENCE: 584

His Xaa Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25
```

```
<210> SEQ ID NO 585
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide Chimera 2-AIB2-K10-acylated
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Acylated with a C18 fatty acyl group
<220> FEATURE:
<221> NAME/KEY: MOD_RES
<222> LOCATION: (24)..(24)
<223> OTHER INFORMATION: Pegylated

<400> SEQUENCE: 585

His Xaa Gln Gly Thr Phe Thr Ser Asp Lys Ser Lys Tyr Leu Asp Glu
1               5                   10                  15

Gln Ala Ala Lys Glu Phe Ile Cys Trp Leu Met Asn Thr
            20                  25

<210> SEQ ID NO 586
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide Chimera 2-AIB2-K30-acylated
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (24)..(24)
<223> OTHER INFORMATION: Pegylated
<220> FEATURE:
<221> NAME/KEY: MOD_RES
<222> LOCATION: (30)..(30)
<223> OTHER INFORMATION: Acylated with a C18 fatty acyl group

<400> SEQUENCE: 586

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr Lys
            20                  25                  30

<210> SEQ ID NO 587
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
```

```
<222> LOCATION: (1)..(1)
<223> OTHER INFORMATION: DMIA

<400> SEQUENCE: 587

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 588
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: DMIA
<220> FEATURE:
<221> NAME/KEY: MOD_RES
<222> LOCATION: (16)..(20)
<223> OTHER INFORMATION: Lactam ring between side chains of amino acids
      at positions 16 and 20

<400> SEQUENCE: 588

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 589
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid

<400> SEQUENCE: 589

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 590
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (24)..(24)
<223> OTHER INFORMATION: Pegylated
```

<400> SEQUENCE: 590

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 591
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide J
<220> FEATURE:
<221> NAME/KEY: MOD_RES
<222> LOCATION: (3)..(3)
<223> OTHER INFORMATION: Xaa is a Glutamine analog
<220> FEATURE:
<221> NAME/KEY: MOD_RES
<222> LOCATION: (27)..(27)
<223> OTHER INFORMATION: Xaa is Norleucine

<400> SEQUENCE: 591

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 592
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide K
<220> FEATURE:
<221> NAME/KEY: MOD_RES
<222> LOCATION: (3)..(3)
<223> OTHER INFORMATION: Xaa is a Glutamine analog
<220> FEATURE:
<221> NAME/KEY: MOD_RES
<222> LOCATION: (16)..(16)
<223> OTHER INFORMATION: Xaa is Aib

<400> SEQUENCE: 592

His Ser Xaa Gly Thr Phe Thr Ser Asp Tyr Ser Lys Tyr Leu Asp Xaa
1               5                   10                  15

Arg Arg Ala Ala Asp Phe Val Ala Trp Leu Met Asp Glu
            20                  25

<210> SEQ ID NO 593
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (27)..(27)
<223> OTHER INFORMATION: Xaa is Norleucine

<400> SEQUENCE: 593

His Ser Gln Gly Thr Phe Thr Ser Asp Tyr Ser Lys Tyr Leu Asp Thr
1               5                   10                  15

-continued

Arg Arg Ala Ala Glu Phe Val Ala Trp Leu Xaa Asp Glu
            20                  25

<210> SEQ ID NO 594
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetamidomethyl-cysteine
<220> FEATURE:
<221> NAME/KEY: MOD_RES
<222> LOCATION: (27)..(27)
<223> OTHER INFORMATION: Xaa is Norleucine

<400> SEQUENCE: 594

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 595
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (27)..(27)
<223> OTHER INFORMATION: Xaa is Norleucine

<400> SEQUENCE: 595

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 596
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is carbamoyldiaminopropanoic acid
<220> FEATURE:
<221> NAME/KEY: MOD_RES
<222> LOCATION: (27)..(27)
<223> OTHER INFORMATION: Xaa is Norleucine

<400> SEQUENCE: 596

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 597
<211> LENGTH: 29
<212> TYPE: PRT
<213> ORGANISM: Artificial Sequence

```
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Methylglutamine
<220> FEATURE:
<221> NAME/KEY: MOD_RES
<222> LOCATION: (27)..(27)
<223> OTHER INFORMATION: Xaa is Norleucine

<400> SEQUENCE: 597

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 598
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Methionine sulfoxide
<220> FEATURE:
<221> NAME/KEY: MOD_RES
<222> LOCATION: (27)..(27)
<223> OTHER INFORMATION: Xaa is Norleucine

<400> SEQUENCE: 598

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 599
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Acetylornithine
<220> FEATURE:
<221> NAME/KEY: MOD_RES
<222> LOCATION: (27)..(27)
<223> OTHER INFORMATION: Xaa is Norleucine

<400> SEQUENCE: 599

His Ser Xaa Gly Thr Phe Thr Ser Asp Tyr Ser Lys Tyr Leu Asp Thr
1               5                   10                  15

Arg Arg Ala Ala Glu Phe Val Ala Trp Leu Xaa Asp Glu
            20                  25

<210> SEQ ID NO 600
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(16)
<223> OTHER INFORMATION: Xaa is Aminoisobutryic Acid

<400> SEQUENCE: 600
```

```
His Ser Gln Gly Thr Phe Thr Ser Asp Tyr Ser Lys Tyr Leu Asp Xaa
1               5                   10                  15

Arg Arg Ala Ala Asp Phe Val Ala Trp Leu Met Asp Glu
            20                  25
```

<210> SEQ ID NO 601
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (16)..(16)
<223> OTHER INFORMATION: Xaa is Aminoisobutyric Acid

<400> SEQUENCE: 601

```
His Ser Xaa Gly Thr Phe Thr Ser Asp Tyr Ser Lys Tyr Leu Asp Xaa
1               5                   10                  15

Arg Arg Ala Ala Asp Phe Val Ala Trp Leu Met Asp Glu
            20                  25
```

<210> SEQ ID NO 602
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Methylglutamine
<220> FEATURE:
<221> NAME/KEY: MOD_RES
<222> LOCATION: (16)..(16)
<223> OTHER INFORMATION: Xaa is Aminoisobutyric Acid

<400> SEQUENCE: 602

```
His Ser Xaa Gly Thr Phe Thr Ser Asp Tyr Ser Lys Tyr Leu Asp Xaa
1               5                   10                  15

Arg Arg Ala Ala Asp Phe Val Ala Trp Leu Met Asp Glu
            20                  25
```

<210> SEQ ID NO 603
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (16)..(16)
<223> OTHER INFORMATION: Xaa is Aminoisobutryic Acid

<400> SEQUENCE: 603

```
His Ser Xaa Gly Thr Phe Thr Ser Asp Tyr Ser Lys Tyr Leu Asp Xaa
1               5                   10                  15

Arg Arg Ala Ala Asp Phe Val Ala Trp Leu Leu Asp Glu
            20                  25
```

```
<210> SEQ ID NO 604
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (16)..(16)
<223> OTHER INFORMATION: Xaa is Aminoisobutyric Acid

<400> SEQUENCE: 604

His Ser Xaa Gly Thr Phe Thr Ser Asp Tyr Ser Lys Tyr Leu Asp Xaa
1               5                   10                  15

Arg Arg Ala Ala Asp Phe Val Ala Trp Leu Leu Asp Thr Gly Pro Ser
            20                  25                  30

Ser Gly Ala Pro Pro Pro Ser
        35

<210> SEQ ID NO 605
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (16)..(16)
<223> OTHER INFORMATION: Xaa is Aminoisobutryic Acid

<400> SEQUENCE: 605

His Ser Xaa Gly Thr Phe Thr Ser Asp Tyr Ser Lys Tyr Leu Asp Xaa
1               5                   10                  15

Arg Arg Ala Ser Asp Phe Val Ser Trp Leu Leu Asp Glu
            20                  25

<210> SEQ ID NO 606
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa is Acetyldiaminobutanoic acid
<220> FEATURE:
<221> NAME/KEY: MOD_RES
<222> LOCATION: (16)..(16)
<223> OTHER INFORMATION: Xaa is Aminoisobutryic Acid

<400> SEQUENCE: 606

His Ser Xaa Gly Thr Phe Thr Ser Asp Tyr Ser Lys Tyr Leu Asp Xaa
1               5                   10                  15

Arg Arg Ala Thr Asp Phe Val Thr Trp Leu Leu Asp Glu
            20                  25

<210> SEQ ID NO 607
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MOD_RES
<222> LOCATION: (10)..(10)
<223> OTHER INFORMATION: Covalently bound to a C14 fatty acyl group
<220> FEATURE:
<221> NAME/KEY: MOD_RES
<222> LOCATION: (16)..(20)
<223> OTHER INFORMATION: Lactam ring between side chains of amino acids
      at positions 16 and 20

<400> SEQUENCE: 607

Xaa Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 608
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: DMIA
<220> FEATURE:
<221> NAME/KEY: MOD_RES
<222> LOCATION: (10)..(10)
<223> OTHER INFORMATION: Covalently bound to C16 fatty acyl group
<220> FEATURE:
<221> NAME/KEY: MOD_RES
<222> LOCATION: (16)..(20)
<223> OTHER INFORMATION: Lactam ring between side chains of amino acids
      at positions 16 and 20

<400> SEQUENCE: 608

Xaa Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 609
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: DMIA
<220> FEATURE:
<221> NAME/KEY: MOD_RES
<222> LOCATION: (10)..(10)
<223> OTHER INFORMATION: Covalently bound to C18 fatty acyl group
<220> FEATURE:
```

```
<221> NAME/KEY: MOD_RES
<222> LOCATION: (16)..(20)
<223> OTHER INFORMATION: Lactam ring between side chains of amino acids
      at positions 16 and 20

<400> SEQUENCE: 609

Xaa Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 610
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Covalently bound to C14 fatty acyl group
<220> FEATURE:
<221> NAME/KEY: MOD_RES
<222> LOCATION: (16)..(16)
<223> OTHER INFORMATION: Aminoisobutryic Acid

<400> SEQUENCE: 610

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 611
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Covalently bound to C16 fatty acyl group
<220> FEATURE:
<221> NAME/KEY: MOD_RES
<222> LOCATION: (16)..(16)
<223> OTHER INFORMATION: Aminoisobutryic Acid

<400> SEQUENCE: 611

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 612
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Covalently bound to C18 fatty acyl group
<220> FEATURE:
<221> NAME/KEY: MOD_RES
<222> LOCATION: (16)..(16)
<223> OTHER INFORMATION: Aminoisobutryic Acid

<400> SEQUENCE: 612

His Xaa Gln Gly Thr Phe Thr Ser Asp Lys Ser Lys Tyr Leu Asp Xaa
 1               5                  10                  15
Arg Arg Ala Gln Asp Phe Val Gln Trp Leu Met Asn Thr
            20                  25

<210> SEQ ID NO 613
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Covalently bound to C14 fatty acyl group

<400> SEQUENCE: 613

His Xaa Gln Gly Thr Phe Thr Ser Asp Lys Ser Lys Tyr Leu Asp Glu
 1               5                  10                  15
Arg Arg Ala Lys Asp Phe Val Gln Trp Leu Met Asn Thr
            20                  25

<210> SEQ ID NO 614
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Covalently bound to C16 fatty acyl group

<400> SEQUENCE: 614

His Xaa Gln Gly Thr Phe Thr Ser Asp Lys Ser Lys Tyr Leu Asp Glu
 1               5                  10                  15
Arg Arg Ala Lys Asp Phe Val Gln Trp Leu Met Asn Thr
            20                  25
```

```
<210> SEQ ID NO 615
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Covalently bound to a C18 fatty acyl group

<400> SEQUENCE: 615

His Xaa Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 616
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Covalently bound to a C14 fatty acyl group
<220> FEATURE:
<221> NAME/KEY: MOD_RES
<222> LOCATION: (16)..(16)
<223> OTHER INFORMATION: Aminoisobutyric Acid

<400> SEQUENCE: 616

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 617
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Covalently bound to C14 fatty acyl group via
      gamma-Glu-gamma-Glu spacer
<220> FEATURE:
<221> NAME/KEY: MOD_RES
<222> LOCATION: (16)..(16)
```

<223> OTHER INFORMATION: Aminoisobutryic Acid

<400> SEQUENCE: 617

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 618
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutryic Acid
<220> FEATURE:
<221> NAME/KEY: MOD_RES
<222> LOCATION: (10)..(10)
<223> OTHER INFORMATION: Covalently bound to C14 fatty acyl group via
      Ala-Ala spacer
<220> FEATURE:
<221> NAME/KEY: MOD_RES
<222> LOCATION: (16)..(16)
<223> OTHER INFORMATION: Aminoisobutryic Acid

<400> SEQUENCE: 618

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 619
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Covalently bound to C16 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Aminoisobutyric Acid

<400> SEQUENCE: 619

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 620
<211> LENGTH: 29
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Covelently bound to C16 fatty acyl group via
      Ala-Ala spacer
<220> FEATURE:
<221> NAME/KEY: MOD_RES
<222> LOCATION: (16)..(16)
<223> OTHER INFORMATION: Aminoisobutyric Acid

<400> SEQUENCE: 620

His Xaa Gln Gly Thr Phe Thr Ser Asp Lys Ser Lys Tyr Leu Asp Xaa
1               5                   10                  15
Arg Arg Ala Gln Asp Phe Val Cys Trp Leu Met Asn Thr
            20                  25

<210> SEQ ID NO 621
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Covelently bound to C16 fatty acyl group
<220> FEATURE:
<221> NAME/KEY: MOD_RES
<222> LOCATION: (16)..(16)
<223> OTHER INFORMATION: Aminoisobutyric Acid

<400> SEQUENCE: 621

His Xaa Gln Gly Thr Phe Thr Ser Asp Lys Ser Lys Tyr Leu Asp Xaa
1               5                   10                  15
Arg Arg Ala Gln Asp Phe Val Cys Trp Leu Met Asn Thr
            20                  25

<210> SEQ ID NO 622
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Aminoisobutyric Acid
<220> FEATURE:
<221> NAME/KEY: MOD_RES
<222> LOCATION: (10)..(10)
<223> OTHER INFORMATION: Covelently bound to C16 fatty acyl group
<220> FEATURE:
<221> NAME/KEY: MOD_RES
<222> LOCATION: (16)..(16)
<223> OTHER INFORMATION: Aminoisobutyric Acid
```

```
<400> SEQUENCE: 622

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr Lys
            20                  25                  30

<210> SEQ ID NO 623
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: beta-Ala-beta-Ala - C16 Glucagon Amide
<220> FEATURE:
<221> NAME/KEY: MISC_FEATURE
<223> OTHER INFORMATION: c-term amidation
<220> FEATURE:
<221> NAME/KEY: MISC_FEATURE
<222> LOCATION: (10)..(10)
<223> OTHER INFORMATION: Acylated with a C16 fatty acyl group via
      beta-Ala-beta-Ala spacer

<400> SEQUENCE: 623

His Ser Gln Gly Thr Phe Thr Ser Asp Lys Ser Lys Tyr Leu Asp Ser
1               5                   10                  15

Arg Arg Ala Gln Asp Phe Val Gln Trp Leu Met Asn Thr
            20                  25

<210> SEQ ID NO 624
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera-2 Aib2C24Mal40KPEG
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with a maleimide-activated PEG
<220> FEATURE:
<221> NAME/KEY: MOD_RES
<222> LOCATION: (29)..(29)
<223> OTHER INFORMATION: AMIDATION

<400> SEQUENCE: 624

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 625
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera-2 Aib2E16K20lactamC24Mal40KPEG
<220> FEATURE:
<221> NAME/KEY: MOD_RES
<222> LOCATION: (2)..(2)
```

<223> OTHER INFORMATION: Xaa is Aib
<220> FEATURE:
<221> NAME/KEY: MISC_FEATURE
<222> LOCATION: (16)..(20)
<223> OTHER INFORMATION: Lactam ring between side chains of the amino
      acids at positions 16 and 20
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with a maleimide-activated PEG
<220> FEATURE:
<221> NAME/KEY: MOD_RES
<222> LOCATION: (29)..(29)
<223> OTHER INFORMATION: AMIDATION

<400> SEQUENCE: 625

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 626
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Aib2E16K20lactamC24amideMal40KPEG
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MISC_FEATURE
<222> LOCATION: (16)..(20)
<223> OTHER INFORMATION: Lactam ring between side chains of amino acids
      at positions 16 and 20
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with a maleimide-activated PEG
<220> FEATURE:
<221> NAME/KEY: MOD_RES
<222> LOCATION: (29)..(29)
<223> OTHER INFORMATION: AMIDATION

<400> SEQUENCE: 626

His Xaa Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 627

<400> SEQUENCE: 627

000

<210> SEQ ID NO 628
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Dmia1E16K20lactamC24Mal40KPEG
<220> FEATURE:
<221> NAME/KEY: MOD_RES

```
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains of amino acids
      at positions 16 and 20
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with a maleimide-activated PEG
<220> FEATURE:
<221> NAME/KEY: MOD_RES
<222> LOCATION: (29)..(29)
<223> OTHER INFORMATION: AMIDATION

<400> SEQUENCE: 628

Xaa Ser Gln Gly Thr Phe Thr Ser Asp Tyr Ser Lys Tyr Leu Asp Glu
1               5                   10                  15
Arg Arg Ala Lys Asp Phe Val Cys Trp Leu Met Asn Thr
            20                  25

<210> SEQ ID NO 629
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Dmia1E16K20lactamC24Mal40KPEG
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains of amino acids
      at positions 16 and 20
<220> FEATURE:
<221> NAME/KEY: MISC_FEATURE
<222> LOCATION: (24)..(24)
<223> OTHER INFORMATION: Covalently bound to 40kDa PEG via thioether
      made by reaction of peptide with a maleimide-activated PEG

<400> SEQUENCE: 629

Xaa Ser Gln Gly Thr Phe Thr Ser Asp Tyr Ser Lys Tyr Leu Asp Glu
1               5                   10                  15
Arg Arg Ala Lys Asp Phe Val Cys Trp Leu Met Asn Thr
            20                  25

<210> SEQ ID NO 630
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Dmia1E16K20lactamC24thioether40KPEG
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains of amino acids
      at position 16 and 20
<220> FEATURE:
<221> NAME/KEY: MOD_RES
<222> LOCATION: (24)..(24)
```

```
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (29)..(29)
<223> OTHER INFORMATION: AMIDATION

<400> SEQUENCE: 630

Xaa Ser Gln Gly Thr Phe Thr Ser Asp Tyr Ser Lys Tyr Leu Asp Glu
1               5                   10                  15

Arg Arg Ala Lys Asp Phe Val Cys Trp Leu Met Asn Thr
            20                  25

<210> SEQ ID NO 631
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Chimera2 Aib2E3C24-Thioether40K PEG(NOF)
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (29)..(29)
<223> OTHER INFORMATION: AMIDATION

<400> SEQUENCE: 631

His Xaa Glu Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 632
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MOD_RES
<222> LOCATION: (24)..(24)
<223> OTHER INFORMATION: Covalently bound to 40kDa PEG
<220> FEATURE:
<221> NAME/KEY: MOD_RES
<222> LOCATION: (29)..(29)
<223> OTHER INFORMATION: AMIDATION

<400> SEQUENCE: 632

Xaa Ser Glu Gly Thr Phe Thr Ser Asp Tyr Ser Lys Tyr Leu Glu Glu
1               5                   10                  15

Arg Arg Ala Lys Asp Phe Val Cys Trp Leu Met Asn Thr
            20                  25

<210> SEQ ID NO 633
<211> LENGTH: 29
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Glucagon Aib2Aib16C24K10(rErE-C16) C24PEG40K
      amide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Covalently bound to C14 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (29)..(29)
<223> OTHER INFORMATION: AMIDATION

<400> SEQUENCE: 633

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 634
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Aib2Aib16K10(AA-C14)C24PEG40K TE amide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Covalently bound to C14 fatty acyl group via
      Ala-Ala spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (29)..(29)
<223> OTHER INFORMATION: AMIDATION

<400> SEQUENCE: 634

His Xaa Gln Gly Thr Phe Thr Ser Asp Lys Ser Lys Tyr Leu Asp Xaa
1               5                   10                  15

Arg Arg Ala Gln Asp Phe Val Cys Trp Leu Met Asn Thr
            20                  25

<210> SEQ ID NO 635
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Aib2Aib16K10(AA-C16) amide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Covalently bound to C16 fatty acyl group via
      Ala-Ala spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: AMIDATION

<400> SEQUENCE: 635

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 636
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Glucagon Aib2Aib16K10(rErE-C16) amide
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Covalently bound to C16 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: AMIDATION

<400> SEQUENCE: 636

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 637
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
```

```
<223> OTHER INFORMATION: Xaa is Aib
<220> FEATURE:
<221> NAME/KEY: MOD_RES
<222> LOCATION: (16)..(16)
<223> OTHER INFORMATION: Xaa is Aib
<220> FEATURE:
<221> NAME/KEY: MOD_RES
<222> LOCATION: (29)..(29)
<223> OTHER INFORMATION: AMIDATION

<400> SEQUENCE: 637

His Xaa Gln Gly Thr Phe Thr Ser Asp Tyr Ser Lys Tyr Leu Asp Xaa
 1               5                  10                  15

Arg Arg Ala Gln Asp Phe Val Gln Trp Leu Met Asn Thr
            20                  25

<210> SEQ ID NO 638
<211> LENGTH: 20
<212> TYPE: DNA
<213> ORGANISM: Artificial Sequence
<220> FEATURE:
<223> OTHER INFORMATION: Synthetic primer

<400> SEQUENCE: 638
caaggtccag ggaggttgtg                                               20

<210> SEQ ID NO 639
<211> LENGTH: 24
<212> TYPE: DNA
<213> ORGANISM: Artificial Sequence
<220> FEATURE:
<223> OTHER INFORMATION: Synthetic primer

<400> SEQUENCE: 639
ccaaaggtaa gctgtccata agga                                          24

<210> SEQ ID NO 640
<211> LENGTH: 22
<212> TYPE: DNA
<213> ORGANISM: Artificial Sequence
<220> FEATURE:
<223> OTHER INFORMATION: Synthetic primer

<400> SEQUENCE: 640
ctctcccaag agtcacatgt cc                                            22

<210> SEQ ID NO 641
<211> LENGTH: 22
<212> TYPE: DNA
<213> ORGANISM: Artificial Sequence
<220> FEATURE:
<223> OTHER INFORMATION: Synthetic primer

<400> SEQUENCE: 641
caataactcg gtcccctaca ac                                            22

<210> SEQ ID NO 642
<211> LENGTH: 29
<212> TYPE: PRT
<213> ORGANISM: Artificial Sequence
<220> FEATURE:
<223> OTHER INFORMATION: Synthetic peptide

<400> SEQUENCE: 642

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asp Thr
            20                  25
```

```
                    20                  25

<210> SEQ ID NO 643
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via
      gamma-Glu spacer

<400> SEQUENCE: 643

His Xaa Gln Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 644
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer

<400> SEQUENCE: 644

His Xaa Gln Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 645
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu spacer

<400> SEQUENCE: 645
```

His Xaa Gln Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 646
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer

<400> SEQUENCE: 646

His Xaa Gln Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 647
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group

<400> SEQUENCE: 647

His Xaa Glu Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 648
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer -continued

```
<400> SEQUENCE: 648

His Xaa Glu Gly Thr Phe Thr Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 649
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu spacer

<400> SEQUENCE: 649

His Xaa Gln Gly Thr Phe Ile Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 650
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer

<400> SEQUENCE: 650

His Xaa Gln Gly Thr Phe Ile Ser Asp Lys Ser Lys Tyr Leu Asp Glu
1               5                   10                  15

Gln Ala Ala Lys Glu Phe Ile Ala Trp Leu Met Asn Thr
            20                  25

<210> SEQ ID NO 651
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Xaa is Dmia
<220> FEATURE:
```

```
<221> NAME/KEY: MOD_RES
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (16)..(20)
<223> OTHER INFORMATION: Lactam ring between side chains of amino acids
      at positions 16 and 20

<400> SEQUENCE: 651

Xaa Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 652
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(20)
<223> OTHER INFORMATION: Lactam ring between side chains of amino acids
      at positions 16 and 20

<400> SEQUENCE: 652

Xaa Ser Gln Gly Thr Phe Thr Ser Asp Lys Ser Lys Tyr Leu Asp Glu
1               5                   10                  15

Arg Arg Ala Lys Asp Phe Val Gln Trp Leu Met Asn Thr
            20                  25

<210> SEQ ID NO 653
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains of amino acids
      at positions 16 and 20
<220> FEATURE:
<221> NAME/KEY: MOD_RES
<222> LOCATION: (29)..(29)
<223> OTHER INFORMATION: Acylated with a C16 fatty acyl group via
      gamma-Glu spacer

<400> SEQUENCE: 653

Xaa Ser Gln Gly Thr Phe Thr Ser Asp Tyr Ser Lys Tyr Leu Asp Glu
1               5                   10                  15
```

```
Arg Arg Ala Lys Asp Phe Val Gln Trp Leu Met Asn Lys
            20                  25

<210> SEQ ID NO 654
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (1)..(1)
<223> OTHER INFORMATION: Xaa is Dmia
<220> FEATURE:
<221> NAME/KEY: MISC_FEATURE
<222> LOCATION: (16)..(20)
<223> OTHER INFORMATION: Lactam ring between side chains of amino acids
      at positions 16 and 20
<220> FEATURE:
<221> NAME/KEY: MOD_RES
<222> LOCATION: (29)..(29)
<223> OTHER INFORMATION: Acylated with a C16 fatty acyl group via
      gamma-Glu-gamma-Glu spacer

<400> SEQUENCE: 654

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Lys
            20                  25

<210> SEQ ID NO 655
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MOD_RES
<222> LOCATION: (16)..(16)
<223> OTHER INFORMATION: Xaa is Aib

<400> SEQUENCE: 655

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25

<210> SEQ ID NO 656
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: c-term amidation
<220> FEATURE:
```

```
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (10)..(10)
<223> OTHER INFORMATION: Acylated with a C16 fatty acyl group via
      gamma-Glu spacer
<220> FEATURE:
<221> NAME/KEY: MOD_RES
<222> LOCATION: (16)..(16)
<223> OTHER INFORMATION: Xaa is Aib

<400> SEQUENCE: 656

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr
            20                  25
```